US009808502B2

(12) United States Patent
Berghard et al.

(10) Patent No.: US 9,808,502 B2
(45) Date of Patent: Nov. 7, 2017

(54) POLYPEPTIDES BINDING TO HUMAN COMPLEMENT C5

(71) Applicant: Swedish Orphan Biovitrum AB (publ), Stockholm (SE)

(72) Inventors: Charlotta Berghard, Stockholm (SE); Magnus Berglund, Vendelso (SE); Patrik Strömberg, Sollentuna (SE); Malin Lindborg, Saltsjo-Boo (SE); Elin Gunneriusson, Saltsjobaden (SE); Joachim Feldwisch, Tyreso (SE)

(73) Assignee: Swedish Orphan Biovitrum AB (publ), Stockholm (SE)

( * ) Notice: Subject to any disclaimer, the term of this patent is extended or adjusted under 35 U.S.C. 154(b) by 371 days.

(21) Appl. No.: 14/378,522

(22) PCT Filed: Feb. 19, 2013

(86) PCT No.: PCT/SE2013/050139
§ 371 (c)(1),
(2) Date: Aug. 13, 2014

(87) PCT Pub. No.: WO2013/126006
PCT Pub. Date: Aug. 29, 2013

(65) Prior Publication Data
US 2015/0011474 A1 Jan. 8, 2015

(30) Foreign Application Priority Data
Feb. 20, 2012 (SE) .................................... 1250145

(51) Int. Cl.
*A61K 38/16* (2006.01)
*C07K 14/00* (2006.01)
*C07K 14/47* (2006.01)
*C07K 14/195* (2006.01)
*C07K 14/315* (2006.01)
*A61K 38/00* (2006.01)

(52) U.S. Cl.
CPC ............ *A61K 38/164* (2013.01); *A61K 38/16* (2013.01); *C07K 14/00* (2013.01); *C07K 14/195* (2013.01); *C07K 14/315* (2013.01); *C07K 14/47* (2013.01); *A61K 38/00* (2013.01)

(58) Field of Classification Search
CPC ................................. A61K 38/16; C07K 14/00
See application file for complete search history.

(56) References Cited

U.S. PATENT DOCUMENTS

| 9,187,535 B2 * | 11/2015 | Lindborg ............... C07K 14/31 |
| 2005/0090448 A1 | 4/2005 | Johnson et al. |
| 2014/0140366 A1 | 5/2014 | Tamatani et al. |
| 2016/0200772 A1 | 7/2016 | Nordling et al. |
| 2016/0311870 A1 | 10/2016 | Nilsson et al. |

FOREIGN PATENT DOCUMENTS

| WO | 9101743 A1 | 2/1991 |
| WO | 9529697 A1 | 11/1995 |
| WO | 0230985 A2 | 4/2002 |
| WO | 02059148 A2 | 8/2002 |
| WO | 03015819 A1 | 2/2003 |
| WO | 2004007553 A1 | 1/2004 |
| WO | 2005023866 A2 | 3/2005 |
| WO | 2005075507 | 8/2005 |
| WO | 2007028968 A1 | 3/2007 |
| WO | 2007106585 A1 | 9/2007 |
| WO | 2009016043 A2 | 2/2009 |
| WO | 2009077175 A1 | 6/2009 |
| WO | 2009080810 A1 | 7/2009 |
| WO | 2010015608 A1 | 2/2010 |
| WO | 2011063980 A1 | 6/2011 |
| WO | 2012004384 A2 | 1/2012 |
| WO | 2013126006 A1 | 8/2013 |
| WO | 2014096163 A1 | 6/2014 |

OTHER PUBLICATIONS

Larghi et al., "Modulatiors of Complement Activation: A Patent Review", Expert Opinion on Therapeutic Patents; vol. 24; No. 6; Jun. 1, 2014; pp. 665-686.
Stromberg et al., "Development of Affibody C5 Inhibitors for Versatile and Efficient Therapeutic Targeting of the Terminal Complement Pathway", Abstracts/Molecular Immunology; vol. 61; No. 2; Oct. 1, 2014; p. 256.
Supplementary European Search Report of the European Searching Authority for European Patent Application No. 13752233.0; dated Aug. 5, 2015; 10 Pages.
International Search Report for the International Searching Authority for International Patent Application No. PCT/SE2013/050139; International Filing Date: Feb. 19, 2013; dated May 28, 2013; 6 Pages.
Written Opinion of the International Sarching Authority for International Patent Application No. PCT/SE2013/050139; International Filing Date: Feb. 19, 2013; dated May 28, 2013; 5 Pages.
A. Lapeyraque et al., "Eculizumab in Severe Shiga-Toxin-Associated HUS," New England Journal of Medicine; Jun. 30, 2011, pp. 2561-2563, vol. 364, No. 26.
A. Manderson et al., "The Role of Complement in the Development of Systemic Lupus Erythematosus," Annual Review of Immunology; 2004, pp. 431-456, vol. 22.

(Continued)

*Primary Examiner* — Jeffrey E Russel
(74) *Attorney, Agent, or Firm* — Wolf, Greenfield & Sacks, P.C.

(57) ABSTRACT

The present invention relates to C5 binding polypeptides, comprising a C5 binding motif, BM, which motif consists of an amino acid sequence selected from i) $EX_2X_3X_4A X_6X_7EID X_{11}LPNL X_{16}X_{17}X_{18}QW X_{21}AFIX_{25}X_{26}LX_{28}D$, and ii) an amino acid sequence which has at least 86% identity to the sequence defined in i), wherein the polypeptide binds to C5. The present invention moreover relates to C5 binding polypeptides for use in therapy, such as for use in treatment of a C5 related condition, and to methods of treatments.

35 Claims, 53 Drawing Sheets

(56) References Cited

OTHER PUBLICATIONS

B. Tack et al., "Fifth Component of Human Complement: Purification from Plasma and Polypeptide Chain Structure," American Chemical Society; 1979, pp. 1490-1497, vol. 18, No. 8.
C. Gronwall et al., "Selection and Characterization of Affibody Ligands Binding to Alzheimer Amyloid B Peptides;" Journal of Biotechnology; 2007, pp. 162-183, vol. 128.
D. Copland et al., "Systemic and Local Anti-C5 Therapy Reduces the Disease Severity in Experimental Autoimmune Uveoretinitis," Clinical and Experimental Immunology 2009, pp. 303-314, vol. 159.
D. Haviland et al., "Cellular Expression of the C5a Anaphylatoxin Recepter (C5aR): Demonstration of C5aR on Nonmyeloid Cells of the Liver and Lung," The Journal of Immunology; 1995, pp. 1861-1869, vol. 154.
D. Ricklin et al., "Complement—A Key System for Immune Surveillance and homeostasis," Sep. 2010, pp. 785-797, vol. 11, No. 9.
F. Fredslund et al., "Structure of and Influence of a Tick Complement Inhibitor on Human Complement Component 5," Nature Immunology; Jul. 2008, pp. 753-760, vol. 9., No. 7.
G. Cazander et al., "Complement Activation and Inhibition in Wound Healing," Clincial and Development Immunology; 2012, pp. 1-14, vol. 2012, Article ID: 534291.
J. Howard Jr. et al., "A Randomized, Double-Blind, Placebo-Controlled Phase II Study of Eculizumab in Patients with Refractory Generalized Myasthenia Gravis," Muscle & Nerve; Jul. 2013, pp. 76-84.
K. Kaida et al., "Antibodies to Gangliosides and Ganglioside Complexes in Guillain-Barre Syndrome and Fisher Syndrome: Mini-review," Journal of Neuroimmunology; 2010, pp. 5-12, vol. 223.
M. Chen et al., "The Complement System in Systemic Autoimmune Disease," Journal of Autoimmunity; 2010, pp. J276-J286, vol. 34.
M. Fung et al., "Pre-neutralization of C5a-mediated Effects by the Monoclonal Antibody 137-26 Reacting with the C5a Moiety of Native C5 Without Preventing C5 Cleavage," Clin. Exp Immunol; 2003, pp. 160-169, vol. 133.
M. Markiewski et al., "Modulation of the Anti-tumor Immune Response by Complement," Nature Immunology; Nov. 2008, pp. 1225-1235, vol. 9, No. 11.
M. Nunn, et al., Complement Inhibitor of C5 Activation from the Soft Tick *Ornithodoros moubata*,: The Journal of Immunology; 2005, pp. 2084-2091, vol. 174.
M. Stegall et al., "Terminal Complement Inhibition Decreases Antibody-Mediated Rejection in Sensitized Renal Transplant Recipients," American Journal of Transplantation; 2011, pp. 2405-2413, vol. 11.
S. Pittock et al., "Eculizumab in AQP4-IgG-positive Relapsing Neuromyelitis Optica Spectrum Disorders: An Open-label Pilot Study," Lancet Neurology; Jun. 2013, pp. 554-562, vol. 12.
T. Abe et al., "Local Complement-Targeted Intervention in Periodontitis: Proof-of-Concept Using a C5a Receptor (CD88) Antagonist," The Journal of Immunology; 2012, pp. 5442-5448, vol. 189, No. 11.
T. Woodruff et al., "Inhibiting the C5-C5a Receptor Axis," Molecular Immunology; 2011, pp. 1631-1642, vol. 48.
Unknown [online]; [retrieved on Mar. 17, 2017]; retrieved from the internet https://www.ncbi.nlm.nih.gov/protein/NP_001726.2. NCBI. "Complement C5 Isoform 1 Preproprotein [*Homo sapiens*]," NCBI Reference Sequence: NP_0017262., Oct. 6, 2016.
"Mutant *Streptococcus* G148 ABD/SPA Z domain fusion protein"; XP002731913; retreived from EBI accession No. GSP: AAB01886, revised Sep. 12, 2003.
International Preliminary Report on Patentability for International Application No. PCT/EP2014/068259; International Filing Date Aug. 28, 2014; dated Mar. 10, 2016; 5 pages.
International Preliminary Report on Patentability for International Application No. PCT/EP2014/068282; International Filing Date Aug. 28, 2014; dated Nov. 5, 2015; 10 pages.
International Search Report and Written Opinion of the International Searching Authority for International Application No. PCT/EP2014/068282; International Filing Date Aug. 28, 2014; dated Jan. 7, 2015; 14 pages.
International Search Report for International Application No. PCT/EP2014/068259; International Filing Date Aug. 28, 2014; dated Nov. 18, 2014; 4 pages.
Written Opinion for International Application No. PCT/EP2014/068259; International Filing Date Aug. 28, 2014; dated Nov. 18, 2014; 4 pages.
Written Opinion of the International Preliminary Examining Authority for International Application No. PCT/EP2014/068282; International Filing Date Aug. 28, 2014; dated Jul. 30, 2015; 8 pages.
Frankel et al.; "Characterization of diphtheria fusion proteins targeted to the human interleukin-3 receptor"; Protein Eng., vol. 13, No. 8; 2000; pp. 575-581.
Paukla et al.; Abstract of "Genetic analysiws of protein stability and function"; Annu. Rev. Genet., vol. 23; 1989; 1 page.

* cited by examiner

Fig. 1A

| Polypeptide | Amino Acid Sequence | SEQ ID NO: |
|---|---|---|
| CBM06175 | EVLEAWDEIDRLPNLTIEQWLAFINKLDD | 1 |
| CBM08044 | EVLEAWNEIDRLPNLTIEQWLAFINKLDD | 2 |
| CBM05998 | EVIEAWNEIDRLPNLTIEQWLAFINKLDD | 3 |
| CBM06009 | EVLEAWDEIDRLPNLTLDQWLAFINKLDD | 4 |
| CBM06079 | EVLDAWDEIDALPNLTIEQWLAFINKLDD | 5 |
| CBM06126 | EVIDAWDEIDRLPNLTLDQWLAFINKLDD | 6 |
| CBM06140 | ETLEAWDEIDRLPNLTIEQWLAFINKLDD | 7 |
| CBM06189 | EVIDAWNEIDALPNLTLDQWLAFINKLDD | 8 |
| CBM06214 | EVLDAWNEIDKLPNLTIDQWLAFINKLDD | 9 |
| CBM06215 | EVLEAWDEIDHLPNLTLDQWLAFINKLDD | 10 |
| CBM06226 | EVLEAWDEIDALPNLTIEQWLAFINKLDD | 11 |
| CBM06018 | EVLDAWDEIDKLPNLTIEQWLAFINKLDD | 12 |
| CBM05477 | ETITAWDEIDKLPNLTIEQWLAFIGKLED | 13 |
| CBM05363 | ESMKAWDEIDRLPNLNINQWVAFIDSLYD | 14 |
| CBM05483 | ESIEAWTEIDHLPNLTIEQWLAFINKLTD | 15 |
| CBM05538 | EVLDAWHEIDTLPNLTVRQWLAFISKLED | 16 |
| CBM05692 | EHIQANEEIDRLPNLTIKQWLAFINKLHD | 17 |
| CBM05994 | EVLHAWAEIDALPNLTIEQWLAFINKLDD | 18 |
| CBM05995 | EVLAAWDEIDSLPNLTLQQWLAFINKLDD | 19 |
| CBM05996 | EVIDAWNEIIDALPNLTLEQWLAFINKLDD | 20 |
| CBM05997 | EVLDAWNEIDALPNLTIDQWLAFINKLSD | 21 |
| CBM05999 | EVIEAWDEIDGLPNLTIEQWLAFINKLDD | 22 |
| CBM06000 | EVLEAWDEIDHLPNLTLQQWLAFINKLDD | 23 |

Fig. 1B

| | | |
|---|---|---|
| CBM06001 | EVIEAWNEIDALPNLTIEQWLAFINKLDD | 24 |
| CBM06002 | EVIAAWNEIDRLPNLTLTQWLAFINKLDD | 25 |
| CBM06003 | EVIEAWDEIDALPNLTLQQWLAFINKLDD | 26 |
| CBM06004 | EVIAAWDEIDKLPNLTIEQWLAFINKLDD | 27 |
| CBM06005 | EVIAAWDEIDKLPNLTLQQWLAFINKLDD | 28 |
| CBM06006 | ETIAAWDEIDKLPNLTIEQWLAFINKLDD | 29 |
| CBM06007 | ETIEAWNEIDRLPNLTIEQWLAFINKLDD | 30 |
| CBM06008 | EVLEAWREIDALPNLTIQQWLAFINKLDD | 31 |
| CBM06010 | EVIEAWDEIDQLPNLTIEQWLAFINKLDD | 32 |
| CBM06011 | EVLRAWDEIDHLPNLTLEQWLAFINKLDD | 33 |
| CBM06012 | EVLEAWDEIDRLPNLTLNQWLAFINKLDD | 34 |
| CBM06013 | EVLDAWNEIDHLPNLTIEQWLAFINKLDD | 35 |
| CBM06014 | EVIDAWNEIDKLPNLTIEQWLAFINKLDD | 36 |
| CBM06015 | ETLEAWDEIDQLPNLTLQQWLAFINKLDD | 37 |
| CBM06016 | EVIEAWNEIDALPNLTLDQWLAFINKLDD | 38 |
| CBM06017 | EVIDAWNEIDRLPNLTLQQWLAFINKLDD | 39 |
| CBM06019 | EVIDAWNEIDQLPNLTLEQWLAFINKLDD | 40 |
| CBM06020 | ETIAAWDEIDHLPNLTLEQWLAFINKLDD | 41 |
| CBM06024 | EVLQAWDEIDHLPNLTIQQWLAFINKLSD | 42 |
| CBM06025 | ETLHAWAEIDRLPNLTIEQWLAFINKLDD | 43 |
| CBM06026 | EVLEAWDEIDHLPNLTLAQWLAFINKLDD | 44 |
| CBM06027 | EVIEAWDEIDKLPNLTIAQWLAFINKLDD | 45 |
| CBM06028 | EVLDAWDEIDHLPNLTLQQWLAFINKLDD | 46 |
| CBM06029 | ETIEAWNEIDKLPNLTLTQWLAFINKLDD | 47 |

Fig. 1C

| | | |
|---|---|---|
| CBM06030 | EVLEAWNEIDLLPNLTIEQWLAFINKLDD | 48 |
| CBM06031 | EVIEAWDEIDHLPNLTIDQWLAFINKLDD | 49 |
| CBM06032 | EVISAWNEIDALPNLTLQQWLAFINKLDD | 50 |
| CBM06033 | EVIAAWNEIDKLPNLTIEQWLAFINKLDD | 51 |
| CBM06034 | ETIEAWNEIDSLPNLTLDQWLAFINKLDD | 52 |
| CBM06035 | EVLDAWNEIDQLPNLTLQQWLAFINKLDD | 53 |
| CBM06037 | EVLAAWNEIDHLPNLTIEQWLAFINKLDD | 54 |
| CBM06038 | EVLEAWDEIDHLPNLTITQWLAFINKLDD | 55 |
| CBM06039 | ETIDAWNEIDHLPNLTIEQWLAFINKLDD | 56 |
| CBM06040 | EVIEAWNEIDHLPNLTIQQWLAFINKLDD | 57 |
| CBM06041 | EVIQAWNEIDALPNLTISQWLAFINKLDD | 58 |
| CBM06043 | EVIAAWDEIDSLPNLTIEQWLAFINKLDD | 59 |
| CBM06044 | EHIEAWNEIDALPNLTIEQWLAFINKLQD | 60 |
| CBM06045 | EVLEAWNEIDKLPNLTLDQWLAFINKLDD | 61 |
| CBM06047 | EVIDAWNEIDHLPNLTIEQWLAFINKLAD | 62 |
| CBM06048 | ETIDAWDEIDKLPNLTIEQWLAFINKLDD | 63 |
| CBM06049 | EVIAAWDEIDLLPNLTLQQWLAFINKLAD | 64 |
| CBM06050 | EVIHAWDEIDKLPNLTIEQWLAFINKLDD | 65 |
| CBM06051 | EVIAAWNEIDHLPNLTLEQWLAFINKLDD | 66 |
| CBM06052 | ETLDAWNEIDKLPNLTLSQWLAFINKLDD | 67 |
| CBM06053 | EVLEAWNEIDALPNLTLEQWLAFINKLDD | 68 |
| CBM06054 | EVIQAWDEIDHLPNLTISQWLAFINKLDD | 69 |
| CBM06055 | EVLQAWDEIDSLPNLTIEQWLAFINKLDD | 70 |
| CBM06056 | ETLEAWDEIDHLPNLTIAQWLAFINKLDD | 71 |

Fig. 1D

| | | |
|---|---|---|
| CBM06057 | ETIDAWNEIDRLPNLTISQWLAFINKLDD | 72 |
| CBM06058 | EVLDAWHEIDHLPNLTIQQWLAFINKLDD | 73 |
| CBM06059 | EQIRAWDEIDKLPNLTIEQWLAFINKLAD | 74 |
| CBM06060 | ETLYAWNEIDKLPNLTIEQWLAFIEKLQD | 75 |
| CBM06061 | EVIEAWNEIDALPNLTIDQWLAFINKLDD | 76 |
| CBM06062 | EVLEAWNEIDHLPNLTIQQWLAFINKLDD | 77 |
| CBM06063 | ETIEAWDEIDALPNLTIEQWLAFINKLDD | 78 |
| CBM06065 | EVIEAWNEIDHLPNLTIQQWLAFINKLDD | 79 |
| CBM06066 | EVIEAWNEIDKLPNLTIQQWLAFINKLDD | 80 |
| CBM06068 | ETLDAWAEIDHLPNLTLDQWLAFINKLDD | 81 |
| CBM06069 | EHIDAWNEIDALPNLTLSQWLAFINKLDD | 82 |
| CBM06070 | EVLDAWNEIDKLPNLTIAQWLAFINKLDD | 83 |
| CBM06071 | EVIEAWTEIDYLPNLTLQQWLAFINKLDD | 84 |
| CBM06072 | ETIEAWNEIDHLPNLTIAQWLAFINKLDD | 85 |
| CBM06073 | EVIQAWNEIDKLPNLTLEQWLAFINKLDD | 86 |
| CBM06074 | EVIEAWDEIDHLPNLTIEQWLAFINKLDD | 87 |
| CBM06075 | ETIDAWNEIDLLPNLTIEQWLAFINKLDD | 88 |
| CBM06076 | EHIDAWNEIDKLPNLTLDQWLAFINKLDD | 89 |
| CBM06077 | EVVAAWNEIDALPNLTIEQWLAFINKLND | 90 |
| CBM06080 | EVIEAWNEIDALPNLTIAQWLAFINKLDD | 91 |
| CBM06081 | EVLQAWDEIDRLPNLTLDQWLAFINKLDD | 92 |
| CBM06082 | EVIDAWDEIDHLPNLTIEQWLAFINKLSD | 93 |
| CBM06083 | EVVEAWNEIDQLPNLTIEQWLAFINKLDD | 94 |
| CBM06084 | EVIQAWNEIDALPNLTIEQWLAFINKLDD | 95 |

Fig. 1E

| | | |
|---|---|---|
| CBM06085 | EVIQAWDEIDKLPNLTIDQWLAFINKLAD | 96 |
| CBM06086 | EVVAAWDEIDALPNLTLTQWLAFINKLDD | 97 |
| CBM06087 | EVIQAWNEIDGLPNLTLSQWLAFINKLDD | 98 |
| CBM06088 | ETIEAWDEIDALPNLTITQWLAFINKLDD | 99 |
| CBM06089 | EVIDAWNEIDHLPNLTIQQWLAFINKLAD | 100 |
| CBM06090 | ETIEAWNEIDALPNLTIDQWLAFINKLED | 101 |
| CBM06091 | EHIHAWNEIDELPNLTIEQWLAFINKLAD | 102 |
| CBM06092 | EVIDAWDEIDHLPNLTIDQWLAFINKLSD | 103 |
| CBM06093 | EVIDANDEIDALPNLTIAQWLAFINKLHD | 104 |
| CBM06095 | ETIEAWDEIDKLPNLTIEQWLAFINKLDD | 105 |
| CBM06097 | EVLLAWDEIDHLPNLTLEQWLAFINKLDD | 106 |
| CBM06098 | EHIDAWNEIDGLPNLTLEQWLAFINKLDD | 107 |
| CBM06099 | EVIEAWSEIDALPNLTIDQWLAFINKLAD | 108 |
| CBM06100 | EQLNAWAEIDALPNLTIEQWLAFINKLDD | 109 |
| CBM06101 | EVIDAWNEIDALPNLTIAQWLAFINKLDD | 110 |
| CBM06103 | ETIDAWNEIDQLPNLTIEQWLAFINKLDD | 111 |
| CBM06104 | EVIEAWDEIDKLPNLTLAQWLAFINKLDD | 112 |
| CBM06105 | EVLYAWAEIDHLPNLTIEQWLAFINKLDD | 113 |
| CBM06107 | EQIDAWNEIDRLPNLTIQQWLAFINKLDD | 114 |
| CBM06108 | EVLAAWDEIDRLPNLTIEQWLAFINKLDD | 115 |
| CBM06109 | EVIEAWDEIDHLPNLTLHQWLAFINKLDD | 116 |
| CBM06110 | EVIEAWNEIDKLPNLTLQQWLAFINKLDD | 117 |
| CBM06111 | EVIDANDEIDALPNLTIEQWLAFINKLHD | 118 |
| CBM06112 | EVIAAWDEIDALPNLTIEQWLAFINKLDD | 119 |

Fig. 1F

| | | |
|---|---|---|
| CBM06113 | EVIEAWTEIDQLPNLTLDQWLAFINKLDD | 120 |
| CBM06114 | EVINAWNEIDALPNLTLQQWLAFINKLDD | 121 |
| CBM06115 | EHIEAWDEIDHLPNLTIDQWLAFINKLAD | 122 |
| CBM06116 | EHLEAWREIDALPNLTIEQWLAFINKLDD | 123 |
| CBM06117 | EVLDAWNEIDKLPNLTLQQWLAFINKLDD | 124 |
| CBM06118 | EVIAAWDEIDHLPNLTIQQWLAFINKLDD | 125 |
| CBM06119 | EVIQAWNEIDALPNLTLEQWLAFINKLDD | 126 |
| CBM06121 | EVIDAWNEIDHLPNLTIAQWLAFINKLDD | 127 |
| CBM06122 | EQLDAWDEIDHLPNLTIDQWLAFINKLSD | 128 |
| CBM06123 | EVLNAWDEIDKLPNLTIEQWLAFINKLDD | 129 |
| CBM06124 | EVLEAWNEIDHLPNLTIDQWLAFINKLDD | 130 |
| CBM06125 | EVLLAWDEIDRLPNLTIDQWLAFINKLAD | 131 |
| CBM06127 | EVIAAWNEIDQLPNLTLDQWLAFINKLDD | 132 |
| CBM06128 | ETLLAWDEIDALPNLTIEQWLAFINKLDD | 133 |
| CBM06129 | EVIDAWNEIDTLPNLTLEQWLAFINKLDD | 134 |
| CBM06131 | EVLHAWDEIDHLPNLTLNQWLAFINKLQD | 135 |
| CBM06132 | EVIQAWNEIDALPNLTIAQWLAFINKLDD | 136 |
| CBM06133 | ETVDAWNEIDALPNLTIEQWLAFINKLDD | 137 |
| CBM06134 | EVIQAWDEIDHLPNLTIDQWLAFINKLDD | 138 |
| CBM06135 | EVLDAWNEIDALPNLTLDQWLAFINKLDD | 139 |
| CBM06136 | ETIEAWNEIDALPNLTLDQWLAFINKLDD | 140 |
| CBM06137 | EVIEAWDEIDALPNLTIDQWLAFINKLDD | 141 |
| CBM06138 | EVIEAWNEIDQLPNLTIQQWLAFINKLDD | 142 |
| CBM06139 | EVIEAWTEIDHLPNLTIEQWLAFINKLDD | 143 |

Fig. 1G

| | | |
|---|---|---|
| CBM06141 | EVIQAWNEIDHLPNLTLQQWLAFINKLED | 144 |
| CBM06142 | EVIQANNEIDQLPNLTIEQWLAFINKLHD | 145 |
| CBM06143 | EVLHAWSEIDKLPNLTIEQWLAFINKLDD | 146 |
| CBM06144 | ETIQAWDEIDKLPNLTLDQWLAFINKLSD | 147 |
| CBM06145 | ETLRAWDEIDKLPNLTIQQWLAFINKLAD | 148 |
| CBM06146 | EVIDAWNEIDHLPNLTIEQWLAFINKLED | 149 |
| CBM06147 | EVIDAWNEIDHLPNLTLQQWLAFINKLAD | 150 |
| CBM06148 | ETIDAWNEIDALPNLTLDQWLAFINKLDD | 151 |
| CBM06149 | EVIEAWNEIDQLPNLTIEQWLAFINKLDD | 152 |
| CBM06150 | EVIRAWDEIDQLPNLTLSQWLAFINKLDD | 153 |
| CBM06151 | EVIEAWNEIDRLPNLTIHQWLAFINKLDD | 154 |
| CBM06152 | ETIEAWNEIDQLPNLTIEQWLAFINKLDD | 155 |
| CBM06153 | EVLTAWAEIDALPNLTLSQWLAFINKLDD | 156 |
| CBM06154 | EVIEAWDEIDKLPNLTVDQWLAFINKLDD | 157 |
| CBM06155 | EVIDAWNEIDHLPNLTLTQWLAFINKLDD | 158 |
| CBM06156 | EVIEAWNEIDQLPNLTLDQWLAFINKLDD | 159 |
| CBM06157 | ETLQAWDEIDHLPNLTLNQWLAFINKLDD | 160 |
| CBM06158 | EVIDAWNEIDHLPNLTIEQWLAFINKLDD | 161 |
| CBM06159 | EVIEAWNEIDLLPNLTLSQWLAFINKLDD | 162 |
| CBM06160 | EVIDAWDEIDRLPNLTLKQWLAFINKLDD | 163 |
| CBM06161 | ETLHAWDEIDKLPNLTIEQWLAFINKLDD | 164 |
| CBM06162 | EVIKAWDEIDHLPNLTLNQWLAFINKLDD | 165 |
| CBM06163 | EVIEAWNEIDHLPNLTLAQWLAFINKLDD | 166 |
| CBM06164 | EVIQAWNEIDHLPNLTIDQWLAFITKLED | 167 |

Fig. 1H

| | | |
|---|---|---|
| CBM06165 | EVIEAWNEIDRLPNLTIKQWLAFINKLDD | 168 |
| CBM06167 | EVIEAWNEIDSLPNLTLQQWLAFINKLDD | 169 |
| CBM06168 | ETIDAWNEIDKLPNLTIEQWLAFINKLDD | 170 |
| CBM06169 | EVLEAWAEIDALPNLTIAQWLAFINKLDD | 171 |
| CBM06170 | ETIDAWNEIDRLPNLTIEQWLAFINKLDD | 172 |
| CBM06171 | ETLKAWDEIDRLPNLTLEQWLAFINKLDD | 173 |
| CBM06172 | ETIAAWNEIDALPNLTLQQWLAFINKLDD | 174 |
| CBM06173 | EVLQAWNEIDHLPNLTIQQWLAFINKLDD | 175 |
| CBM06174 | EVIEAWSEIDHLPNLTLQQWLAFINKLDD | 176 |
| CBM06176 | EVIDAWNEIDGLPNLTIEQWLAFINKLDD | 177 |
| CBM06178 | EVIHAWNEIDHLPNLTLNQWLAFINKLED | 178 |
| CBM06179 | EVLDAWNEIDSLPNLTLDQWLAFINKLDD | 179 |
| CBM06180 | EQIEAWNEIDRLPNLTLEQWLAFINKLDD | 180 |
| CBM06181 | EVVDAWNEIDALPNLTIEQWLAFINKLDD | 181 |
| CBM06182 | EVIEAWNEIDKLPNLTIEQWLAFINKLDD | 182 |
| CBM06183 | EVIEANDEIDRLPNLTIEQWLAFINKLDD | 183 |
| CBM06184 | ETLQAWDEIDKLPNLTIEQWLAFINKLHD | 184 |
| CBM06185 | EVIEAWDEIDHLPNLTIDQWLAFINKLAD | 185 |
| CBM06186 | EVIEAWNEIDHLPNLTLQQWLAFINKLAD | 186 |
| CBM06187 | ETIDAWNEIDKLPNLTIEQWLAFINKLDD | 187 |
| CBM06188 | EVIDAWDEIDKLPNLTLAQWLAFINKLDD | 188 |
| CBM06190 | EVLQAWDEIDKLPNLTIQQWLAFINKLDD | 189 |
| CBM06191 | EVIAAWNEIDGLPNLTLQQWLAFINKLDD | 190 |
| CBM06192 | ETLNAWNEIDALPNLTLQQWLAFINKLDD | 191 |

Fig. 1I

| | | |
|---|---|---|
| CBM06193 | EVLSAWNEIDQLPNLTLEQWLAFINKLDD | 192 |
| CBM06194 | ETLEAWDEIDHLPNLTLHQWLAFINKLDD | 193 |
| CBM06195 | EQIEAWNEIDHLPNLTLQQWLAFINKLAD | 194 |
| CBM06196 | EVVEAWDEIDKLPNLTIEQWLAFINKLDD | 195 |
| CBM06197 | EVLEAWNEIDELPNLTIEQWLAFINKLDD | 196 |
| CBM06198 | EVIDAWNEIDQLPNLTLQQWLAFINKLDD | 197 |
| CBM06199 | ETIDAWDEIDKLPNLTLSQWLAFINKLDD | 198 |
| CBM06200 | ETIDAWNEIDQLPNLTLQQWLAFINKLDD | 199 |
| CBM06201 | EVIQAWDEIDALPNLTLNQWLAFINKLDD | 200 |
| CBM06202 | EVLDAWAEIDQLPNLTLQQWLAFINKLDD | 201 |
| CBM06203 | EHIAAWDEIDALPNLTIEQWLAFINKLDD | 202 |
| CBM06206 | EVIRAWDEIDALPNLTIEQWLAFINKLDD | 203 |
| CBM06207 | EVIDAWDEIDALPNLTIDQWLAFINKLAD | 204 |
| CBM06208 | EVIDAWNEIDRLPNLTIQQWLAFINKLDD | 205 |
| CBM06209 | EVITAWNEIDHLPNLTLSQWLAFINKLDD | 206 |
| CBM06210 | EVIDAWNEIDALPNLTIHQWLAFINKLDD | 207 |
| CBM06211 | EQLKAWDEIDKLPNLTIEQWLAFIEKLQD | 208 |
| CBM06212 | EHIDAWTEIDHLPNLTIEQWLAFINKLDD | 209 |
| CBM06213 | EQLRAWDEIDKLPNLTIEQWLAFINKLQD | 210 |
| CBM06216 | EVLEAWREIDSLPNLTIAQWLAFINKLDD | 211 |
| CBM06217 | EVIQAWNEIDKLPNLTIEQWLAFINKLDD | 212 |
| CBM06218 | EHVEAWNEIDQLPNLTIEQWLAFINKLAD | 213 |
| CBM06219 | EVIDAWDEIDALPNLTIDQWLAFINKLSD | 214 |
| CBM06220 | EVIEAWNEIDHLPNLTIEQWLAFINKLDD | 215 |

Fig. 1J

| | | |
|---|---|---|
| CBM06221 | EVLQAWDEIDKLPNLTIEQWLAFINKLSD | 216 |
| CBM06222 | EVIKAWNEIDSLPNLTIEQWLAFINKLDD | 217 |
| CBM06223 | EVLEAWHEIDLLPNLTIQQWLAFINKLDD | 218 |
| CBM06224 | EVLEAWTEIDRLPNLTLDQWLAFINKLDD | 219 |
| CBM06225 | EQLYAWNEIDHLPNLTIEQWLAFIEKLQD | 220 |
| CBM06227 | EVLNAWDEIDKLPNLTIKQWLAFINKLDD | 221 |
| CBM06228 | EVIRAWDEIDKLPNLTVEQWLAFINKLDD | 222 |
| CBM06230 | EVVQAWDEIDQLPNLTLEQWLAFINKLDD | 223 |
| CBM06231 | EVIRAWDEIDQLPNLTLEQWLAFINKLDD | 224 |
| CBM06232 | ETIDAWNEIDHLPNLTLDQWLAFINKLDD | 225 |
| CBM06233 | EVVAAWTEIDLLPNLTLDQWLAFINKLED | 226 |
| CBM06234 | EVVAAWDEIDALPNLTIEQWLAFINKLSD | 227 |
| CBM06235 | ETLEAWREIDSLPNLTLEQWLAFINKLDD | 228 |
| CBM06236 | EVIKAWNEIDHLPNLTLDQWLAFINKLDD | 229 |
| CBM06237 | EVLEAWTEIDKLPNLTIDQWLAFINKLDD | 230 |
| CBM06238 | ETLEAWDEIDKLPNLTIDQWLAFINKLDD | 231 |
| CBM06239 | EVIEAWNEIDKLPNLTIDQWLAFINKLDD | 232 |
| CBM06240 | ETIDAWNEIDKLPNLTLEQWLAFINKLDD | 233 |
| CBM06241 | ETLDAWDEIDALPNLTIDQWLAFINKLED | 234 |
| CBM06242 | EVLSAWNEIDHLPNLTIQQWLAFINKLDD | 235 |
| CBM06244 | EVIQANDEIDKLPNLTIEQWLAFIHKLHD | 236 |
| CBM06245 | EHLDAWDEIDHLPNLTIQQWLAFINKLAD | 237 |
| CBM06246 | EVIQAWNEIDQLPNLTIEQWLAFINKLDD | 238 |
| CBM06247 | EVIEAWNEIDYLPNLTIAQWIAFINKLDD | 239 |

Fig. 1K

| | | |
|---|---|---|
| CBM06248 | ETIQAWDEIDRLPNLTLQQWLAFINKLDD | 240 |
| CBM06249 | ETIQAWDEIDKLPNLTIEQWLAFINKLDD | 241 |
| CBM06250 | ETLDAWAEIDHLPNLTIEQWLAFINKLDD | 242 |
| CBM06251 | EVIEAWDEIDKLPNLTLNQWLAFINKLDD | 243 |
| CBM06252 | EVLDAWNEIDQLPNLTIEQWLAFINKLDD | 244 |
| CBM06253 | EVLHAWNEIDHLPNLTIEQWLAFIEKLED | 245 |
| CBM06254 | EVIEAWQEIDKLPNLTIDQWLAFINKLDD | 246 |
| CBM06257 | EVVDAWNEIDQLPNLTIEQWLAFINKLDD | 247 |
| CBM06258 | EQIEAWNEIDALPNLTIEQWLAFINKLAD | 248 |
| P06175 | KEVLEAWDEIDRLPNLTIEQWLAFINKLDDDPSQSSELLSEAKKLNDSQ | 249 |
| P08044 | KEVLEAWNEIDRLPNLTIEQWLAFINKLDDDPSQSSELLSEAKKLNDSQ | 250 |
| P05998 | KEVIEAWNEIDRLPNLTIEQWLAFINKLDDDPSQSSELLSEAKKLNDSQ | 251 |
| P06009 | KEVLEAWDEIDRLPNLTLDQWLAFINKLDDDPSQSSELLSEAKKLNDSQ | 252 |
| P06079 | KEVLDAWDEIDALPNLTIEQWLAFINKLDDDPSQSSELLSEAKKLNDSQ | 253 |
| P06126 | KEVLDAWDEIDRLPNLTLDQWLAFINKLDDDPSQSSELLSEAKKLNDSQ | 254 |
| P06140 | KETLEAWDEIDRLPNLTIEQWLAFINKLDDDPSQSSELLSEAKKLNDSQ | 255 |
| P06189 | KEVIDAWNEIDALPNLTLDQWLAFINKLDDDPSQSSELLSEAKKLNDSQ | 256 |
| P06214 | KEVLDAWDEIDKLPNLTIDQWLAFINKLDDDPSQSSELLSEAKKLNDSQ | 257 |
| P06215 | KEVLEAWDEIDHLPNLTLDQWLAFINKLDDDPSQSSELLSEAKKLNDSQ | 258 |
| P06226 | KEVLEAWDEIDALPNLTIEQWLAFINKLDDDPSQSSELLSEAKKLNDSQ | 259 |
| P06018 | KEVLDAWDEIDKLPNLTLEQWLAFINKLDDDPSQSSELLSEAKKLNDSQ | 260 |
| P05477 | KETITAWDEIDKLPNLTIEQWLAFIGKLEDDPSQSSELLAEAKKLNDAQ | 261 |
| P05363 | KESMKAWDEIDRLPNLNINQWVAFIDSLYDDPSQSANLLAEAKKLNDAQ | 262 |
| P05483 | KESIEAWTEIDHLPNLTIEQWLAFINKLTDDPSQSSELLAEAKKLNDAQ | 263 |

Fig. 1L

| | | |
|---|---|---|
| P05538 | KEVLDAWHEIDTLPNLTVRQWLAFISKLEDDPSQSSELLAEAKKLNDAQ | 264 |
| P05692 | KEHIQANEEIDRLPNLTIKQWLAFINKLHDDPSQSSELLAEAKKLNDAQ | 265 |
| P05994 | KEVLHAWAEIDALPNLTIEQWLAFINKLDDDPSQSSELLSEAKKLNDSQ | 266 |
| P05995 | KEVLAAWDEIDSLPNLTLQQWLAFINKLDDDPSQSSELLSEAKKLNDSQ | 267 |
| P05996 | KEVIDAWNEIDALPNLTLEQWLAFINKLDDDPSQSSELLSEAKKLNDSQ | 268 |
| P05997 | KEVLDAWNEIDALPNLTIDQWLAFINKLSDDPSQSSELLSEAKKLNDSQ | 269 |
| P05999 | KEVIEAWDEIDGLPNLTIEQWLAFINKLDDDPSQSSELLSEAKKLNDSQ | 270 |
| P06000 | KEVLEAWDEIDHLPNLTLQQWLAFINKLDDDPSQSSELLSEAKKLNDSQ | 271 |
| P06001 | KEVIEAWNEIDALPNLTIEQWLAFINKLDDDPSQSSELLSEAKKLNDSQ | 272 |
| P06002 | KEVIAAWNEIDRLPNLTLTQWLAFINKLDDDPSQSSELLSEAKKLNDSQ | 273 |
| P06003 | KEVIEAWDEIDALPNLTLQQWLAFINKLDDDPSQSSELLSEAKKLNDSQ | 274 |
| P06004 | KEVIAAWDEIDKLPNLTIEQWLAFINKLDDDPSQSSELLSEAKKLNDSQ | 275 |
| P06005 | KEVIAAWDEIDKLPNLTLQQWLAFINKLDDDPSQSSELLSEAKKLNDSQ | 276 |
| P06006 | KETIAAWDEIDKLPNLTIEQWLAFINKLDDDPSQSSELLSEAKKLNDSQ | 277 |
| P06007 | KETIEAWNEIDRLPNLTIEQWLAFINKLDDDPSQSSELLSEAKKLNDSQ | 278 |
| P06008 | KEVLEAWREIDALPNLTIQQWLAFINKLDDDPSQSSELLSEAKKLNDSQ | 279 |
| P06010 | KEVIEAWDEIDQLPNLTIEQWLAFINKLDDDPSQSSELLSEAKKLNDSQ | 280 |
| P06011 | KEVLRAWDEIDHLPNLTLEQWLAFINKLDDDPSQSSELLSEAKKLNDSQ | 281 |
| P06012 | KEVLEAWDEIDRLPNLTLNQWLAFINKLDDDPSQSSELLSEAKKLNDSQ | 282 |
| P06013 | KEVLDAWNEIDHLPNLTIEQWLAFINKLDDDPSQSSELLSEAKKLNDSQ | 283 |
| P06014 | KEVIDAWNEIDKLPNLTIEQWLAFINKLDDDPSQSSELLSEAKKLNDSQ | 284 |
| P06015 | KETLEAWDEIDQLPNLTLQQWLAFINKLDDDPSQSSELLSEAKKLNDSQ | 285 |
| P06016 | KEVIEAWNEIDALPNLTLDQWLAFINKLDDDPSQSSELLSEAKKLNDSQ | 286 |
| P06017 | KEVIDAWNEIDRLPNLTLQQWLAFINKLDDDPSQSSELLSEAKKLNDSQ | 287 |

Fig. 1M

| | | |
|---|---|---|
| P06019 | KEVIDAWNEIDQLPNLTLEQWLAFINKLDDDPSQSSELLSEAKKLNDSQ | 288 |
| P06020 | KETIAAWDEIDHLPNLTLEQWLAFINKLDDDPSQSSELLSEAKKLNDSQ | 289 |
| P06024 | KEVLQAWDEIDHLPNLTIQQWLAFINKLSDDPSQSSELLSEAKKLNDSQ | 290 |
| P06025 | KETLHAWAEIDRLPNLTIEQWLAFINKLDDDPSQSSELLSEAKKLNDSQ | 291 |
| P06026 | KEVLEAWNEIDHLPNLTLAQWLAFINKLDDDPSQSSELLSEAKKLNDSQ | 292 |
| P06027 | KEVIEAWDEIDKLPNLTIAQWLAFINKLDDDPSQSSELLSEAKKLNDSQ | 293 |
| P06028 | KEVLDAWDEIDHLPNLTLQQWLAFINKLDDDPSQSSELLSEAKKLNDSQ | 294 |
| P06029 | KETIEAWNEIDKLPNLTLTQWLAFINKLDDDPSQSSELLSEAKKLNDSQ | 295 |
| P06030 | KEVLEAWNEIDLLPNLTIEQWLAFINKLDDDPSQSSELLSEAKKLNDSQ | 296 |
| P06031 | KEVIEAWDEIDHLPNLTIDQWLAFINKLDDDPSQSSELLSEAKKLNDSQ | 297 |
| P06032 | KEVISAWNEIDALPNLTLQQWLAFINKLDDDPSQSSELLSEAKKLNDSQ | 298 |
| P06033 | KEVIAAWNEIDKLPNLTLEQWLAFINKLDDDPSQSSELLSEAKKLNDSQ | 299 |
| P06034 | KETIEAWNEIDSLPNLTLDQWLAFINKLDDDPSQSSELLSEAKKLNDSQ | 300 |
| P06035 | KEVLDAWNEIDQLPNLTLQQWLAFINKLDDDPSQSSELLSEAKKLNDSQ | 301 |
| P06037 | KEVLAAWNEIDHLPNLTIEQWLAFINKLDDDPSQSSELLSEAKKLNDSQ | 302 |
| P06038 | KEVLEAWDEIDHLPNLTITQWLAFINKLDDDPSQSSELLSEAKKLNDSQ | 303 |
| P06039 | KETIDAWNEIDHLPNLTIEQWLAFINKLDDDPSQSSELLSEAKKLNDSQ | 304 |
| P06040 | KEVIEAWNEIDHLPNLTIQQWLAFINKLDDDPSQSSELLSEAKKLNDSQ | 305 |
| P06041 | KEVIQAWNEIDALPNLTISQWLAFINKLDDDPSQSSELLSEAKKLNDSQ | 306 |
| P06043 | KEVIAAWDEIDSLPNLTIEQWLAFINKLDDDPSQSSELLSEAKKLNDSQ | 307 |
| P06044 | KEHIEAWNEIDALPNLTIEQWLAFINKLQDDPSQSSELLSEAKKLNDSQ | 308 |
| P06045 | KEVLEAWNEIDKLPNLTLDQWLAFINKLDDDPSQSSELLSEAKKLNDSQ | 309 |
| P06047 | KEVIDAWNEIDHLPNLTIEQWLAFINKLADDPSQSSELLSEAKKLNDSQ | 310 |
| P06048 | KETIDAWDEIDKLPNLTIEQWLAFINKLDDDPSQSSELLSEAKKLNDSQ | 311 |

Fig. 1N

| | | |
|---|---|---|
| P06049 | KEVIAAWDEIDLLPNLTLQQWLAFINKLADDPSQSSELLSEAKKLNDSQ | 312 |
| P06050 | KEVIHAWDEIDKLPNLTIEQWLAFINKLDDDPSQSSELLSEAKKLNDSQ | 313 |
| P06051 | KEVIAAWNEIDHLPNLTLEQWLAFINKLDDDPSQSSELLSEAKKLNDSQ | 314 |
| P06052 | KETLDAWNEIDKLPNLTLSQWLAFINKLDDDPSQSSELLSEAKKLNDSQ | 315 |
| P06053 | KEVLEAWNEIDALPNLTEQWLAFINKLDDDPSQSSELLSEAKKLNDSQ | 316 |
| P06054 | KEVIQAWDEIDHLPNLTISQWLAFINKLDDDPSQSSELLSEAKKLNDSQ | 317 |
| P06055 | KEVLQAWDEIDSLPNLTIEQWLAFINKLDDDPSQSSELLSEAKKLNDSQ | 318 |
| P06056 | KETLEAWDEIDHLPNLTIAQWLAFINKLDDDPSQSSELLSEAKKLNDSQ | 319 |
| P06057 | KETIDAWNEIDRLPNLTISQWLAFINKLDDDPSQSSELLSEAKKLNDSQ | 320 |
| P06058 | KVLDAWHEIDHLPNLTIQQWLAFINKLDDDPSQSSELLSEAKKLNDSQ | 321 |
| P06059 | KEQIRAWDEIDKLPNLTIEQWLAFINKLADDPSQSSELLSEAKKLNDSQ | 322 |
| P06060 | KETLYAWNEIDKLPNLTIAFIEKLQDDPSQSSELLSEAKKLNDSQ | 323 |
| P06061 | KEVIEAWNEIDALPNLTIDQWLAFINKLDDDPSQSSELLSEAKKLNDSQ | 324 |
| P06062 | KEVLEAWNEIDHLPNLTIEQWLAFINKLDDDPSQSSELLSEAKKLNDSQ | 325 |
| P06063 | KETIEAWDEIDALPNLTIEQWLAFINKLDDDPSQSSELLSEAKKLNDSQ | 326 |
| P06065 | KEVIEAWNEIDHLPNLTIQQWLAFINKLDDDPSQSSELLSEAKKLNDSQ | 327 |
| P06066 | KEVIEAWNEIDKLPNLTIQQWLAFINKLDDDPSQSSELLSEAKKLNDSQ | 328 |
| P06068 | KETLDAWAEIDHLPNLTLDQWLAFINKLDDDPSQSSELLSEAKKLNDSQ | 329 |
| P06069 | KEHIDAWNEIDALPNLTISQWLAFINKLDDDPSQSSELLSEAKKLNDSQ | 330 |
| P06070 | KEVLDAWNEIDKLPNLTIAQWLAFINKLDDDPSQSSELLSEAKKLNDSQ | 331 |
| P06071 | KEVIEAWTEIDYLPNLTLQQWLAFINKLDDDPSQSSELLSEAKKLNDSQ | 332 |
| P06072 | KETIEAWNEIDHLPNLTIAQWLAFINKLDDDPSQSSELLSEAKKLNDSQ | 333 |
| P06073 | KEVIQAWNEIDKLPNLTLEQWLAFINKLDDDPSQSSELLSEAKKLNDSQ | 334 |
| P06074 | KEVIEAWDEIDHLPNLTIEQWLAFINKLDDDPSQSSELLSEAKKLNDSQ | 335 |

Fig. 10

| | | |
|---|---|---|
| P06075 | KETIDAWNEIDLLPNLTIEQWLAFINKLDDDPSQSSELLSEAKKLNDSQ | 336 |
| P06076 | KEHIDAWNEIDKLPNLTLDQWLAFINKLDDDPSQSSELLSEAKKLNDSQ | 337 |
| P06077 | KEVAAWNEIDALPNLTIEQWLAFINKLNDDPSQSSELLSEAKKLNDSQ | 338 |
| P06080 | KEVIEAWNEIDALPNLTLAQWLAFINKLDDDPSQSSELLSEAKKLNDSQ | 339 |
| P06081 | KEVLQAWDEIDRLPNLTLDQWLAFINKLDDDPSQSSELLSEAKKLNDSQ | 340 |
| P06082 | KEVIDAWDEIDHLPNLTIEQWLAFINKLSDDPSQSSELLSEAKKLNDSQ | 341 |
| P06083 | KEVVEAWNEIDQLPNLTIEQWLAFINKLDDDPSQSSELLSEAKKLNDSQ | 342 |
| P06084 | KEVIQAWNEIDALPNLTIEQWLAFINKLDDDPSQSSELLSEAKKLNDSQ | 343 |
| P06085 | KEVIQAWDEIDKLPNLTIDQWLAFINKLADDPSQSSELLSEAKKLNDSQ | 344 |
| P06086 | KEVVAAWDEIDALPNLTLTQWLAFINKLDDDPSQSSELLSEAKKLNDSQ | 345 |
| P06087 | KEVIQAWNEIDGLPNLTLSQWLAFINKLDDDPSQSSELLSEAKKLNDSQ | 346 |
| P06088 | KETIEAWDEIDALPNLTITQWLAFINKLDDDPSQSSELLSEAKKLNDSQ | 347 |
| P06089 | KEVIDAWNEIDHLPNLTIQQWLAFINKLADDPSQSSELLSEAKKLNDSQ | 348 |
| P06090 | KETIEAWNEIDALPNLTLDQWLAFINKLEDDPSQSSELLSEAKKLNDSQ | 349 |
| P06091 | KEHIHAWNEIDELPNLTIEQWLAFINKLADDPSQSSELLSEAKKLNDSQ | 350 |
| P06092 | KEVIDAWDEIDHLPNLTIDQWLAFINKLSDDPSQSSELLSEAKKLNDSQ | 351 |
| P06093 | KEVIDANDEIDALPNLTIAQWLAFINKLHDDPSQSSELLSEAKKLNDSQ | 352 |
| P06095 | KETIEAWDEIDKLPNLTIEQWLAFINKLDDDPSQSSELLSEAKKLNDSQ | 353 |
| P06097 | KEVLLAWDEIDHLPNLTLEQWLAFINKLDDDPSQSSELLSEAKKLNDSQ | 354 |
| P06098 | KEHIDAWNEIDGLPNLTLEQWLAFINKLDDDPSQSSELLSEAKKLNDSQ | 355 |
| P06099 | KEVIEAWSEIDALPNLTIDQWLAFINKLADDPSQSSELLSEAKKLNDSQ | 356 |
| P06100 | KEQLNAWAEIDALPNLTIEQWLAFINKLDDDPSQSSELLSEAKKLNDSQ | 357 |
| P06101 | KEVIDAWNEIDALPNLTIAQWLAFINKLDDDPSQSSELLSEAKKLNDSQ | 358 |
| P06103 | KETIDAWNEIDQLPNLTIEQWLAFINKLDDDPSQSSELLSEAKKLNDSQ | 359 |

Fig. 1P

| | | |
|---|---|---|
| P06104 | KEVIEAWDEIDKLPNLTLAQWLAFINKLDDDPSQSSELLSEAKKLNDSQ | 360 |
| P06105 | KEVLYAWAEIDHLPNLTIEQWLAFINKLDDDPSQSSELLSEAKKLNDSQ | 361 |
| P06107 | KEQIDAWNEIDRLPNLTIQQWLAFINKLDDDPSQSSELLSEAKKLNDSQ | 362 |
| P06108 | KEVLAAWDEIDRLPNLTIEQWLAFINKLDDDPSQSSELLSEAKKLNDSQ | 363 |
| P06109 | KEVIEAWDEIDHLPNLTLHQWLAFINKLDDDPSQSSELLSEAKKLNDSQ | 364 |
| P06110 | KEVIEAWNEIDKLPNLTLQQWLAFINKLDDDPSQSSELLSEAKKLNDSQ | 365 |
| P06111 | KEVIDANDEIDALPNLTIEQWLAFINKLHDDPSQSSELLSEAKKLNDSQ | 366 |
| P06112 | KEVIAAWDEIDALPNLTIEQWLAFINKLDDDPSQSSELLSEAKKLNDSQ | 367 |
| P06113 | KEVIEAWTEIDQLPNLTLDQWLAFINKLDDDPSQSSELLSEAKKLNDSQ | 368 |
| P06114 | KEVINAWNEIDALPNLTLQQWLAFINKLDDDPSQSSELLSEAKKLNDSQ | 369 |
| P06115 | KEHIEAWDEIDHLPNLTIDQWLAFINKLADDPSQSSELLSEAKKLNDSQ | 370 |
| P06116 | KEHLEAWREIDALPNLTIEQWLAFINKLDDDPSQSSELLSEAKKLNDSQ | 371 |
| P06117 | KEVLDAWNEIDKLPNLTLQQWLAFINKLDDDPSQSSELLSEAKKLNDSQ | 372 |
| P06118 | KEVIAAWDEIDHLPNLTIQQWLAFINKLDDDPSQSSELLSEAKKLNDSQ | 373 |
| P06119 | KEVIQAWNEIDALPNLTLEQWLAFINKLDDDPSQSSELLSEAKKLNDSQ | 374 |
| P06121 | KEVIDAWNEIDHLPNLTIAQWLAFINKLDDDPSQSSELLSEAKKLNDSQ | 375 |
| P06122 | KEQLDAWDEIDHLPNLTIDQWLAFINKLSDDPSQSSELLSEAKKLNDSQ | 376 |
| P06123 | KEVLNAWDEIDHLPNLTIEQWLAFINKLDDDPSQSSELLSEAKKLNDSQ | 377 |
| P06124 | KEVLEAWNEIDHLPNLTIDQWLAFINKLADDPSQSSELLSEAKKLNDSQ | 378 |
| P06125 | KEVLLAWDEIDRLPNLTIDQWLAFINKLADDPSQSSELLSEAKKLNDSQ | 379 |
| P06127 | KEVIAAWNEIDQLPNLTLDQWLAFINKLDDDPSQSSELLSEAKKLNDSQ | 380 |
| P06128 | KETLLAWDEIDALPNLTIEQWLAFINKLDDDPSQSSELLSEAKKLNDSQ | 381 |
| P06129 | KEVIDAWNEIDTLPNLTLEQWLAFINKLDDDPSQSSELLSEAKKLNDSQ | 382 |
| P06131 | KEVLHAWNEIDHLPNLTLNQWLAFINKLQDDPSQSSELLSEAKKLNDSQ | 383 |

Fig. 1Q

| | | |
|---|---|---|
| P06132 | KEVIQAWNEIDALPNLTIAQWLAFINKLDDDPSQSSELLSEAKKLNDSQ | 384 |
| P06133 | KETVDAWNEIDALPNLTIEQWLAFINKLDDDPSQSSELLSEAKKLNDSQ | 385 |
| P06134 | KEVIQAWDEIDHLPNLTIDQWLAFINKLDDDPSQSSELLSEAKKLNDSQ | 386 |
| P06135 | KEVLDAWNEIDQLPNLTIQQWLAFINKLDDDPSQSSELLSEAKKLNDSQ | 387 |
| P06136 | KETIEAWNEIDALPNLTLDQWLAFINKLDDDPSQSSELLSEAKKLNDSQ | 388 |
| P06137 | KEVIEAWDEIDALPNLTIDQWLAFINKLDDDPSQSSELLSEAKKLNDSQ | 389 |
| P06138 | KEVIEAWNEIDQLPNLTIQQWLAFINKLDDDPSQSSELLSEAKKLNDSQ | 390 |
| P06139 | KEVIEAWTEIDHLPNLTIEQWLAFINKLDDDPSQSSELLSEAKKLNDSQ | 391 |
| P06141 | KEVIQANNEIDHLPNLTIQQWLAFINKLEDDPSQSSELLSEAKKLNDSQ | 392 |
| P06142 | KEVIQANNEIDQLPNLTIEQWLAFINKLHDDPSQSSELLSEAKKLNDSQ | 393 |
| P06143 | KEVLHAWSEIDKLPNLTIEQWLAFINKLDDDPSQSSELLSEAKKLNDSQ | 394 |
| P06144 | KETIQAWDEIDKLPNLTLDQWLAFINKLSDDPSQSSELLSEAKKLNDSQ | 395 |
| P06145 | KETLRAWDEIDKLPNLTIQQWLAFINKLADDPSQSSELLSEAKKLNDSQ | 396 |
| P06146 | KEVIDAWNEIDHLPNLTIEQWLAFINKLEDDPSQSSELLSEAKKLNDSQ | 397 |
| P06147 | KEVIDAWNEIDHLPNLTLQQWLAFINKLADDPSQSSELLSEAKKLNDSQ | 398 |
| P06148 | KETIDAWNEIDALPNLTLDQWLAFINKLDDDPSQSSELLSEAKKLNDSQ | 399 |
| P06149 | KEVIEAWNEIDQLPNLTIEQWLAFINKLDDDPSQSSELLSEAKKLNDSQ | 400 |
| P06150 | KEVIRAWDEIDQLPNLTLSQWLAFINKLDDDPSQSSELLSEAKKLNDSQ | 401 |
| P06151 | KEVIEAWNEIDRLPNLTIHQWLAFINKLDDDPSQSSELLSEAKKLNDSQ | 402 |
| P06152 | KETIEAWNEIDQLPNLTIEQWLAFINKLDDDPSQSSELLSEAKKLNDSQ | 403 |
| P06153 | KEVLTAWAEIDALPNLTLSQWLAFINKLDDDPSQSSELLSEAKKLNDSQ | 404 |
| P06154 | KEVIEAWDEIDKLPNLTVDQWLAFINKLDDDPSQSSELLSEAKKLNDSQ | 405 |
| P06155 | KEVIDAWNEIDHLPNLTLTQWLAFINKLDDDPSQSSELLSEAKKLNDSQ | 406 |
| P06156 | KEVIEAWNEIDQLPNLTLDQWLAFINKLDDDPSQSSELLSEAKKLNDSQ | 407 |

Fig. 1R

| | | |
|---|---|---|
| P06157 | KETLQAWDEIDHLPNLTLNQWLAFINKLDDDPSQSSELLSEAKKLNDSQ | 408 |
| P06158 | KEVIDAWNEIDHLPNLTIEQWLAFINKLDDDPSQSSELLSEAKKLNDSQ | 409 |
| P06159 | KEVIEAWNEIDLLPNLTLSQWLAFINKLDDDPSQSSELLSEAKKLNDSQ | 410 |
| P06160 | KEVIDAWDEIDRLPNLTLKQWLAFINKLDDDPSQSSELLSEAKKLNDSQ | 411 |
| P06161 | KETLHAWDEIDKLPNLTIEQWLAFINKLDDDPSQSSELLSEAKKLNDSQ | 412 |
| P06162 | KEVIKAWDEIDHLPNLTLNQWLAFINKLDDDPSQSSELLSEAKKLNDSQ | 413 |
| P06163 | KEVIEAWNEIDHLPNLTLAQWLAFINKLDDDPSQSSELLSEAKKLNDSQ | 414 |
| P06164 | KEVIQAWNEIDHLPNLTIDQWLAFITKLEDDPSQSSELLSEAKKLNDSQ | 415 |
| P06165 | KEVIEAWNEIDRLPNLTIKQWLAFINKLDDDPSQSSELLSEAKKLNDSQ | 416 |
| P06167 | KEVIEAWNEIDSLPNLTLQQWLAFINKLDDDPSQSSELLSEAKKLNDSQ | 417 |
| P06168 | KETIDAWNEIDKLPNLTIEQWLAFINKLDDDPSQSSELLSEAKKLNDSQ | 418 |
| P06169 | KEVLEAWAEIDALPNLTIAQWLAFINKLDDDPSQSSELLSEAKKLNDSQ | 419 |
| P06170 | KETIDAWNEIDRLPNLTIEQWLAFINKLDDDPSQSSELLSEAKKLNDSQ | 420 |
| P06171 | KETLKAWDEIDRLPNLTLEQWLAFINKLDDDPSQSSELLSEAKKLNDSQ | 421 |
| P06172 | KETIAAWNEIDALPNLTLQQWLAFINKLDDDPSQSSELLSEAKKLNDSQ | 422 |
| P06173 | KEVIQAWNEIDHLPNLTIQQWLAFINKLDDDPSQSSELLSEAKKLNDSQ | 423 |
| P06174 | KEVIEAWSEIDHLPNLTLQQWLAFINKLDDDPSQSSELLSEAKKLNDSQ | 424 |
| P06176 | KEVIDAWNEIDGLPNLTIEQWLAFINKLDDDPSQSSELLSEAKKLNDSQ | 425 |
| P06178 | KEVIHAWNEIDHLPNLTLNQWLAFINKLEDDPSQSSELLSEAKKLNDSQ | 426 |
| P06179 | KEVLDAWNEIDSLPNLTLDQWLAFINKLDDDPSQSSELLSEAKKLNDSQ | 427 |
| P06180 | KEQIEAWNEIDRLPNLTIEQWLAFINKLDDDPSQSSELLSEAKKLNDSQ | 428 |
| P06181 | KEVVDAWNEIDALPNLTLQQWLAFINKLDDDPSQSSELLSEAKKLNDSQ | 429 |
| P06182 | KEVIEAWNEIDKLPNLTIEQWLAFINKLDDDPSQSSELLSEAKKLNDSQ | 430 |
| P06183 | KEVIEANDEIDRLPNLTIEQWLAFINKLHDDPSQSSELLSEAKKLNDSQ | 431 |

Fig. 1S

| | | |
|---|---|---|
| P06184 | KETLQAWDEIDKLPNLTIEQWLAFINKLDDDPSQSSELLSEAKKLNDSQ | 432 |
| P06185 | KEVIEAWDEIDHLPNLTIDQWLAFINKLADDPSQSSELLSEAKKLNDSQ | 433 |
| P06186 | KETIDAWNEIDHLPNLTLQQWLAFINKLADDPSQSSELLSEAKKLNDSQ | 434 |
| P06187 | KEVIDAWDEIDKLPNLTIEQWLAFINKLDDDPSQSSELLSEAKKLNDSQ | 435 |
| P06188 | KEVIEAWNEIDKLPNLTLAQWLAFINKLDDDPSQSSELLSEAKKLNDSQ | 436 |
| P06190 | KEVLQAWDEIDKLPNLTIQQWLAFINKLDDDPSQSSELLSEAKKLNDSQ | 437 |
| P06191 | KEVIAAWNEIDGLPNLTLQQWLAFINKLDDDPSQSSELLSEAKKLNDSQ | 438 |
| P06192 | KETLNAWNEIDALPNLTLQQWLAFINKLDDDPSQSSELLSEAKKLNDSQ | 439 |
| P06193 | KEVLSAWNEIDQLPNLTIEQWLAFINKLDDDPSQSSELLSEAKKLNDSQ | 440 |
| P06194 | KETLEAWDEIDHLPNLTLHQWLAFINKLDDDPSQSSELLSEAKKLNDSQ | 441 |
| P06195 | KEQIEAWNEIDHLPNLTLQQWLAFINKLADDPSQSSELLSEAKKLNDSQ | 442 |
| P06196 | KEVVEAWDEIDKLPNLTIEQWLAFINKLDDDPSQSSELLSEAKKLNDSQ | 443 |
| P06197 | KEVLEAWNEIDELPNLTIEQWLAFINKLDDDPSQSSELLSEAKKLNDSQ | 444 |
| P06198 | KEVIDAWNEIDQLPNLTLQQWLAFINKLDDDPSQSSELLSEAKKLNDSQ | 445 |
| P06199 | KETIDAWDEIDKLPNLTLSQWLAFINKLDDDPSQSSELLSEAKKLNDSQ | 446 |
| P06200 | KETIDAWNEIDQLPNLTLQQWLAFINKLDDDPSQSSELLSEAKKLNDSQ | 447 |
| P06201 | KEVIQAWDEIDALPNLTINQWLAFINKLDDDPSQSSELLSEAKKLNDSQ | 448 |
| P06202 | KEVLDAWAEIDQLPNLTIQQWLAFINKLDDDPSQSSELLSEAKKLNDSQ | 449 |
| P06203 | KEHIAAWDEIDALPNLTIEQWLAFINKLDDDPSQSSELLSEAKKLNDSQ | 450 |
| P06206 | KEVIRAWDEIDALPNLTIEQWLAFINKLDDDPSQSSELLSEAKKLNDSQ | 451 |
| P06207 | KEVIDAWDEIDALPNLTIDQWLAFINKLADDPSQSSELLSEAKKLNDSQ | 452 |
| P06208 | KEVIDAWNEIDRLPNLTIQQWLAFINKLDDDPSQSSELLSEAKKLNDSQ | 453 |
| P06209 | KEVITAWNEIDHLPNLTLSQWLAFINKLDDDPSQSSELLSEAKKLNDSQ | 454 |
| P06210 | KEVIDAWNEIDALPNLTIHQWLAFINKLDDDPSQSSELLSEAKKLNDSQ | 455 |

Fig. 1T

| | | |
|---|---|---|
| P06211 | KEQLKAWDEIDKLPNLTIEQWLAFIEKLQDDPSQSSELLSEAKKLNDSQ | 456 |
| P06212 | KEHIDAWTEIDHLPNLTIEQWLAFINKLDDDPSQSSELLSEAKKLNDSQ | 457 |
| P06213 | KEQLRAWDEIDKLPNLTIEQWLAFINKLQDDPSQSSELLSEAKKLNDSQ | 458 |
| P06216 | KEVLEAWREIDSLPNLTIAQWLAFINKLDDDPSQSSELLSEAKKLNDSQ | 459 |
| P06217 | KEVIQAWNEIDKLPNLTIEQWLAFINKLDDDPSQSSELLSEAKKLNDSQ | 460 |
| P06218 | KEHVEAWNEIDQLPNLTIEQWLAFINKLADDPSQSSELLSEAKKLNDSQ | 461 |
| P06219 | KEVIDAWDEIDALPNLTIDQWLAFINKLSDDPSQSSELLSEAKKLNDSQ | 462 |
| P06220 | KEVIEAWNEIDHLPNLTIEQWLAFINKLDDDPSQSSELLSEAKKLNDSQ | 463 |
| P06221 | KEVLQAWDEIDKLPNLTIEQWLAFINKLSDDPSQSSELLSEAKKLNDSQ | 464 |
| P06222 | KEVIKAWNEIDSLPNLTIEQWLAFINKLDDDPSQSSELLSEAKKLNDSQ | 465 |
| P06223 | KEVLEAWHEIDLLPNLTIQQWLAFINKLDDDPSQSSELLSEAKKLNDSQ | 466 |
| P06224 | KEVLEAWTEIDRLPNLTLDQWLAFINKLDDDPSQSSELLSEAKKLNDSQ | 467 |
| P06225 | KEQLYAWNEIDHLPNLTIEQWLAFIEKLQDDPSQSSELLSEAKKLNDSQ | 468 |
| P06227 | KEVLNAWDEIDKLPNLTIKQWLAFINKLDDDPSQSSELLSEAKKLNDSQ | 469 |
| P06228 | KEVIRAWDEIDKLPNLTVEQWLAFINKLDDDPSQSSELLSEAKKLNDSQ | 470 |
| P06230 | KEVVQAWDEIDQLPNLTLEQWLAFINKLDDDPSQSSELLSEAKKLNDSQ | 471 |
| P06231 | KEVIRAWDEIDQLPNLTIEQWLAFINKLDDDPSQSSELLSEAKKLNDSQ | 472 |
| P06232 | KETIDAWNEIDHLPNLTLDQWLAFINKLDDDPSQSSELLSEAKKLNDSQ | 473 |
| P06233 | KEVVAAWTEIDLLPNLTLDQWLAFINKLEDDPSQSSELLSEAKKLNDSQ | 474 |
| P06234 | KEVVAAWDEIDALPNLTIEQWLAFINKLSDDPSQSSELLSEAKKLNDSQ | 475 |
| P06235 | KETLEAWREIDSLPNLTLEQWLAFINKLDDDPSQSSELLSEAKKLNDSQ | 476 |
| P06236 | KEVIKAWNEIDHLPNLTLDQWLAFINKLDDDPSQSSELLSEAKKLNDSQ | 477 |
| P06237 | KEVLEAWTEIDKLPNLTIDQWLAFINKLDDDPSQSSELLSEAKKLNDSQ | 478 |
| P06238 | KETLEAWDEIDKLPNLTIDQWLAFINKLDDDPSQSSELLSEAKKLNDSQ | 479 |

Fig. 1U

| | | |
|---|---|---|
| P06239 | KEVIEAWNEIDKLPNLTIDQWLAFINKLDDDPSQSSELLSEAKKLNDSQ | 480 |
| P06240 | KETIDAWNEIDKLPNLTLEQWLAFINKLDDDPSQSSELLSEAKKLNDSQ | 481 |
| P06241 | KETLDAWDEIDALPNLTIDQWLAFINKLEDDPSQSSELLSEAKKLNDSQ | 482 |
| P06242 | KEVLSAWNEIDHLPNLTIQQWLAFINKLDDDPSQSSELLSEAKKLNDSQ | 483 |
| P06244 | KEVIQANDEIDKLPNLTIEQWLAFIHKLHDDPSQSSELLSEAKKLNDSQ | 484 |
| P06245 | KEHLDAWDEIDHLPNLTIQQWLAFINKLADDPSQSSELLSEAKKLNDSQ | 485 |
| P06246 | KEVIQAWNEIDQLPNLTIEQWLAFINKLDDDPSQSSELLSEAKKLNDSQ | 486 |
| P06247 | KEVIEAWNEIDYLPNLTIAQWIAFINKLDDDPSQSSELLSEAKKLNDSQ | 487 |
| P06248 | KETIQAWDEIDRLPNLTLQQWLAFINKLDDDPSQSSELLSEAKKLNDSQ | 488 |
| P06249 | KETIQAWDEIDKLPNLTIEQWLAFIEKLEDDPSQSSELLSEAKKLNDSQ | 489 |
| P06250 | KETLDAWAEIDHLPNLTIEQWLAFINKLDDDPSQSSELLSEAKKLNDSQ | 490 |
| P06251 | KEVIEAWDEIDKLPNLTLNQWLAFINKLDDDPSQSSELLSEAKKLNDSQ | 491 |
| P06252 | KEVLDAWNEIDQLPNLTIEQWLAFINKLDDDPSQSSELLSEAKKLNDSQ | 492 |
| P06253 | KEVLHAWNEIDHLPNLTIEQWLAFIEKLEDDPSQSSELLSEAKKLNDSQ | 493 |
| P06254 | KEVIEAWQEIDKLPNLTIDQWLAFINKLDDDPSQSSELLSEAKKLNDSQ | 494 |
| P06257 | KEVVDAWNEIDQLPNLTIEQWLAFINKLDDDPSQSSELLSEAKKLNDSQ | 495 |
| P06258 | KEQIEAWNEIDALPNLTIEQWLAFINKLADDPSQSSELLSEAKKLNDSQ | 496 |
| Z06175 | VDAKYAKEVLEAWDEIDRLPNLTIEQWLAFINKLDDDPSQSSELLSEAKKLNDSQAPK | 497 |
| Z08044 | VDAKYAKEVLEAWNEIDRLPNLTIEQWLAFINKLDDDPSQSSELLSEAKKLNDSQAPK | 498 |
| Z05998 | VDAKYAKEVIEAWNEIDRLPNLTIEQWLAFINKLDDDPSQSSELLSEAKKLNDSQAPK | 499 |
| Z06009 | VDAKYAKEVIEAWNEIDRLPNLTLDQWLAFINKLDDDPSQSSELLSEAKKLNDSQAPK | 500 |
| Z06079 | VDAKYAKEVLDAWDEIDALPNLTLEQWLAFINKLDDDPSQSSELLSEAKKLNDSQAPK | 501 |
| Z06126 | VDAKYAKEVIDAWDEIDRLPNLTLDQWLAFINKLDDDPSQSSELLSEAKKLNDSQAPK | 502 |
| Z06140 | VDAKYAKETLEAWDEIDRLPNLTIEQWLAFINKLDDDPSQSSELLSEAKKLNDSQAPK | 503 |

Fig. 1V

| | | |
|---|---|---|
| Z06189 | VDAKYAKEVIDAWNEIDALPNLTLDQWLAFINKLDDDPSQSSELLSEAKKLNDSQAPK | 504 |
| Z06214 | VDAKYAKEVLDAWDEIDKLPNLTIDQWLAFINKLDDDPSQSSELLSEAKKLNDSQAPK | 505 |
| Z06215 | VDAKYAKEVLEAWDEIDHLPNLTLDQWLAFINKLDDDPSQSSELLSEAKKLNDSQAPK | 506 |
| Z06226 | VDAKYAKEVLEAWDEIDALPNLTIEQWLAFINKLDDDPSQSSELLSEAKKLNDSQAPK | 507 |
| Z06018 | VDAKYAKEVLDAWDEIDKLPNLTLEQWLAFINKLDDDPSQSSELLSEAKKLNDAQAPK | 508 |
| Z05477 | VDAKYAKETITAWDEIDKLPNLTIEQWLAFIGKLEDDPSQSSELLAEAKKLNDAQAPK | 509 |
| Z05363 | VDNKFNKESMKAWDEIDRLPNLNINQWVAFIDSLYDDPSQSANILAEAKKLNDAQAPK | 510 |
| Z05483 | VDAKYAKESIEAWTEIDHLPNLTIEQWLAFINKLTDDPSQSSELLAEAKKLNDAQAPK | 511 |
| Z05538 | VDAKYAKEVLDAWHEIDTLPNLTVRQWLAFISKLEDDPSQSSELLAEAKKLNDAQAPK | 512 |
| Z05692 | VDAKYAKEHIQANEEIDRLPNLTIKQWLAFINKLHDDPSQSSELLSEAKKLNDAQAPK | 513 |
| Z05994 | VDAKYAKEVLHAWAEIDALPNLTIEQWLAFINKLDDDPSQSSELLSEAKKLNDSQAPK | 514 |
| Z05995 | VDAKYAKEVLAAWDEIDSLPNLTLQQWLAFINKLDDDPSQSSELLSEAKKLNDSQAPK | 515 |
| Z05996 | VDAKYAKEVIDAWNEIDALPNLTLEQWLAFINKLDDDPSQSSELLSEAKKLNDSQAPK | 516 |
| Z05997 | VDAKYAKEVLDAWNEIDALPNLTIDQWLAFINKLSDDPSQSSELLSEAKKLNDSQAPK | 517 |
| Z05999 | VDAKYAKEVIEAWDEIDGLPNLTIEQWLAFINKLDDDPSQSSELLSEAKKLNDSQAPK | 518 |
| Z06000 | VDAKYAKEVLEAWDEIDHLPNLTLQQWLAFINKLDDDPSQSSELLSEAKKLNDSQAPK | 519 |
| Z06001 | VDAKYAKEVIEAWNEIDALPNLTLTQWLAFINKLDDDPSQSSELLSEAKKLNDSQAPK | 520 |
| Z06002 | VDAKYAKEVIAAWNEIDRLPNLTLTQWLAFINKLDDDPSQSSELLSEAKKLNDSQAPK | 521 |
| Z06003 | VDAKYAKEVIEAWDEIDALPNLTLQQWLAFINKLDDDPSQSSELLSEAKKLNDSQAPK | 522 |
| Z06004 | VDAKYAKEVIAAWDEIDKLPNLTIEQWLAFINKLDDDPSQSSELLSEAKKLNDSQAPK | 523 |
| Z06005 | VDAKYAKEVIAAWDEIDKLPNLTLQQWLAFINKLDDDPSQSSELLSEAKKLNDSQAPK | 524 |
| Z06006 | VDAKYAKETIAAWDEIDKLPNLTIEQWLAFINKLDDDPSQSSELLSEAKKLNDSQAPK | 525 |
| Z06007 | VDAKYAKETIEAWNEIDRLPNLTIEQWLAFINKLDDDPSQSSELLSEAKKLNDSQAPK | 526 |
| Z06008 | VDAKYAKEVLEAWREIDALPNLTIQQWLAFINKLDDDPSQSSELLSEAKKLNDSQAPK | 527 |

Fig. 1W

| ID | Sequence | # |
|---|---|---|
| Z06010 | VDAKYAKEVIEAWDEIDQLPNLTIEQWLAFINKLDDDPSQSSELLSEAKKLNDSQAPK | 528 |
| Z06011 | VDAKYAKEVLRAWDEIDHLPNLTLEQWLAFINKLDDDPSQSSELLSEAKKLNDSQAPK | 529 |
| Z06012 | VDAKYAKEVLEAWDEIDRLPNLTLNQWLAFINKLDDDPSQSSELLSEAKKLNDSQAPK | 530 |
| Z06013 | VDAKYAKEVLDAWNEIDHLPNLTIEQWLAFINKLDDDPSQSSELLSEAKKLNDSQAPK | 531 |
| Z06014 | VDAKYAKEVIDAWNEIDKLPNLTIEQWLAFINKLDDDPSQSSELLSEAKKLNDSQAPK | 532 |
| Z06015 | VDAKYAKETLEAWDEIDQLPNLTLQQWLAFINKLDDDPSQSSELLSEAKKLNDSQAPK | 533 |
| Z06016 | VDAKYAKEVIEAWNEIDALPNLTLDQWLAFINKLDDDPSQSSELLSEAKKLNDSQAPK | 534 |
| Z06017 | VDAKYAKEVIDAWNEIDRLPNLTLQQWLAFINKLDDDPSQSSELLSEAKKLNDSQAPK | 535 |
| Z06019 | VDAKYAKEVIDAWNEIDQLPNLTLEQWLAFINKLDDDPSQSSELLSEAKKLNDSQAPK | 536 |
| Z06020 | VDAKYAKETIAAWDEIDHLPNLTLEQWLAFINKLDDDPSQSSELLSEAKKLNDSQAPK | 537 |
| Z06024 | VDAKYAKEVLQAWDEIDHLPNLTIQQWLAFINKLSDDPSQSSELLSEAKKLNDSQAPK | 538 |
| Z06025 | VDAKYAKETLHAWAEIDRLPNLTIEQWLAFINKLDDDPSQSSELLSEAKKLNDSQAPK | 539 |
| Z06026 | VDAKYAKEVLEAWNEIDHLPNLTLAQWLAFINKLDDDPSQSSELLSEAKKLNDSQAPK | 540 |
| Z06027 | VDAKYAKEVIEAWDEIDKLPNLTIAQWLAFINKLDDDPSQSSELLSEAKKLNDSQAPK | 541 |
| Z06028 | VDAKYAKEVLDAWDEIDHLPNLTLQQWLAFINKLDDDPSQSSELLSEAKKLNDSQAPK | 542 |
| Z06029 | VDAKYAKETIEAWNEIDKLPNLTLTQWLAFINKLDDDPSQSSELLSEAKKLNDSQAPK | 543 |
| Z06030 | VDAKYAKEVLEAWNEIDLLPNLTIEQWLAFINKLDDDPSQSSELLSEAKKLNDSQAPK | 544 |
| Z06031 | VDAKYAKEVIEAWDEIDHLPNLTIDQWLAFINKLDDDPSQSSELLSEAKKLNDSQAPK | 545 |
| Z06032 | VDAKYAKEVISAWNEIDALPNLTLQQWLAFINKLDDDPSQSSELLSEAKKLNDSQAPK | 546 |
| Z06033 | VDAKYAKEVIAAWNEIDKLPNLTLEQWLAFINKLDDDPSQSSELLSEAKKLNDSQAPK | 547 |
| Z06034 | VDAKYAKETIEAWNEIDSLPNLTLDQWLAFINKLDDDPSQSSELLSEAKKLNDSQAPK | 548 |
| Z06035 | VDAKYAKEVLDAWNEIDQLPNLTLQQWLAFINKLDDDPSQSSELLSEAKKLNDSQAPK | 549 |
| Z06037 | VDAKYAKEVLAAWNEIDHLPNLTIEQWLAFINKLDDDPSQSSELLSEAKKLNDSQAPK | 550 |
| Z06038 | VDAKYAKEVLEAWDEIDHLPNLTITQWLAFINKLDDDPSQSSELLSEAKKLNDSQAPK | 551 |

Fig. 1X

| | | |
|---|---|---|
| Z06039 | VDAKYAKETIDAWNEIDHLPNLTIEQWLAFINKLDDDPSQSSELLSEAKKLNDSQAPK | 552 |
| Z06040 | VDAKYAKEVLEAWNEIDHLPNLTIQQWLAFINKLDDDPSQSSELLSEAKKLNDSQAPK | 553 |
| Z06041 | VDAKYAKEVIQAWNEIDALPNLTISQWLAFINKLDDDPSQSSELLSEAKKLNDSQAPK | 554 |
| Z06043 | VDAKYAKEVIAAWDEIDSLPNLTIEQWLAFINKLDDDPSQSSELLSEAKKLNDSQAPK | 555 |
| Z06044 | VDAKYAKEHIEAWNEIDALPNLTIEQWLAFINKLQDDPSQSSELLSEAKKLNDSQAPK | 556 |
| Z06045 | VDAKYAKEVLEAWNEIDKLPNLTLDQWLAFINKLDDDPSQSSELLSEAKKLNDSQAPK | 557 |
| Z06047 | VDAKYAKEVIDAWNEIDHLPNLTIEQWLAFINKLADDPSQSSELLSEAKKLNDSQAPK | 558 |
| Z06048 | VDAKYAKETIDAWDEIDKLPNLTIEQWLAFINKLDDDPSQSSELLSEAKKLNDSQAPK | 559 |
| Z06049 | VDAKYAKEVIAAWDEIDLLPNLTLQQWLAFINKLADDPSQSSELLSEAKKLNDSQAPK | 560 |
| Z06050 | VDAKYAKEVIHAWDEIDKLPNLTIEQWLAFINKLDDDPSQSSELLSEAKKLNDSQAPK | 561 |
| Z06051 | VDAKYAKEVIAAWNEIDKLPNLTLEQWLAFINKLDDDPSQSSELLSEAKKLNDSQAPK | 562 |
| Z06052 | VDAKYAKETLDAWNEIDKLPNLTLSQWLAFINKLDDDPSQSSELLSEAKKLNDSQAPK | 563 |
| Z06053 | VDAKYAKEVLEAWNEIDALPNLTIEQWLAFINKLDDDPSQSSELLSEAKKLNDSQAPK | 564 |
| Z06054 | VDAKYAKEVIQAWDEIDHLPNLTISQWLAFINKLDDDPSQSSELLSEAKKLNDSQAPK | 565 |
| Z06055 | VDAKYAKEVLQAWDEIDSLPNLTIEQWLAFINKLDDDPSQSSELLSEAKKLNDSQAPK | 566 |
| Z06056 | VDAKYAKETLEAWDEIDHLPNLTIAQWLAFINKLDDDPSQSSELLSEAKKLNDSQAPK | 567 |
| Z06057 | VDAKYAKETIDAWNEIDRLPNLTISQWLAFINKLDDDPSQSSELLSEAKKLNDSQAPK | 568 |
| Z06058 | VDAKYAKEVLDAWHEIDHLPNLTIQQWLAFINKLDDDPSQSSELLSEAKKLNDSQAPK | 569 |
| Z06059 | VDAKYAKEQIRAWDEIDKLPNLTIEQWLAFINKLADDPSQSSELLSEAKKLNDSQAPK | 570 |
| Z06060 | VDAKYAKETLYAWNEIDKLPNLTIEQWLAFIEKLQDDPSQSSELLSEAKKLNDSQAPK | 571 |
| Z06061 | VDAKYAKEVIEAWNEIDALPNLTIDQWLAFINKLDDDPSQSSELLSEAKKLNDSQAPK | 572 |
| Z06062 | VDAKYAKEVLEAWNEIDHLPNLTIQQWLAFINKLDDDPSQSSELLSEAKKLNDSQAPK | 573 |
| Z06063 | VDAKYAKETIEAWDEIDALPNLTIEQWLAFINKLDDDPSQSSELLSEAKKLNDSQAPK | 574 |
| Z06065 | VDAKYAKEVIEAWNEIDHLPNLTLQQWLAFINKLDDDPSQSSELLSEAKKLNDSQAPK | 575 |

Fig. 1Y

| | | |
|---|---|---|
| Z06066 | VDAKYAKEVIEAWNEIDKLPNLTIQQWLAFINKLDDDPSQSSELLSEAKKLNDSQAPK | 576 |
| Z06068 | VDAKYAKETLDAWAEIDHLPNLTLDQWLAFINKLDDDPSQSSELLSEAKKLNDSQAPK | 577 |
| Z06069 | VDAKYAKEHIDAWNEIDALPNLTLSQWLAFINKLDDDPSQSSELLSEAKKLNDSQAPK | 578 |
| Z06070 | VDAKYAKEVLDAWNEIDKLPNLTIAQWLAFINKLDDDPSQSSELLSEAKKLNDSQAPK | 579 |
| Z06071 | VDAKYAKEVIEAWTEIDYLPNLTLPNLTIQQWLAFINKLDDDPSQSSELLSEAKKLNDSQAPK | 580 |
| Z06072 | VDAKYAKETIEAWNEIDHLPNLTIAQWLAFINKLDDDPSQSSELLSEAKKLNDSQAPK | 581 |
| Z06073 | VDAKYAKEVIQAWNEIDKLPNLTLEQWLAFINKLDDDPSQSSELLSEAKKLNDSQAPK | 582 |
| Z06074 | VDAKYAKEVIEAWDEIDHLPNLTIEQWLAFINKLDDDPSQSSELLSEAKKLNDSQAPK | 583 |
| Z06075 | VDAKYAKETIDAWNEIDLLPNLTIEQWLAFINKLDDDPSQSSELLSEAKKLNDSQAPK | 584 |
| Z06076 | VDAKYAKEHIDAWNEIDKLPNLTLDQWLAFINKLDDDPSQSSELLSEAKKLNDSQAPK | 585 |
| Z06077 | VDAKYAKEVVAAWNEIDALPNLTIEQWLAFINKLNDDPSQSSELLSEAKKLNDSQAPK | 586 |
| Z06080 | VDAKYAKEVIEAWNEIDALPNLTLAQWLAFINKLDDDPSQSSELLSEAKKLNDSQAPK | 587 |
| Z06081 | VDAKYAKEVLQAWDEIDRLPNLTLDQWLAFINKLDDDPSQSSELLSEAKKLNDSQAPK | 588 |
| Z06082 | VDAKYAKEVIDAWDEIDHLPNLTIEQWLAFINKLSDDPSQSSELLSEAKKLNDSQAPK | 589 |
| Z06083 | VDAKYAKEVVEAWNEIDQLPNLTIEQWLAFINKLDDDPSQSSELLSEAKKLNDSQAPK | 590 |
| Z06084 | VDAKYAKEVIQAWNEIDALPNLTIEQWLAFINKLDDDPSQSSELLSEAKKLNDSQAPK | 591 |
| Z06085 | VDAKYAKEVIQAWDEIDKLPNLTIDQWLAFINKLDDDPSQSSELLSEAKKLNDSQAPK | 592 |
| Z06086 | VDAKYAKEVVAAWDEIDALPNLTLTQWLAFINKLDDDPSQSSELLSEAKKLNDSQAPK | 593 |
| Z06087 | VDAKYAKEVIQAWNEIDGLPNLTLSQWLAFINKLDDDPSQSSELLSEAKKLNDSQAPK | 594 |
| Z06088 | VDAKYAKETIEAWDEIDALPNLTITQWLAFINKLDDDPSQSSELLSEAKKLNDSQAPK | 595 |
| Z06089 | VDAKYAKEVIDAWNEIDHLPNLTIQQWLAFINKLAFINKLADDPSQSSELLSEAKKLNDSQAPK | 596 |
| Z06090 | VDAKYAKETIEAWNEIDALPNLTLDQWLAFINKLEDDPSQSSELLSEAKKLNDSQAPK | 597 |
| Z06091 | VDAKYAKEHIHAWNEIDELPNLTIEQWLAFINKLADDPSQSSELLSEAKKLNDSQAPK | 598 |
| Z06092 | VDAKYAKEVIDAWDEIDHLPNLTIDQWLAFINKLSDDPSQSSELLSEAKKLNDSQAPK | 599 |

Fig. 1Z

| | | |
|---|---|---|
| Z06093 | VDAKYAKEVIDANDEIDALPNLTIAQWLAFINKLHDDPSQSSELLSEAKKLNDSQAPK | 600 |
| Z06095 | VDAKYAKETIEAWDEIDKLPNLTIEQWLAFINKLDDDPSQSSELLSEAKKLNDSQAPK | 601 |
| Z06097 | VDAKYAKEVLLAWDEIDHLPNLTLEQWLAFINKLDDDPSQSSELLSEAKKLNDSQAPK | 602 |
| Z06098 | VDAKYAKEHIDAWNEIDGLPNLTLEQWLAFINKLDDDPSQSSELLSEAKKLNDSQAPK | 603 |
| Z06099 | VDAKYAKEVIEAWSEIDALPNLTIDQWLAFINKLADDPSQSSELLSEAKKLNDSQAPK | 604 |
| Z06100 | VDAKYAKEQLNAWAEIDALPNLTIEQWLAFINKLDDDPSQSSELLSEAKKLNDSQAPK | 605 |
| Z06101 | VDAKYAKEVIDAWNEIDALPNLTIAQWLAFINKLDDDPSQSSELLSEAKKLNDSQAPK | 606 |
| Z06103 | VDAKYAKETIDAWNEIDQLPNLTIEQWLAFINKLDDDPSQSSELLSEAKKLNDSQAPK | 607 |
| Z06104 | VDAKYAKEVIEAWDEIDKLPNLTLAQWLAFINKLDDDPSQSSELLSEAKKLNDSQAPK | 608 |
| Z06105 | VDAKYAKEVLYAWAEIDHLPNLTIEQWLAFINKLDDDPSQSSELLSEAKKLNDSQAPK | 609 |
| Z06107 | VDAKYAKEQIDAWNEIDRLPNLTIQQWLAFINKLDDDPSQSSELLSEAKKLNDSQAPK | 610 |
| Z06108 | VDAKYAKEVLAAWDEIDRLPNLTIEQWLAFINKLDDDPSQSSELLSEAKKLNDSQAPK | 611 |
| Z06109 | VDAKYAKEVIEAWDEIDHLPNLTLHQWLAFINKLDDDPSQSSELLSEAKKLNDSQAPK | 612 |
| Z06110 | VDAKYAKEVIEAWNEIDKLPNLTLQQWLAFINKLDDDPSQSSELLSEAKKLNDSQAPK | 613 |
| Z06111 | VDAKYAKEVIDANDEIDALPNLTIEQWLAFINKLHDDPSQSSELLSEAKKLNDSQAPK | 614 |
| Z06112 | VDAKYAKEVIAAWDEIDALPNLTIEQWLAFINKLDDDPSQSSELLSEAKKLNDSQAPK | 615 |
| Z06113 | VDAKYAKEVIEAWTEIDQLPNLTLDQWLAFINKLDDDPSQSSELLSEAKKLNDSQAPK | 616 |
| Z06114 | VDAKYAKEVINAWNEIDALPNLTLDQWLAFINKLADDPSQSSELLSEAKKLNDSQAPK | 617 |
| Z06115 | VDAKYAKEHIEAWDEIDHLPNLTLEQWLAFINKLDDDPSQSSELLSEAKKLNDSQAPK | 618 |
| Z06116 | VDAKYAKEHLEAWREIDALPNLTIEQWLAFINKLDDDPSQSSELLSEAKKLNDSQAPK | 619 |
| Z06117 | VDAKYAKEVLDAWNEIDKLPNLTLQQWLAFINKLDDDPSQSSELLSEAKKLNDSQAPK | 620 |
| Z06118 | VDAKYAKEVIAAWDEIDHLPNLTIQQWLAFINKLDDDPSQSSELLSEAKKLNDSQAPK | 621 |
| Z06119 | VDAKYAKEVIQAWNEIDALPNLTLEQWLAFINKLDDDPSQSSELLSEAKKLNDSQAPK | 622 |
| Z06121 | VDAKYAKEVIDAWNEIDHLPNLTIAQWLAFINKLDDDPSQSSELLSEAKKLNDSQAPK | 623 |

Fig. 1AA

| ID | Sequence | # |
|---|---|---|
| Z06122 | VDAKYAKEQLDAWDEIDHLPNLTIDQWLAFINKLSDDPSQSSELLSEAKKLNDSQAPK | 624 |
| Z06123 | VDAKYAKEVLNAWDEIDKLPNLTIEQWLAFINKLDDDPSQSSELLSEAKKLNDSQAPK | 625 |
| Z06124 | VDAKYAKEVLEAWNEIDHLPNLTIDQWLAFINKLDDDPSQSSELLSEAKKLNDSQAPK | 626 |
| Z06125 | VDAKYAKEVLLAWDEIDRLPNLTIDQWLAFINKLADDPSQSSELLSEAKKLNDSQAPK | 627 |
| Z06127 | VDAKYAKEVIAAWNEIDQLPNLTLDQWLAFINKLDDDPSQSSELLSEAKKLNDSQAPK | 628 |
| Z06128 | VDAKYAKETLLAWDEIDALPNLTIEQWLAFINKLDDDPSQSSELLSEAKKLNDSQAPK | 629 |
| Z06129 | VDAKYAKEVIDAWNEIDTLPNLTLEQWLAFINKLDDDPSQSSELLSEAKKLNDSQAPK | 630 |
| Z06131 | VDAKYAKEVLHAWNEIDHLPNLTLNQWLAFINKLQDDPSQSSELLSEAKKLNDSQAPK | 631 |
| Z06132 | VDAKYAKEVIQAWNEIDALPNLTIAQWLAFINKLDDDPSQSSELLSEAKKLNDSQAPK | 632 |
| Z06133 | VDAKYAKETVDAWNEIDALPNLTIEQWLAFINKLDDDPSQSSELLSEAKKLNDSQAPK | 633 |
| Z06134 | VDAKYAKEVIQAWDEIDHLPNLTIDQWLAFINKLDDDPSQSSELLSEAKKLNDSQAPK | 634 |
| Z06135 | VDAKYAKEVLDAWNEIDQLPNLTIQQWLAFINKLDDDPSQSSELLSEAKKLNDSQAPK | 635 |
| Z06136 | VDAKYAKETIEAWNEIDAIPNLTLDQWLAFINKLDDDPSQSSELLSEAKKLNDSQAPK | 636 |
| Z06137 | VDAKYAKEVIEAWDEIDALPNLTIDQWLAFINKLDDDPSQSSELLSEAKKLNDSQAPK | 637 |
| Z06138 | VDAKYAKEVIEAWNEIDQLPNLTIQQWLAFINKLDDDPSQSSELLSEAKKLNDSQAPK | 638 |
| Z06139 | VDAKYAKEVIEAWTEIDHLPNLTIEQWLAFINKLDDDPSQSSELLSEAKKLNDSQAPK | 639 |
| Z06141 | VDAKYAKEVIQAWNEIDHLPNLTLQQWLAFINKLEDDPSQSSELLSEAKKLNDSQAPK | 640 |
| Z06142 | VDAKYAKEVIQANNEIDQLPNLTIEQWLAFINKLHDDPSQSSELLSEAKKLNDSQAPK | 641 |
| Z06143 | VDAKYAKEVLHAWSEIDKLPNLTIEQWLAFINKLDDDPSQSSELLSEAKKLNDSQAPK | 642 |
| Z06144 | VDAKYAKETIQAWDEIDKLPNLTLDQWLAFINKLSDDPSQSSELLSEAKKLNDSQAPK | 643 |
| Z06145 | VDAKYAKETLRAWDEIDKLPNLTIQQWLAFINKLADDPSQSSELLSEAKKLNDSQAPK | 644 |
| Z06146 | VDAKYAKEVIDAWNEIDHLPNLTIEQWLAFINKLEDDPSQSSELLSEAKKLNDSQAPK | 645 |
| Z06147 | VDAKYAKEVIDAWNEIDHLPNLTLQQWLAFINKLADDPSQSSELLSEAKKLNDSQAPK | 646 |
| Z06148 | VDAKYAKETIDAWNEIDALPNLTLDQWLAFINKLDDDPSQSSELLSEAKKLNDSQAPK | 647 |

Fig. 1AB

| | | |
|---|---|---|
| Z06149 | VDAKYAKEVIEAWNEIDQLPNLTTEQWLAFINKLDDDPSQSSELLSEAKKLNDSQAPK | 648 |
| Z06150 | VDAKYAKEVIRAWDEIDQLPNLTLSQWLAFINKLDDDPSQSSELLSEAKKLNDSQAPK | 649 |
| Z06151 | VDAKYAKEVIEAWNEIDRLPNLTIHQWLAFINKLDDDPSQSSELLSEAKKLNDSQAPK | 650 |
| Z06152 | VDAKYAKETIEAWNEIDQLPNLTIEQWLAFINKLDDDPSQSSELLSEAKKLNDSQAPK | 651 |
| Z06153 | VDAKYAKEVLTAWAEIDALPNLTLSQWLAFINKLDDDPSQSSELLSEAKKLNDSQAPK | 652 |
| Z06154 | VDAKYAKEVIEAWDEIDKLPNLTVDQWLAFINKLDDDPSQSSELLSEAKKLNDSQAPK | 653 |
| Z06155 | VDAKYAKEVIDAWNEIDHLPNLTLTQWLAFINKLDDDPSQSSELLSEAKKLNDSQAPK | 654 |
| Z06156 | VDAKYAKEVIEAWNEIDQLPNLTLDQWLAFINKLDDDPSQSSELLSEAKKLNDSQAPK | 655 |
| Z06157 | VDAKYAKETLQAWDEIDHLPNLTLNQWLAFINKLDDDPSQSSELLSEAKKLNDSQAPK | 656 |
| Z06158 | VDAKYAKEVIDAWNEIDHLPNLTIEQWLAFINKLDDDPSQSSELLSEAKKLNDSQAPK | 657 |
| Z06159 | VDAKYAKEVIEAWNEIDLLPNLTLSQWLAFINKLDDDPSQSSELLSEAKKLNDSQAPK | 658 |
| Z06160 | VDAKYAKEVIDAWDEIDRLPNLTLKQWLAFINKLDDDPSQSSELLSEAKKLNDSQAPK | 659 |
| Z06161 | VDAKYAKETLHAWDEIDKLPNLTIEQWLAFINKLDDDPSQSSELLSEAKKLNDSQAPK | 660 |
| Z06162 | VDAKYAKEVIKAWDEIDHLPNLTLNQWLAFINKLDDDPSQSSELLSEAKKLNDSQAPK | 661 |
| Z06163 | VDAKYAKEVIEAWNEIDHLPNLTLAQWLAFINKLDDDPSQSSELLSEAKKLNDSQAPK | 662 |
| Z06164 | VDAKYAKEVIQAWNEIDHLPNLTIDQWLAFITKLEDDPSQSSELLSEAKKLNDSQAPK | 663 |
| Z06165 | VDAKYAKEVIEAWNEIDRLPNLTIKQWLAFINKLDDDPSQSSELLSEAKKLNDSQAPK | 664 |
| Z06167 | VDAKYAKEVIEAWNEIDSLPNLTLQQWLAFINKLDDDPSQSSELLSEAKKLNDSQAPK | 665 |
| Z06168 | VDAKYAKETIDAWNEIDKLPNLTIEQWLAFINKLDDDPSQSSELLSEAKKLNDSQAPK | 666 |
| Z06169 | VDAKYAKEVLEAWAEIDALPNLTIAQWLAFINKLDDDPSQSSELLSEAKKLNDSQAPK | 667 |
| Z06170 | VDAKYAKETIDAWNEIDRLPNLTIEQWLAFINKLDDDPSQSSELLSEAKKLNDSQAPK | 668 |
| Z06171 | VDAKYAKEVIDAWNEIDRLPNLTIEQWLAFINKLDDDPSQSSELLSEAKKLNDSQAPK | 669 |
| Z06172 | VDAKYAKETLKAWDEIDRLPNLTLQQWLAFINKLDDDPSQSSELLSEAKKLNDSQAPK | 670 |
| Z06173 | VDAKYAKEVLQAWNEIDHLPNLTIQQWLAFINKLDDDPSQSSELLSEAKKLNDSQAPK | 671 |

Fig. 1AC

| | | |
|---|---|---|
| Z06174 | VDAKYAKEVIEAWSEIDHLPNLTLQQWLAFINKLDDDPSQSSELLSEAKKLNDSQAPK | 672 |
| Z06176 | VDAKYAKEVIDAWNEIDGLPNLTIEQWLAFINKLDDDPSQSSELLSEAKKLNDSQAPK | 673 |
| Z06178 | VDAKYAKEVIHAWNEIDHLPNLTLNQWLAFINKLEDDPSQSSELLSEAKKLNDSQAPK | 674 |
| Z06179 | VDAKYAKEVLDAWNEIDSLPNLTLDQWLAFINKLDDDPSQSSELLSEAKKLNDSQAPK | 675 |
| Z06180 | VDAKYAKEQIEAWNEIDRLPNLTLEQWLAFINKLDDDPSQSSELLSEAKKLNDSQAPK | 676 |
| Z06181 | VDAKYAKEVVDAWNEIDALPNLTLQQWLAFINKLDDDPSQSSELLSEAKKLNDSQAPK | 677 |
| Z06182 | VDAKYAKEVIEAWNEIDKLPNLTIEQWLAFINKLDDDPSQSSELLSEAKKLNDSQAPK | 678 |
| Z06183 | VDAKYAKEVIEANDEIDRLPNLTIEQWLAFINKLHDDPSQSSELLSEAKKLNDSQAPK | 679 |
| Z06184 | VDAKYAKETLQAWDEIDKLPNLTIEQWLAFINKLDDDPSQSSELLSEAKKLNDSQAPK | 680 |
| Z06185 | VDAKYAKEVIEAWDEIDHLPNLTIDQWLAFINKLADDPSQSSELLSEAKKLNDSQAPK | 681 |
| Z06186 | VDAKYAKETIDAWNEIDHLPNLTLQQWLAFINKLDDDPSQSSELLSEAKKLNDSQAPK | 682 |
| Z06187 | VDAKYAKEVIDAWDEIDKLPNLTIEQWLAFINKLDDDPSQSSELLSEAKKLNDSQAPK | 683 |
| Z06188 | VDAKYAKEVIEAWNEIDKLPNLTLAQWLAFINKLDDDPSQSSELLSEAKKLNDSQAPK | 684 |
| Z06190 | VDAKYAKEVLQAWDEIDKLPNLTIQQWLAFINKLDDDPSQSSELLSEAKKLNDSQAPK | 685 |
| Z06191 | VDAKYAKEVIAAWNEIDGLPNLTLQQWLAFINKLDDDPSQSSELLSEAKKLNDSQAPK | 686 |
| Z06192 | VDAKYAKETLNAWNEIDALPNLTLQQWLAFINKLDDDPSQSSELLSEAKKLNDSQAPK | 687 |
| Z06193 | VDAKYAKEVLSAWNEIDQLPNLTLEQWLAFINKLDDDPSQSSELLSEAKKLNDSQAPK | 688 |
| Z06194 | VDAKYAKETLEAWDEIDHLPNLTLHQWLAFINKLDDDPSQSSELLSEAKKLNDSQAPK | 689 |
| Z06195 | VDAKYAKEQIEAWNEIDHLPNLTIEQWLAFINKLADDPSQSSELLSEAKKLNDSQAPK | 690 |
| Z06196 | VDAKYAKEVVEAWDEIDKLPNLTIEQWLAFINKLDDDPSQSSELLSEAKKLNDSQAPK | 691 |
| Z06197 | VDAKYAKEVLEAWNEIDELPNLTIEQWLAFINKLDDDPSQSSELLSEAKKLNDSQAPK | 692 |
| Z06198 | VDAKYAKEVIDAWNEIDQLPNLTLQQWLAFINKLDDDPSQSSELLSEAKKLNDSQAPK | 693 |
| Z06199 | VDAKYAKETIDAWDEIDKLPNLITLSQWLAFINKLDDDPSQSSELLSEAKKLNDSQAPK | 694 |
| Z06200 | VDAKYAKETIDAWNEIDQLPNLTLQQWLAFINKLDDDPSQSSELLSEAKKLNDSQAPK | 695 |

Fig. 1AD

| | | |
|---|---|---|
| Z06201 | VDAKYAKEVIQAWDEIDALPNLTLNQWLAFINKLDDDPSQSSELLSEAKKLNDSQAPK | 696 |
| Z06202 | VDAKYAKEVLDAWAEIDQLPNLTLQQWLAFINKLDDDPSQSSELLSEAKKLNDSQAPK | 697 |
| Z06203 | VDAKYAKEHIAAWDEIDALPNLTIEQWLAFINKLDDDPSQSSELLSEAKKLNDSQAPK | 698 |
| Z06206 | VDAKYAKEVIRAWDEIDALPNLTIEQWLAFINKLDDDPSQSSELLSEAKKLNDSQAPK | 699 |
| Z06207 | VDAKYAKEVIDAWDEIDALPNLTIDQWLAFINKLADDPSQSSELLSEAKKLNDSQAPK | 700 |
| Z06208 | VDAKYAKEVIDAWNEIDRLPNLTIQQWLAFINKLDDDPSQSSELLSEAKKLNDSQAPK | 701 |
| Z06209 | VDAKYAKEVITAWNEIDHLPNLTLSQWLAFINKLDDDPSQSSELLSEAKKLNDSQAPK | 702 |
| Z06210 | VDAKYAKEVIDAWNEIDALPNLTIHQWLAFINKLDDDPSQSSELLSEAKKLNDSQAPK | 703 |
| Z06211 | VDAKYAKEQLKAWDEIDKLPNLTIEQWLAFIEKLQDDPSQSSELLSEAKKLNDSQAPK | 704 |
| Z06212 | VDAKYAKEHIDAWTEIDHLPNLTIEQWLAFINKLDDDPSQSSELLSEAKKLNDSQAPK | 705 |
| Z06213 | VDAKYAKEQLRAWDEIDKLPNLTIEQWLAFINKLQDDPSQSSELLSEAKKLNDSQAPK | 706 |
| Z06216 | VDAKYAKEVLEAWREIDSLPNLTIAQWLAFINKLDDDPSQSSELLSEAKKLNDSQAPK | 707 |
| Z06217 | VDAKYAKEVIQAWNEIDKLPNLTIEQWLAFINKLDDDPSQSSELLSEAKKLNDSQAPK | 708 |
| Z06218 | VDAKYAKEHVEAWNEIDQLPNLTIEQWLAFINKLADDPSQSSELLSEAKKLNDSQAPK | 709 |
| Z06219 | VDAKYAKEVIDAWDEIDALPNLTIDQWLAFINKLSDDPSQSSELLSEAKKLNDSQAPK | 710 |
| Z06220 | VDAKYAKEVIEAWNEIDHLPNLTIEQWLAFINKLDDDPSQSSELLSEAKKLNDSQAPK | 711 |
| Z06221 | VDAKYAKEVLQAWDEIDKLPNLTIEQWLAFINKLSDDPSQSSELLSEAKKLNDSQAPK | 712 |
| Z06222 | VDAKYAKEVIKAWNEIDSLPNLTIEQWLAFINKLDDDPSQSSELLSEAKKLNDSQAPK | 713 |
| Z06223 | VDAKYAKEVLEAWHEIDLLPNLTIQQWLAFINKLDDDPSQSSELLSEAKKLNDSQAPK | 714 |
| Z06224 | VDAKYAKEVLEAWTEIDRLPNLTIKQWLAFINKLDDDPSQSSELLSEAKKLNDSQAPK | 715 |
| Z06225 | VDAKYAKEQLYAWNEIDHLPNLTIEQWLAFIEKLQDDPSQSSELLSEAKKLNDSQAPK | 716 |
| Z06227 | VDAKYAKEVLNAWDEIDKLPNLTIKQWLAFINKLDDDPSQSSELLSEAKKLNDSQAPK | 717 |
| Z06228 | VDAKYAKEVIRAWDEIDKLPNLTVEQWLAFINKLDDDPSQSSELLSEAKKLNDSQAPK | 718 |
| Z06230 | VDAKYAKEVVQAWDEIDQLPNLTLEQWLAFINKLDDDPSQSSELLSEAKKLNDSQAPK | 719 |

Fig. 1AE

| | | |
|---|---|---|
| Z06231 | VDAKYAKEVIRAWDEIDQLPNLTLEQWLAFINKLDDDPSQSSELLSEAKKLNDSQAPK | 720 |
| Z06232 | VDAKYAKETIDAWNEIDHLPNLTLDQWLAFINKLDDDPSQSSELLSEAKKLNDSQAPK | 721 |
| Z06233 | VDAKYAKEVVAAWTEIDLLPNLTLDQWLAFINKLEDDPSQSSELLSEAKKLNDSQAPK | 722 |
| Z06234 | VDAKYAKEVVAAWDEIDALPNLTIEQWLAFINKLSDDPSQSSELLSEAKKLNDSQAPK | 723 |
| Z06235 | VDAKYAKETLEAWREIDSLPNLTLEQWLAFINKLDDDPSQSSELLSEAKKLNDSQAPK | 724 |
| Z06236 | VDAKYAKEVIKAWNEIDHLPNLTLDQWLAFINKLDDDPSQSSELLSEAKKLNDSQAPK | 725 |
| Z06237 | VDAKYAKEVLEAWTEIDKLPNLTIDQWLAFINKLDDDPSQSSELLSEAKKLNDSQAPK | 726 |
| Z06238 | VDAKYAKETLEAWDEIDKLPNLTIDQWLAFINKLDDDPSQSSELLSEAKKLNDSQAPK | 727 |
| Z06239 | VDAKYAKEVIEAWNEIDKLPNLTIDQWLAFINKLDDDPSQSSELLSEAKKLNDSQAPK | 728 |
| Z06240 | VDAKYAKETIDAWNEIDKLPNLTLEQWLAFINKLDDDPSQSSELLSEAKKLNDSQAPK | 729 |
| Z06241 | VDAKYAKETLDAWDEIDALPNLTIDQWLAFINKLEDDPSQSSELLSEAKKLNDSQAPK | 730 |
| Z06242 | VDAKYAKEVLSAWNEIDHLPNLTIQQWLAFINKLDDDPSQSSELLSEAKKLNDSQAPK | 731 |
| Z06244 | VDAKYAKEVIQANDEIDKLPNLTIEQWLAFIHKLHDDPSQSSELLSEAKKLNDSQAPK | 732 |
| Z06245 | VDAKYAKEHLDAWDEIDHLPNLTIQQWLAFINKLADDPSQSSELLSEAKKLNDSQAPK | 733 |
| Z06246 | VDAKYAKEVIQAWNEIDQLPNLTIEQWLAFINKLDDDPSQSSELLSEAKKLNDSQAPK | 734 |
| Z06247 | VDAKYAKEVIEAWNEIDYLPNLTIAQWIAFINKLDDDPSQSSELLSEAKKLNDSQAPK | 735 |
| Z06248 | VDAKYAKETIQAWDEIDRLPNLTLQQWLAFINKLDDDPSQSSELLSEAKKLNDSQAPK | 736 |
| Z06249 | VDAKYAKETIQAWDEIDKLPNLTIEQWLAFINKLDDDPSQSSELLSEAKKLNDSQAPK | 737 |
| Z06250 | VDAKYAKETLDAWAEIDHLPNLTIEQWLAFINKLDDDPSQSSELLSEAKKLNDSQAPK | 738 |
| Z06251 | VDAKYAKEVIEAWDEIDKLPNLTLNQWLAFINKLDDDPSQSSELLSEAKKLNDSQAPK | 739 |
| Z06252 | VDAKYAKEVLDAWNEIDQLPNLTIEQWLAFINKLDDDPSQSSELLSEAKKLNDSQAPK | 740 |
| Z06253 | VDAKYAKEVLHAWNEIDHLPNLTIEQWLAFIEKLEDDPSQSSELLSEAKKLNDSQAPK | 741 |
| Z06254 | VDAKYAKEVIEAWQEIDKLPNLTIDQWLAFINKLDDDPSQSSELLSEAKKLNDSQAPK | 742 |
| Z06257 | VDAKYAKEVVDAWNEIDQLPNLTIEQWLAFINKLDDDPSQSSELLSEAKKLNDSQAPK | 743 |

Fig. 1AF

| | | |
|---|---|---|
| Z06258 | VDAKYAKEQIEAWNEIDALPNLTIEQWLAFINKLADDPSQSSELLSEAKKLNDSQAPK | 744 |
| Z05477a | VDAKYAKETITAWDEIDKLPNLTIEQWLAFIGKLEDDPSQSSELLAEAKKLNDAQAPKVD | 745 |
| Z05998a | AEAKYAKEVIEAWNEIDRLPNLTIEQWLAFINKLDDDPSQSSELLSEAKKLNDSQAPKVD | 746 |
| Z08044a | AEAKYAKEVLEAWNEIDRLPNLTIEQWLAFINKLDDDPSQSSELLSEAKKLNDSQAPKVD | 747 |
| Z06009a | AEAKYAKEVLEAWDEIDRLPNLTLDQWLAFINKLDDDPSQSSELLSEAKKLNDSQAPKVD | 748 |
| Z06018a | AEAKYAKEVLDAWDEIDKLPNLTLEQWLAFINKLDDDPSQSSELLSEAKKLNDSQAPKVD | 749 |
| Z06079a | AEAKYAKEVLDAWDEIDALPNLTLEQWLAFINKLDDDPSQSSELLSEAKKLNDSQAPKVD | 750 |
| Z06126a | AEAKYAKEVIDAWDEIDRLPNLTLDQWLAFINKLDDDPSQSSELLSEAKKLNDSQAPKVD | 751 |
| Z06140a | AEAKYAKETLEAWDEIDRLPNLTIEQWLAFINKLDDDPSQSSELLSEAKKLNDSQAPKVD | 752 |
| Z06175a | AEAKYAKEVLEAWDEIDRLPNLTIEQWLAFINKLDDDPSQSSELLSEAKKLNDSQAPKVD | 753 |
| Z06189a | AEAKYAKEVIDAWNEIDALPNLTLDQWLAFINKLDDDPSQSSELLSEAKKLNDSQAPKVD | 754 |
| Z06214a | AEAKYAKEVLDAWDEIDKLPNLTIDQWLAFINKLDDDPSQSSELLSEAKKLNDSQAPKVD | 755 |
| Z06215a | AEAKYAKEVLEAWDEIDHLPNLTLDQWLAFINKLDDDPSQSSELLSEAKKLNDSQAPKVD | 756 |
| Z06226a | AEAKYAKEVLEAWDEIDALPNLTIEQWLAFINKLDDDPSQSSELLSEAKKLNDSQAPKVD | 757 |
| Z00000 | VDNKFNKEQQNAFYEILHLPNLNEEQRNAFIQSLKDDPSQSANLLAEAKKLNDAQAPK | 758 |
| ABD094 | LAEAKEAANAELDSYGVSDFYKRLIDKAKTVEGVEALKDAILAALP | 759 |

Fig. 1AG

| | | |
|---|---|---|
| Human C5 | MGLLGILCFLIFLGKTWGQEQTYVISAPKIFRVGASENIVIQVYGYTEAFDATISIKSYPDKKFSYSSGHVHLSSENKFQ<br>NSAILTIQPKQLPGGQNPVSYVYLEVVSKHFSKSKRMPITYDNGFLFIHTDKPVYTPDQSVKVRVYSLNDDLKPAKRETV<br>LTFIDPEGSEVDMVEEIDHIGIISFPDFKIPSNPRYGMWTIKAKYKEDFSTTGTAYFEVKEYVLPHFSVSIEPEYNFIGY<br>KNFKNFEITIKARYFYNKVTEADVYITFGIREDLKDDQKEMMQTAMQNTMLINGIAQVTFDSETAVKELSYYSLEDLNN<br>KYLYIAVTVIESTGGFSEEAEIPGIKVVLSPYKLNLVATPLFLKPGIPYPIKVQVKDSLDQLVGGVPVTLNAQTIDVNQE<br>TSDLDPSKSVTRVDDGVASFVLNLPSGVTVLEFNVKTDAPDLPEENQAREGYRAIAYSSLSQSYLYIDWTDNHKALLVGE<br>HLNIIVTPKSPYIDKITHYNYLILSKGKIIHFGTREKFSDASYQSINIPVTQNMVPSSRLLVYIVTGEQTAELVSDSVW<br>LNIEEKCGNQLQVHLSPDADAYSPGQTVSLNMATGMDSWVALAAVDSAVYGVQRGAKKPLERVFQFLEKSDLGCGAGGGL<br>NNANVFHLAGLLTFLTNANADDSQENDEPCKEILRPRRTLQKKIEEIAAKYKHSVVKKCCYDGACVNDETCEQRAARISL<br>GPRCIKAFTECCVVASQLRANISHKDMQLGRLHMKTLLPVSKPEIRSYFPESWLWEVHLVPRRKQLQFALPDSLTTWEIQ<br>GVGISNTGICVADTVKAKVFKDVFLEMNIPYSVVRGEQIQLKGTVYNYRTSGMQFCVKMSAVEGICTSESPVIDHQGTKS<br>SKCVRQKVEGSSSHLVTFTVLPLEIGLHNINFSLETWFGKEILVKTLRVVPEGVKRESYSGVTLDPRGIYGTISRRKEFP<br>YRIPLDLVPKTEIKRILSVKGLLVGEILSAVLSQEGINILTHLPKGSAEAELMSVVPVFYVFHYLETGNHWNIFHSDPLI<br>EKQKLKKKLKEGMLSIMSYRNADYSYSVWKGGSASTWLTAFALRVLGQVNKYVEQNQNSICNSLLWLVENYQLDNGSFKE<br>NSQYQPIKLQGTLPVEARENSLYLTAFTVIGIRKAFDICPLVKIDTALIKADNFLLENTLPAQSTFTLAISAYALSLGDK<br>THPQFRSIVSALKREALVKGNPPIYRFWKDNLQHKDSSVPNTGTARMVETTAYALLTSLNLKDINYVNPVIKWLSEEQRY<br>GGGFYSTQDTINAIEGLTEYSLLVKQLRLSMDIDVSYKHKGALHNYKMTDKNFLGRPVEVLLNDDLIVSTGFGSGLATVH<br>VTTVVHKTSTSEEVCSFYLKIDTQDIEASHYRGYGNSDYKRIVACASYKPSREESSSGSSHAVMDISLPTGISANEEDLK<br>ALVEGVDQLFTDYQIKDGHVILQLNSIPSSDFLCVRFRIFELFEVGFLSPATFTVYEYHRPDKQCTMFYSTSNIKIQKVC<br>EGAACKCVEADCGQMQEELDLTISAETRKQTACKPEIAYAYKVSITSITVENVFVKYKATLLDIYKTGEAVAEKDSEITF<br>IKKVTCTNAELVKGRQYLIMGKEALQIKYNFSFRYIYPLDSLTWIEYWPRDTTCSSCQAFLANLDEFAEDIFLNGC | 760 |
| OmCI – His6 | MDSESDCTGSEPVDAFQAFSEGKEAYVLVRSTDPKARDCLKGEPAGEKQDNTLPVMMTFKNGTDWASTDWTFTLDGAKVT<br>ATLGNLTQNREVVYDSQSHHCHVDKVEKEVPDYEMWMLDAGGLEVECCRQKLEELASGRNQMYPHLKDCGGGSENLY<br>FQGSHHHHHH | 761 |

Fig.1AH

| Cynomolgus C5 | MGLLGILCFLIFLGKTWGQEQTYVISAPKIFRVGASENIVIQVYGYTEAFDATISIKSYPDKXFSYSSGHVHLSSENKFQ NSAVLTIQPKQLPGGQNQVSYVYLEVVSKHFSKSKKIPITYDNGFLFIHTDKPVYTPDQSVKVRVYSLNDDLKPAKRETV LTFIDPEGSEIDMVEEIDHIGIISFPDFKIPSNPRYGMWTIQAKYKEDFSTTGTAFFEVKEYVLPHFSVSVEPESNFIGY KNFKNFEITIKARIFYNKVVTEADVYITFGIREDLKDDQKEMMQTAMQNTMLINGIAEVTFDSETAVKELSYYSLEDLNN KYLYIAVTVIESTGGFSEEAEIPGIKYVLSPYKLNIVATPLFLKPGIPYSIKVQVKDALDQLVGGVPVTLNAQTIDVNQE TSDLEPRKSVTRVDDGVASFVVNLPSGVTVLEFNVKTDAPDLPDENQAREGYRAIAYSSLSQSYLYIDWTDNHKALLVGE YLNIIVTPKSPYIDKITHYNYLILSKGKIIHFGTREKLSDASYQSINIPVTQNMVPSSRLLVYYIVTGEQTAELVSDSVW LNIEEKCGNQLQVHLSPDADTYSPGQTVSLNMVTGMDSWVALTAVDSAVYGVQRRAKKPLERVFQFLEKSDLGCGAGGGL NNANVFHLAGLTFLTNANADDSQENDEPCKEIIRPRRMLQEKIEEIAAKYKHLVVKKCCYDGVRINHDETCEQRAARISV GPRCVKAFTECCVVASQLRANNSHKDLQLGRLHMKTLLPVSKPEIRSYFPESWLWEVHLVPRRKQLQFALPDSVTTWEIQ GVGISNSGICVADTIKAKVFKDVFLEMNIPYSVVRGEQVQLKGTVYNYRTSGMQFCVKMSAVEGICTSESPVIDHQGTKS SKCVRQKVEGSSNHLVTFTVLPLEIGLQNINFSLETSFGKEILVKSLRVVPEGVKRESYSGITLDPRGIYGTISRRKEFP YRIPLDIVPKTEIKRILSVKGLLIVGEILSAVLSREGINILITHLPKGSAEAELMSVVPVFYVFHYLETGNHWNIFHSDPLI EKRNLEKKLKEGMVSIMSYRNADYSYSVWKGGSASTWLTAFALRVLGQVHKYVEQNQNSICNSLLWIVENYQLDNGSFKE NSQYQPIKLQGTLPVEARENSLYLTAFTVIGIRKAFDICPLVKINTALIKADTFLLENTLPAQSTFTLAISAYALSLGDK THPQFRSIVSALKREALVKGNPPIYRFWKDSLQHKDSSVPNTGTARMVETTAYALLTSLNLKDINYVNPIIKWLSEEQRY GGGFYSTQDTINAIEGLTEYSLLVKQLRLNMDIDVAYKHKGPLHNYKMTDKNFLGRPVEVLLNDDXVVSTGFGSGLATVH VTTVHKTSTSEEVCSFYLKIDTQDVEASHYRGYGNSDYKRIVACASYKPSKEESSGSSHAVMDISLPTGINANEEDLK ALVEGVDQLFTDYQIKDGHVILQLNSIPSSDFLCVRFIFELFEVGFLSPATFTVYEYHRPDKQCTMFYSTSNIKIQKVC EGATCKCIEADCGQMQKELDLTISAETRKQTACNPEIAYAYKVIITSITTENVFVKYKATLLDIYKTGEAVAEKDSEITF IKKVTCTNAELVKGRQYLIMGKEALQIKYNFTFRYIYPLDSLTWIEYWPRDTTCSSCQAFLANLDEFAEDIFLNGC | 762 |

POLYPEPTIDES BINDING TO HUMAN COMPLEMENT C5

CROSS-REFERENCE TO RELATED APPLICATIONS

This Application is a U.S. National Stage Application of PCT/SE2013/050139 filed Feb. 19, 2013 which is incorporated by reference in its entirety.

TECHNICAL FIELD

The present disclosure relates to polypeptides that bind to human complement component 5 (C5) and to the use of such polypeptides in therapy.

BACKGROUND

The complement protein C5 is a central component of the complement system; a key part of the innate immune system. The complement system is an intricate immune survival system with numerous tasks in tightly controlled, diverse processes. One of its functions is as first line host defense against infection by other organisms by discriminating healthy host tissues from cellular debris and apoptotic and necrotic cells. Furthermore, it is involved in clearance of immune complexes, regulation of the adaptive immune response, promotion of tissue regeneration, angiogenesis, mobilization of stem cells and development of the central nervous system (Woodruff et al. Mol Immunol 2011, 48 (14):1631-1642); Ricklin et al. Nat Immunol 2010, 11(9): 785-795). Any trigger, for example erroneous or unrestricted activation or insufficient regulation, that disturbs the fine balance of complement activation and regulation may lead to pathologic conditions including self-attack of the host's cells leading to extensive tissue damage.

The complement system consists of about 30 proteins. There are three pathways to initiate complement immunity; the classical pathway that employs C1q to recognize immune complexes on the surface of cells, the lectin pathway that is initiated when mannose-binding lectin (MBL) recognizes certain sugars and the alternative pathway that is initiated spontaneously by hydrolysis of complement factor 3 (C3), a process suppressed by certain mammalian cell surface molecules not present on invading pathogens. The alternative pathway also acts as an amplification loop for the complement system. All three pathways converge at the level of C3. Cleavage of C3 into C3a and C3b leads to the formation of a convertase that in turn cleaves complement factor 5 (C5) into C5a and C5b. C5a is a very potent attractant of various immune cells while C5b oligomerizes with C6-9 to form a pore known as the membrane attack complex (MAC) or sometimes the terminal complement complex (TCC). Activation of the complement system leads to a number of mechanisms with the purpose of neutralizing the pathogen; formation of MAC on the surface of a cell such as an invading bacteria lead to lysis, deposition of C3 and C4 cleavage products C3b and C4b aids opsonization leading to phagocytosis of the pathogen by macrophages and anaphylatoxins such as C3a and C5a attracts monocytes and neutrophils to the site of activation, upregulates surface markers leading to increased immunologic susceptibility and to the release of cytokines.

C5 is a 190-kDa glycoprotein comprised of 2 disulfide-linked polypeptide chains, alpha and beta, with a molecular mass of 115 and 75 kDa, respectively (Tack et al. Biochem 1979, 18:1490-1497). Haviland et al. (J Immun 1991, 146: 362-368) constructed the complete cDNA sequence of human complement pro-05, which is predicted to encode a 1,676-amino acid pro-molecule that contains an 18-amino acid leader peptide and a 4-amino acid linker separating the beta and alpha chains. Blockade of C5 cleavage into C5a and C5b prevents MAC formation and formation of the pro-inflammatory C5a but leaves the upstream complement effector system intact allowing the C3/C4 mediated opsonization.

The complement system's key role in the defense against pathogens in general makes it an interesting target for pharmaceutical intervention. This is emphasized by the fact that many mutations or impaired regulation of complement is involved in various diseases and conditions. These include increased susceptibility to auto-immune diseases such as systemic lupus erythematosis (SLE) where deposition of immune complexes triggers the classical pathway (Manderson et al. Annu Rev Immunol 2004, 22:431-456). In addition, mutations of the complement proteins C1-C5 often result in SLE or SLE like symptoms. Other autoimmune diseases with a strong involvement of the complement system are rheumatoid arthritis (RA) where immune complexes may activate complement in the RA joint, Sjögren's syndrome, dermatomyositis and other autoantibody driven diseases such as Guillain-Barré syndrome (GBS), Fisher syndrome (Kaida et al. J. Neuroimmun 2010, 223:5-12) different types of vasculitis, systemic sclerosis, anti-glomerular basement membrane (anti-GBM) and anti-phospholipid syndrome (APS) (Chen et al. J Autoimmun 2010, 34:J276-J286).

The complement system is furthermore involved in neurodegenerative disorders such as Alzheimer's disease (AD) where Aβ plaques directly activate the complement system leading to C5a mediated recruitment of microglia. This was further confirmed when a C5aR antagonist was shown to be neuroprotective in a mouse model of AD (Fonseca et al. J Immunol 2009, 183:1375-1383). Auto-antibodies against the acetylcholine receptor and subsequent complement activation is the most common cause to myasthenia gravis, a disease that affects the neuromuscular junction (Toyka and Gold, Schweizer Archive Neurol Psych 2007, 158:309-321). MAC formation is involved in the pathophysiology of multiple sclerosis (MS) (Oh et al. Immunol Res 2008, 40:224-234). Also in Parkinson's disease, Huntington's disease and prion diseases such as Creutzfeld-Jacob disease, complement activation is a part of the pathology (Bonifati and Kishore, Mol Immunol 2007, 44:999-1010). In wound healing, inflammatory responses are a key component to restore tissue homeostasis and the complement system is involved in the early recognition of damaged tissue. However, in models of chronic wounds and severe burns, for example, inhibition of complement by e. g. C1 inhibitor resulted in improved healing and decreased tissue damage suggesting that complement. Furthermore, various complement deficiencies, such as exemplified by the C4 knockout mouse, have been found to be protective against long-term tissue damage resulting from wounds (reviewed in Cazender et al. Clinical and Developmental Immunology 2012, on-line publication). Lately it has been shown that tumor growth and proliferation is facilitated by complement activation, in particular by C5a, and that blockade of the C5a receptor slows down this process. In addition, mice lacking C3 display significantly slower tumor growth than wild-type littermates (Markiewski et al. Nat Immunol 2008, 9:1225-1235).

Dysfunctional complement regulation is the cause of several rare to ultra-rare conditions, such as paroxysmal nocturnal hemoglobinuria (PNH) and atypical hemolytic uremic syndrome (aHUS), where hemolysis is a key feature in the pathology. In PNH, a clone of hematopoetic stem cells with mutated PIG-A gene encoding phosphatidylinositol N-acetylglucosaminyltransferase subunit A take over the pool of blood cells. This mutation leads to loss of GPI anchored proteins such as the complement regulators CD55 and CD59. Red blood cells lacking CD55 and CD59 on the surface are exposed for complement mediated lysis by MAC. Clinically, PNH is manifested by hemolysis leading to anemia, thrombosis and bone marrow failure. Atypical HUS is caused by mutations in regulatory proteins of mainly the alternative pathway, such as by mutations in factor H.

The eye is strongly indicated as a site for complement driven pathology. The most common cause of visual loss is age-related macular degeneration (AMD) where, in its more severe form (exudative or wet AMD), pathologic choridal neurovascular membranes develop under the retina. In the US, about 10% of the population aged 65-74 shows sign of macular degeneration and as many as 5% have visual impairment as a result to AMD. These numbers increase dramatically with age, but there are also genetic factors. Among the genes strongest associated with AMD are complement factor H, factor B and C3 and the C1 inhibitor (Bradley et al. Eye 2011, 25:683-693). Furthermore, several studies and clinical trials using various complement blocking molecules have proven beneficial, suggesting that a C5 blocking molecule could help these patient groups. However, the current treatments of advanced AMD aims at inhibition of vascular endothelial growth factor (VEGF) induced vascularization by intravitreal injections of e.g. Ranibizumab (a monoclonal antibody fragment) and Bevacizumab (monoclonal antibody). In animal models of uveitis, inflammation of the eye due to immune responses to ocular antigens, blocking antibodies against alternative pathway factor B (Manickam et al. J Biol Chem 2011, 286:8472-8480) as well as against C5 (Copland et al. Clin Exp Immunol 2009, 159:303-314), improved the disease state.

In transplantation of solid organs, there are two major mechanistic pathways leading to rejection or delayed/impaired function of the graft: 1) the immunologic barriers between donor and recipient with respect to blood group (ABO) and MHC classes as well as extent of pre-sensitization of the recipient against the donor, i.e. occurrence of donor specific antibodies (DSA) leading to acute antibody mediated rejection (AMR); and 2) the condition of the transplanted organ as well as the period of time it has been kept without constant blood perfusion, i.e. the degree of ischemic damage or ischemia reperfusion injury (IRI) of the graft. In both AMR and IRI, the complement system is attacking the organ recognized as foreign and, therefore, an entity that should be rejected. In AMR, the pre-existing anti-donor antibodies rapidly form immune complexes on the surface of the foreign organ leading to recognition by C1q and subsequent activation of the complement system via the classical pathway. This process, known as hyperacute rejection happens within minutes and, therefore modern transplantation of mismatched organs includes elimination of DSA prior to transplantation by plasmapheresis or plasma exchange and intravenous IgG combined with different immunosuppressants. Novel treatments also include B-cell depletion via usage of the anti-CD20 antibody Rituximab (Genberg et al. Transplant 2008, 85:1745-1754). These protocols have vastly eliminated the occurrence of hyperacute rejection but still, in highly sensitized patients, the incidence of acute AMR (weeks-months) is as high as 40% (Burns et al. Am J Transplant 2008, 6:2684-2694; Stegall et al. Am J Transplant 2011, early on-line publication). With respect to IRI, most evidence points at the terminal pathway with subsequent MAC formation and lysis as the main cause of tissue damage. Thus, a C5 blocking polypeptide would be protective against rejection regardless of the cause being AMR, IRI or, as often happens, a combination of both AMR and IRI. As expected, highly perfused organs, such as the liver (Qin et al. Cell Mol Immunol 2006, 3:333-340), the heart and the kidneys are particularly susceptible to complement mediated damage.

The central placement of the C5 protein; connecting the proximal and the terminal parts of the complement cascade, makes it an attractive target for pharmaceutical intervention. Since C5 is common to all pathways of complement activation, blocking of C5 will stop the progression of the cascade regardless of the stimuli and thereby prevent the deleterious properties of terminal complement activation while leaving the immunoprotective and immunoregulatory functions of the proximal complement cascade intact.

Antibodies targeted to human complement C5 are known from, e.g., WO 95/29697; WO 02/30985; and WO 2004/007553. Eculizumab (SOLIRIS) is a humanized monoclonal antibody directed against protein C5 and prevents cleavage of C5 into C5a and C5b. Eculizumab has been shown to be effective in treating PNH, a rare and sometimes life threatening disease of the blood characterized by intravascular hemolytic anemia, thrombophilia and bone marrow failure, and is approved for this indication. Eculizumab was also recently approved by the FDA for treatment of atypical hemolytic syndrome (aHUS), a rare but life threatening disease caused by loss of control of the alternative complement pathway leading to over-activation manifested as thrombotic microangiopathy (TMA) leading to constant risk of damage to vital organs such as kidney, heart and the brain. In aHUS, transplantation of the damaged organ only temporarily helps the patient as the liver continues to produce the mutated form of controlling protein (most often complement factor H or other proteins of the alternative pathway). A related disease with a transient acute pathophysiology is HUS caused by infection of Shiga toxin positive *E. coli* (STEC-HUS) and there are promising clinical data suggesting efficacy also for this condition (Lapeyraque et al, N Engl J Med 2011, 364:2561-2563). Finally, the C5 blocking antibody Eculizumab has proven efficacious in preventing AMR in recipients of highly mismatched kidneys (Stegall, M. D. et al. Am J Transplant 2011, 11:2405-2413).

Apart from full length antibodies, single-chain variable fragments (scFV), minibodies and aptamers targeting C5 are described in literature. These C5 inhibitors may bind to different sites (epitopes) on the C5 molecule and may have different modes of action. For example, whereas Eculizumab interacts with C5 at some distance of the convertase cleavage site, the minibody MUBODINA interacts with the cleavage site of C5. The C5 inhibitory protein *Ornithodoros moubata* Complement Inhibitor (OmCI, Nunn, M. A. et al. J Immunol 2005, 174:2084-2091) from soft tic *Ornithodoros moubata* has been hypothesized to bind to the distal end of the CUB-C5d-MG8 superdomain, which is close to the convertase cleavage site (Fredslund et al. Nat Immunol 2008, 9 (7):753-760). In contrast to the three proteins mentioned above inhibiting cleavage of C5, the monoclonal antibody TNX-558 binds to a C5a epitope present both on intact C5 and released C5a without inhibiting the cleavage of C5. (Fung et al. Clin Exp Immunol 2003, 133 (2):160-169).

Antibodies with their large, multidomain structure, 12 intra-chain and 4 inter-chain disulfide bridges and complex glycosylation patterns, have a number of intrinsic disadvantages related to their molecular structure. For example, the size of Eculizumab is about 148 kDa. The concentration of C5 in human blood is about 400 nM and in order to block C5 activity entirely, the concentration of the inhibitor must be at least equal or higher than that. Therefore, the standard life-long treatment regimen of PNH using SOLIRIS is intravenous infusions of 900 mg protein every second week, a treatment that mainly take place in the clinic leading to great inconvenience to the patient and cost to the society. SOLIRIS has also been reported to cause chest pain, fever, chills, itching, hives, flushing of the face, rash, dizziness, troubled breathing, or swelling of the face, tongue, and throat, although the reasons for these side effects are not clear. Furthermore, Eculizumab is not active in any tested animal model, including primates, making animal studies with the active drug impossible. As mentioned above, the current treatments of AMD are also antibody dependent and, thus, treatments based on injections or other routes of administration with molecules of lower molecular weight, are highly required.

In addition, antibody production is more difficult and more expensive than production of small proteins (Kenanova et al. Expert Opin Drug Deliv 2006, 3 (1):53-70). Other drawbacks generally related to antibodies are listed by Reilly et al. (Clin Pharmacokinet 1995, 28:126-142), such as cross-reactivity and non-specific binding to normal tissues, increased metabolism of injected antibodies and formation of human anti-human antibodies (HAMA) causing decreased or loss of the therapeutic effect.

Thus, continued provision of agents with comparable C5 blocking activity remains a matter of substantial interest within the field. In particular, there is a continued need for molecules that prevent the terminal complement cascade as well as the formation of the pro-inflammatory molecule C5a. Of great interest is also a provision of uses of such molecules in the treatment of disease.

DESCRIPTION

It is an object of the invention to provide new C5 binding agents. It is moreover an object of the invention to provide new C5 binding agents for use in therapeutic applications.

In one aspect, there is provided a C5 binding polypeptide, comprising a C5 binding motif, BM, which motif consists of the amino acid sequence selected from i)
(SEQ ID NO. 763)
$EX_2X_3X_4A$ $X_6X_7EID$ $X_{11}LPNL$ $X_{16}X_{17}X_{18}QW$ $X_{21}AFIX_{25}$ $X_{26}LX_{28}D$, wherein, independently of each other,
$X_2$ is selected from H, Q, S, T and V;
$X_3$ is selected from I, L, M and V;
$X_4$ is selected from A, D, E, H, K, L, N, Q, R, S, T and Y;
$X_6$ is selected from N and W;
$X_7$ is selected from A, D, E, H, N, Q, R, S and T;
$X_{11}$ is selected from A, E, G, H, K, L, Q, R, S, T and Y;
$X_{16}$ is selected from N and T;
$X_{17}$ is selected from I, L and V;
$X_{18}$ is selected from A, D, E, H, K, N, Q, R, S and T;
$X_{21}$ is selected from I, L and V;
$X_{25}$ is selected from D, E, G, H, N, S and T;
$X_{26}$ is selected from K and S;
$X_{28}$ is selected from A, D, E, H, N, Q, S, T and Y;
and ii) an amino acid sequence which has at least 86% identity to the sequence defined in i), wherein the polypeptide binds to C5.

The above defined class of sequence related polypeptides having a binding affinity for C5 is derived from a common parent polypeptide sequence. More specifically, the definition of the class is based on an analysis of a large number of random polypeptide variants of the parent polypeptide that were selected for their interaction with C5 in selection experiments. The identified C5 binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. By random variation of binding surface residues and subsequent selection of variants, the Fc interaction capacity of the binding surface has been replaced with a capacity for interaction with C5.

As accounted for in the following Examples, selection of C5 binding polypeptide variants may for example be achieved by phage display for selection of naïve variants of a protein scaffold optionally followed by affinity maturation and cell display for selection of affinity maturated C5 binding variants. It is however understood that any selection system, whether phage-based, bacterial-based, cell-based or other, may be used for selection of C5 binding polypeptides.

The terms "C5 binding" and "binding affinity for C5" as used in this specification refers to a property of a polypeptide which may be tested for example by the use of surface plasmon resonance technology, such as in a Biacore instrument (GE Healthcare). C5 binding affinity may e.g. be tested in an experiment in which C5 is immobilized on a sensor chip of a Biacore instrument, and the sample containing the polypeptide to be tested is passed over the chip. Alternatively, the polypeptide to be tested is immobilized on a sensor chip of the instrument, and a sample containing C5, or fragment thereof, is passed over the chip. The skilled person may then interpret the results obtained by such experiments to establish at least a qualitative measure of the binding of the polypeptide to C5. If a quantitative measure is desired, for example to determine the apparent equilibrium dissociation constant $K_D$ for the interaction, surface plasmon resonance methods may also be used. Binding values may for example be defined in a Biacore 2000 instrument (GE Healthcare). C5 is immobilized on a sensor chip of the measurement, and samples of the polypeptide whose affinity is to be determined are prepared by serial dilution and injected over the chip. $K_D$ values may then be calculated from the results using for example the 1:1 Langmuir binding model of the BIAevaluation software provided by the instrument manufacturer. The C5 or fragment thereof used in the $K_D$ determination may for example comprise the amino acid sequence represented by SEQ ID NO:760.

In one embodiment of the C5 binding polypeptide according to the present invention, the C5 binding polypeptide binds to C5 such that the $K_D$ value of the interaction is at most $1\times10^{-6}$ M, such as at most $1\times10^{-7}$ M, $1\times10^{-8}$ M, or $1\times10^{-9}$ M.

A C5 binding polypeptide according to the present invention may be used as an alternative to conventional antibodies or low molecular weight substances in various medical, veterinary and diagnostic applications. In particular, the C5 binding polypeptide may be useful in any method requiring affinity for C5 of a reagent. Accordingly, the C5 binding polypeptide may be used as a detection reagent, a capture reagent, a separation reagent, a diagnostic agent or a therapeutic agent in such methods.

As the skilled person will realize, the function of any polypeptide, such as the C5 binding capacity of the polypeptides as defined herein, is dependent on the tertiary structure of the polypeptide. It is therefore possible to make minor changes to the amino acid sequence of a polypeptide without largely affecting the tertiary structure and the function thereof. Thus, in one embodiment, the polypeptide comprises modified variants of the BM of i), which are such that the resulting sequence is at least 89% identical to a sequence belonging to the class defined by i), such as at least 93% identical, such as at least 96% identical to a sequence belonging to the class defined by i). For example, it is possible that an amino acid residue belonging to a certain functional grouping of amino acid residues (e.g. hydrophobic, hydrophilic, polar etc) could be exchanged for another amino acid residue from the same functional group.

In another embodiment of the C5 binding polypeptide as defined above, the amino acid sequence is selected from i) as defined above, and iii) an amino acid sequence which in the 13 variable positions as denoted by $X_n$, wherein n is 2-4, 6-7, 11, 16-18, 21, 25-26 and 28, has at least 84% identity to the sequence defined in i), and which in positions 1, 5, 8-10, 12-15, 19-20, 22-24, 27 and 29 has at least 87% identity to the sequence defined in i).

In one embodiment of the polypeptide according to the present invention, $X_2$ is selected from H, T and V. In another embodiment, $X_2$ is selected from T and V. In yet another embodiment, $X_2$ is V.

In one embodiment of the polypeptide according to the present invention, $X_3$ is selected from I, L and V. In another embodiment, $X_3$ is selected from I and L. In yet another embodiment, $X_3$ is I. In an alternative embodiment, $X_3$ is L.

In one embodiment of the polypeptide according to the present invention, $X_4$ is selected from A, D, E, K, L, Q and R. In another embodiment, $X_4$ is selected from A, D, E, K and R. In yet another related embodiment, $X_4$ is selected from D and E.

In one embodiment of the polypeptide according to the present invention, $X_6$ is W.

In one embodiment of the polypeptide according to the present invention, $X_7$ is selected from A, D, N and T. In another embodiment, $X_7$ is selected from D and N. In yet another related embodiment, $X_7$ is D. In an alternative embodiment, $X_7$ is N.

In one embodiment of the polypeptide according to the present invention, $X_{11}$ is selected from A, H, K, Q, R and S. In another embodiment, $X_{11}$ is selected from A, H, K and R. In yet another related embodiment, $X_{11}$ is selected from A, K and R. In yet another related embodiment, $X_{11}$ is selected from K and R.

In one embodiment of the polypeptide according to the present invention, $X_{16}$ is T.

In one embodiment of the polypeptide according to the present invention, $X_{17}$ is selected from I and L. In another embodiment, $X_{17}$ is I. In an alternative embodiment, $X_{17}$ is L.

In one embodiment of the polypeptide according to the present invention, $X_{18}$ is selected from A, D, E, N, Q, S and T. In another embodiment, $X_{18}$ is selected from A, D, E, Q and S. In yet another related embodiment, $X_{18}$ is selected from D, E and Q. In yet another related embodiment, $X_{18}$ is selected from D and E. In yet another related embodiment, $X_{18}$ is D. In an alternative embodiment, $X_{18}$ is E.

In one embodiment of the polypeptide according to the present invention, $X_{21}$ is selected from I and L. In another embodiment, $X_{21}$ is I. In an alternative embodiment, $X_{21}$ is L.

In one embodiment of the polypeptide according to the present invention, $X_{25}$ is selected from E, H, N and T. In another embodiment, $X_{25}$ is selected from E and N. In yet another related embodiment, $X_{25}$ is N.

In one embodiment of the polypeptide according to the present invention, $X_{26}$ is K.

In one embodiment of the polypeptide according to the present invention, $X_{28}$ is selected from A, D, E, H, N, Q and S. In another embodiment of the above disclosed polypeptide, $X_{28}$ is selected from A, D, E and S. In yet another related embodiment, $X_{28}$ is selected from A, D and E. In yet another related embodiment, $X_{28}$ is selected from D and E. In yet another related embodiment, $X_{28}$ is D.

In one embodiment of the polypeptide according to the present invention, $X_3X_4$ is selected from LE and LD.

In one embodiment of the polypeptide according to the present invention, $X_{17}X_{18}$ is selected from IE and LD.

In the above embodiments of the first aspect, examples of C5 binding polypeptides falling within the class of polypeptides are identified. It is contemplated that the above individual embodiments may be combined in all conceivable ways and still fall within the scope of the present invention. Such combinations of individual embodiments define a restricted, in one or more of the positions $X_2$-$X_{28}$, amino acid sequence as compared to the amino acid definition in i).

The above embodiments of a C5 binding polypeptide may for example be combined such that the amino acid i) fulfils at least four of the following eight conditions I-VIII:

I. $X_2$ is V;
II. $X_3$ is selected from I and L;
III. $X_6$ is W;
IV. $X_7$ is selected from D and N;
V. $X_{17}$ is selected from I and L;
VI. $X_{21}$ is L;
VII. $X_{25}$ is N;
VIII. $X_{28}$ is D.

In some examples of a C5 binding polypeptide according to the first aspect, the amino acid sequence i) fulfils at least five of the eight conditions I-VIII. More specifically, the amino acid sequence i) may fulfill at least six of the eight conditions I-VIII, such at least seven of the eight conditions I-VIII, such as all of the eight conditions I-VIII.

As described in the following Examples, the selection of C5 binding variants has led to the identification of individual C5 binding motif (BM) sequences. These sequences constitute individual embodiments of C5 binding polypeptides according to this aspect. The sequences of individual C5 binding motifs are presented in FIG. 1 and as SEQ ID NO:1-248. In some embodiments of this aspect, the BM sequence i) is selected from any one of SEQ ID NO:1-12, SEQ ID NO:20, SEQ ID NO:23-24, SEQ ID NO:26-28, SEQ ID NO:32-35, SEQ ID NO:38-39, SEQ ID NO:41, SEQ ID NO:46, SEQ ID NO:49, SEQ ID NO:56-57, SEQ ID NO:59, SEQ ID NO:66, SEQ ID NO:78-79, SEQ ID NO:87, SEQ ID NO:92, SEQ ID NO:106, SEQ ID NO:110, SEQ ID NO:119, SEQ ID NO:125, SEQ ID NO:141, SEQ ID NO:151, SEQ ID NO:161, SEQ ID NO:166, SEQ ID NO:187, SEQ ID NO:197, SEQ ID NO:203, SEQ ID NO:205, SEQ ID NO:215 and SEQ ID NO:243. More specifically, the BM sequence i) is selected from any one of SEQ ID NO:1-12, such as from SEQ ID NO:1, SEQ ID NO:2, SEQ ID NO:3, SEQ ID NO:4 and SEQ ID NO:5. In particular, the BM sequence i) may be selected from SEQ ID NO:1 and SEQ ID NO:4.

In particular embodiments, the C5 binding motif (BM) forms part of a three-helix bundle protein domain. For example, the BM may essentially constitute two alpha helices with an interconnecting loop, within said three-helix bundle protein domain.

The three-helix bundle protein domain is, in another embodiment, selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from said domain B of staphylococcal Protein A.

In embodiments where the C5 binding polypeptide of the invention forms part of a three-helix bundle protein domain, the C5 binding polypeptide may comprise an amino acid sequence selected from:

i)
(SEQ ID NO. 764)

K-[BM]-DPSQS $X_aX_b$LL$X_c$ EAKKL ND$X_d$Q;

wherein

[BM] is a C5 binding motif as defined above;

$X_a$ is selected from A and S;

$X_b$ is selected from N and E;

$X_c$ is selected from A, S and C;

$X_d$ is selected from A and S;

and ii) an amino acid sequence which has at least 79% identity to any one of the sequences defined above. Said amino acid sequence may have at least 81%, such as at least 83%, such as at least 85%, such as at least 87%, such as at least 89%, such as at least 91%, such as at least 93%, such as at least 95%, such as at least 97% identity to any one of the sequences defined above.

In one embodiment of the C5 binding polypeptide as defined above, $X_a$ is A. In an alternative embodiment of the C5 binding polypeptide as defined above, $X_a$ is S.

In one embodiment of the C5 binding polypeptide as defined above, $X_b$ is N. In an alternative embodiment, $X_b$ is E.

In one embodiment of the C5 binding polypeptide as defined above, $X_b$ is A. In an alternative embodiment, $X_c$ is S. In yet another alternative embodiment, $X_c$ is C.

In one embodiment of the C5 binding polypeptide as defined above, $X_d$ is A. In an alternative embodiment, $X_d$ is S.

In one embodiment of the C5 binding polypeptide as defined above, $X_a$ is A; $X_b$ is N; $X_c$ is A and $X_d$ is A.

In a further embodiment of the C5 binding polypeptide as defined above, $X_a$ is A; $X_b$ is N; $X_c$ is C and $X_d$ is A.

In a further embodiment of the C5 binding polypeptide as defined above, $X_a$ is S; $X_b$ is E; $X_c$ is S and $X_d$ is S.

In a further embodiment of the C5 binding polypeptide as defined above, $X_a$ is S; $X_b$ is E; $X_c$ is C and $X_d$ is S.

In yet a further embodiment, the amino acid sequence of the C5 binding polypeptide as defined above is selected from SEQ ID NO:249-496, in particular from SEQ ID NO:249-260, SEQ ID NO:268, SEQ ID NO:271-272, SEQ ID NO:274-276, SEQ ID NO:280-283, SEQ ID NO:286-287, SEQ ID NO:289, SEQ ID NO:294, SEQ ID NO:297, SEQ ID NO:304-305, SEQ ID NO:307, SEQ ID NO:314, SEQ ID NO:326-327, SEQ ID NO:335, SEQ ID NO:340, SEQ ID NO:354, SEQ ID NO:358, SEQ ID NO:367, SEQ ID NO:373, SEQ ID NO:389, SEQ ID NO:399, SEQ ID NO:409, SEQ ID NO:414, SEQ ID NO:435, SEQ ID NO:445, SEQ ID NO:451, SEQ ID NO:453, SEQ ID NO:463 and SEQ ID NO:491, such as from SEQ ID NO:249-260. In a further embodiment, the amino acid sequence is selected from SEQ ID NO:249, SEQ ID NO:250, SEQ ID NO:251, SEQ ID NO:252 and SEQ ID NO:253, such as from SEQ ID NO:249 and SEQ ID NO:252.

Thus, in a further embodiment, there is provided a C5 binding polypeptide which comprises an amino acid sequence selected from:

i)

(SEQ ID NO 765)

YAK-[*BM*]-DPSQS SELL$X_c$ EAKKL NDSQA P;

wherein [BM] is a C5 binding motif as defined above and $X_c$ is selected from S and C; and ii) an amino acid sequence which has at least 81% identity to any one of the sequences defined in i) above.

Alternatively, there is provided a C5 binding polypeptide which comprises an amino acid sequence selected from:

i)

(SEQ ID NO. 766)

FNK-[*BM*]-DPSQS ANLL$X_c$ EAKKL NDAQA P;

wherein [BM] is a C5 binding motif as defined above and $X_c$ is selected from A and C; and ii) an amino acid sequence which has at least 81% identity to any one of the sequences defined in i) above.

As discussed above, polypeptides comprising minor changes as compared to the above amino acid sequences without largely affecting the tertiary structure and the function thereof are also within the scope of the present application. Thus, in some embodiments, the C5 binding polypeptides as defined above may for example have a sequence which is at least 83%, at least 84%, at least 86%, at least 88%, at least 90%, at least 92%, at least 94%, at least 96% or at least 98% identical to the sequence defined in i).

In some embodiments and as disclosed in the Examples below, the C5 binding motif may form part of a 58 or 60 amino acid polypeptide. Such a polypeptide may e.g. comprise a sequence selected from any one of SEQ ID NO:497-757, in particular a sequence selected from any one of SEQ ID NO:497-508, SEQ ID NO:516, SEQ ID NO:519-520, SEQ ID NO:522-524, SEQ ID NO:528-531, SEQ ID NO:534-535, SEQ ID NO:537, SEQ ID NO:542, SEQ ID NO:545, SEQ ID NO:552-553, SEQ ID NO:555, SEQ ID NO:562, SEQ ID NO:574-575, SEQ ID NO:583, SEQ ID NO:588, SEQ ID NO:602, SEQ ID NO:606, SEQ ID NO:615, SEQ ID NO:621, SEQ ID NO:637, SEQ ID NO:647, SEQ ID NO:657, SEQ ID NO:662, SEQ ID NO:683, SEQ ID NO:693, SEQ ID NO:699, SEQ ID NO:701, SEQ ID NO:711, SEQ ID NO:739 and SEQ ID NO:745-757, such as a sequence selected from SEQ ID NO:497-508 and SEQ ID NO:745-757. In another embodiment, the amino acid sequence is selected from SEQ ID NO:497, SEQ ID NO:498, SEQ ID NO:499, SEQ ID NO:500, SEQ ID NO:501, SEQ ID NO:746, SEQ ID NO:747, SEQ ID NO:748, SEQ ID NO:750 and SEQ ID NO:753, such as from any one of SEQ ID NO:497, SEQ ID NO:500, SEQ ID NO:748 and SEQ ID NO:753.

Binding of a molecule to C5 does not necessarily inhibit cleavage of C5. Inhibition is dependent on binding site, and since it is not entirely clear what effects interaction with specific regions of C5 have, some C5 binding molecules may interact with C5 without inhibiting its cleavage into C5a and C5b. In one embodiment of the present invention, the C5 binding polypeptide, when e.g. administered to a mammalian subject, inhibits cleavage of C5. The C5 binding polypeptide according to the invention may more specifically inhibit cleavage of human C5 when administered to a human subject.

The structure of C5 differs somewhat between species, and thus, a C5 binder found to bind C5 of one species may be inactive in another species. The humanized antibody Eculizumab, for example, binds to a domain of C5 often referred to as MG7. This region is highly variable between species and, therefore, Eculizumab binding is restricted to human C5. The C5 binding polypeptide of the present invention, however, is not restricted to human C5 but exhibits activity in animal models as well, as demonstrated in the appended Examples.

The skilled person will understand that various modifications and/or additions can be made to a C5 binding polypeptide according to any aspect disclosed herein in order to tailor the polypeptide to a specific application without departing from the scope of the present invention. For example, a C5 binding polypeptide according to any aspect may comprise further C terminal and/or N terminal amino acids. Such a polypeptide should be comprehended as a polypeptide having additional amino acids residues at the very first and/or the very last position in the polypeptide chain, i.e. at the N- and/or C-terminus. Thus, a C5 binding polypeptide may comprise any suitable number of additional amino acid residues, for example at least one additional amino acid residue. Each additional amino acid residue may individually or collectively be added in order to, for example, improve production, purification, stabilization in vivo or in vitro, coupling, or detection of the polypeptide. Such additional amino acid residues may comprise one or more amino acid residues added for the purpose of chemical coupling. One example of this is the addition of a cysteine residue. Such additional amino acid residues may also provide a "tag" for purification or detection of the polypeptide, such as a $His_6$ tag or a "myc" (c-myc) tag or a "FLAG" tag for interaction with antibodies specific to the tag or immobilized metal affinity chromatography (IMAC) in the case of the $His_6$-tag.

The further amino acids as discussed above may be coupled to the C5 binding polypeptide by means of chemical conjugation (using known organic chemistry methods) or by any other means, such as expression of the C5 binding polypeptide as a fusion protein.

The further amino acids as discussed above may for example comprise one or more polypeptide domain(s) A further polypeptide domain may provide the C5 binding polypeptide with another function, such as for example another binding function, or an enzymatic function, or a toxic function (e.g. an immunotoxin), or a fluorescent signaling function, or combinations thereof.

A further polypeptide domain may moreover provide the C5 binding polypeptide with the same binding function. Thus, in a further embodiment, there is provided a C5 binding polypeptide comprising at least two C5 binding polypeptide monomer units, the amino acid sequences of which may be the same or different. Multimeric forms of the polypeptides may comprise a suitable number of domains, each having a C5 binding motif, and each forming a "monomer" within the multimer. These domains may all have the same amino acid sequence, but alternatively, they may have different amino acid sequences. In particular, the C5 binding polypeptide of the invention may form homo- or heterodimers.

The further polypeptide domain(s) as described above may be joined to the C5 binding polypeptide by covalent coupling using known organic chemistry methods. Alternatively, the C5 binding polypeptide comprising the further polypeptide domain(s) may be expressed as one or more fusion polypeptides, for example in a system for recombinant expression of polypeptides, or joined in any other fashion, either directly or via a linker, for example an amino acid linker.

In some embodiments, the further polypeptide domain(s) may comprise a half-life extending moiety which increases the half life of the C5 binding polypeptide in vivo. As understood by the skilled person, increased, or extended, half life means slower clearance of a particular molecule from blood. There are a number of known strategies for prolonging the half life of a particular polypeptide in vivo, such as coupling to the Fc domain of an antibody (Fc conjugation) or coupling to albumin Another example is coupling to a half life extending moiety, e.g. a peptide or protein, that will associate to serum albumin in vivo. In particular, the half life extending moiety may be an albumin binding moiety. An albumin binding moiety may e.g. consist of a naturally occurring polypeptide, or an albumin binding fragment thereof, or an engineered polypeptide. An engineered polypeptide may be derived from a naturally occurring starting polypeptide through subjecting it to protein engineering techniques, such as mutations and alterations in a site-directed or randomized approach, with a view to create novel or enhanced properties, such as binding affinity for a molecule such as albumin. Such an engineered albumin binding polypeptide may for example be a variant of a protein scaffold, which variant has been selected for its specific binding affinity for albumin. In a specific embodiment, the protein scaffold may be selected from domains of streptococcal Protein G or derivatives thereof, such as for example domain GA1, domain GA2 and domain GM of Protein G from *Streptococcus* strain G148, in particular domain GA3.

Accordingly, in one embodiment of the C5 binding polypeptide, the further amino acids improves stabilization in vivo or in vitro and comprise an albumin binding domain (ABD) of streptococcal protein G, or a derivative thereof. One example of an albumin binding domain which may be comprised as a further polypeptide domain in the C5 binding polypeptide of the invention is set out in SEQ ID NO:759. Other examples of suitable albumin binding domains are disclosed in WO 2009/016043 and WO 2012/004384. Such an ABD-extended polypeptide binds to serum albumin in vivo, and benefits from its longer half life, which increases the net half life of the polypeptide itself (see e.g. WO 91/01743). The pharmacokinetic profile of a C5 binding polypeptide comprising an albumin binding moiety as defined above thus resembles that of serum albumin when administered for example to a mammalian subject. ABD and derivatives thereof bind very strongly to human serum albumin (HSA) as well as to serum albumin from other species, such as mouse and rat.

ABD of streptococcal protein G is 46 amino acid long, and thus when a C5 binding polypeptide according to the invention comprises an ABD moiety or a derivative thereof, the overall size of the C5 binding polypeptide is relatively small. When administered for example to a mammalian subject, such as a human subject, the albumin binding part of the C5 binding polypeptide will associate non-covalently with serum albumin and the polypeptide may thereby benefit from decreased renal clearance and increased recirculation in epithelial cells. Tissue penetration may however still be fast due to extravasating properties of serum albumin. Furthermore, a C5 binding polypeptide comprising a half life extending moiety may not only display an extended half life in vivo, but also a reduced immunologic response in vivo, as compared to a polypeptide lacking a corresponding half life extending moiety (see e.g. WO 2005/097202).

In a related aspect, there is provided a C5 binding compound, comprising at least one C5 binding polypeptide according to any preceding claim; at least one albumin binding domain of streptococcal protein G, or a derivative thereof, and at least one linking moiety for linking said at least one domain or derivative thereof to the C or N terminus of said at least one C5 binding polypeptide. Such a C5 binding compound has high affinity for C5 as well as for serum albumin in vivo, when administered e.g. to a mammalian subject, and binding to serum albumin does not interfere with the interaction with C5, as demonstrated in the following Examples.

In one embodiment, the C5 binding compound has a structure selected from

[CBP1]-[L1]-[ALBD];
[CBP1]-[CBP2]-[L1]-[ALBD];
[CBP1]-[L1]-[ALBD]-[L2]-[CBP2];
[ALBD]-[L1]-[CBP1];
[ALBD]-[L1]-[CBP1]-[CBP2];
[CBP1]-[L1]-[CBP2]-[L2]-[ALBD]; and
[ALBD]-[L1]-[CBP1]-[L2]-[CBP2]
wherein, independently of each other,
[CBP1] and [CBP2] are C5 binding polypeptides which may be the same or different;
[L1] and [L2] are linking moieties which may be the same or different; and
[ALBD] is an albumin binding domain of streptococcal protein G, or derivative thereof.

Preferred C5 binding compounds have a structure selected from
[CBP1]-[CBP2]-[L1]-[ALBD];
[CBP1]-[L1]-[ALBD]-[L2]-[CBP2]; and most preferably,
[CBP1]-[L1]-[ALBD].

Examples of linking moieties that may be used in such C5 binding compounds are selected from G, GS; $[G_2S]_n$; $[G_3S]_n$ (SEQ ID NO: 783); $[G_4S]_n$ (SEQ ID NO: 784); $GS[G_4S]_n$ (SEQ ID NO: 785), wherein n is 0-7 (preferably, n is 0-2); $[S_2G]_m$; $[S_3G]_m$ (SEQ ID NO: 786); $[S_4G]_m$ (SEQ ID NO: 787); wherein m is 0-7, and VDGS (SEQ ID NO: 788). Preferred linkers are GS and $GS[G_4S]_2$ (SEQ ID NO: 785).

Examples of albumin binding domains or derivatives thereof that may be comprised in a C5 binding compound are as described above. In particular, one example of an albumin binding domain is set out in SEQ ID NO:759.

Particularly preferred C5 binding compounds have the structure [CBP1]-[L1]-[ALBD], wherein [CBP1] is a polypeptide selected from SEQ ID NO:748 and SEQ ID NO:753, [L1] is GS, and [ALBD] is a polypeptide shown as SEQ ID NO:759.

The C5 binding polypeptide(s) comprised in a C5 binding polypeptide are, in one embodiment, independently selected from 58-mer or 60-mer C5 binding polypeptides as previously described. In particular, the C5 binding compound may comprise one or more C5 binding polypeptides independently selected from any one of SEQ ID NO:497-508, SEQ ID NO:516, SEQ ID NO:519-520, SEQ ID NO:522-524, SEQ ID NO:528-531, SEQ ID NO:534-535, SEQ ID NO:537, SEQ ID NO:542, SEQ ID NO:545, SEQ ID NO:552-553, SEQ ID NO:555, SEQ ID NO:562, SEQ ID NO:574-575, SEQ ID NO:583, SEQ ID NO:588, SEQ ID NO:602, SEQ ID NO:606, SEQ ID NO:615, SEQ ID NO:621, SEQ ID NO:637, SEQ ID NO:647, SEQ ID NO:657, SEQ ID NO:662, SEQ ID NO:683, SEQ ID NO:693, SEQ ID NO:699, SEQ ID NO:701, SEQ ID NO:711, SEQ ID NO:739 and SEQ ID NO:746-757, such as a sequence selected from SEQ ID NO:497-508 and SEQ ID NO:746-757. In another embodiment, the amino acid sequence is selected from SEQ ID NO:497, SEQ ID NO:498, SEQ ID NO:499, SEQ ID NO:500, SEQ ID NO:501, SEQ ID NO:746, SEQ ID NO:747, SEQ ID NO:748, SEQ ID NO:750 and SEQ ID NO:753, such as from any one of SEQ ID NO:497, SEQ ID NO:500, SEQ ID NO:748 and SEQ ID NO:753.

In a further aspect, there is provided a polynucleotide encoding a C5 binding polypeptide or a compound as described above. An expression vector comprising such a polynucleotide may enable production of a C5 binding polypeptide or a C5 binding compound, for example by expression in a host cell.

It should be understood that the C5 binding polypeptide according to the present invention may be useful as a therapeutic or diagnostic agent in its own right or as a means for targeting other therapeutic or diagnostic agents, with e.g. direct or indirect effects on the complement protein C5. A direct therapeutic effect may for example be accomplished by inhibiting C5 cleavage. In one embodiment, there is thus provided a combination of a C5 binding polypeptide or a C5 binding compound according to the invention with a therapeutic agent. Non-limiting examples of therapeutic agents that may prove useful in such a combination are immunostimulatory agents and radionuclides.

Thus, the C5 binding polypeptide as such, or as comprised in a C5 binding compound or a combination according to the invention, is in one embodiment provided for use in therapy, for example for the treatment of a C5 related condition, such as a C5 related condition in a mammal, such as a human subject. In one embodiment, said C5 related condition is selected from inflammatory disease, such as antigen-induced arthritis, sepsis, synovial inflammation, vasculitis and asthma; autoimmune disease, such as systemic lupus erythematosus (SLE), cold agglutinin disease, rheumatoid arthritis, multiple sclerosis (MS), Sjögren's syndrome, dermatomyositis, myasthenia gravis and other autoantibody driven diseases such as Guillain-Barré syndrome (GBS), Fisher syndrome, systemic sclerosis, anti-glomerular basement membrane (anti-GBM) and anti-phospholipid syndrome (APS); infectious disease, such as hemolytic-uremic syndrome (HUS), viral infections, bacterial infections and fungal infections; cardiovascular disease, such as (acute) myocardial infarction (undergoing revascularization either by fibrinolysis or percutaneous coronary intervention (PCI)); neurodegenerative disorders such as Alzheimer's disease (AD), Huntington's disease, Creutzfeld-Jacob disease and Parkinson's disease; cancers; wounds; graft injury, such as ischemia reperfusion injury (IRI) and acute antibody mediated rejection (AMR); eye disease, such as age-related macular degeneration (AMD), uveitis, diabetic ocular diseases and disorders, and retinopathy of prematurity; kidney disease, such as membranous glomerulonephritis, membranous nephritis, immunoglobulin A nephropathy, Lupus nephritis, Goodpasture syndrome and post-streptococcal glomerulonephritis; pulmonary diseases, such as adult respiratory distress syndrome, chronic obstructive pulmonary disease and cystic fibrosis; hematological diseases; such as hemolytic anaemia, paroxysmal cold hemoglobinuria, atypical hemolytic uremic syndrome (aHUS) and paroxysmal nocturnal hemoglobinuria (PNH); allergic diseases, such as anaphylactic shock, allergy and asthma; and dermatological diseases, such as pemphigus, bullous pemphigoid, phototoxic reactions and psoriasis. In a more particular embodiment, the C5 binding polypeptide, compound or combination according to the invention is used for treatment of paroxysmal nocturnal hemoglobinuria (PNH).

As mentioned when discussing organ transplantation in the background section above, differences between donor and recipient (e.g. ABO and MHC classes) as well as the condition of the transplanted organ may lead to delayed functioning or even rejection of the transplanted organ. Treatment may thus be necessary to eliminate anti-donor antibodies despite a positive donor-recipient crossmatch or to eliminate ABO antibodies when transplantation occurs against the ABO barrier. Such treatment typically includes immunoadsorption, e.g. by use of affinity chromatography techniques, prior to as well as after transplantation or plasmapheresis. Such procedures however runs the risk of eliminating nearly all antibodies present in the circulation, thus including therapeutic antibodies. The C5 binding polypeptides or compounds of the invention are however not affected by any antibody removing procedures, and may thus be exploited in these treatments.

In some C5 related conditions where a more local acute pathology in readily accessible tissues, such as lung and the blood stream, dominates rather than systemic pathologies, a drug with a very short half-life could be advantageous over one with a slow elimination. Thus, in such C5 related conditions, a C5 binding polypeptide without a half-life extending moiety may be beneficial. As previously accounted for, a C5 binding polypeptide according to the invention will, due to its relatively small size, exhibit a relatively rapid pharmacokinetic profile when administered to a mammal such as a human. The C5 binding polypeptide according to the invention may potentially be active in treatment of C5 related conditions such as asthma (Zhang et al. Expert Rev Clin Immunol 2010, 6:269-277), sepsis (Ward et al. The Sci World J 2010, 10:2395-2402), and hypersensitivity syndrome including the C activation-related pseudoallergy (CARPA, a reaction to certain therapeutic liposomes and lipid excipient-based drugs that in rare cases can lead to life threatening cardiopulmonary distress (Szebeni et al. Adv Drug Delivery Rev 2011, 63:1020-1030). In addition, a C5 binding polypeptide according to the invention may be used for complement inhibition when a recipient of blood transfusion has received blood of an incompatible type (a situation occurring in about 1:14000 transfusion units in the US which is associated with high mortality, Goodnough et al. Lancet 2003, 361:161-169).

In a related aspect, there is provided a method of treatment of a C5 related condition, comprising administering of a C5 binding polypeptide, or combination as described above to a mammalian subject in need thereof. Consequently, in the method of treatment, the subject is treated with a C5 binding polypeptide, a C5 binding compound or a combination according to the invention. In a more specific embodiment of said method, the binding of the C5 binding polypeptide or the combination, to a C5 expressed on a cell surface in the subject inhibits C5 cleavage. In one embodiment of the method of treatment, the C5 related condition is selected from inflammatory disease; autoimmune disease; infectious disease; cardiovascular disease; neurodegenerative disorders; cancers; wounds; graft injury; eye disease; kidney disease; pulmonary diseases; hematological diseases; allergic diseases and dermatological diseases. In particular the C5 related condition may be as defined above in relation to therapeutic use of a C5 binding polypeptide, compound or combination according to the invention. The C5 related condition may for example be paroxysmal nocturnal hemoglobinuria (PNH). In one embodiment of the method of treatment, the said C5 binding polypeptide is administered intravenously, subcutaneously, by inhalation, nasally, orally, intravitreally, or topically.

The invention will now be further illustrated by the following non-limiting Examples.

BRIEF DESCRIPTION OF THE FIGURES

FIG. 1A-1AH is a listing of the amino acid sequences of examples of C5 binding motifs comprised in C5 binding polypeptides of the invention (SEQ ID NO:1-248), examples of 49-mer C5 binding polypeptides according to the invention (SEQ ID NO:249-496), examples of 58-mer C5 binding polypeptides according to the invention (SEQ ID NO:497-744) and examples of 60-mer C5 binding polypeptides according to the invention (SEQ ID NO:745-757), as well as the sequences of protein Z (SEQ ID NO:758), an albumin binding domain (ABD094, SEQ ID NO:759), the Swiss-Prot entry P01031 of human C5 (amino acid residues 1-1676, SEQ ID NO:760; of which the α-chain corresponds to amino acid residues 678-1676 and the β-chain corresponds to amino acid residues 19-673), the sequence of the $His_6$-tagged tic protein OmCI used herein (SEQ ID NO:761) and cynomolgus C5 (SEQ ID NO:762) derived from genomic sequence (published on-line at www.ebi.ac.uk/ena; Ebeling et al. (2001) Genome Res. 21(10):1746-1756) using human C5 as template. The sequence contains two unknown amino acids "X" in positions 63 and 1346.

FIG. 7A shows C5 binding of different Z variants (SEQ ID NO:745, SEQ ID NO:748-757) in fusion with ABD094 (SEQ ID NO:759) compared to C5 binding of the tick protein OmCI (SEQ ID NO:761).

EXAMPLES

Figure 2:
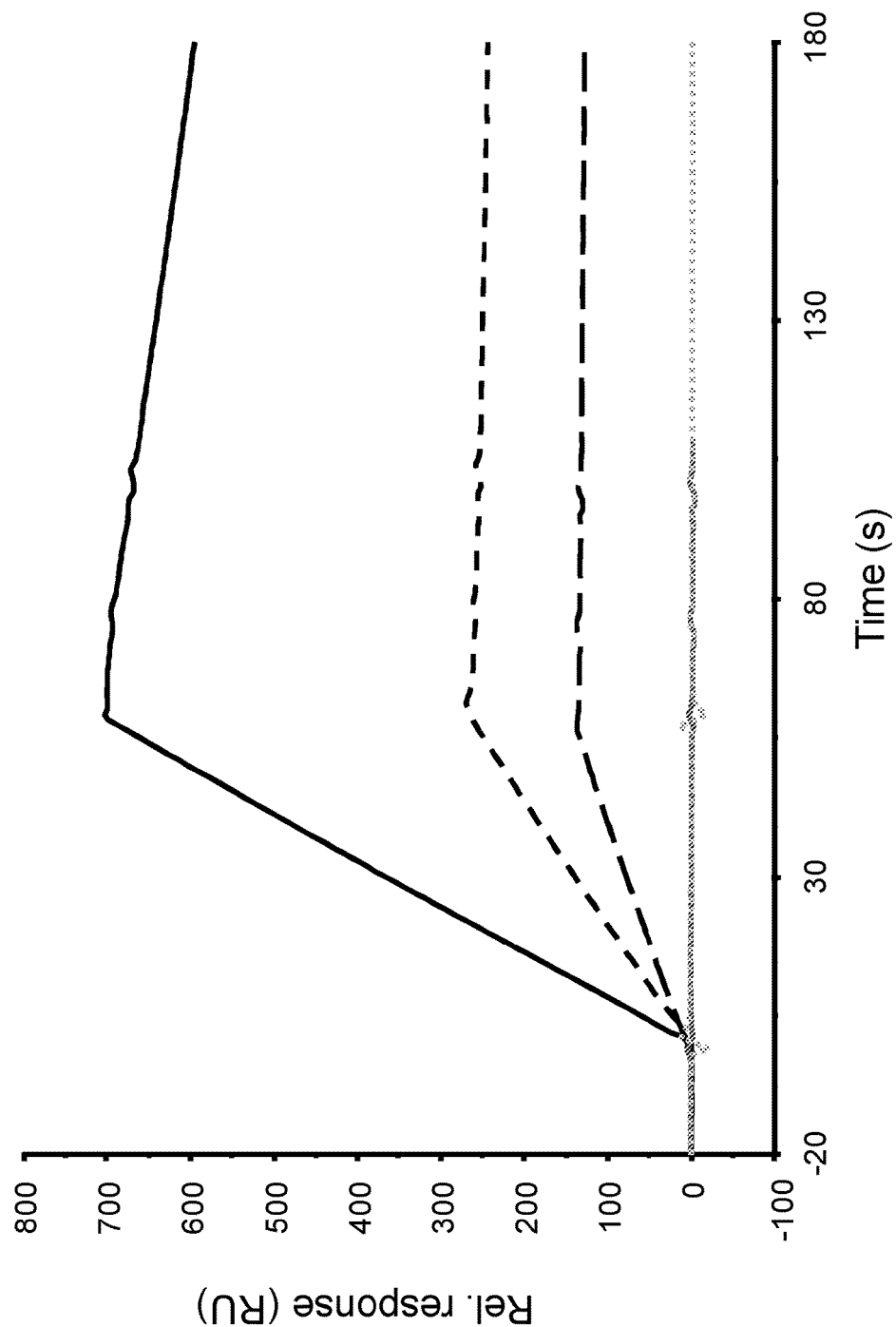
FIG. 2 shows the result of a typical binding analysis performed in a Biacore instrument as described in Example 2. Sensorgrams were obtained by injection of human C5 (hC5; black solid curve), cynomolgus C5 (cC5; black short-dashed curve), rat C5 (rC5; black long-dashed curve), human MG7 domain (hMG7; gray dotted curve), and human immunoglobulin G (hIgG; gray solid curve), respectively, over an immobilized dimeric Z variant (Z05477, SEQ ID NO:509).
Figure 3:
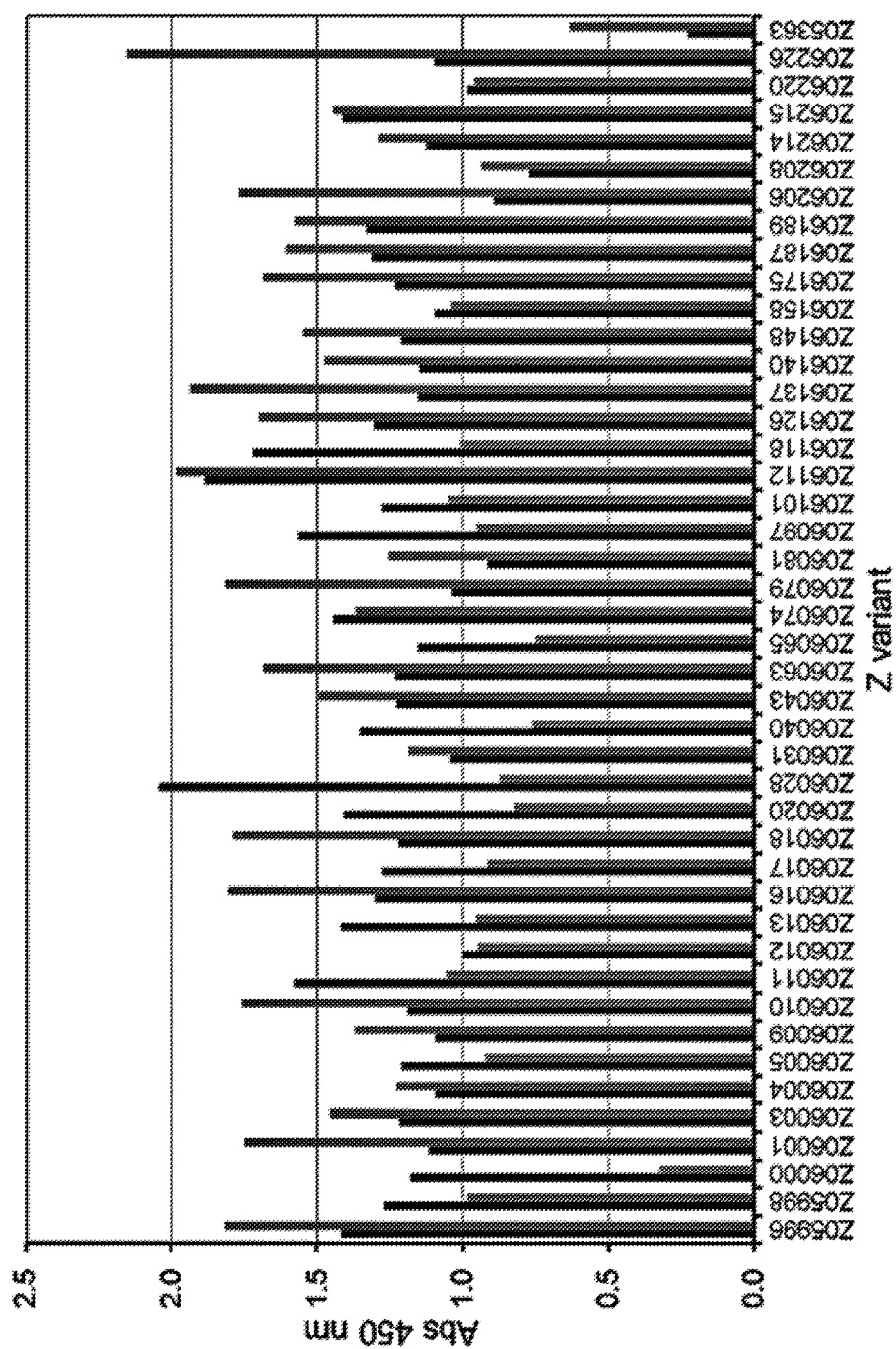
FIG. 3 is a column chart showing the response in ELISA against hC5 and rC5, respectively, for selected maturated Z variants. The black columns corresponds to the absorbance at 450 nm obtained using 0.05 µg/ml hC5 (left column in each group) and to the absorbance at 450 nm obtained using 4 µg/ml rC5 for each Z variant (right column in each group), as described in Example 4. The responses for the Z variant Z05363 (SEQ ID NO:510) are plotted as a positive control.

The following materials were used throughout this work except where otherwise noted.

*Escherichia coli* strain RR1ΔM15 (Rüther, Nucleic Acids Res 10:5765-5772, 1982).

*Escherichia coli* strain XL1-Blue (Agilent Technologies, cat. no. 200268).

Human complement protein C5 (hC5). The full 1676 amino acid pro-protein has GenBank accession number: NP_001726 (SEQ ID NO:760) wherein amino acids 19-673 is the beta chain and amino acids 678-1676 is the alpha chain. Human C5 used herein was purchased from Quidel (cat. no. A403)

Cynomolgus complement protein C5 (cC5; SEQ ID NO:762). The cC5 sequence was derived from the Cynomolgus (*Macaca fascicularis*) genomic sequence (www.ebi.ac.uk/ena; Ebeling et al. (2001) Genome Res. 21(10):1746-1756). The coding region of human C5 was retrieved from www.ensembl.org, and the C5 gene was localized to chromosome 15. The region containing the gene is approximately 110 000 bases long and is contained in contigs CAEC01154150 to CAEC01154178. The contigs were manually joined to a single file and used as a genomic context for the sim4 software to align the coding region of human C5 to the raw Cynomolgus genomic material. Cynomolgus C5 used herein was purified in-house from serum using a three-step procedure; PEG6000 precipitation, ion exchange and OmCI affinity chromatography.

Rat Complement protein C5 (rC5; GenBank accession number: XP_001079130) Rat C5 used herein was purified in-house from serum using a three-step procedure; PEG6000 precipitation, ion exchange and OmCI affinity chromatography.

Human MG7 (hMG7) domain of complement protein C5, corresponding to amino acid residues 822-931 of human C5 (SEQ ID NO:760; Fredslund et al. (2008) Nature Immunology 9: 753-760) produced in-house in Freestyle HEK293 cells.

hMG7 binding protein.

OmCI (AF2999, Nunn, M. A. et al. supra) from soft tick *Ornithodoros moubata* OmCI with a $His_6$ tag in the C-terminus (SEQ ID NO:761) was produced in-house in *E. coli* strain Origami(DE3) and purified on a His-Trap1 column.

Example 1: Selection and Screening of Complement Protein C5 Binding Polypeptides Materials and Methods
Biotinylation of Target Protein hC5:

hC5 was biotinylated according to the manufacturer's recommendations at room temperature (RT) for 40 min using No-Weigh EZ-Link Sulfo-NHS-LC-Biotin (Pierce, cat. no. 21327) at a ten times (10×) molar excess. Subsequent buffer exchange to PBS (10 mM phosphate, 137 mM NaCl, 2.68 mM KCl, pH 7.4) was performed using Protein Desalting Spin Columns (Pierce, cat. no. 89849) according to the manufacturer's instructions.

Phage Display Selection of C5-Binding Polypeptides:

Libraries of random variants of protein Z displayed on bacteriophage, constructed in phagemid pAffi1/pAY00065/pAY02947/pAY02592 essentially as described in Grönwall et al. J Biotechnol 2007, 128:162-183), were used to select C5 binding polypeptides. Three different library vectors were used. Two of these utilize an albumin binding domain (ABD, GA3 of protein G from *Streptococcus* strain G148) as fusion partner to the Z variants generating the libraries Zlib003Naive.I and Zlib006Naive.II. The third library, Zlib004Naive.I utilizes the Taq DNA polymerase binding molecule Z03639 (denoted $Z_{TaqS1-1}$ in Gunneriusson et al. Protein Eng 1999, 12:873-878) as fusion partner. The libraries had the following actual sizes: $3 \times 10^9$ (Zlib003Naive.I); $1.5 \times 10^{10}$ (Zlib006Naive.II); and $1.4 \times 10^{10}$ (Zlib004Naive.I), the number referring to the amount of variants.

Phage stocks were prepared either in shake flasks (Zlib003Naive.I) as described in Grönwall et al. supra or in a 20 l fermenter (Zlib006Naive.II and Zlib004Naive.I). Cells from a glycerol stock containing the phagemid library Zlib004Naive.I were inoculated in 20 l of TSB-YE (Tryptic Soy Broth-Yeast Extract; 30 g/l TSB, 5 g/l yeast extract) supplemented with 2% glucose and 100 µg/ml ampicillin. Cells from a glycerol stock containing the phagemid library Zlib006Naive.II were inoculated in 20 l of a defined proline free medium [dipotassium hydrogenphosphate 7 g/l, trisodium citrate dihydrate 1 g/l, uracil 0.02 g/l, YNB (Difco™ Yeast Nitrogen Base w/o amino acids, Becton Dickinson) 6.7 g/l, glucose monohydrate 5.5 g/l, L-alanine 0.3 g/l, L-arginine monohydrochloride 0.24 g/l, L-asparagine monohydrate 0.11 g/l, L-cysteine 0.1 g/l, L-glutamic acid 0.3 g/l, L-glutamine 0.1 g/l, glycine 0.2 g/l, L-histidine 0.05 g/l, L-isoleucine 0.1 g/l, L-leucine 0.1 g/l, L-lysine monohydrochloride 0.25 g/l, L-methionine 0.1 g/l, L-phenylalanine 0.2 g/l, L-serine 0.3 g/l, L-threonine 0.2 g/l, L-tryptophane 0.1 g/l, L-tyrosine 0.05 g/l, L-valine 0.1 g/l] supplemented with 100 µg/ml ampicillin. The cultivations were grown at 37° C. in a fermenter (Belach Bioteknik, BR20). When the cells reached an optical density (OD) of 0.7-0.8, approximately 2.6 l of the cultivation was infected using a 10× molar excess of M13K07 helper phage (New England Biolabs #N03155). The cells were incubated for 30 minutes, whereupon the fermenter were filled up to 20 l with TSB-YE supplemented with 100 µM IPTG (isopropyl-β-D-1-thiogalactopyranoside, for induction of expression), 25 µg/ml kanamycin and 12.5 µg/ml carbenicillin and grown at 30° C. for 22 h. The cells in the cultivation were pelleted by centrifugation at 15,900 g and the phage particles remaining in the medium were thereafter precipitated twice in PEG/NaCl (polyethylene glycol/sodium chloride), filtered and dissolved in PBS and glycerol as described in Grönwall et al. supra. Phage stocks were stored at −80° C. before use.

Selections were performed in four cycles against biotinylated hC5. Phage stock preparation, selection procedure and amplification of phage between selection cycles were performed essentially as described in WO 2009/077175. PBS supplemented with 3% bovine serum albumin (BSA) and 0.1% Tween20 was used as selection buffer and the target-phage complexes were directly captured by DYNABEADS M-280 Streptavidin (Dynal, cat. no. 112.06). 1 mg beads per 10 µg complement protein C5 was used. *E. coli* strain RR1ΔM15 was used for phage amplification. In cycle 1 of the selections, 100 nM hC5 was used and two washes with PBST 0.1% (PBS supplemented with 0.1% Tween-20) were performed. An increased stringency, using a lowered target concentration and an increased number of washes, was applied in the subsequent three cycles. In cycle 2, 3 and 4; 50 or 33 nM hC5, 25 or 11 nM hC5 and 12.5 or 3.7 nM hC5 were used. In cycle 2, 3 and 4; 4, 6 and 8 washes were performed, using PBST 0.1% in all cycles or PBST 0.2%, 0.3% and 0.4% in cycle 2, 3 and 4.

ELISA Screening of Z Variants:

To test if the selected Z variant molecules could indeed interact with human complement protein C5, ELISA assays were performed. The Z variants were produced by inoculating single colonies from the selections into 1 ml TSB-YE medium supplemented with 100 µg/ml ampicillin and 0.1 mM IPTG in deep-well plates (Nunc, cat. no. 278752). The plates were incubated for 18-24 h at 37° C. Cells were pelleted by centrifugation, re-suspended in 300 µl PBST 0.05% and frozen at −80° C. to release the periplasmic fraction of the cells. Frozen samples were thawed in a water bath and cells were pelleted by centrifugation. The periplasmic supernatant contained the Z variants as fusions to an albumin binding domain (GM of protein G from *Streptococcus* strain G148), expressed as AQHDEALE-[Z#####]-VDYV-[ABD]-YVPG (SEQ ID NO. 767) (Grönwall et al, supra), or to the Taq DNA polymerase binding molecule Z03639, expressed as AQHDEALE-[Z#####]-VDYV-[Z03639]-YVPG (SEQ ID NO. 768). Z##### refers to individual 58 amino acid residues Z variants.

Half-area 96-well ELISA plates (Costar, cat. no. 3690) were coated with 50 µl/well of coating buffer (50 mM sodium carbonate, pH 9.6) containing 4 µg/ml of an antibody specific for Z variants (Affibody, cat. no. 20.1000.01.0005) and incubated over-night at 4° C. The antibody solution was poured off and the wells were blocked with 100 µl of PBSC (PBS supplemented with 0.5% casein (Sigma, cat. no. C8654) for 1-2 h at RT. The blocking solution was discarded and 50 µl periplasmic solution was added to the wells and incubated for 1 h at RT under slow shaking. The supernatants were poured off and the wells were washed 4 times with PBST 0.05%. Then 50 μl of biotinylated complement protein hC5, at a concentration of 5 μg/ml in PBSC, was added to each well. The plates were incubated for 1.5 h at RT followed by washes as described above. Streptavidin-HRP (Horseradish peroxidase; Dako, cat. no. P0397) was diluted 1:10,000 in PBSC, added to the wells which were then incubated for 45 min. After washing as described above, 50 μl ImmunoPure TMB substrate (Thermo Scientific, cat. no. 34021) was added to the wells and the plates were treated according to the manufacturer's recommendations. Absorbance of the wells was measured at 450 nm using a multi-well plate reader, Victor$^3$ (Perkin Elmer).

As positive control, a periplasmic fraction also containing the PSMA binding molecule Z03938 expressed as AQH-DEALE-[Z03938]-VDYV-[Z03639]-YVPG (SEQ ID NO. 769) was assayed against 5 μg/ml biotinylated PSMA protein. As negative control; the same periplasmic preparation was assayed against complement protein hC5. Sequencing was performed for the clones with positive absorbance values against hC5.

Sequencing:

PCR fragments were amplified from single colonies using a standard PCR program and the primers AFFI-21 (5'-tgcttccggctcgtatgttgtgtg) (SEQ ID NO. 770) and AFFI-22 (5'-cggaaccagagccaccaccgg) (SEQ ID NO. 771). Sequencing of amplified fragments was performed using the biotinylated oligonucleotide AFFI-72 (5'-biotin-cggaaccagagccaccaccgg) (SEQ ID NO. 772) and a BIGDYE Terminator v3.1 Cycle Sequencing Kit (Applied Biosystems), used in accordance with the manufacturer's protocol. The sequencing reactions were purified by binding to magnetic streptavidin coated beads (Detach Streptavidin Beads, Nordiag, cat. no. 2012-01) using a Magnatrix 8000 (Magnetic Biosolution), and analyzed on ABI PRISM 3100 Genetic Analyzer (PE Applied Biosystems).

Blocking ELISA:

Clones found positive for hC5 in the ELISA screening were subjected to an ELISA blocking assay in order to elucidate if their target binding was affected by the presence of the hC5 binding proteins OmCI and/or hMG7 binding protein. The blocking ELISA was run using Z variants expressed in periplasmic fractions as described in the section for ELISA screening above, but setting up 5 ml cultures in 12 ml round-bottom tubes and using 2 ml PBST 0.05% for pellet dissolution. The ELISA blocking assay was run as the ELISA screening assay, with a protocol modification introduced at the target step; OmCI or hMG7 binding protein were mixed with the target protein before addition to the assay plate. 5 μg/ml biotinylated hC5 was mixed with 5 times or 20 times molar excess of OmCI or hMG7 binding protein, respectively, then incubated 1 h at RT to allow complex formation before addition to the plate. For each clone, a reference (1), a negative control (2) and a background (3) response/signal, respectively, were obtained as follows: at the target step, solely hC5 was added to the Z variants (as in the screening ELISA) (1); the irrelevant protein PSMA (in house produced) was added to complement protein hC5, instead of OmCI or hMG7 binding protein (2); only buffer was added to the Z variants (3).

Results

Phage Display Selection of Complement Protein C5 Binding Polypeptides:

Individual clones were obtained after two-four cycles of phage display selections against biotinylated hC5.

ELISA Screening of Z Variants:

The clones obtained after four cycles of selection were produced in 96-well plates and screened for complement protein C5 binding activity in ELISA. In total, nearly 400 clones were screened. The absorbance measurements showed many clearly hC5 positive clones. The result from a selection of clones is displayed in Table 1; the Z05363 (SEQ ID NO:510) variant is tagged with ABD, whereas the other listed Z variants are tagged with the Taq binding molecule Z03639 as described in the methods section. The PSMA specific molecule Z03938 used as a negative control gave a positive signal for PSMA, whereas no signal was obtained against hC5.

Blocking ELISA:

Clones positive for hC5 were subjected to a blocking assay using the hC5 binding proteins OmCI and hMG7 binding protein. For five clones, the binding signal to complement protein C5 was completely extinguished by the presence of OmCI, reaching the same level as the background (Table 1). One of these clones, namely the Z05363 variant (SEQ ID NO:510), was also tested for its ability to bind hC5 in the presence of hMG7 binding protein. The hMG7 binding protein did not inhibit the binding of Z05363 to hC5.

TABLE 1

Response in ELISA to target, with or without blocking molecule for a number of Z variants.

| Z variant | SEQ ID NO: # | hC5 (OD 450 nm) | OmCI-block |
| --- | --- | --- | --- |
| Z05363 | SEQ ID NO: 510 | 3.143 | complete |
| Z05477 | SEQ ID NO: 509 | 2.872 | complete |
| Z05483 | SEQ ID NO: 511 | 0.531 | complete |
| Z05538 | SEQ ID NO: 512 | 0.099 | complete |
| Z05692 | SEQ ID NO: 513 | 0.944 | complete |

Sequencing:

Sequencing was performed for the clones with positive absorbance values against complement protein C5 in the ELISA screening. Each variant was given a unique identification number #####, and individual variants are referred to as Z#####. The amino acid sequences of the 58 amino acid residues long Z variants are listed in FIG. 1 and in the sequence listing as SEQ ID NO:509-513. The deduced complement protein C5 binding motifs of these Z variants are listed in FIG. 1 and in the sequence listing as SEQ ID NO:13-17. The amino acid sequences of the 49 amino acid residues long polypeptides predicted to constitute the complete three-helix bundle within each of these Z variants are listed in FIG. 1 and in the sequence listing as SEQ ID NO:261-265.

Example 2: Production and Characterization of Z Variants

Materials and Methods

Subcloning of Z Variants, Protein Expression and Purification:

Five complement protein C5 binding Z variants (Z05363 (SEQ ID NO:510); Z05477 (SEQ ID NO:509); Z05483 (SEQ ID NO:511); Z05538 (SEQ ID NO:512) and Z05692 (SEQ ID NO:513)) were amplified from pAffi1/pAY00065/pAY02947 library vectors. A subcloning strategy for construction of dimeric Affibody molecules with N-terminal His$_6$ tags was applied using standard molecular biology techniques and as described in detail in WO 2009/077175.

The Z gene fragments were subcloned into the expression vector pAY01448 resulting in the encoded sequence MGSSHHHHHHLQ-[Z#####][Z#####]-VD (SEQ ID NO. 773).

The subcloned Z variants were transformed into *E. coli* BL21(DE3) and expressed in the multifermenter system Greta (Belach Bioteknik). In brief, cultures were grown at 37° C. in 800 ml TSB-YE-medium containing 50 µg/ml kanamycin. At an $OD_{600}$ of ~1, the cultures were induced through the automatic addition of IPTG to a final concentration of 0.05 mM. Cultures were cooled down to approximately 10° C. after 5 h of induction, and harvested by centrifugation (20 min, 15,900 g). Supernatants were discarded and the cell pellets were collected and stored at −20° C. until further use. Expression levels and the degree of solubility were estimated by SDS-PAGE analysis on 4-12% NUPAGE gels (Invitrogen) using Coomassie blue staining.

For Z variants expressed mainly as soluble protein, the cell pellets were resuspended in binding buffer (20 mM sodium phosphate, 0.5 M NaCl, 20 mM imidazole, pH 7.4) with an addition of 1000 U BENZONASE (Merck, cat. no. 1.01654.001) and disrupted by ultrasonication. For each of the Z variants, the sonicated suspension was clarified by centrifugation (40 min, 25,000 g, 4° C.) and the supernatant was loaded onto a 1 ml His GRAVITRAP column (GE Healthcare). The column was washed with wash buffer (20 mM sodium phosphate, 0.5 M NaCl, 60 mM imidazole, pH 7.4), before eluting the Z variants with 3 ml elution buffer (20 mM sodium phosphate, 0.5 M NaCl, 0.5 M imidazole, pH 7.4). Z variants which expressed mainly as insoluble protein were purified likewise, but 8 M urea was included in the binding and wash buffer. If required, the Z variants were further purified by reversed phase chromatography (RPC) on 1 ml RESOURCE columns (GE Healthcare) using water including 0.1% TFA (trifluoroacetic acid) as mobile phase and elution with an appropriate gradient (typically 0-50% over 20 column volumes) of acetonitrile including 0.1% TFA.

The buffer was exchanged to PBS using PD-10 columns (GE Healthcare).

Protein Characterization:

The concentration of the purified Z variants was determined by absorbance measurements at 280 nm using theoretical extinction coefficients. The purity was estimated by SDS-PAGE analysis on 4-12% NUPAGE gels (Invitrogen) using Coomassie blue staining. To verify the identity and to determine the molecular weights of purified Z variants, LC/MS-analyses were performed on an Agilent 1100 LC/MSD system (Agilent Technologies).

CD Analysis:

The purified Z variants were diluted to 0.5 mg/ml in PBS. For each diluted Z variant, a CD spectrum was recorded between 250-195 nm at a temperature of 20° C. In addition, a variable temperature measurement (VTM) was performed to determine the melting temperature (Tm). In the VTM, the absorbance was measured at 221 nm while the temperature was raised from 20 to 90° C., with a temperature slope of 5° C./min. The ability of the Z variant to refold was assessed by collecting an additional CD spectrum at 250-195 nm after cooling to 20° C. The CD measurements were performed on a Jasco J-810 spectropolarimeter (Jasco Scandinavia AB) using a cell with an optical path length of 1 mm.

Biacore Binding Analysis:

The interactions of the five subcloned $His_6$-tagged dimeric hC5-binding Z variants with hC5, cC5, rC5, hMG7 and hIgG (Sigma, cat. no. G4386) were analyzed in a Biacore instrument (GE Healthcare). The Z variants were immobilized in different flow cells on the carboxylated dextran layer of several CM5 chip surfaces (GE Healthcare). The immobilization was performed using amine coupling chemistry according to the manufacturer's protocol. One flow cell surface on each chip was activated and deactivated for use as blank during analyte injections. The analytes, diluted in HBS-EP running buffer (GE Healthcare) to a final concentration of 100 nM, were injected at a flow rate of 10 µl/min for 1 min. After 2 min of dissociation, the surfaces were regenerated with one injection of 10 mM HCl. The results were analyzed in BiaEvaluation software (GE Healthcare). Curves of the blank surface were subtracted from the curves of the ligand surfaces.

Results

Subcloning of Z Variants:

Five selected unique clones (Z05477 (SEQ ID NO:509), Z05363 (SEQ ID NO:510), Z05483 (SEQ ID NO:511), Z05538 (SEQ ID NO:512) and Z05692 (SEQ ID NO:513)) were chosen for subcloning as dimers in the expression vector pAY01448 and were subsequently verified by sequencing.

Protein Production:

The histidine-tagged dimeric Z variants yielded acceptable expression levels of soluble gene product. The purity of produced batches was estimated to exceed 90% as assessed by SDS-PAGE analysis. LC/MS analysis verified the correct molecular weight for all Z variant molecules.

CD Analysis:

The melting temperatures (Tm) of the different Z variants were calculated by determining the midpoint of the transition in the CD signal vs. temperature plot. The results for a number of reversibly folding Z variants are summarized in Table 2 below.

TABLE 2

Melting temperatures for a number of Z variants.

| Z variant | SEQ ID NO: # of monomeric Z variant | Tm (° C.) |
|---|---|---|
| $His_6$-(Z05477)$_2$ | SEQ ID NO: 509 | 45 |
| $His_6$-(Z05363)$_2$ | SEQ ID NO: 510 | 35 |
| $His_6$-(Z05483)$_2$ | SEQ ID NO: 511 | 44 |
| $His_6$-(Z05538)$_2$ | SEQ ID NO: 512 | 54 |
| $His_6$-(Z05692)$_2$ | SEQ ID NO: 513 | 52 |

Biacore Binding Analysis:

The binding of the five subcloned dimeric Z variants to different species of C5 and MG7, a subdomain of hC5, as well as the background binding to IgG was tested in a Biacore instrument by injecting the different proteins over surfaces containing the Z variants. The ligand immobilization levels for the different Z variants on the surfaces were: Z05363: 2080 RU, Z05477: 2180 RU, Z05483: 2010 RU, Z05538: 2570 RU and Z05692: 3270 RU. The different Z variants were tested for binding to different sets of proteins injected at concentrations of 100 nM, see Table 3. The result for the tested Z variants is displayed in the table as a +/− outcome for each protein. As an example of the Biacore binding analysis, FIG. 2 shows the sensorgrams obtained from immobilized dimeric Z05477 assayed against hC5, cC5, rC5, hMG7 and hIgG.

TABLE 3

Biacore response of different Z variants against C5 from various species and relevant selected background proteins.

| Z variant | SEQ ID NO: # of monomeric Z variant | hC5 | cC5 | rC5 | hMG7 | hIgG |
|---|---|---|---|---|---|---|
| His$_6$-(Z05477)$_2$ | SEQ ID NO: 509 | + | + | + | − | − |
| His$_6$-(Z05363)$_2$ | SEQ ID NO: 510 | + | + | + | − | − |
| His$_6$-(Z05483)$_2$ | SEQ ID NO: 511 | + | + | + | − | − |
| His$_6$-(Z05538)$_2$ | SEQ ID NO: 512 | + | + | + | − | − |
| His$_6$-(Z05692)$_2$ | SEQ ID NO: 513 | + | + | − | − | − |

Example 3: Design and Construction of a Maturated Library of Complement Protein C5 Binding Z Variants In this Example, a maturated library was constructed. The library was used for selections of hC5-binding polypeptides. Selections from maturated libraries are usually expected to result in binders with increased affinity (Orlova et al. Cancer Res 2006, 66(8):4339-48). In this study, randomized double stranded linkers were generated by the SLONOMICS technology which enables incorporation of randomized sets of trinucleotide building blocks using ligations and restrictions of the subsequently built up double stranded DNA.

Materials and Methods
Library Design:

The library was based on a selection of sequences of the hC5 binding Z variants described in Examples 1 and 2. In the new library, 13 variable positions in the Z molecule scaffold were biased towards certain amino acid residues, according to a strategy based on the Z variant sequences defined in SEQ ID NO:509-513 (Z05477, Z05363, Z05483, Z05538, Z05692). A SLONOMAX library of double-stranded DNA, containing the 147 bp partially randomized helix 1 and 2 of the amino acid sequence 5'-AA ATA AAT CTC GAG GTA GAT GCC AAA TAC GCC AAA GAA/GAG NNN NNN NNN GCA/GCC NNN NNN GAG/GAA ATC/ATT NNN NNN TTA/CTG CCT AAC TTA ACC/ACT NNN NNN CAA/CAG TGG NNN GCC/GCG TTC ATC/ATT NNN AAA/AAG TTA/CTG NNN GAT/GAC GAC CCA AGC CAG AGC TCA TTA TTT A-3' (SEQ ID NO. 774) (randomized codons are illustrated as NNN) flanked with restriction sites XhoI and SacI, was ordered from Sloning Bio-Technology GmbH (Pucheim, Germany). The theoretical distributions of amino acid residues in the new library finally including 12 variable Z positions are given in Table 4.

TABLE 4

| Library design. | | | |
|---|---|---|---|
| Amino acid position in the Z variant molecule | Randomization (amino acid abbreviations) | No of amino acids | Pro-portion |
| 9 | H, Q, S, T, V | 5 | 1/5 |
| 10 | I, L, V, W | 4 | 1/4 |
| 11 | A, D, E, H, K, L, N, R, S, T, Y | 12 | 1/12 |
| 13 | N, Q, W, Y | 4 | 1/4 |
| 14 | A, D, E, H, I, K, L, N, Q, R, S, T, V, W, Y | 15 | 1/14 |
| 17 | D, E | 2 | 1/2 |
| 18 | A, D, E, G, H, I, K, L, Q, R, S, T, V, Y | 14 | 1/14 |
| 24 | I, L, V | 3 | 1/3 |
| 25 | A, D, E, H, K, N, Q, R, S, T, Y | 11 | 1/11 |
| 28 | I, L, V | 3 | 1/3 |
| 32 | A, D, E, F, G, H, K, L, N, Q, R, S, T, V | 14 | 1/14 |
| 35 | A, D, E, H, K, N, Q, R, S, T, W, Y | 12 | 1/12 |

Library Construction:

The library was amplified using AmpliTaq Gold polymerase (Applied Biosystems, cat. no. 4311816) during 12 cycles of PCR and pooled products were purified with QIAquick PCR Purification Kit (QIAGEN, cat. no. 28106) according to the supplier's recommendations. The purified pool of randomized library fragments was digested with restriction enzymes XhoI and SacI (New England Biolabs, cat. no. R01460L, and cat. no. R0156L) and purified once more with PCR Purification Kit. Subsequently, the product was purified using preparative gel electrophoresis on a 1% agarose gel.

The phagemid vector pAY02592 (essentially as pAffi1 described in Grönwall et al. supra) was restricted with the same enzymes, purified using phenol/chloroform extraction and ethanol precipitation. The restricted fragments and the restricted vector were ligated in a molar ratio of 5:1 with T4 DNA ligase (New England Biolabs, cat. no. M0202S), for 2 hours at RT followed by overnight incubation at 4° C. The ligated DNA was recovered by phenol/chloroform extraction and ethanol precipitation, followed by dissolution in 10 mM Tris-HCl, pH 8.5.

The ligation reactions (approximately 250 ng DNA/transformation) were electroporated into electrocompetent E. coli RR1ΔM15 cells (100 µl). Immediately after electroporation, approximately 1 ml of SOC medium (TSB-YE media, 1% glucose, 50 µM MgCl$_2$, 50 µM MgSO$_4$, 50 µM NaCl and 12.5 µM KCl) was added. The transformed cells were incubated at 37° C. for 50 min Samples were taken for titration and for determination of the number of transformants. The cells were thereafter pooled and cultivated overnight at 37° C. in 71 of TSB-YE medium, supplemented with 2% glucose and 100 µg/ml ampicillin. The cells were pelleted for 15 min at 4,000 g, resuspended in a PBS/glycerol solution (approximately 40% glycerol). The cells were aliquoted and stored at −80° C. Clones from the library of Z variants were sequenced in order to verify the content and to evaluate the outcome of the constructed library vis-à-vis the library design. Sequencing was performed as described in Example 1 and the amino acid distribution was verified.

Preparation of Phage Stock:

Cells from the glycerol stock containing the C5 phagemid library were inoculated in 20 l of a defined proline free medium (described in Example 1) supplemented with 100 µg/ml ampicillin, and grown at 37° C. in a fermenter (Belach Bioteknik, BR20). All steps were performed as described in Example 1 for the library Zlib006Naive.II. After cultivation, the cells were pelleted by centrifugation at 15,900 g and the phage particles remaining in the medium were thereafter precipitated twice in PEG/NaCl, filtered and dissolved in PBS and glycerol as described in Example 1. Phage stocks were stored at −80° C. until use in selection.

Results
Library Construction:

The new library was designed based on a set of OmCI-blocked C5 binding Z variants with verified binding properties (Example 1 and 2). The theoretical size of the designed library was $6.7\times10^9$ Z variants. The actual size of the library, determined by titration after transformation to *E. coli*. RR1ΔM15 cells, was $1.4\times10^9$ transformants.

The library quality was tested by sequencing of 64 transformants and by comparing their actual sequences with the theoretical design. The contents of the actual library compared to the designed library were shown to be satisfying. The locked position in the designed amino acid sequence (W in position 27) was reflected in the actual sequence in that only the expected amino acid occurred in that position. A maturated library of hC5 binding polypeptides was thus successfully constructed.

Example 4: Selection, Screening and Characterization of Z Variants from a Maturated Library Materials and Methods Phage Display Selection of Complement Protein C5 Binding Polypeptides:

The target protein hC5 was biotinylated as described in Example 1. Phage display selections were performed against hC5 essentially as described in Example 1 using the new library of Z variant molecules described in Example 3. *E. coli* XL1-Blue was used for phage amplification. Selection was initially performed in two parallel tracks. In one track, the time of selection was 2 h, while in the other track, shorter selection times were used: 20 min in the first cycle and 10 min for subsequent cycles 2-4. These two tracks (1 and 2) were further divided in the second cycle, resulting in totally six tracks (1a-c and 2a-c, differing in target concentration and wash conditions). Selection was performed in a total of four cycles. In cycle 1 of the selections, 25 nM complement protein C5 was used and five washes with PBST 0.1% were performed. An increased stringency, using a lowered target concentration and an increased number of washes, was applied in the subsequent three cycles. In cycle 2, 3 and 4; 10, 5 or 2.5 nM complement protein C5, 4, 1 or 0.25 nM complement protein C5 and 1.6, 0.2 or 0.05 nM complement protein C5 were used. In cycle 2, 3 and 4; 10, 15 and 20 washes were performed using PBST 0.1%. In addition, the second last wash was prolonged to 3 h with a 50× excess of non-biotinylated hC5 in the washing solution for two of the tracks (1c and 2c).

Sequencing of Potential Binders:

Individual clones from the different selection tracks were picked for sequencing. All clones run in the ELISA screening were sequenced. Amplification of gene fragments and sequence analysis of gene fragments were performed as described in Example 1.

ELISA Screening of Z Variants:

Single colonies containing Z variants were randomly picked from the selected clones of the complement protein C5 maturated library and grown in 1 ml cultivations as described in Example 1. Periplasmic proteins were released by 8 repeated freeze-thawing cycles. ELISA screenings were performed essentially as described in Example 1 with the following exceptions. Half-area 96-well ELISA plates were coated with 2 μg/ml of an ABD specific goat antibody (in house produced) diluted in coating buffer. Biotinylated hC5 was used at a concentration of 0.15 μg/ml and incubation performed for 1.5-2 h. Streptavidin conjugated HRP was obtained from Thermo Scientific (cat. no. N100). The Z variant Z05363 (SEQ ID NO:510) originating from the primary selections (Example 1) was used as a positive control as well as a negative control omitting hC5.

Selected maturated Z variants were subjected to a second screen against hC5 at a lower concentration and compared to rC5. The assay was essentially performed as described above. hC5 and rC5 was used at a concentration of 0.05 μg/ml and 4 μg/ml, respectively. The Z variant Z05363 (SEQ ID NO:510) was used as a positive control in this experiment as well. As a negative control, a Z variant binding to PDGF-Rβ (Z01977; described in WO 2009/077175) was assayed against biotinylated hC5 or rC5.

In deep sequence analysis of selected Z variants and correlation of amino acids in the 13 randomized positions with measured melting temperatures and $IC_{50}$ values for human C5 and mouse C5 in the hemolysis assay (described in Example 6) suggested a favorable Z variant not identified among the 558 sequenced clones. Based on the Z variant Z05998 (SEQ ID No:499), a single amino acid, Ile in position 10 was substituted with Leu using conventional technology for site directed mutagenesis. The new variant is referred to as Z08044 (SEQ ID NO:498). The deduced complement protein C5 binding motif of this Z variant is listed in FIG. 1 and in the sequence listing as SEQ ID NO:2. The amino acid sequences of the 49 amino acid residues long polypeptide predicted to constitute the complete three-helix bundle within these Z variant is listed in FIG. 1 and in the sequence listing as SEQ ID NO:250.

Results

Phage Display Selection of Complement Protein C5 Binding Polypeptides:

Selection was performed in totally six parallel tracks containing four cycles each. The different selection tracks differed in target concentration and wash conditions as follows: 1a) 2 h selection time, high concentration, standard wash, 1b) 2 h selection time, low concentration, standard wash, 1c) 2 h selection time, medium concentration, long wash, 2a) 10 min selection time, high concentration, standard wash, 2b) 10 min selection time, low concentration, standard wash, and 2c) 10 min selection time, medium concentration, long wash. For each selection cycle, the target concentration was decreased and the washing conditions were more stringent. All tracks gave in each round sufficient amounts of phage particles in the eluate. Most phage particles were found in tracks 1a and 2a, representing the highest target concentration and mildest wash conditions.

Sequencing:

Randomly picked clones (558) were sequenced. Each individual Z variant was given an identification number, Z#####, as described in Example 1. In total, 242 new unique Z variant molecules were identified. The amino acid sequences of the 58 amino acid residues long Z variants are listed in FIG. 1 and in the sequence listing as SEQ ID NO:497, SEQ ID NO:499-508 and SEQ ID NO:514-744. The deduced complement protein C5 binding motifs of these Z variants are listed in FIG. 1 and in the sequence listing as SEQ ID NO:1, SEQ ID NO:3-12 and SEQ ID NO:18-248. The amino acid sequences of the 49 amino acid residues long polypeptides predicted to constitute the complete three-helix bundle within each of these Z variants are listed in FIG. 1 and in the sequence listing as SEQ ID NO:249, SEQ ID NO:251-260 and SEQ ID NO:266-496. Among the sequenced clones, 63 sequences occurred two or more times.

ELISA Screening of Z Variants:

Clones obtained after four selection cycles were produced in 96-well plates and screened for hC5-binding activity using ELISA. All randomly picked clones were analyzed. 229 of the 242 unique Z variants were found to give a higher response (0.3-3.1 AU) against hC5 at a concentration of 0.15 µg/ml compared to the positive control clone Z05363 (SEQ ID NO:510; an average absorbance signal of 0.3 AU), obtained from the primary selections (Example 1). Clones from all selection tracks showed positive signals. The negative controls had an absorbance of approximately 0.1 AU.

Z variants were selected based on their performance in the ELISA screen against hC5 and the occurrence frequency. 43 unique Z variants were assayed against a lower concentration of hC5 (0.05 μg/ml) as well as rC5 (4 μg/ml). A positive result against rC5 was obtained for 40 of the tested Z variants, defined as 2× the signal for the negative control (0.4 AU). The results for all the tested Z variants against the lower concentration of hC5 as well as against rC5 are shown in FIG. 3.

Example 5: Subcloning, Production and Characterization of a Subset of Complement Protein C5 Binding Z Variants Materials and Methods Subcloning of Z Variant Molecules into Expression Vectors:

Based on sequence analysis and the performance in the ELISA against human and rat complement protein C5, 45 clones were selected for subcloning into the expression vector pAY01448. Monomer Z variant fragments were amplified from the phagemid vector pAY02592 and the subcloning into pAY01448 was performed as described in Example 2, resulting in a vector encoding the protein sequence MGSSHHHHHHLQ-[Z#####]-VD (SEQ ID NO. 775).

Protein Expression and Purification:

The 45 Z variants in the $His_6$-(Z#####) format, were expressed in an automated multifermenter system as described in Example 2 or similarly in a small scale set-up of 100 ml cultures in shaker flasks induced manually with IPTG to a final concentration of 0.4 mM. Purification was performed using 1 ml His GRAVITRAP columns essentially as described in Example 2 or in a smaller scale using 0.1 ml His SpinTrap (GE Healthcare, cat. no. 28-4013-53). Buffer was exchanged to PBS using PD-10 columns or PD SpinTrap G-25 (GE Healthcare, cat. no. 28-9180-04) according to the manufacturer's instructions. The concentration of purified Z variants was determined by absorbance measurements at 280 nm and the purity and identity was assessed by SDS-PAGE and LC/MS as described in Example 2. Samples were aliquoted and stored at −80° C. until further use.

CD Analysis:

The CD analysis for determination of melting temperatures and folding reversibility was performed as described in Example 2.

Results

Protein Expression and Purification:

All 45 subcloned Z variants could be expressed and the in vitro solubility for all purified variants was good. The purity was estimated by LC/MS to exceed 90% for all variants. The correct molecular weights were verified by LC-MS.

CD Analysis:

CD spectrum measurements performed at 20° C. confirmed the α-helical structure of the Z variants at this temperature. An overlay of the spectrums obtained after the variable temperature measurements (heating to 90° C. followed by cooling to 20° C.) on the spectrums obtained before the variable temperature measurement showed that all Z variants fold back completely, or nearly completely, to their α-helical structures after heating to 90° C. (results not shown). The melting temperatures for a set of Z variants were determined from the variable temperature measurements and are shown in Table 5.

TABLE 5

Melting temperatures of maturated Z variants with a histidine tag fused directly to the amino terminus of SEQ ID NO: 497 and SEQ ID NO: 499-508.

| Z variant | SEQ ID NO: # of Z variant | Tm (° C.) |
|---|---|---|
| $His_6$-Z06175 | SEQ ID NO: 497 | 44 |
| $His_6$-Z05998 | SEQ ID NO: 499 | 45 |
| $His_6$-Z06009 | SEQ ID NO: 500 | 45 |
| $His_6$-Z06079 | SEQ ID NO: 501 | 46 |
| $His_6$-Z06126 | SEQ ID NO: 502 | 44 |
| $His_6$-Z06140 | SEQ ID NO: 503 | 42 |
| $His_6$-Z06189 | SEQ ID NO: 504 | 47 |
| $His_6$-Z06214 | SEQ ID NO: 505 | 44 |
| $His_6$-Z06215 | SEQ ID NO: 506 | 41 |
| $His_6$-Z06226 | SEQ ID NO: 507 | 44 |
| $His_6$-Z06018 | SEQ ID NO: 508 | 46 |

Example 6: In Vitro Characterization of C5 Binding Z Variants

Materials and Methods

Cloning and Protein Production:

DNA encoding a subset of C5 binding Z variants (SEQ ID NO:745-757) where *E. coli* codon optimized and synthesized by GeneArt, GmbH. The synthetic genes representing the C5 binding Z variants were subcloned and expressed in *E. coli*. The expression vectors encoding constructs of monomers or dimers of Z variants optionally linked to an albumin binding domain (ABD094, SEQ ID NO:759) are schematically illustrated in FIG. 4.

Intracellularly expressed Z variants were purified using conventional chromatography methods. Homogenization and clarification was performed by sonication followed by centrifugation and filtration. Anion exchange chromatography was used as capture step. Further purification was obtained by hydrophobic interaction chromatography. The purifications were executed at acidic conditions (pH 5.5). Polishing and buffer exchange was performed by size exclusion chromatography. Before concentration to final protein content, the endotoxin level was reduced by polymyxin B affinity chromatography. Produced proteins were analyzed by MALDI-TOF MS and on SDS-PAGE.

In addition, recombinantly expressed OmCI protein (SEQ ID NO:761) was used as a reference molecule in the in vitro studies.

Inhibition of Hemolysis:

For studies of classical complement pathway function and inhibition thereof by C5 binding polypeptides, sheep erythrocytes were prepared from fresh sheep whole blood in Alsever's solution (Swedish National Veterinary Institute) and thereafter treated with rabbit anti-sheep erythrocyte antiserum (Sigma) to become antibody sensitized sheep erythrocyte (EA). The whole process was conducted under aseptic conditions. All other reagents were from commercial sources.

The in vitro assay was run in 96-well U-form microtiter plate by consecutive additions of a test protein, a complement serum and EA suspension. The final concentrations of all reagents, in a total reaction volume of 50 μl per well and at pH 7.3-7.4, were: 0.15 mM $CaCl_2$; 0.5 mM $MgCl_2$; 3 mM $NaN_3$; 138 mM NaCl; 0.1% gelatin; 1.8 mM sodium barbital; 3.1 mM barbituric acid; 5 million EA; complement protein C5 serum at suitable dilution, and C5 binding Z variant at desired concentrations. Different species of complement sera were used in the assay to define cross-species potencies of the Z variants. For mouse serum, a C5 depleted human serum (C5D from Quidel cat. no. A501) had to be supplemented in an equal amount.

The Z variants were pre-incubated with the above described complement serum for 20 min on ice prior to starting the reaction by the addition of EA suspension. The hemolytic reaction was allowed to proceed at 37° C. during agitation for 45 min and was then optionally ended by addition of 100 µl ice-cold saline containing 0.02% Tween 20. The cells were centrifuged to the bottom and the upper portion, corresponding to 100 µl supernatant, was transferred to a transparent microplate having half-area and flat-bottom wells. The reaction results were analyzed as optical density using a microtiter plate reader at a wavelength of 415 nm.

On all test occasions, controls, vehicle and OmCI (SEQ ID NO:761), were included in each plate to define the values of uninhibited and fully inhibited reactions, respectively. These values were used to calculate the % inhibition of the complement hemolysis at any given sample concentration. The inhibitory potencies ($IC_{50}$ values) of tested Z variants were defined by applying the same assay in the presence of a controlled concentration of human C5 added to C5 depleted serum. For highly potent inhibitors (low nanomolar to sub-nanomolar), a final C5 concentration of the reaction mixture was controlled at 0.1 nM, which was optionally established by using C5 depleted or deficient sera.

In Vitro Kinetics and Affinity of C5 Binding Z Variants to Immobilized hC5:

The binding affinity of a number of C5 binding Z variants (SEQ ID NO:748-757) to hC5 were analyzed using a Biacore T200 instrument (GE Healthcare). Human C5 (A403, Quidel Corporation) was coupled to a CM5 sensor chip (900 RU) using amine coupling chemistry according to the manufacturer's protocol. The coupling was performed by injecting hC5 at a concentration of 7.5 µg/ml in 10 mM Na-acetate buffer pH 5 (GE Healthcare). The reference cell was treated with the same reagents but without injecting human C5.

All experiments were performed in 10 mM HEPES pH 7.4, 150 mM NaCl, 3 mM EDTA, 0.005% Surfactant P20 (HBS-EP buffer, GE Healthcare). For kinetic analyses, the flow rate was 30 µl/min and data were collected at 25° C. Data from the reference cell were subtracted to compensate for bulk refractive index changes. In most cases, an injection of HBS-EP was also included as control so that the sensorgrams were double blanked. The surfaces were regenerated in HBS-EP buffer.

Binding of Z variants to immobilized hC5 was studied with the single cycle kinetics method, in which five concentrations of sample are injected one after the other in the same cycle without regeneration between injections. Kinetic constants were calculated from the sensorgrams using the Langmuir 1:1 or bivalent analyte model of Biacore T200 Evaluation Software version 1.0.

In Vitro Kinetics and Affinity of C5 Binding Z-ABD Molecules to Immobilized hC5:

Binding of Z-ABD molecules (SEQ ID NO:748-757 fused to ABD094 (SEQ ID NO:759) by a GS linker), to immobilized hC5 was evaluated using a Biacore T200 instrument (GE Healthcare).

Figure 4:
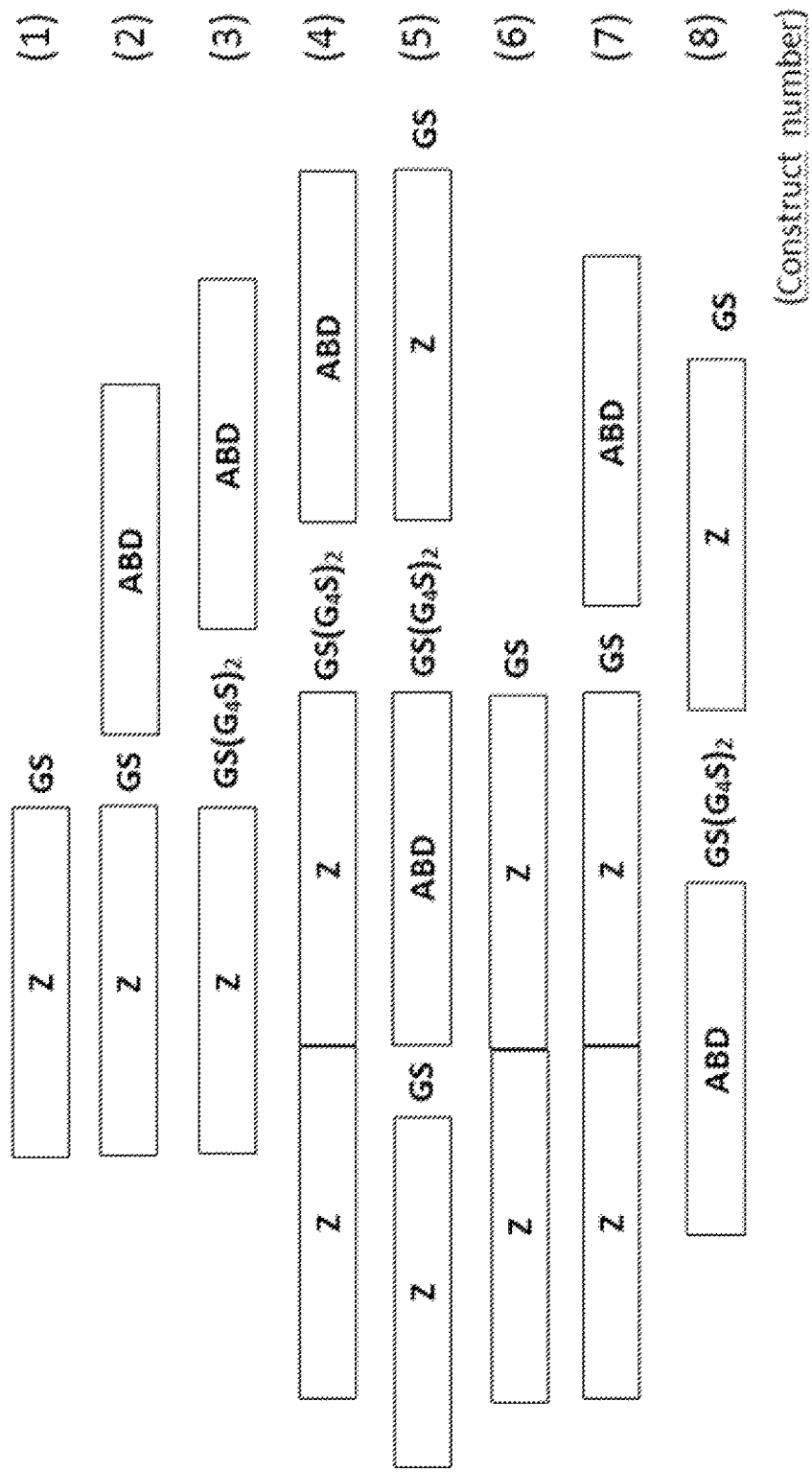
FIG. 4 schematically shows different constructs encompassing one or several C5 binding Z variants selected from SEQ ID NO:745-757, optionally linked to ABD094 (SEQ ID NO:759).

Z-ABD constructs where Z06175a (SEQ ID NO:753) as a monomer or dimer have been fused to ABD094 (SEQ ID NO:759) either in the N-terminus or the C-terminus via different linkers as specified in FIG. 4 (constructs 2, 7, 5 and 4) were also pre-incubated with recombinant human albumin (Cell Prime rAlbumin AF-G, 9301, Novozymes), diluted and then injected over immobilized human C5 according to the single-cycle kinetics method as described above. As a comparison, the same constructs were injected in the absence of HSA. Two constructs, Z06175a-GS (FIG. 4, construct 1) and Z06175a-GSGGGGSGGGGS-ABD094 (SEQ ID NO. 776) (FIG. 4, construct 3) were only tested in the absence of HSA.

Steady State Binding of C5 Binding Z Variants to C5 Coated ECL Plates:

The affinity of a number of C5 binding constructs comprising Z variants (SEQ ID NO:745, SEQ ID NO:748-757 optionally fused to ABD094 (SEQ ID NO:759) in constructs as specified in FIG. 4) to human C5 was measured by displacement of a ruthenium labeled C5 binding Z-ABD variant (SEQ ID NO:748 fused to SEQ ID NO:759 by a GS-linker).

The Z-ABD variant (SEQ ID NO:748 fused to SEQ ID NO:759 by a GS-linker) to be used as tracer was labeled at a molar ratio 1:12 to 1:20 (protein: SULFO-TAG NHS-Ester, Meso Scale Discovery, cat. no. R91AN-1). The labeling reaction was performed on ice for two hours. Unbound SULFO-TAG was removed using a ZEBA spin desalting column (Thermo Scientific, cat no. 89889) and final protein concentration was measured by using Bradford reagent (Bradford, M. M., Anal. Biochem. 72: 248-254, 1976). The affinity (dissociation constant, $K_D$) of the SULFO-TAG labeled Z-ABD variant was determined by saturation binding analysis of increasing concentrations of the labeled Z-ABD variant to C5 coated electrochemoluminescence wells (ECL, Meso Scale Discovery). The labeled Z-ABD variant was further analyzed by LC/MS in order to determine the distribution of SULFO-TAG molecules on the Z-ABD variant.

Displacement was carried out by coating ECL, Multi-array 96-well high-bind, non-coated (Meso Scale Discovery, cat. no. L15XB) plates with 50 fmol/well hC5 over night at 4° C. Subsequently, non-specific sites were blocked with PBS with 1% Casein for two hours at RT. Different Z variants optionally fused with ABD094 (SEQ ID NO:759) (see FIG. 4) were incubated at different concentrations along with approximately 100 pM of the SULFO-TAG labeled C5 binding Z-ABD variant in PBS with 1% Casein. Incubation lasted three hours at RT while agitating the plate at 300 rpm. Finally, incubation was terminated by washing 3 times with 150 µl ice-cold PBS-Tween20. Immediately after the final wash, 150 µl 2× reading buffer (4× reading buffer T, Meso Scale Discovery cat. no. R92TC-3 diluted 1:1 in ultrapure $H_2O$) was added to each well and the signal was detected using a plate reader (SECTOR Imager 2400, Meso Scale Discovery). The naturally occurring C5 binding protein OmCI (Nunn et al. supra, SEQ ID NO:761) was included in the displacement assay as a positive control. Binding affinity of competing C5 binding constructs and controls to C5 was determined by non-linear regression analysis using Excel plugin XLfit5 and GraphPad Prism 4.

Selectivity of Z-ABD Binding to C5 Over C3, C4 and IgG:

Binding of one Z-ABD variant (SEQ ID NO:748 fused to SEQ ID NO:759 by a GS-linker) to the closely related complement proteins C3 and C4 from human as well as binding to human IgG (since the origin of the Z-domain, Staphylococcal protein A, is an IgG binding protein) was addressed by surface plasmon resonance (SPR) using a Biacore 2000 instrument (GE Healthcare). The Z-ABD construct was immobilized on a CM5 chip (GE-Healthcare) using amine coupling (70 RU). 40 nM and 400 nM of each of human C3 (A401, Quidel), C4 (A402, Quidel) and IgG (12511, Sigma) diluted in HBS-P buffer (GE Healthcare) were injected over the surface. Each injection was followed by a regeneration cycle with 20 mM NaOH injected for 30 s. Human C5 at the same concentrations was run in parallel as a positive control.

Results

Figure 5:
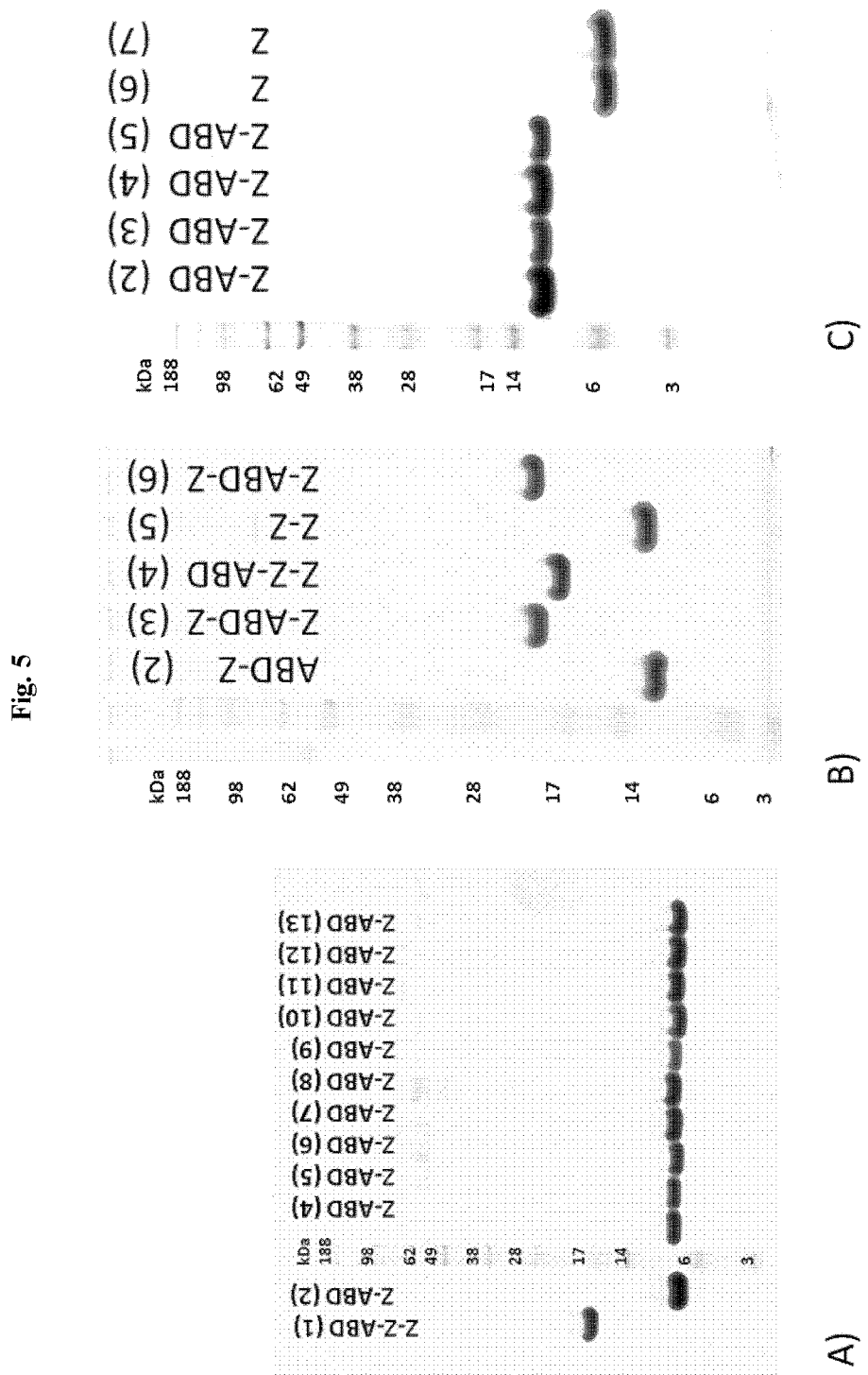
FIG. 5 shows SDS-PAGE analyses of purified C5 binding Z variants (reduced condition) visualized by Instant Blue, as described in Example 6. A) represents one example of dimeric Z-Z-ABD (lane 1 where Z is equal to SEQ ID NO:745 and ABD is equal to SEQ ID NO:759) compared with different Z-ABD fusion proteins (where Z is equal to SEQ ID NO:745 (lane 2), SEQ ID NO:748-757 (lanes 4-13) fused to ABD094 (SEQ ID NO:759) by a GS linker); B) represents one C5 binding Z variant (SEQ ID NO:753) in different constructs, and C) represents two different C5 binding Z variants (SEQ ID NO:748, lanes 2-3 and 6 and SEQ ID NO:753, lanes 4-5 and 7), in monomeric form (lanes 6-7) and in fusion with ABD094 (SEQ ID NO:759) via a GS(G$_4$S)$_2$ linker (lanes 2-5).

Cloning and Protein Production:

Produced protein variants as schematically described in FIG. 4 where "Z" can be represented by SEQ ID NO:745 and SEQ ID NO:748-757 were analyzed by MALDI-TOF MS and on SDS-PAGE. (FIG. 5)

Figure 6A:
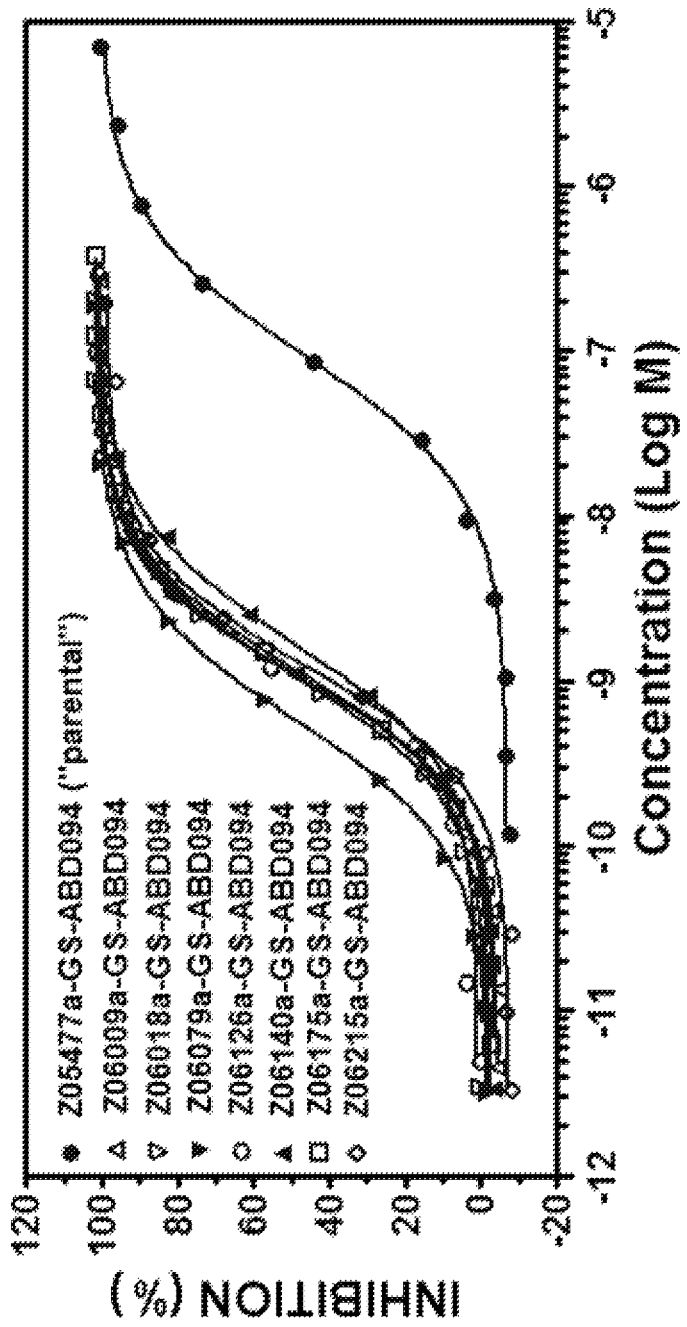
FIGS. 6A and B are diagrams showing exemplary data of dose-response characterization of the potency of different C5 binding Z variants to inhibit complement activation as seen in a hemolytic assay, described in Example 6. C5 deficient serum was diluted 63-fold and supplemented with 0.1 nM hC5. A) shows effect of different Z-ABD fusion proteins (Z variants corresponding to SEQ ID NO:745, SEQ ID NO:748-753 and SEQ ID NO:756 fused to ABD094 (SEQ ID NO:759) by a GS linker) to hC5, whereas B) shows effect of different C5 binding constructs comprising the same C5 binding Z variant (Z06175a, SEQ ID NO:753) as monomer or dimer, in fusion with ABD094 (SEQ ID NO:759), or as provided with a His$_6$-tag (six histidine residues), compared to the C5 binding tick protein OmCI (SEQ ID NO:761).
Figure 6B:
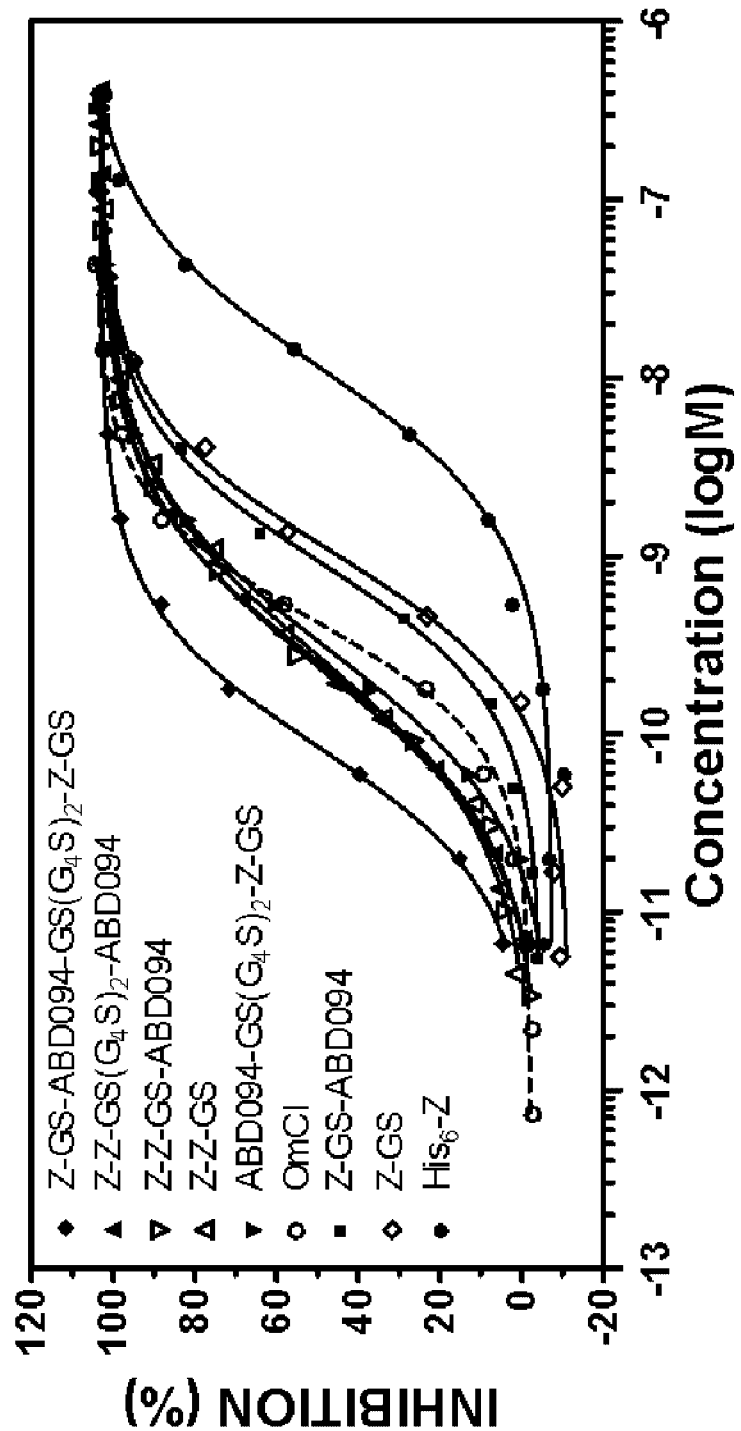

Inhibition of Hemolysis:

A subset of C5 binding Z variants were assayed for C5 binding activity in vitro and inhibition of hemolysis in sheep erythrocytes. The concentration of Z variant resulting in 50% inhibition of hemolysis ($IC_{50}$) or 50% inhibition of tracer binding to human C5 was calculated. Representative concentration-response curves for Z variants shown as SEQ ID NO:745 and SEQ ID NO:748-757 inhibiting hemolysis as described in the methods section are shown in FIGS. 6A and 6B. The result for different Z variants fused to ABD094 (SEQ ID NO:759) via a short GS-linker are shown in FIG. 6A.

The parental Z variant Z05477a (SEQ ID NO:745) fused to ABD094 (SEQ ID NO:759) separated by a short GS linker exhibited an $IC_{50}$ value of about 100 nM, whereas the tested second-generation C5 binding Z-ABD variants typically inhibited hemolysis with $IC_{50}$ values around or below 1 nM. This suggests a more than 100-fold increase in potency for the C5 binding Z variants identified in the maturation selection and subsequent screening.

In FIG. 6B, C5 binding is shown for various combinations of one representative Z variant (Z06175a; SEQ ID NO:753) alone, as a dimer and in fusion with ABD094 (SEQ ID NO:759) either in the N-terminus or the C-terminus via different linkers as specified in the figure. The C5 binding combinations exhibited $IC_{50}$ values ranging from 86 pM to 12 nM with human serum as measured using the above described assay. The corresponding value for the tic protein OmCI was typically 300 to 500 pM.

In Vitro Kinetics:

Kinetic studies of binding characteristics for a number of Z variants (SEQ ID NO:748-757) optionally fused to ABD094 (SEQ ID NO:759), to immobilized hC5, as well as to C5 in the presence of human albumin, were performed using the Biacore T200 instrument.

Data for ten different Z variants fused to ABD094 via a GS linker are presented in Table 6.

TABLE 6

Human C5-binding characteristics for different Z-ABD fusions

| Construct | SEQ ID NO: # of Z variant | $k_a$ (1/Ms) | $k_d$ (1/s) | $K_D$ (M) |
|---|---|---|---|---|
| Z-GS-ABD094 | SEQ ID NO: 748 | $6.93 \times 10^5$ | $9.04 \times 10^{-4}$ | $1.31 \times 10^{-9}$ |
| | SEQ ID NO: 749 | $6.75 \times 10^5$ | $1.23 \times 10^{-3}$ | $1.83 \times 10^{-9}$ |
| | SEQ ID NO: 750 | $7.65 \times 10^5$ | $1.34 \times 10^{-3}$ | $1.75 \times 10^{-9}$ |
| | SEQ ID NO: 751 | $6.90 \times 10^5$ | $1.29 \times 10^{-3}$ | $1.87 \times 10^{-9}$ |
| | SEQ ID NO: 752 | $7.02 \times 10^5$ | $1.81 \times 10^{-3}$ | $2.58 \times 10^{-9}$ |
| | SEQ ID NO: 753 | $7.90 \times 10^5$ | $1.01 \times 10^{-3}$ | $1.18 \times 10^{-9}$ |
| | SEQ ID NO: 754 | $5.00 \times 10^5$ | $1.14 \times 10^{-3}$ | $2.28 \times 10^{-9}$ |
| | SEQ ID NO: 755 | $6.84 \times 10^5$ | $2.08 \times 10^{-3}$ | $3.05 \times 10^{-9}$ |
| | SEQ ID NO: 756 | $3.17 \times 10^5$ | $6.37 \times 10^{-3}$ | $2.01 \times 10^{-9}$ |
| | SEQ ID NO: 757 | $4.63 \times 10^5$ | $1.08 \times 10^{-3}$ | $2.34 \times 10^{-9}$ |

Binding of the same Z variant (SEQ ID NO:753) but in different constructs; i.e. with/without ABD and different linkers, were also analyzed using Biacore T200. In addition, the effect of albumin on some Z-ABD fusions was also assessed by running the same analysis in the absence and in the presence of human albumin. These data are presented below in Table 7.

TABLE 7

Human C5-binding characteristics for a Z-ABD fusion variant Z06175a (SEQ ID NO: 753, abbreviated Z) comprised in different constructs.

| Construct | Human albumin | $k_a$ (1/Ms) | $k_d$ (1/s) | $K_D$ (M) |
|---|---|---|---|---|
| Z-GS-ABD094 | − | $7.37 \times 10^5$ | $1.06 \times 10^{-3}$ | $1.43 \times 10^{-9}$ |
| Z-GS-ABD094 | + | $6.74 \times 10^5$ | $9.62 \times 10^{-4}$ | $1.43 \times 10^{-9}$ |
| Z-Z-GS-ABD094 | − | $5.93 \times 10^5$ | $3.74 \times 10^{-4}$ | $6.30 \times 10^{-10}$ |
| Z-Z-GS-ABD094 | + | $6.02 \times 10^5$ | $4.67 \times 10^{-4}$ | $7.76 \times 10^{-10}$ |
| Z-GS-ABD094-GSGGGGSGGGGS-Z (SEQ ID NO. 777) | − | $8.69 \times 10^5$ | $5.75 \times 10^{-4}$ | $6.62 \times 10^{-10}$ |
| Z-GS-ABD094-GSGGGGSGGGGS-Z (SEQ ID NO. 777) | + | $6.55 \times 10^5$ | $3.83 \times 10^{-4}$ | $5.86 \times 10^{-10}$ |
| Z-Z-GSGGGGSGGGGS-ABD094 (SEQ ID NO. 778) | − | $4.59 \times 10^5$ | $6.32 \times 10^{-4}$ | $1.38 \times 10^{-9}$ |

TABLE 7-continued

Human C5-binding characteristics for a Z-ABD fusion
variant Z06175a (SEQ ID NO: 753, abbreviated Z)
comprised in different constructs.

| Construct | Human albumin | $k_a$ (1/Ms) | $k_d$ (1/s) | $K_D$ (M) |
|---|---|---|---|---|
| Z-Z-GSGGGGSGGGGS-ABD094 (SEQ ID NO. 778) | + | $8.32 \times 10^5$ | $9.39 \times 10^{-4}$ | $1.13 \times 10^{-9}$ |
| Z-GS | − | $2.42 \times 10^6$ | $1.40 \times 10^{-3}$ | $5.79 \times 10^{-10}$ |
| Z-GSGGGGSGGGGS-ABD094 (SEQ ID NO. 779) | − | $3.64 \times 10^5$ | $1.37 \times 10^{-3}$ | $3.75 \times 10^{-9}$ |

Surprisingly small effects could be seen when comparing the affinities of the constructs for hC5 (SEQ ID NO:760) in the presence and absence of albumin. This suggests that simultaneous binding of albumin to the ABD moiety of the constructs does not interfere with C5 interaction.

Steady State Binding of C5 Binding Z Variants to C5 Coated ECL Plates:

Steady state binding of C5 binding constructs composed of different Z variants (SEQ ID NO:745 and 748-757), optionally fused to ABD094 (SEQ ID NO:759) in constructs as specified in FIG. 4, to hC5 was assessed in a competition assay. By competing for binding to C5 coated on ECL plates with a SULFO-TAG labeled C5 binding Z variants (SEQ ID NO:748) fused to ABD (SEQ ID NO:759), steady state binding of the C5 constructs was evaluated. As a comparison the tic protein OmCI (SEQ ID NO:761) was also included. The labeled Z-ABD variant containing SEQ ID NO:748 had an affinity ($K_d$) of 0.9 nM for hC5. This labeled Z-ABD variant was further found to bind to an antibody specific for the constant region of Z variants in a concentration-dependent manner with a $K_d$ of 0.34 nM.

Figure 7A:
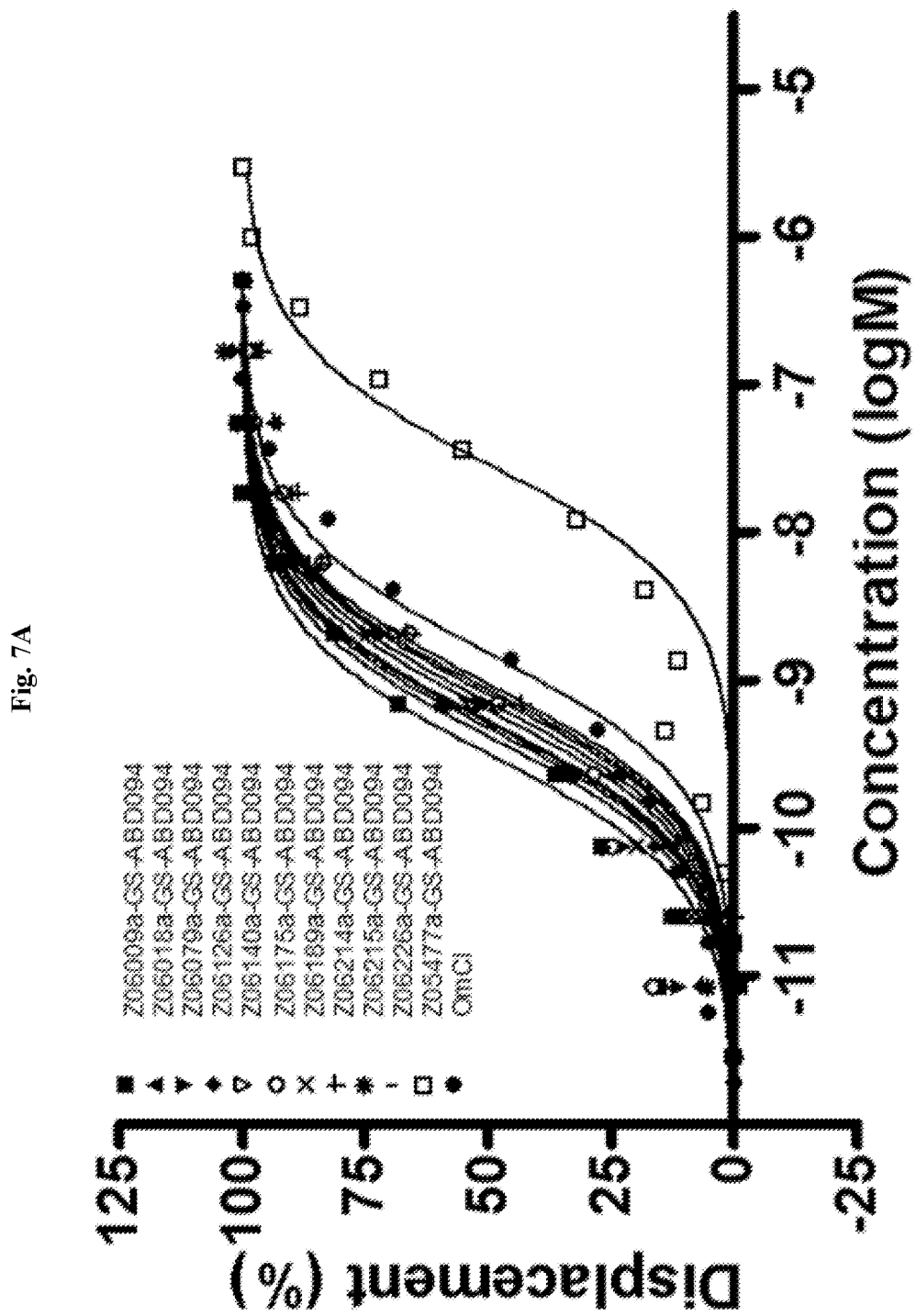
FIGS. 7A and B are diagrams showing exemplary data of equilibrium binding based on the displacement ECL technique described in Example 6.

The C5 binding Z-variants (SEQ ID NO:748-757) fused in the carboxy terminus to ABD094 (SEQ ID NO:759) by a GS linker were found to displace 200 pM SULFO-TAG labeled Z-ABD variant with $IC_{50}$ values ranging from about 300 pM to 1 nM (FIG. 7A), whereas the corresponding construct containing the parental Z variant Z05477a (SEQ ID NO:745) exhibited an affinity $IC_{50}$ value of about 30 nM. In contrast, the naturally occurring C5 binding protein OmCI was found to bind hC5 with an $IC_{50}$ of 1.5 nM (FIG. 7A). Thus, all the tested second-generation Z variants (SEQ ID NO:748-757) exhibited a higher binding affinity for human C5 than the parental Z variant Z05477a (SEQ ID NO:745). In addition, the affinities were higher than that of OmCI binding to human C5 using the same method.

Figure 7B:
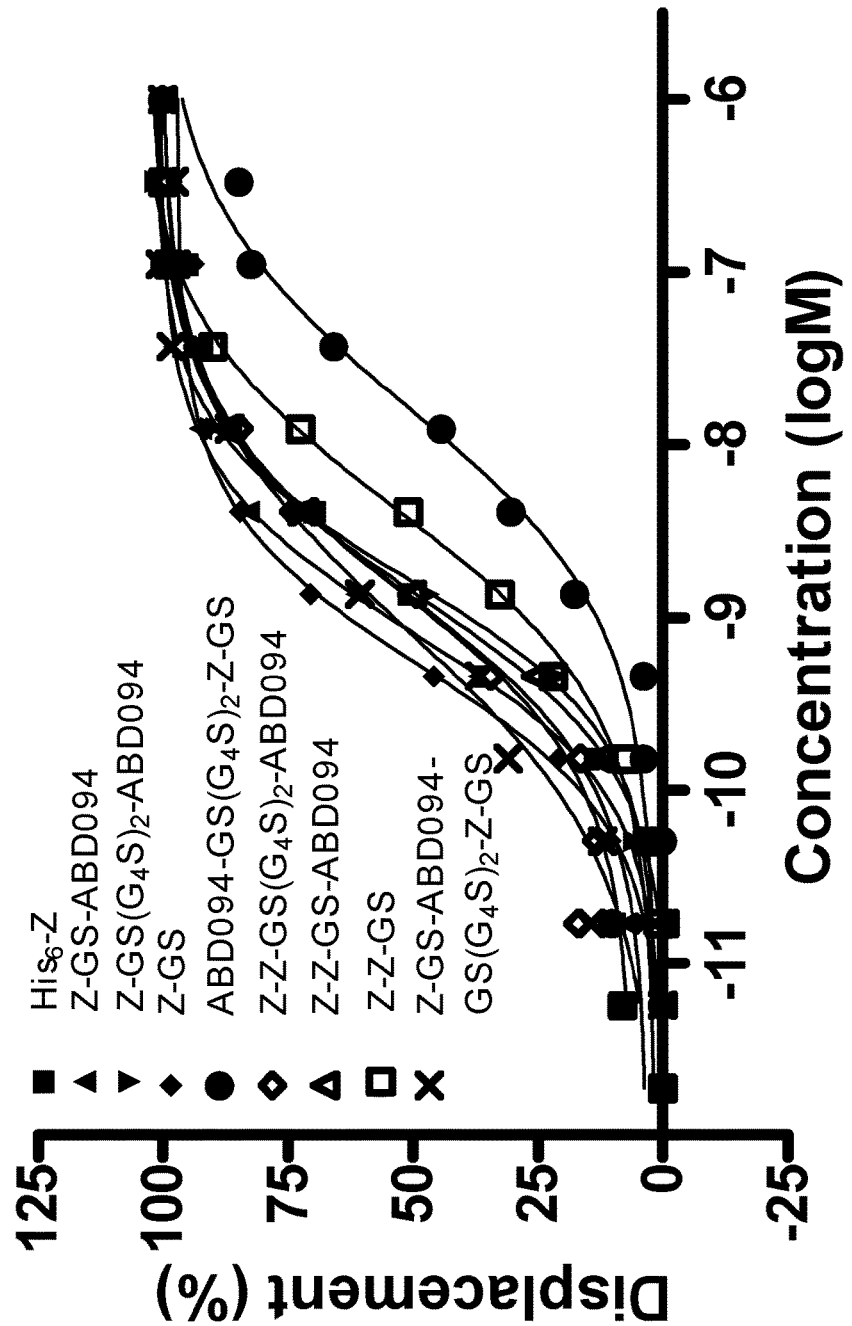
FIG. 7B shows binding of different C5 binding constructs comprising the same C5 binding Z variant (SEQ ID NO:753) as monomer or dimer, in fusion with ABD094 (SEQ ID NO:759) or as provided with a His$_6$-tag.

A number of different constructs containing the same C5 binding domain as a monomer, dimer, with or without ABD as well as a few different linkers between the different domains were also tested (FIG. 7B). Monomeric variants of Z06175a (SEQ ID NO:753, optionally fused to a His$_6$-tag or a C-terminal ABD) and the dimeric variants with a C-terminal ABD linker were found to displace 200 pM SULFO-TAG labeled Z-ABD variant with $IC_{50}$ values ranging from about 500 pM to 1.7 nM whereas the dimeric variant without an ABD and the monomeric variant with a N-terminal ABD displaced 200 pM SULFO-TAG labeled Z-ABD with $IC_{50}$ values of 4 nM and 17 nM, respectively.

Selectivity:

Selectivity was addressed using SPR analysis and the surface with the immobilized Z-ABD variant (SEQ ID NO:748 fused to SEQ ID NO:759 by a GS-linker) displayed no significant SPR signal when subjected to 40 and 400 nM of the C5 paralogs human C3 and C4 as well as human IgG. As a comparison, 400 nM human C5 elicited an SPR response of about 450 RU showing that the tested Z-ABD variant indeed is selective for C5 over C3, C4 and IgG.

Example 7: Interaction Studies of Z-ABD Variants with HSA, BSA and Serum Album from Rat and Mouse Materials and Methods Two different methods, size exclusion chromatography and Biacore, were used to study the interaction between the albumin binding domain ABD094 fused to a C5 binding Z variants.

Size exclusion chromatography (SEC) was employed to study the interaction between Z06175a-GS-ABD094 (SEQ ID NO:753 fused to SEQ ID NO:759 by a GS linker) and HSA. Briefly, equimolar amounts of Z06175a-GS-ABD094 and recombinant HSA (Novozymes) were preincubated in PBS at room temperature for 60 minutes and subsequently run on a Superdex200 column (GE Healthcare) using the SMART system (GE Healthcare). Z06175a-GS-ABD094 and HSA were also run separately as controls.

Binding to immobilized albumin was studied using a Biacore 2000 instrument (GE Healthcare). Recombinant human albumin (RECOMBUMIN, Novozymes) was coupled to a CM5 sensor chip (385 RU) using amine coupling chemistry as described by the manufacturer. The coupling was performed by injecting human albumin in 10 mM Na-acetate buffer pH 4.5 (GE Healthcare). The reference cell was treated with the same reagents but without injecting human albumin Injection of HBS-EP was also included as control so that the sensorgrams were double blanked. Experiments were performed in HBS-EP buffer, 10 mM glycine-HCl pH 2 (GE Healthcare) was used for regeneration, the flow rate was 30 µl/min and data were collected at 25° C. Two different constructs were tested, Z-ABD (Z06175a-GS-ABD094) and Z-ABD-Z (Z06175a-GS-ABD094-GSGGGGSGGGGS-Z06175a) (SEQ ID NO. 780) at three different concentrations; 25 nM, 100 nM and 400 nM. BIAevaluation version 4.1.1 was used for evaluation of sensorgram data. In a similar fashion, binding of Z-ABD (Z06175a-GS-ABD094) to surfaces immobilized with serum albumin from rat (A4538, Sigma), mouse (A3559, Sigma), and cow (BSA, Sigma) was also investigated.

Results

Figure 8A:
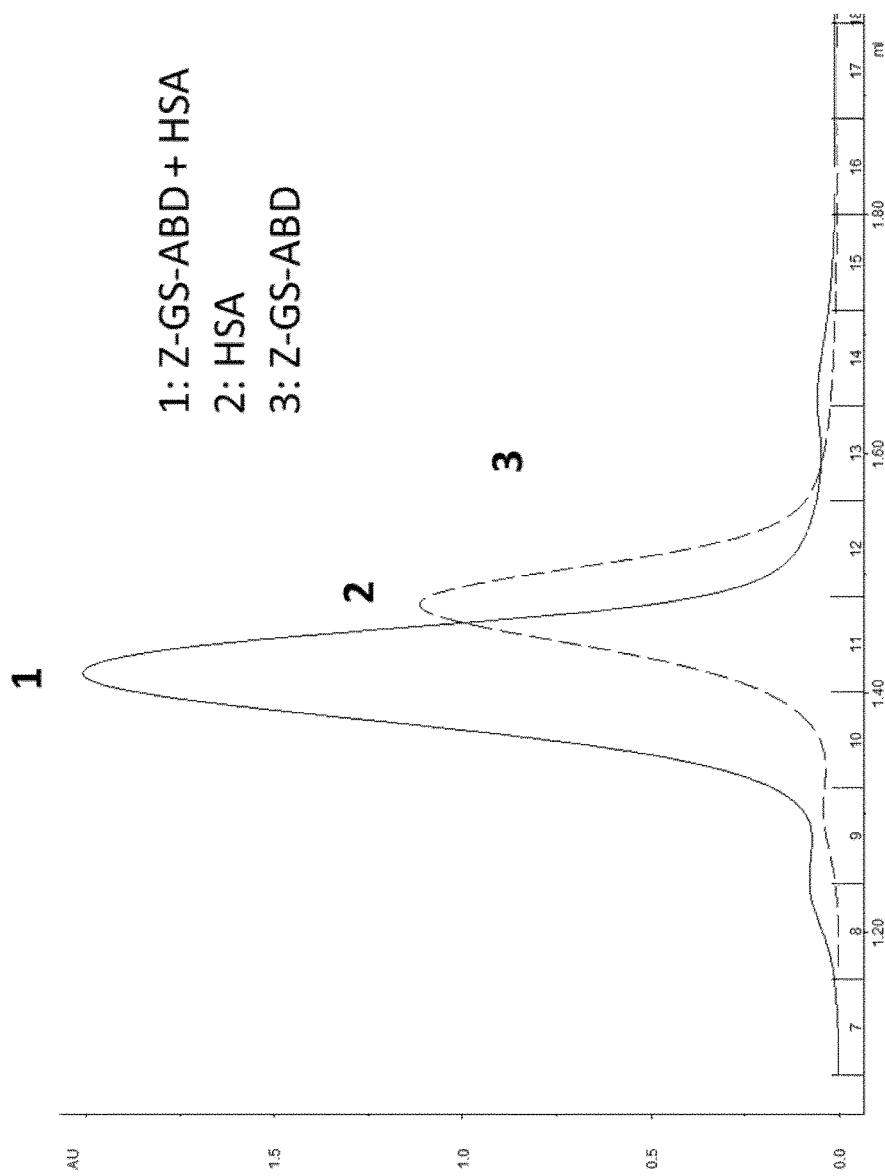
FIGS. 8A and 8B show interactions between Z-ABD variants and human serum albumin (HSA) studied as described in Example 7. A) Size exclusion chromatography (SEC) where Z-ABD (Z06175a (SEQ ID NO:753) fused to ABD094 (SEQ ID NO:759) by a GS linker) has been preincubated with equimolar amounts of HSA (1). As a comparison, the chromatograms for HSA alone (2) and Z-ABD alone (3) are also shown in the graph. B) Biacore sensorgrams of Z-ABD and Z-ABD-Z (Z06175a (SEQ ID NO:753) fused to ABD094 (SEQ ID NO:759) by linkers specified in FIG. 4, in construct 2 and construct 5, respectively) injected over an HSA coated surface. Each of the two constructs was injected at a concentration of 25, 100 and 400 nM.

On a SEC column, larger molecules elute faster than small. As seen in FIG. 8A, the co-injected HSA+ Z06175a-GS-ABD094 elute faster than when HSA is injected alone suggesting that the two molecules behave as a stable complex under these conditions. The smaller Z06175a-GS-ABD094 elute slower than either the complex or HSA alone showing that these proteins alone are smaller than the complex.

Figure 8B:
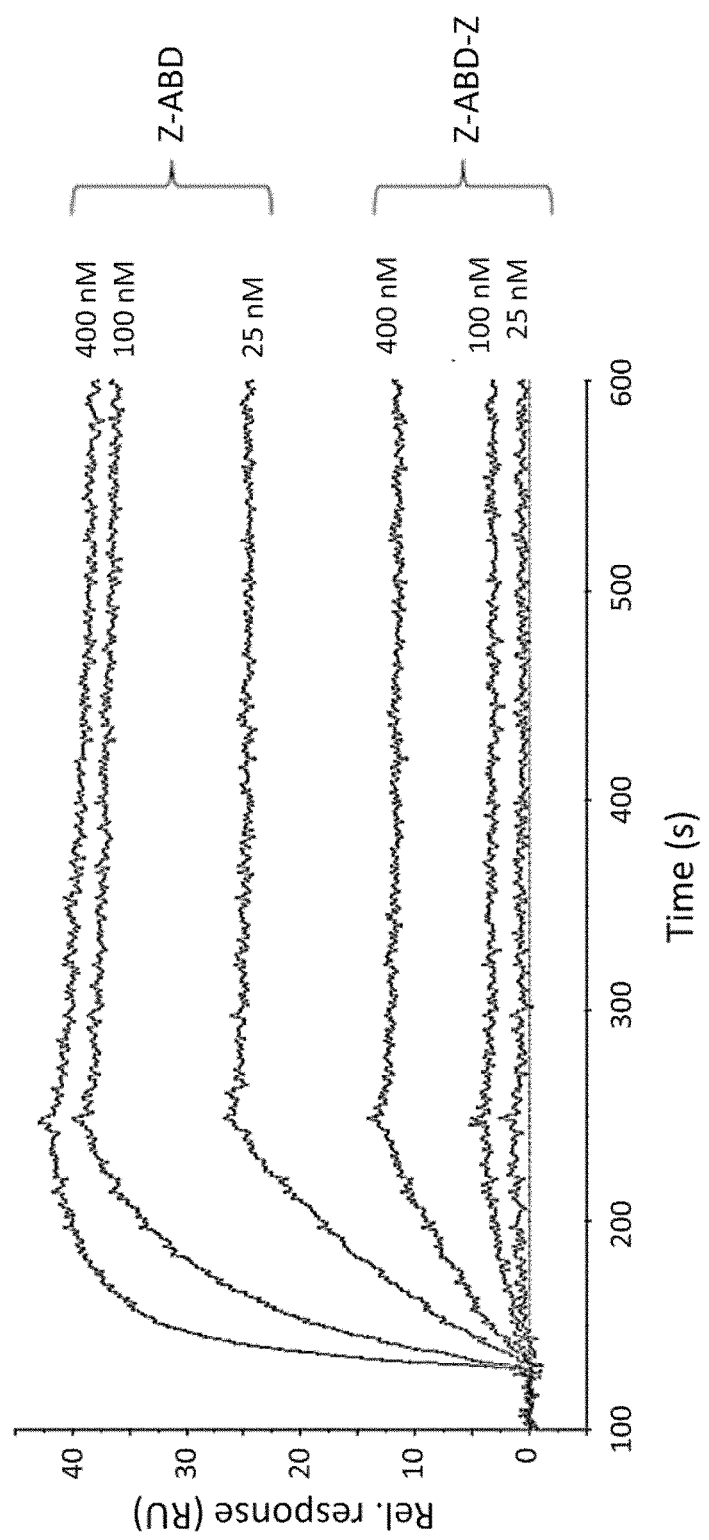

Biacore 2000 data for the analyzed Z-ABD and Z-ABD-Z variants show that the Z-ABD has a faster on-rate than when ABD is flanked by Z-domains on either side (FIG. 8B). Analysis of the binding affinity of ABD fused Z domains points at an affinity below 1 nM for Z-ABD whereas the Z-ABD-Z variant bind to immobilized HSA with a $K_D$ above 1 nM.

Z06175a-GS-ABD094 bound to rat serum albumin with very high affinity (KD<100 pM) whereas the interaction with immobilized mouse serum albumin was weaker (KD of about 4 nM) than both with human and rat serum albumin Interaction with bovine serum albumin was not measurable.

These data agree well with published data on an earlier variant of ABD (Jonsson et al. Protein Engineering, Design & Selection 2008, 21: 515-527) and show that the tested Z-ABD variant is strongly bound to serum albumin in human at clinically relevant concentrations as well as in mouse and rat allowing comparisons of pharmacokinetic data between animals and humans.

Example 8: Pharmacokinetic Studies of C5 Binding Z Variant in Rats

Materials and Methods
Rodent in-Life Phase:

The pharmacokinetics of two C5 binding constructs Z-ABD (Z06175a-GS-ABD094; SEQ ID NO:753 fused to SEQ ID NO:759 by a GS linker, FIG. 4, construct 2) and Z-ABD-Z (Z06175a-GS-ABD094-GSGGGGSGGGGS-Z06175a (SEQ ID NO. 781); (SEQ ID NO:753 fused to SEQ ID NO:759 by a GS linker, followed by a GS($G_4S$)$_2$ linker and a second SEQ ID NO:753 motif, FIG. 4, construct 5) was studied in Male Sprague Dawley (SD) rats (250-300 g body weight). Each rat was given a single dose administration, i.v. (250 nmol/kg) or s.c. (500 nmol/kg), of Z-ABD or A-ABD-Z (n=3 per dose group). Blood samples (200 µL) were drawn at 5, 20, and 45 min, as well as 1.5, 4, 7, 24, 48, 72, 120, 168, 240, and 336 h following administration for the i.v. group and at 15 and 30 min, 1, 2, 4, 7, 24, 48, 72, 120, 168, 240, and 336 h following administration for the s.c. group. Blood was collected in tubes and placed in the fridge for 20 min to allow clotting. Serum was subsequently harvested following centrifugation at 4000 rpm for 10 minutes. Serum samples were kept at −70° C. pending analysis.

Determination of C5 Binding Z Variant Concentrations in Serum Samples from Animals Using LC/LC/MS/MS:

Serum concentrations of the administered C5 binding constructs Z-ABD and Z-ABD-Z, as described above, were determined by mass spectrometry (LC/LC/MS/MS). Serum or plasma samples (25 µl) were diluted with 150 µl of a pepsin agarose (7 mg/ml, Sigma, cat. no. P0609) suspended in 1 M ammonium formate buffer pH 3.0 in a 500 µl Eppendorf tube. The tubes were capped and agitated in an Eppendorf thermomixer compact at 37° C. for 20 min Following agitation, 25 µl of an internal standard solution I($^{13}C_6$;$^{15}N$)NKLDDDPSQSSEL (SEQ ID NO. 782) (amino acids 31-44 of the SEQ ID NO:746-757) (Thermo Fisher Scientific GmbH), diluted to 0.5 µM in 0.1% trifluoroacetic acid (TFA), was added. Following addition of internal standard, the samples were mixed and filtered through 0.45 µm cellulose spin filters (Grace).

Standard samples for calibration were prepared by weighing 20 µl of protein stock solution with known protein concentration (5-10 mg/ml) followed by dilution with blank plasma from the species to be analyzed. The first stock plasma standard (3 µM) was diluted further down to 0.1 µM.

40 µl of the samples were injected into a coupled column system followed by tandem mass spectrometry with multiple reaction monitoring (MRM). The first column was an Ascentis RP-Amide column packed with 5 µm particles (2.1×150 mm, Supelco). An enrichment column; a Brownlee newgard column (3.2×15 mm) packed with 7 µm C18 particles, was used to trap the analyte peptide fraction from the first column. The effluent from the first column was diluted with 1 ml/min water pumped by Shimadzu pump into a whirl mixer (Lee Scientific). The last column was a mixed mode reversed phase and cation exchange column (2.1×100 mm) packed with 5 µm particles Primesep 100 (SIELC Inc).

The mobile phases for the first column (RP-Amide) provided on a first liquid chromatograph (Acquity UPLC) were A: 2% acetonitrile, 0.1% acetic acid, 0.1% TFA, and 97.8% water, and B: acetonitrile with 0.1% acetic acid and 0.02% TFA. The flow was 0.5 ml/min and a linear gradient was used for elution. The sample was eluted at isocratic conditions with 100% A for 1 min, followed by 80% A at 7.9 min. At 8.1 min, the column was washed with 100% B for one minute, followed by reconditioning with 100% A. The effluent from the column was connected to a Valco six port valve controlled from the mass spectrometer software.

The trap column (3.2×15 mm) was connected to the six port valve in back flush mode. The mobile phases for the second column, provided on a second liquid chromatograph (Agilent 1100), were A: 80% acetonitrile, 19.9% water, and 0.1% formic acid, and B: 80% acetonitrile, 19% water, 0.5% acetic acid and 0.5% TFA pumped by an Agilent 1100 liquid chromatograph at 0.5 ml/min and eluted with the following gradient: 100% A during the first 5 minutes followed by B gradually being raised from 0 to 40% from 5 to 10 minutes followed by a raise to 100% B during the next 6 seconds (10 to 10.1 minutes). B was kept at 100% until 11.5 minutes followed by a drop to 0% (100% A) during the next 6 seconds (11.5 to 11.6 minute) and kept at 0% B throughout the cycle until stopped at 13 minutes.

The effluent from the last column was connected to a triple quadrupole mass spectrometer (Sciex API 4000) equipped with an electrospray ion source operated in positive ion mode. The MRM transitions were 780.9>814.4 for the analyte and 784.5>821.4 for the internal standard. The declustering potential was optimized at 55 V and the collision energy to 35 V. The effective collision energy was 70 eV since the precursor ion was doubly charged giving a singly charged fragment ion. The peak area ratios between the analyte and internal standard were used for quantification. Linear calibration curves were obtained with a recovery of 85% and a limit of quantification of about 40 nM.

Ex Vivo Hemolysis:

An ex vivo hemolytic assay for complement activation was performed in order to optimally assemble in vivo conditions for the serum samples from the above described in vivo studies. The serum samples were 5× diluted in a total reaction volume of 25 µl/well comprising 5 million antibody sensitized sheep erythrocytes (EA). In general, a portion of 20 µl EA suspension containing all other components (see Example 6) was mixed (agitation 10 minutes) with 5 µl serum sample to initiate the hemolytic activation at 37° C. For mouse serum samples, such as in example 11, however, 1 µl C5D had to be included in the 20 µl EA suspension. The ex vivo assay was performed essentially as described for the in vitro assay of Example 6. Calculations: Evaluation of the pharmacokinetic parameters was based on individual serum concentration data, the mean (±stdev) is reported for each dose group. Levels below lower limit of quantitation (LLOQ) appearing at terminal sampling points were omitted from the pharmacokinetic analysis. Maximum serum concentration, $C_{max}$, and time to observed maximum serum concentration, $t_{max}$, were obtained directly from the serum concentration data. The pharmacokinetic parameters; area under curve (AUC, $AUC_{0-\infty}$ and $AUC_{0-last}$ calculated by the linear trapezoidal method), subcutaneous bioavailability (F, calculated as $(AUC_{sc}/AUC_{iv})*(Dose_{iv}/Dose_{sc})$), terminal serum half-life ($T_{1/2,z}$, calculated as ln $2/\lambda_z$ where estimation of terminal slope, $\lambda_z$, was based on at least 4 C=f(t) observations), mean residence time (MRT, calculated as AUMC/AUC), serum clearance (CL, calculated as Dose/$AUC_{0-\infty}$), volume of distribution at steady state ($V_{ss}$, calculated as CL*MRT) and volume of distribution at the terminal phase ($V_z$, calculated as CL/2) were calculated using WinNonlin software version 5.2.1 (Pharsight Corp., USA), Non-Compartmental-Analysis.

Results

The pharmacokinetic data for Z-ABD and Z-ABD-Z following i.v. (250 nmol/kg) and s.c. (500 nmol/kg) administration are summarized in Table 8. Z-ABD was quantifiable in serum up to 10-14 days post dose in the i.v. group and 14 days in the s.c. group whereas Z-ABD-Z was quantifiable in serum up to 10 days post dose in both dose groups (FIG. 9). 14 days was the final sampling time point.

Figure 9:
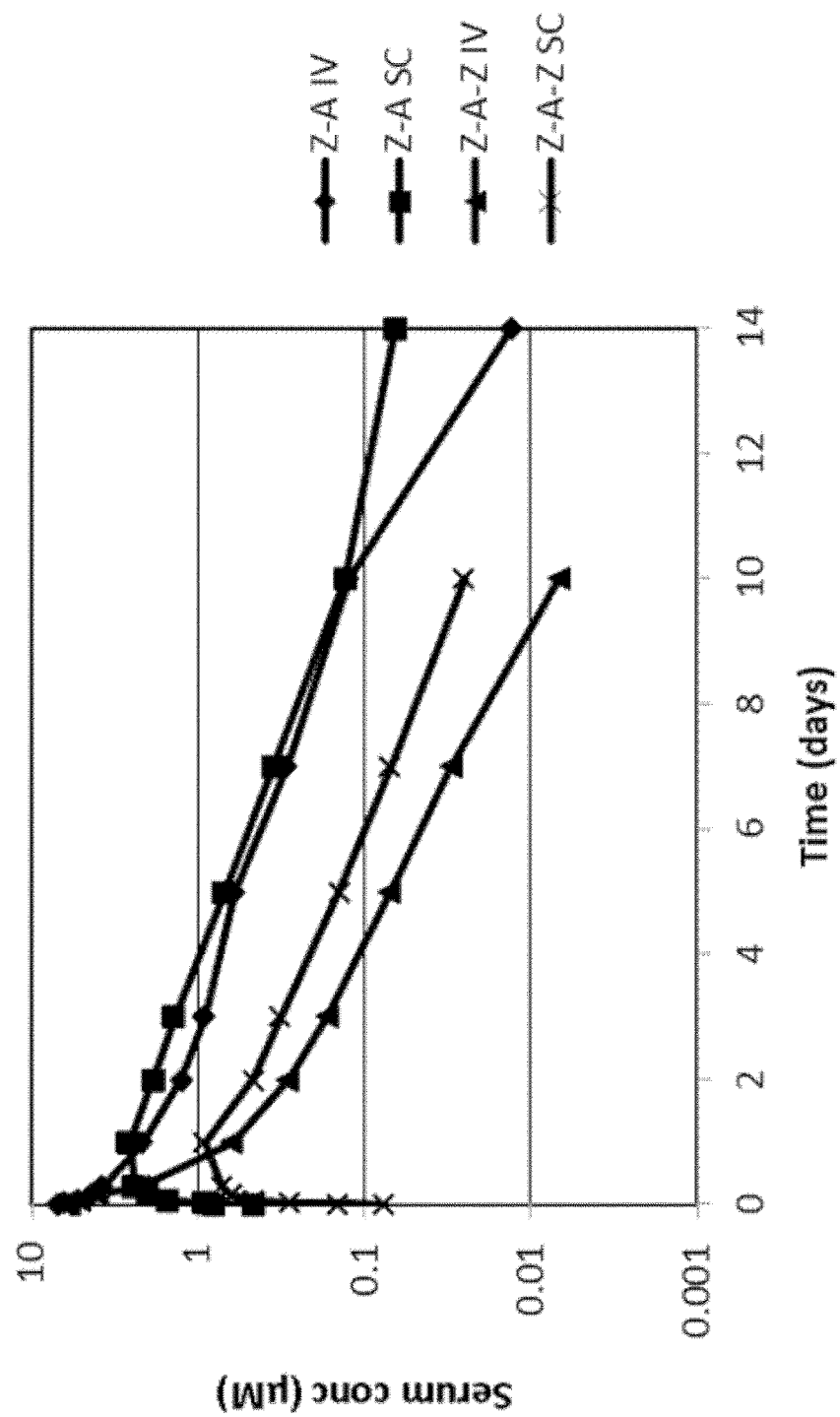
FIG. 9 is a diagram showing the pharmacokinetic profiles for the C5 binding compounds Z-ABD and Z-ABD-Z (Z06175a, SEQ ID NO:753) fused to ABD094 (SEQ ID NO:759) by linkers specified in FIG. 4, in construct 2 and construct 5, respectively) in Male Sprague Dawley rats over time after intravenous (i.v., 0.25 µmol/kg) and subcutaneous (s.c., 0.5 µmol/kg) administration, as described in Example 8. Each data point represents an average from three individual animals at a specific time point ranging from five minutes to two weeks after dosing for animals dosed i.v and from 15 minutes to two weeks for animals dosed s.c.
Figure 10:
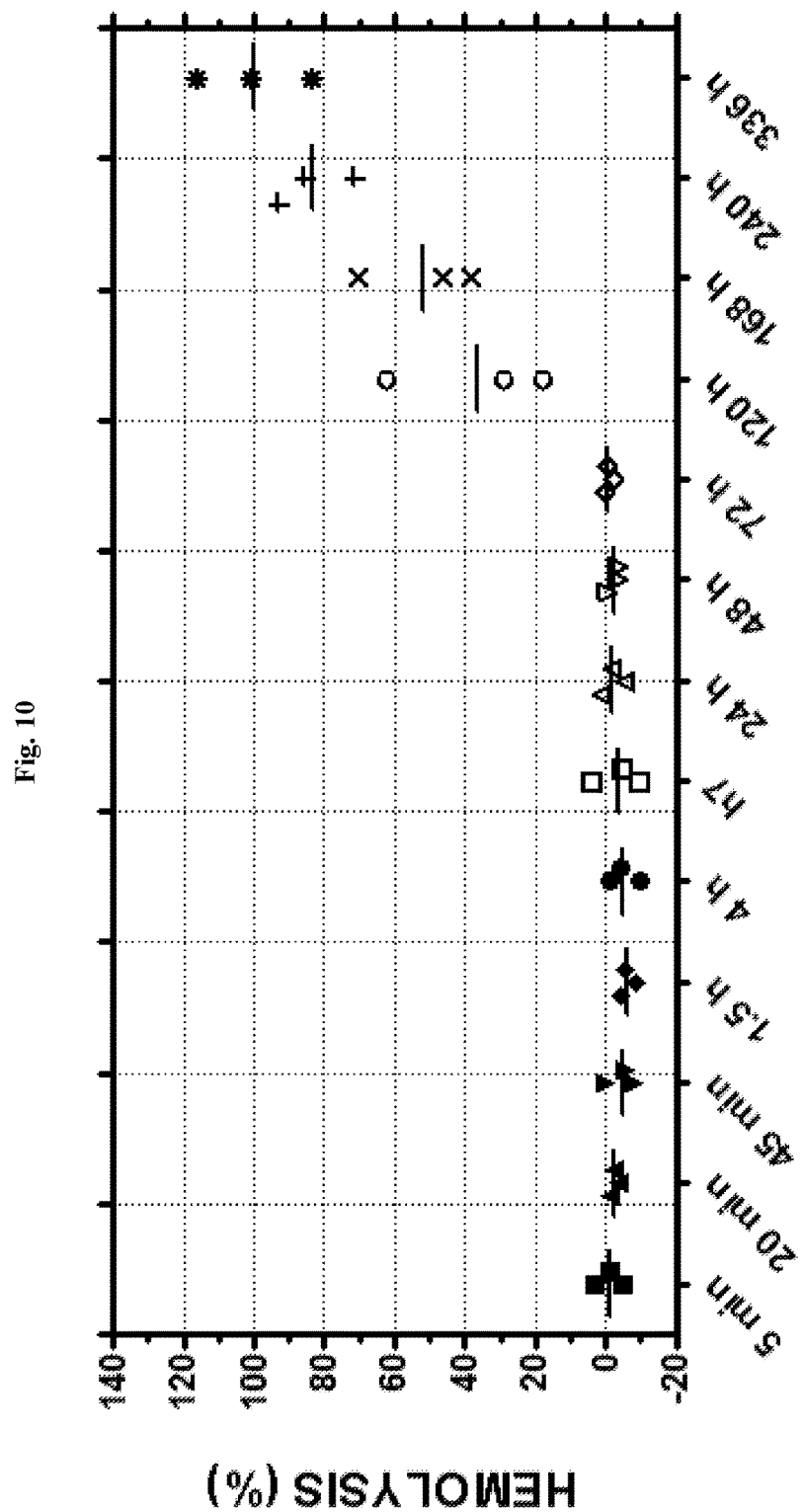
FIG. 10 shows ex vivo hemolysis in sheep erythrocytes after exposure to serum diluted 1:5 from animal samples taken from Sprague Dawley rats after intravenous (i.v.; 0.25 µmol/kg) administration of Z-ABD (Z06175a (SEQ ID NO:753) fused to ABD094 (SEQ ID NO:759) by a GS linker), as described in Example 8. Each dot represents one individual animal at a specific time point ranging from five minutes to two weeks after dosing.
Figure 11:
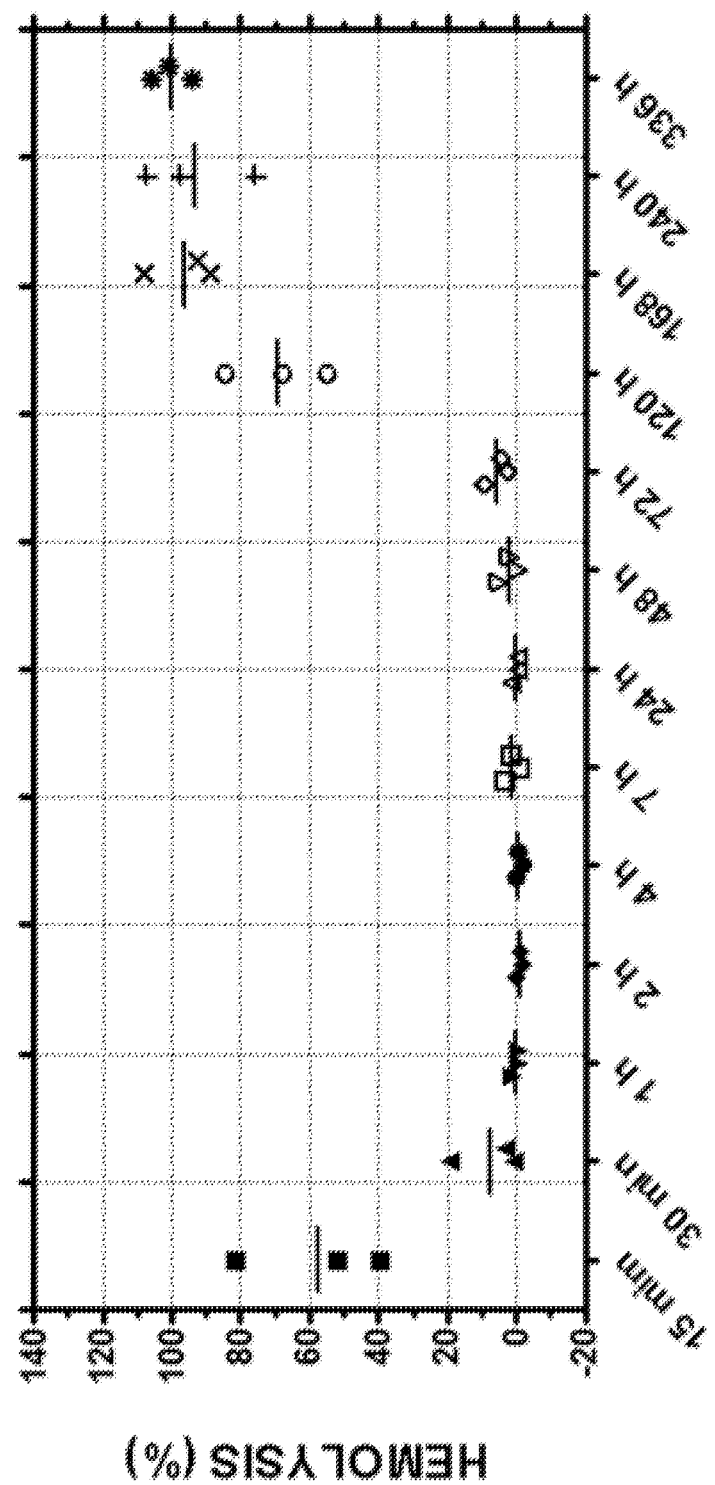
FIG. 11 shows ex vivo hemolysis in sheep erythrocytes after exposure to serum diluted 1:5 from animal samples taken from Sprague Dawley rats after subcutaneous (s.c.; 0.5 µmol/kg) administration of Z-ABD (Z06175a (SEQ ID NO:753) fused to ABD094 (SEQ ID NO:759) by a GS linker), as described in Example 8. Each dot represents one individual animal at a specific time point ranging from 15 minutes to two weeks.
Figure 12:
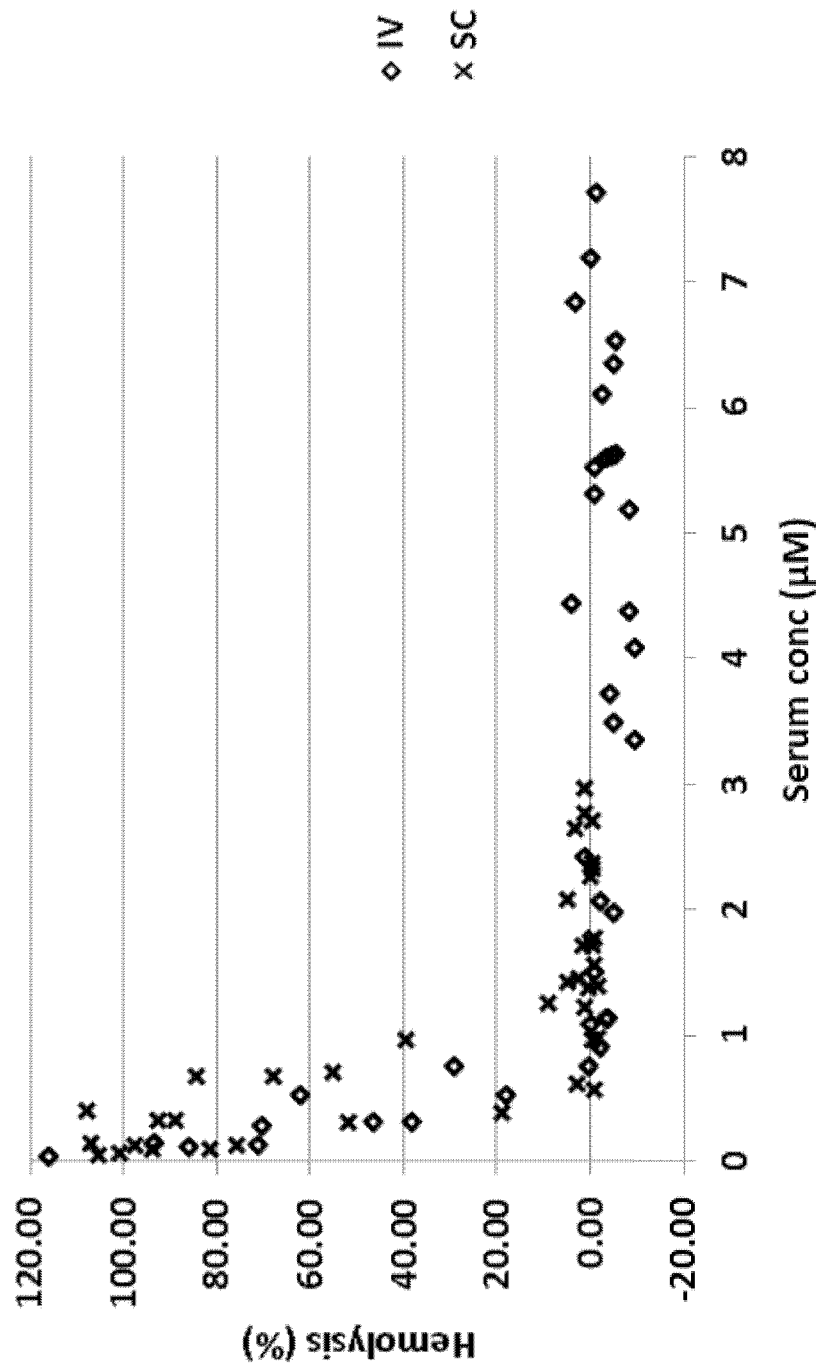
FIG. 12 shows the hemolysis versus Z-ABD (Z06175a (SEQ ID NO:753) fused to ABD094 (SEQ ID NO:759) by a GS linker) serum concentration following i.v. and s.c. administration to male Sprague Dawley rats, as described in Example 8.
Figure 13:
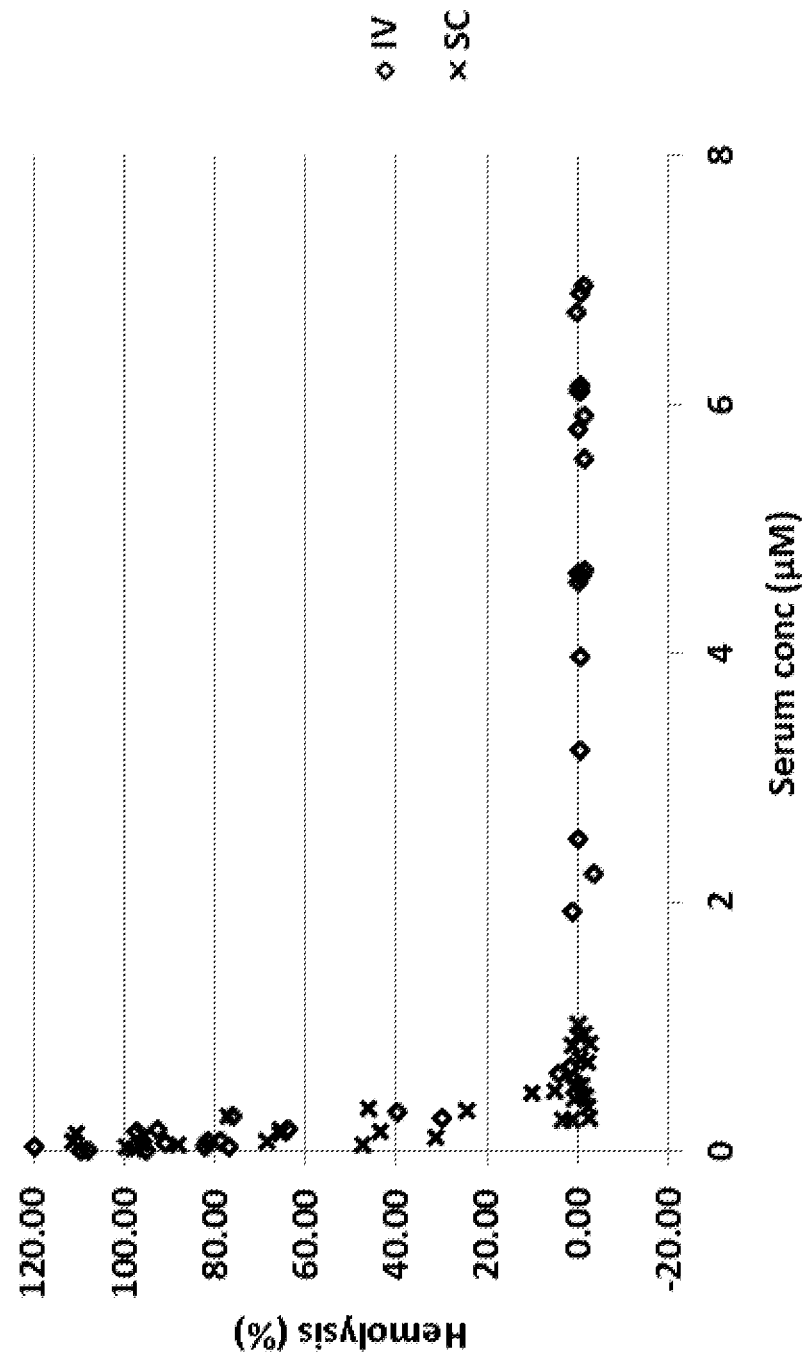
FIG. 13 shows hemolysis in sheep erythrocytes versus Z-ABD-Z (Z06175a (SEQ ID NO:753) fused to ABD094 (SEQ ID NO:759) by linkers specified in FIG. 4, construct 5) serum concentration following i.v. and s.c. administration to male Sprague Dawley rats, as described in Example 8.

Correlating the serum concentration of C5 binding polypeptide with the amount of hemolysis in sheep erythrocytes, it was found that full inhibition of hemolysis under the conditions described (e.g. serum dilution 1:5) was obtained by Z-ABD at serum concentrations above 1 µM (FIG. 12) whereas Z-ABD-Z reached full inhibition at serum concentrations around 0.5 µM (FIG. 13). Surprisingly, as seen in FIG. 9 and Table 8, Z-ABD has a lower serum clearance, a longer terminal serum half-life and a higher bioavailability than Z-ABD-Z. In terms of time this lead to full inhibition of hemolysis for about three days after administration of 250 nmol/kg Z-ABD (FIG. 10) i.v. or 500 nmol/kg s.c (FIG. 11) to S.D.rats.

TABLE 8

Mean (±stdev) pharmacokinetics of Z-ABD and Z-ABD-Z following i.v. and s.c. administration in male Sprague Dawley rats.

| | | Z-ABD | | Z-ABD-Z | |
|---|---|---|---|---|---|
| Administration route | | i.v. | s.c. | i.v. | s.c. |
| Dose | nmol/kg | 250 | 500 | 250 | 500 |
| $C_{max}$ | µM | | 2.8 (0.2) | | 0.90 (0.10) |
| $T_{max}$ | h | | 18 (9.8) | | 17 (12) |
| $AUC_{0-\infty}$ | µM*h | 233 (34) | 252 (11) | 79 (7.5) | 64 (1.2) |
| $AUC_{0-last}$ | µM*h | 226 (37) | 247 (11) | 79 (6.9) | 63 (1.0) |
| F | % | | 55 (3.1) | | 41 (2.6) |
| $T_{1/2, z}$ | h | 58 (4.6) | 57 (4.2) | 36 (0.6) | 46 (1.2) |
| MRT | h | 69 (2.6) | 80 (4.6) | 27 (1.5) | 63 (2.6) |
| CL | mL/h*kg | 1.1 (0.2) | | 3.2 (0.2) | |
| $V_{ss}$ | mL/kg | 73 (12) | | 83 (10) | |
| $V_z$ | mL/kg | 90 (18) | | 159 (12) | |

Example 9: Pharmacokinetic Studies of C5 Binding Z Variants in Monkey

Materials and Methods

The study in life phase was performed at Charles River, Nevada (www.criver.com), formulation of administered drug and analysis of serums samples were performed in house. The pharmacokinetics of a Z-ABD variant (Z06175a (SEQ ID NO:753) fused to ABD094 (SEQ ID NO:759) by a GS linker) was investigated in the male Cynomolgus monkey (n=3) following i.v. (intravenous) and s.c. (subcutaneous) administration. Evaluation of the pharmacokinetic parameters was performed according to Example 8, however following i.v. administration the initial serum half-life ($T_{1/2\alpha}$) corresponding to the initial slope of the log-linear serum concentration-time curve, intermediate serum half-life ($T_{1/2\beta}$) corresponding to the slope of the log-linear serum concentration-time curve associated with the secondary (intermediate) phase and terminal serum half-life ($T_{1/2\gamma}$) corresponding to the terminal slope of the log-linear serum concentration-time curve was determined. $T_{1/2}$ was calculated as ln $2/\lambda$ where estimation of the slope, $\lambda$, was based on at least 4 C=f(t) observations. The pharmacokinetic data presented for sc administration are compensated for pre-dose levels of Z-ABD while the graph displaying serum concentration versus time after sc administration show the actual serum concentrations determined. The monkeys were 2-4 years old with a body weight of 2.3-3 kg. Each monkey received a single i.v. dose (540 nmol/kg) followed by a single s.c. dose (1635 nmol/kg) three weeks after the i.v. administration. Blood samples were taken at 10 and 30 minutes and 1, 2, 4, 8, 24, 48, 72, 120, 168, 240, 336 and 504 hours post dose following both administrations. The blood samples were allowed to clot for 20-40 minutes in room temperature and then centrifuged at 1500 to 2200 RCF at 2-8° C. for 10-15 minutes before the serum was harvested and frozen. The serum samples were stored at a temperature below −20° C. until analysis.

Serum concentrations of Z-ABD were analyzed by LC/LC/MS/MS as described in Example 8. Serum concentrations determined by LC/LC/MS/MS were also confirmed by a quantitative sandwich enzyme immunoassay technique. A polyclonal antibody specific for the Z compartment of Z-ABD was coated on to a microplate. Unbound polyclonal antibody was washed away and casein was added as blocking agent to reduce unspecific binding to the plastic surface. Samples and standards were diluted in PBS containing 0.5% casein and between 1-5% monkey normal serum. After washing away unbound casein, standards and samples were pipetted to the wells allowing any Z-ABD, presumed mainly to be associated with serum albumin, present in the sample to bind to the immobilized antibody. After washing away any unbound Z-ABD, an HRP labeled polyclonal antibody specific for albumin was added to detect the immobilized Z-ABD-albumin complex by colorometric methods. Unbound polyclonal antibody was washed away and a substrate solution was added to the wells and color develops in proportion to the amount of Z-ABD bound. Evaluation and calculation of pharmacokinetic parameters were performed as described in Example 8.

Ex vivo hemolysis in serum from cynomolgus monkeys dosed with above described Z-ABD variant was monitored using the method described in Examples 6 and 8 with the modification that the monkey serum was diluted only two-fold compared to five-fold for rodent serum.

Results

Figure 14:
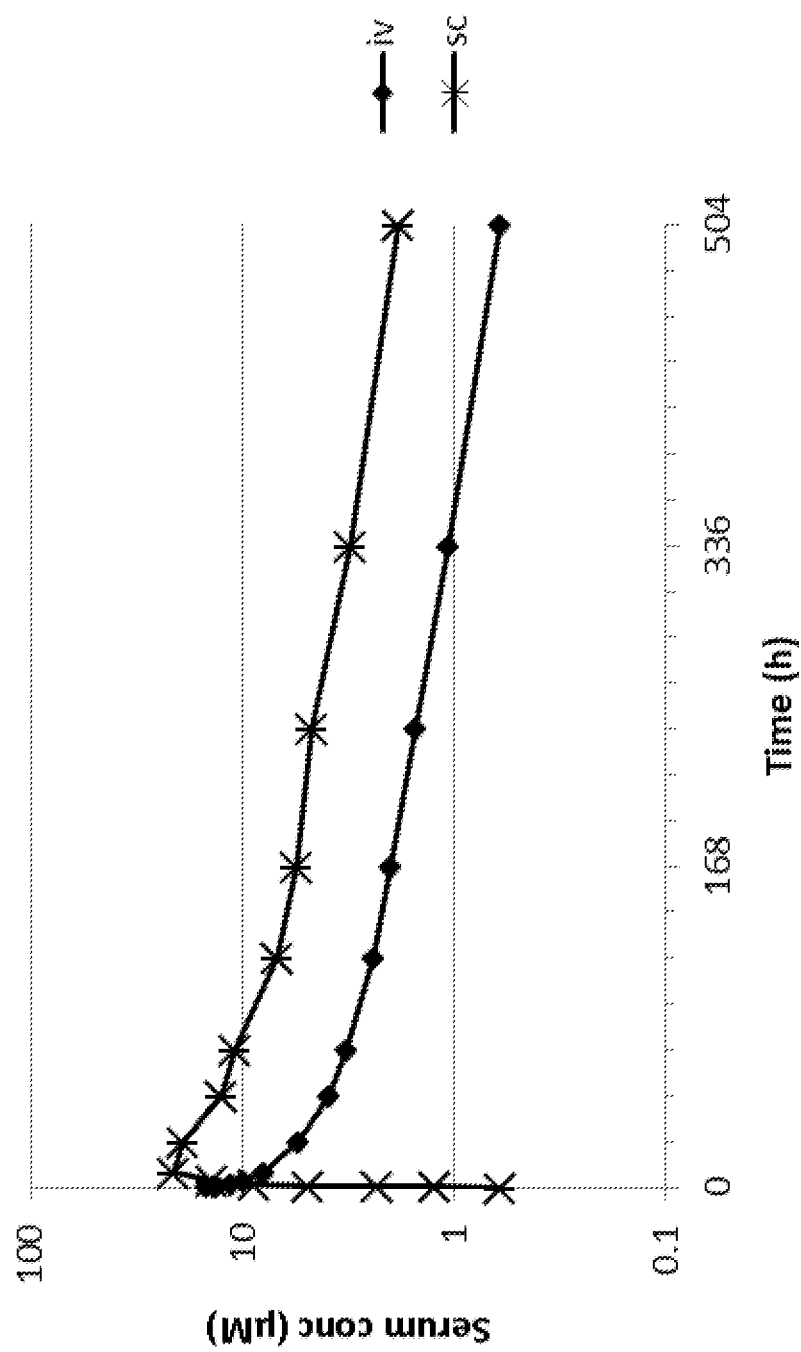
FIG. 14 shows the serum exposure of Z-ABD (Z06175a (SEQ ID NO:753) fused to ABD094 (SEQ ID NO:759) by a GS linker) following i.v. (415 nmol/kg) and s.c. (1250 nmol/kg) administration in male Cynomolgus monkey, as described in Example 9. Each data point represents the mean of three individual animals.

Data on the mean (±stdev) pharmacokinetics of each dose group are presented. Serum concentrations of Z-ABD were quantifiable at all time points following both i.v. and s.c. administration by LC/LC/MS/MS (FIG. 14). ELISA data and LC/LC/MS/MS data correlated linearly by a coefficient of 0.986 but LC/LC/MS/MS data were used for the calculations. Following i.v. administration of Z-ABD the initial serum half-life was 9.1 (0.8) hours, intermediate serum half-life was 84 (4) hours and the terminal serum half-life was 198 (51) hours. The mean residence time was 246 (62) hours. The volume of distribution, $V_{ss}$ and $V_z$ was calculated to 110 (23) ml/kg and 127 (27) ml/kg respectively and clearance was estimated to 0.45 (0.02)mL/h*kg.

Following s c administration, and corrected for pre-dose serum levels remaining from the i v administration, maximum serum concentrations (mean $C_{max}$ 21(3) µM) were reached at 8-24 h after dose. The terminal serum half-life was 206 (40) hours and the mean residence time was 250 (68) hours. The subcutaneous bioavailability was estimated to be above 70%.

The pharmacodynamic effect of the injected Z-ABD variant (Z06175a (SEQ ID NO:753) fused to ABD094 (SEQ ID NO:759) by a GS linker) was monitored by hemolysis. The hemolytic effect in cynomolgus monkey was completely suppressed (<20% of pre-dose) for at least seven days after administration of 5 mg/kg Z-ABD i.v. and 15 mg/kg Z-ABD s.c.

Example 10: In Vivo Studies Using Zymosan Induced Peritonitis

Materials and Methods
Administration to Mice:

C57BL/6 female mice received different concentrations of a Z-ABD fusion molecule (Z06175a-GS-ABD094, SEQ ID NO:753 fused to SEQ ID NO:759 by a GS linker) or the positive control OmCI intraperitoneally (i.p.) 1 hour before induction with zymosan, or subcutaneously (s.c.) 18 hours before induction with zymosan.

0.8 mg/mouse zymosan was administered i.p. 1 hour later orbital blood samples (in serum vials with coagulation activator) were taken under isoflurane anaesthesia. The animals were killed by cervical dislocation. A skin incision was made, and the abdominal muscular wall was visualized. PBS solution (including 2 mM EDTA) was gently injected into the abdominal cavity. The abdomen was massaged and a sample of fluid (1-2 ml) was withdrawn. The samples were transferred to test tubes and stored on wet ice before centrifugation at 600 g for 10 min. Total protein and C5a concentrations in the supernatant were analyzed.

Blood samples were kept in a refrigerator for at least 30 min and centrifugation was thereafter performed at 2000 g. Serum samples were stored in freezer (−70° C.) for later analysis of hemolytic activity and levels of Z06175a-GS-ABD094.
Analysis of Hemolysis Activity in Serum Samples from Animals:

Analysis of hemolysis activity was performed according to the hemolysis assay described in Examples 6 and 7.
Analysis of C5a Concentration in Lavage from Mice Dosed with Zymosan and C5 Binding Z-ABD Fusion Molecules:

For detection of C5a in mouse peritoneal lavage samples, microtiter plates (MaxiSorp, Nunc) were coated overnight at 4° C. with 100 µl/well of anti-05a antibody (cat. no. MAB21501, R&D Systems) at a concentration of 1 µg/ml in 0.05 M sodium carbonate-bicarbonate buffer, pH 9.6 (cat. no. C-3041, Sigma). The plates were washed three times with PBS containing 0.05% Tween 20 (PBST, cat. no. 09-9410-100, Medicago) and blocked with 200 µl/well of 1% BSA (cat. no. A7030, Sigma) in PBST for 1-1.5 h at RT during agitation at 450 rpm. The plate was again washed three times with PBST and then incubated with 100 µl/well of recombinant mouse C5a standard (cat. no. 2150-05, R&D Systems) at various concentrations in PBST with 0.1% BSA or samples for 2 h at RT during agitation at 450 rpm. High concentration samples were also diluted in PBST with 0.1% BSA. The plate was once again washed three times with PBST and then incubated with 100 µl/well of biotinylated anti-C5a antibody (cat. no. BAF2150, R&D Systems) at a concentration of 0.1 µg/ml for 1.5 h at RT while shaking the plate at 450 rpm. Following 3× washing with PBST, the plate was incubated with 100 µl/well of streptavidin-HRP (cat. no. DY998, R&D Systems) at a 200 fold dilution in blocking buffer for 20 min at RT during agitation at 450 rpm. After three final washes, the plate was developed with 100 µl/well TMB substrate (cat. no. T0440, Sigma) and read after 20-30 min at 650 nm using a Spectramax Plus plate reader (Molecular Devices).

A standard curve was constructed by plotting the absorbance at 650 nm for each standard against its concentration (range 0-4000 pg/ml).
Determination of Z Variant Concentration in Serum Samples from Animals Using ECL:

Serum concentrations of administered C5 binding Z06175a-GS-ABD094 (SEQ ID NO:753 fused to SEQ ID NO:759 by a GS linker) and Z06175a-GS-ABD094-GSGGGGSGGGS-Z06175a (SEQ ID NO: 789) (SEQ ID NO:753 fused to SEQ ID NO:759 by a GS linker, followed by a $GS(G_4S)_2$ (SEQ ID NO: 785) linker and a second SEQ ID NO:753 motif, see FIG. 4 for construct description) were determined by ECL. Multi-array 96-well high-bind, non-coated (Meso Scale Discovery cat. no. L15XB) plates were coated with a goat anti-Affibody molecule Ig (Affibody AB, cat. no. 20.1000.01.0005).

In similarity with Example 6, a Z-ABD variant (Z06009a, SEQ ID NO:748 fused to ABD094, SEQ ID NO:759 Multi-array plates were coated with the goat anti-Affibody molecule IgG (Affibody AB) overnight at 4° C., and subsequently non-specific sites were blocked with PBS with 1% Casein for two hours at RT.

Meanwhile, serum samples were thawed from −70° C. and diluted in PBS with casein in serum from the same animal strain. Standards and controls were diluted in the corresponding buffer. Samples and standards were incubated for three hours at RT while shaking the plate at 300 rpm. Incubation was terminated by washing 3×150 µL ice-cold PBS-Tween20. Immediately after the final wash, 150 µl 2× reading buffer (4× reading buffer T, Meso Scale Discovery cat. no. R92TC-3 diluted 1:1 in ultrapure $H_2O$) was added to each well and the signal was detected using a plate reader (SECTOR Imager 2400, Meso Scale Discovery).

In an alternative experiment, plates were coated with human C5 (SEQ ID NO:760, 1 pmol/well). Prior to addition to the coated plate, serum samples and standards, diluted in serum or in serum and PBS with casein (all samples and standards were matched to the same serum concentration), were heated to 60° C. for 30 min in order to denature endogenous C5. This alternative experiment provided a method for exclusive detection of C5 binding proteins, whereas the antibody dependent strategy described above can be applied to all proteins binding to that particular antibody.

Results
Analysis of Serum Concentrations of Z-ABD and Hemolysis Activity in Serum Samples from Animals:

The serum concentrations as well as the ability to affect hemolysis in sheep erythrocytes of the Z-ABD fusion molecule (Z06175a-GS-ABD094, SEQ ID NO:753 fused to SEQ ID NO:759 by a GS linker)) was assessed after administration of a low (20 nmol/kg), medium (100 nmol/kg) and high dose (500 nmol/kg). The serum concentrations were relatively linear with dose, and inhibition of hemolysis confirmed that the molecules in serum were active and that the inhibition of hemolysis indeed also was concentration dependent.

Figure 15:
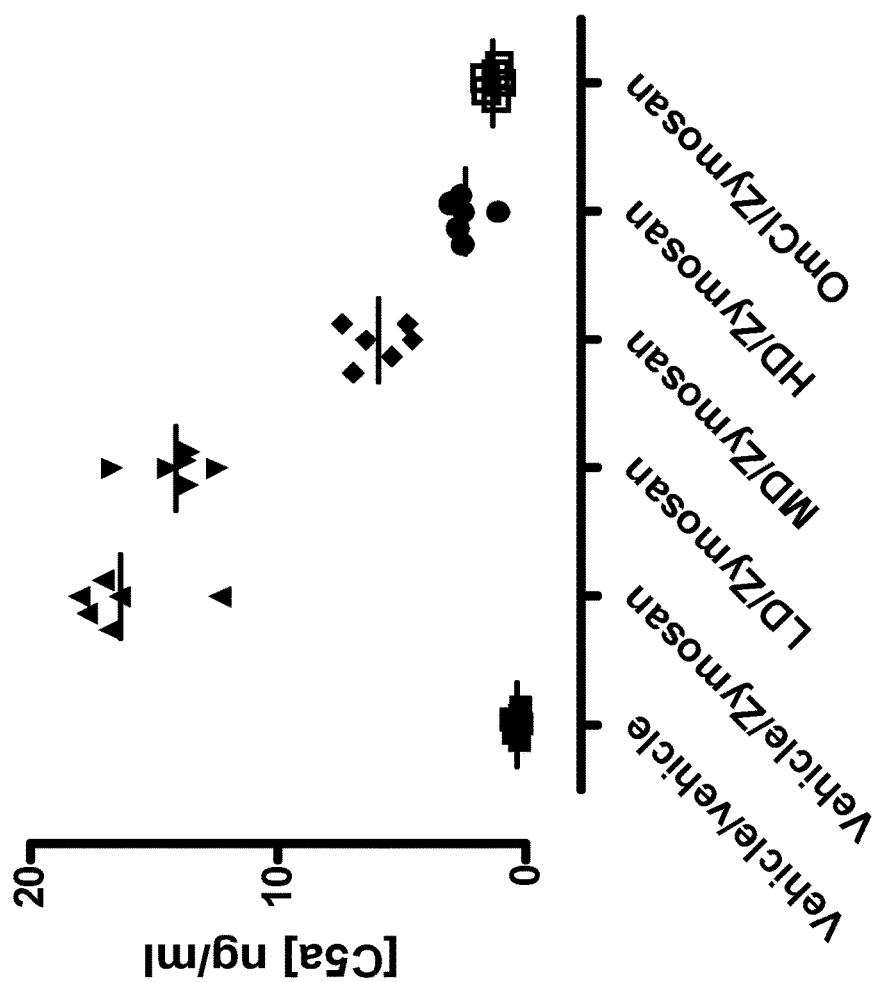
FIG. 15 is a diagram showing the effect (C5a concentration in lavage) of the pro-inflammatory molecule zymosan (40 mg/kg i.p.) alone and in combination with a C5 binding Z-ABD fusion molecule (Z06175a (SEQ ID NO:753) fused to ABD094 (SEQ ID NO:759) by a GS linker)) or OmCI (SEQ ID NO:761) analyzed as described in Example 10. Z-ABD was administered at 20 nmol/kg (LD), 100 nmol/kg (MD) and 500 nmol/kg (HD) s.c. 18 h before induction with zymosan. OmCI (30 nmol/kg) was administered i.p. 1 h before zymosan treatment and samples were taken 1 h after zymosan induction.

Analysis of C5a Concentration in Lavage from Mice Dosed with Zymosan and C5 Binding Z-ABD Fusion Molecules:

The pro-inflammatory molecule zymosan was administered i.p. and in FIG. 15 the effect on the highly inflammatory C5 cleavage product C5a in lavage as a function of zymosan dosing alone and zymosan dosed after a dosing of a C5 binding Z variant at 20, 100 and 500 nmol/kg administered s.c. 18 h before zymosan treatment or OmCI administered i.p. 1 h before zymosan treatment, is shown. Zymosan administration alone leads to a potent elevation of C5a in the lavage. This effect is blocked in a dose dependent manner by the presented C5 binding Z-ABD fusion molecule.

Example 11: Pharmacokinetic Studies of C5 Binding Protein in Mice Following Intratracheal Administration Materials and Methods The pharmacokinetic profile of the C5 binding construct Z06175a-GS-ABD094 (SEQID NO: 753 fused to SEQ ID NO:759 by a GS linker) following intratracheal administration to female C57b1 mice was studied. Temperature, relative humidity and lighting was set to maintain 22±1° C., 55±5% and a 12 h light—12 h dark cycle and diet and water was provided ad libitum. Animals were anesthetized with isoflurane and dosed directly into the lungs using a microspray with 500 nmol/kg Z06175a-GS-ABD094. As much blood as possible was drawn, under anesthesia by isoflurane, from vena cava at 5 min, 30 min, 1 h, 3 h, 7 h, 16 h, 24 h, 48 h and 72 h (three animals/time point) for preparation of serum samples. Serum samples were prepared by collecting blood in tubes and placing the tubes in the fridge for 20 min. Subsequently, the tubes were centrifuged at 4000 rpm for 10 minutes. A minimum of 100 μl serum was prepared from each blood sample. Serum samples were kept at −70° C. prior to analysis. Serum concentrations of Z06175a-GS-ABD094 in each sample was determined by ECL as described in Example 10 and the ability of serum samples to affect hemolysis in sheep erythrocytes was determined as described in Examples 6 and 8.

Results

Figure 16A:
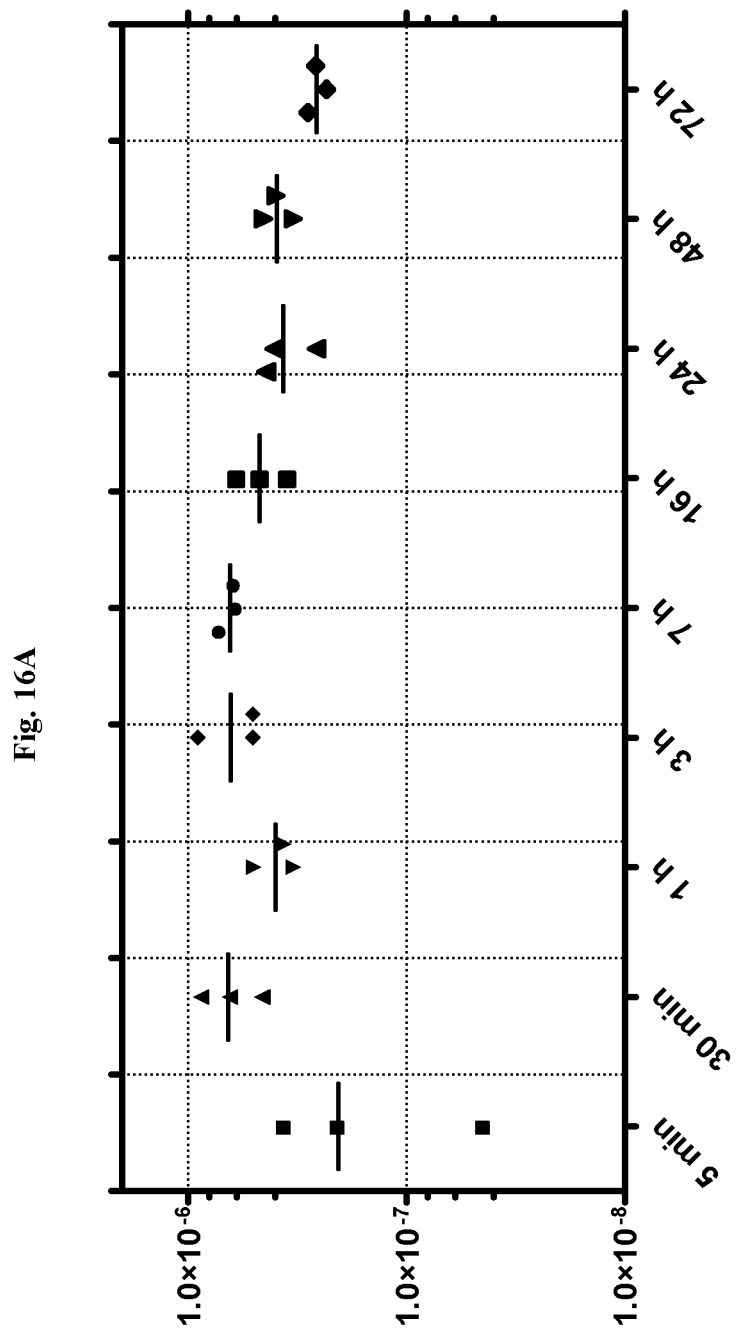
FIGS. 16A and 16B show the pharmacokinetic profile of Z-ABD (Z06175a (SEQ ID NO:753) fused to ABD094 (SEQ ID NO:759) by a GS linker) following intratracheal administration of 500 nmol/kg into female C57b1 mice, as described in Example 11. A) serum concentration in each animal (n=3 for each time point, 27 animals totally) and B) hemolysis in sheep erythrocytes exposed to these serum samples diluted 1:5.
Figure 16B:
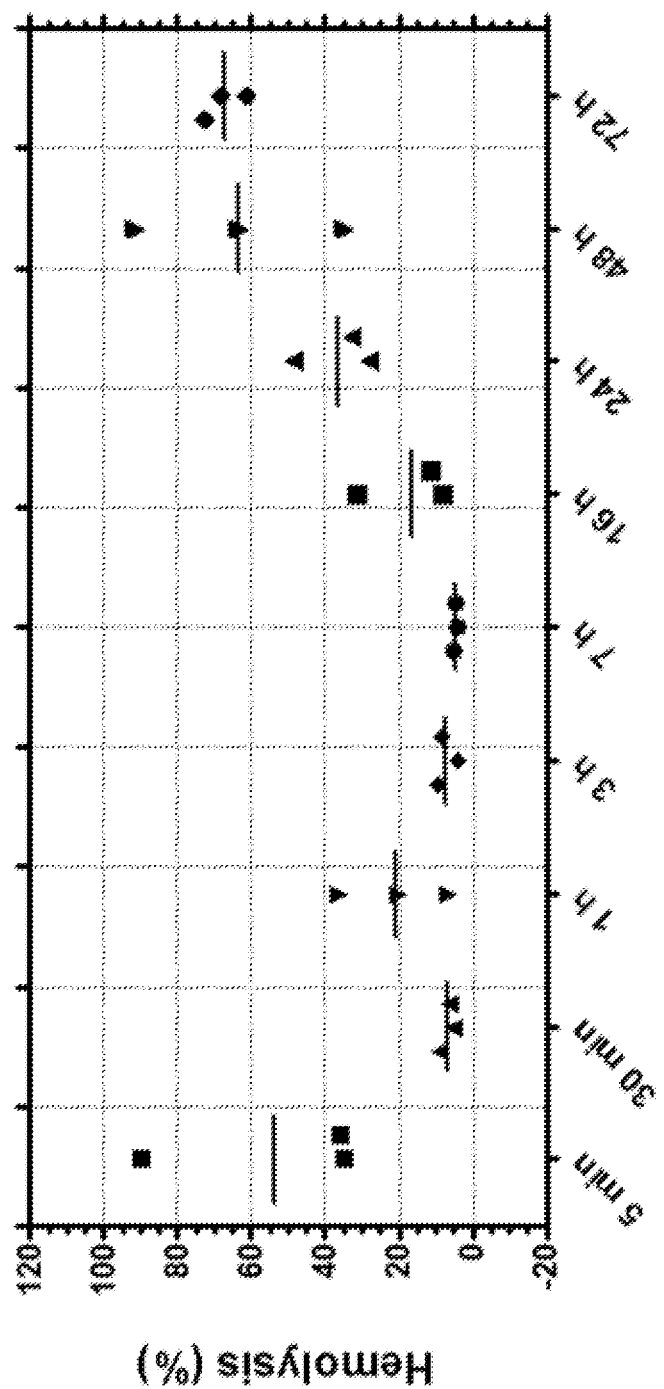

The serum concentration in each sample and the corresponding ability to affect hemolysis in sheep erythrocytes are described in FIG. 16A and FIG. 16B, respectively. Within 30 minutes, a plateau is reached with serum concentrations ranging from 300 to 1000 nM where hemolysis is nearly completely blocked. In serum sampled at time points later than 7 h post-administration, hemolysis is gradually reoccurring. At the final time point three days after dosing, hemolysis was about 70% of control (FIG. 16B). These data clearly demonstrate absorption of Z06175a-GS-ABD094 into the systemic circulation following intratracheal administration and that the molecule functionally inhibits hemolysis.

Example 12: Pharmacokinetic Studies of C5 Binding Z Variant in Rabbit Eye Following Topical and Intravitreal Administration Materials and Methods
Rabbit in-Life Phase:

The pharmacokinetics of a Z variant (Z06175a, SEQ ID NO:753 followed by GS (FIG. 4, construct 1)) was studied in rabbit eye following intra-vitreal administration.

The study in-life phase and dissection of eyes from dosed animals (pigmented rabbits, 2-2.5 kg) was performed at Iris Pharma, La Gaude, France (www.iris-pharma.com). Animals were housed individually at 20±2° C. at 55±10% relative humidity with access to food and water ad lib.

Animals were divided in three groups: 1) intravitreal administration (50 μl in each eye, n=3, six eyes totally) followed by dissection and serum sampling after one day, 2) intravitreal administration (50 μl in each eye, n=3) followed by dissection and serum sampling after four days and 3) untreated animals (n=5).

Four distinct eye compartments were dissected (aqueous humor, vitreous, neuro-retina and RPE-choroid) and immediately frozen at −80° C. Formulation of administered drug (20.2 mg/ml in 10 mM phosphate buffer, 145 mM NaCl, pH 7.4) and analysis of drug in various eye compartments were performed in house.

Analysis of Z-Variant in Dissected Eye Compartments:

Dissected eye compartments were shipped on dry ice and stored at −80° C. until analysis. The retina and choroid samples were thawed in 10 times (volume/weight) PBS containing 1% human serum albumin in Lysing Matrix D tubes (MP Biomedical) containing ceramic beads and agitated at speed 4 for 2×20 s in a Savant Bio 101 homogenizer. The homogenate was removed from the beads using a pipette and transferred to a 1.5 ml Eppendorf tube and centrifuged at 900 rpm for ten minutes. The aqueous humor and vitreous samples were treated the same way as retina and choroid with the exception that no homogenization was needed. The vitreous samples from groups one and two were diluted 10 times further in the same buffer as above. Five standards were prepared in PBS with HSA (35.8 μM, 3.58 μM, 358 nM, 35.8 nM and 17.9 nM). Subsequently, standards and samples were subjected to pepsin digestion and analysis of the concentration of Z variant in tissue extracts was determined using the LC/LC/MS/MS method described in Example 8.

Results

The concentrations of Z variant after intravitreal administration were high in all compartments after one day (6-200 μM) and, surprisingly, remained high 4 days post-administration (1.5-78 μM). In particular, the concentration of the Z molecule in the vitreous ranged from 118 to 201 μM (average 161 μM, n=6 eyes) one day after injection and remained at 26 to 78 μM (average 46 μM, n=6) four days post-injection, pointing at a $T_{1/2}$ of several days. There appears to be an inverse relationship between size and elimination of drugs after intravitreal injection in rabbit eye described by the following examples; Moxifloxacin (MW<0.35 kDa, $T_{1/2}$=1.72 h, Mohan et al. Trans Am Ophthalmol Soc 2005, 103:76-83), ESBA105 (MW=26 kDa, $T_{1/2}$=25 h, Ottiger et al. Investigative Ophthalmology & Visual Science 2009, 50: 779-786) and Ranibizumab (MW=48 kDa, $T_{1/2}$=2.88 days, Bakri et al. American Academy of Ophthalmology 2007, 114:2179-2182). The Z variant tested here had a molecular weight of 7.0 kDa, suggesting that the elimination of the Z molecule was slower than what would be expected for such a small molecule in vitreous.

The invention claimed is:

1. A C5 binding polypeptide, comprising a C5 binding motif, BM, which motif consists of an amino acid sequence selected from i)
$$EX_2X_3X_4A\ X_6X_7EID\ X_{11}LPNL\ X_{16}X_{17}X_{18}QW\ X_{21}AFIX_{25}\ X_{26}LX_{28}D,$$ (SEQ ID NO: 763)

wherein, independently of each other,
$X_2$ is selected from H, Q, S, T and V;
$X_3$ is selected from I, L, M and V;
$X_4$ is selected from A, D, E, H, K, L, N, Q, R, S, T and Y;
$X_6$ is selected from N and W;
$X_7$ is selected from A, D, E, H, N, Q, R, S and T;
$X_{11}$ is selected from A, E, G, H, K, L, Q, R, S, T and Y;
$X_{16}$ is selected from N and T;
$X_{17}$ is selected from I, L and V;
$X_{18}$ is selected from A, D, E, H, K, N, Q, R, S and T;
$X_{21}$ is selected from I, L and V;
$X_{25}$ is selected from D, E, G, H, N, S and T;
$X_{26}$ is selected from K and S;
$X_{28}$ is selected from A, D, E, H, N, Q, S, T and Y; and ii) an amino acid sequence which has at least 86% identity to the sequence defined in i), wherein the polypeptide binds to C5.

2. A C5 binding polypeptide according to claim 1, wherein the amino acid sequence i) fulfills at least four of the following eight conditions I-VIII:
I. $X_2$ is V;
II. $X_3$ is selected from I and L;
III. $X_6$ is
IV. $X_7$ is selected from D and N;
V. $X_{17}$ is selected from I and L;
VI. $X_{21}$ is L;
VII. $X_{25}$ is N;
VIII. $X_{28}$ is D.

3. The C5 binding polypeptide according to claim 1, wherein the amino acid sequence is selected from any one of SEQ ID NO:1-248.

4. The C5 binding polypeptide according to claim 3, wherein the amino acid sequence is selected from any one of SEQ ID NO:1-12, SEQ ID NO:20, SEQ ID NO:23-24, SEQ ID NO:26-28, SEQ ID NO:32-35, SEQ ID NO:38-39, SEQ ID NO:41, SEQ ID NO:46, SEQ ID NO:49, SEQ ID NO:56-57, SEQ ID NO:59, SEQ ID NO:66, SEQ ID NO:78-79, SEQ ID NO:87, SEQ ID NO:92, SEQ ID NO:106, SEQ ID NO:110, SEQ ID NO:119, SEQ ID NO:125, SEQ ID NO:141, SEQ ID NO:151, SEQ ID NO:161, SEQ ID NO:166, SEQ ID NO:187, SEQ ID NO:197, SEQ ID NO:203, SEQ ID NO:205, SEQ ID NO:215 and SEQ ID NO:243.

5. The C5 binding polypeptide according to claim 4, wherein the amino acid sequence is selected from any one of SEQ ID NO:1-12.

6. The C5 binding polypeptide according to claim 1, in which said C5 binding motif forms part of a three-helix bundle protein domain.

7. A C5 binding polypeptide, which comprises the amino acid sequence:

K-[BM]-DPSQS $X_aX_b$LL$X_c$ EAKKL ND$X_d$Q; (SEQ ID NO: 764)

or an amino acid sequence which has at least 79% identity to SEQ ID NO: 764,
wherein
$X_a$ is selected from A and S;
$X_b$ is selected from N and E;
$X_c$ is selected from A, S and C;
$X_d$ is selected from A and S; and
wherein [BM] is a C5 binding motif, which motif consists of the amino acid sequence E$X_2X_3X_4$A $X_6X_7$EID $X_{11}$LPNL$X_{16}X_{17}X_{18}$QW$X_{21}$AFI$X_{25}$ $X_{26}$L$X_{28}$D (SEQ ID NO: 763), or an amino acid sequence which has at least 86% identity to SEQ ID NO:763,
wherein independently of each other:
$X_2$ is selected from H, Q, S, T and V;
$X_3$ is selected from I, L, M and V;
$X_4$ is selected from A, D, E, H, K, L, N, Q, R, S, T and Y;
$X_6$ is selected from N and W;
$X_7$ is selected from A, D, E, H, N, Q, R, S and T;
$X_{11}$ is selected from A, E, G, H, K, L, Q, R, S, T and Y;
$X_{16}$ is selected from N and T;
$X_{17}$ is selected from I, L and V;
$X_{18}$ is selected from A, D, E, H, K, N, Q, R, S and T;
$X_{21}$ is selected from I, L and V;
$X_{25}$ is selected from D, E, G, H, N, S and T;
$X_{26}$ is selected from K and S;
$X_{28}$ is selected from A, D, E, H, N, Q, S, T and Y; and
wherein the [BM] motif binds to C5.

8. The C5 binding polypeptide according to claim 7, wherein the amino acid sequence is selected from any one of SEQ ID NO:249-496.

9. The C5 binding polypeptide according to claim 8, wherein the amino acid sequence is selected from any one of SEQ ID NO:249-260, SEQ ID NO:268, SEQ ID NO:271-272, SEQ ID NO:274-276, SEQ ID NO:280-283, SEQ ID NO:286-287, SEQ ID NO:289, SEQ ID NO:294, SEQ ID NO:297, SEQ ID NO:304-305, SEQ ID NO:307, SEQ ID NO:314, SEQ ID NO:326-327, SEQ ID NO:335, SEQ ID NO:340, SEQ ID NO:354, SEQ ID NO:358, SEQ ID NO:367, SEQ ID NO:373, SEQ ID NO:389, SEQ ID NO:399, SEQ ID NO:409, SEQ ID NO:414, SEQ ID NO:435, SEQ ID NO:445, SEQ ID NO:451, SEQ ID NO:453, SEQ ID NO:463 and SEQ ID NO:491.

10. The C5 binding polypeptide according to claim 9, wherein the amino acid sequence is selected from any one of SEQ ID NO:249-260.

11. The C5 binding polypeptide according to claim 10, wherein the amino acid sequence is selected from any one of SEQ ID NO:497-757.

12. The C5 binding polypeptide according to claim 11, wherein the amino acid sequence is selected from any one of SEQ ID NO:497-508, SEQ ID NO:516, SEQ ID NO:519-520, SEQ ID NO:522-524, SEQ ID NO:528-531, SEQ ID NO:534-535, SEQ ID NO:537, SEQ ID NO:542, SEQ ID NO:545, SEQ ID NO:552-553, SEQ ID NO:555, SEQ ID NO:562, SEQ ID NO:574-575, SEQ ID NO:583, SEQ ID NO:588, SEQ ID NO:602, SEQ ID NO:606, SEQ ID NO:615, SEQ ID NO:621, SEQ ID NO:637, SEQ ID NO:647, SEQ ID NO:657, SEQ ID NO:662, SEQ ID NO:683, SEQ ID NO:693, SEQ ID NO:699, SEQ ID NO:701, SEQ ID NO:711, SEQ ID NO:739 and SEQ ID NO:746-757.

13. The C5 binding polypeptide according to claim 12, wherein the amino acid sequence is selected from any one of SEQ ID NO:497-508 and SEQ ID NO:746-757.

14. The C5 binding polypeptide according to claim 13, wherein the amino acid sequence is selected from any one of SEQ ID NO:497, SEQ ID NO:498, SEQ ID NO:499, SEQ ID NO:500, SEQ ID NO:501, SEQ ID NO:746, SEQ ID NO:747, SEQ ID NO:748, SEQ ID NO:750 and SEQ ID NO:753.

15. The C5 binding polypeptide according to claim 1, which inhibits cleavage of C5.

16. The C5 binding polypeptide according to claim 1, wherein the C5 binding polypeptide binds to C5 such that the $K_D$ value of the interaction is at most $1 \times 10^{-6}$ M.

17. The C5 binding polypeptide according to claim 1, comprising further C terminal and/or N terminal amino acids that improve production, purification, stabilization in vivo or in vitro, coupling, or detection of the polypeptide.

18. The C5 binding polypeptide according to claim 1, wherein the polypeptide is in multimeric form, comprising at least two C5 binding polypeptide monomer units, the amino acid sequences of which may be the same or different.

19. A C5 binding compound, comprising at least one C5 binding polypeptide according to claim 1; at least one albumin binding domain of streptococcal protein G, or a derivative thereof; and at least one linking moiety for linking said at least one albumin binding domain or derivative thereof to the C or N terminal of said at least one C5 binding polypeptide.

20. The C5 binding compound according to claim 19, having a structure selected from

[CBP1]-[L1]-[ALBD];

[CBP1]-[CBP2]-[L1]-[ALBD];

[CBP1]-[L1]-[ALBD]-[L2]-[CBP2];

[ALBD]-[L1]-[CBP1];

[ALBD]-[L1]-[CBP1]-[CBP2];

[CBP1]-[L1]-[CBP2]-[L2]-[ALBD]; and

[ALBD]-[L1]-[CBP1]-[L2]-[CBP2]

wherein, independently of each other,

[CBP1] and [CBP2] are C5 binding polypeptides which may be the same or different;

[L1] and [L2] are linking moieties which may be the same or different; and

[ALBD] is an albumin binding domain of streptococcal protein G, or derivative thereof.

21. The C5 binding compound according to claim 20, wherein the linking moiety is selected from G; GS; $[G_2S]_n$; $[G_3S]_n$ (SEQ ID NO:783); $[G_4S]_n$ (SEQ ID NO:784); $GS[G_4S]_n$ (SEQ ID NO:785); $[S_2G]_m$; $[S_3G]_m$ (SEQ ID NO:786); $[S_4G]_m$ (SEQ ID NO:787); and VDGS (SEQ ID NO:788);

wherein n is 0-7; and wherein m is 0-7.

22. The C5 binding compound according to claim 19, wherein said albumin binding domain is as set out in SEQ ID NO:759.

23. The C5 binding compound according to claim 19, wherein each of said C5 binding polypeptides is independently selected from any one of SEQ ID NO:497-757.

24. A polynucleotide encoding a polypeptide according to claim 1.

25. A polynucleotide encoding a compound according to claim 19.

26. A combination of a C5 binding polypeptide according to claim 1 with a therapeutic agent.

27. A combination of a C5 binding compound according to claim 19 with a therapeutic agent.

28. A method of treatment of a C5 related condition, comprising administering a C5 binding polypeptide according to claim 1, a C5 binding compound according to claim 19, or the combination according to claim 26, to a mammalian subject in need thereof.

29. The method of treatment according to claim 28, in which binding of the C5 binding polypeptide, the C5 binding compound or the combination to C5 inhibits cleavage of C5.

30. The method of treatment according to claim 28, wherein said C5 related condition is selected from inflammatory disease; autoimmune disease; infectious disease; cardiovascular disease; neurodegenerative disorders; cancer; graft injury; wounds; eye disease; kidney disease; pulmonary diseases; hematological diseases; allergic diseases and dermatological diseases.

31. The method of treatment according to claim 30, wherein said C5 related condition is paroxysmal nocturnal hemoglobinuria (PNH).

32. The method of treatment according to claim 28, wherein said C5 binding polypeptide is administered intravenously, subcutaneously, by inhalation, nasally, orally, intravitreally, or topically.

33. The C5 binding polypeptide according to claim 1, wherein the C5 binding polypeptide binds to C5 such that the $K_D$ value of the interaction is at most $1 \times 10^{-7}$ M.

34. The C5 binding polypeptide according to claim 1, wherein the C5 binding polypeptide binds to C5 such that the $K_D$ value of the interaction is at most $1 \times 10^{-8}$ M.

35. The C5 binding polypeptide according to claim 1, wherein the C5 binding polypeptide binds to C5 such that the $K_D$ value of the interaction is at most $1 \times 10^{-9}$ M.

* * * * *

```
                          SEQUENCE LISTING

<160> NUMBER OF SEQ ID NOS: 789

<210> SEQ ID NO 1
<211> LENGTH: 29
<212> TYPE: PRT
<213> ORGANISM: artificial sequence
<220> FEATURE:
<223> OTHER INFORMATION: Modified bacterial sequence

<400> SEQUENCE: 1

Glu Val Leu Glu Ala Trp Asp Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 2
<211> LENGTH: 29
<212> TYPE: PRT
<213> ORGANISM: artificial sequence
<220> FEATURE:
<223> OTHER INFORMATION: Modified bacterial sequence

<400> SEQUENCE: 2

Glu Val Leu Glu Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 3
<211> LENGTH: 29
<212> TYPE: PRT
<213> ORGANISM: artificial sequence
<220> FEATURE:
<223> OTHER INFORMATION: Modified bacterial sequence

<400> SEQUENCE: 3

Glu Val Ile Glu Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 4
<211> LENGTH: 29
<212> TYPE: PRT
<213> ORGANISM: artificial sequence
<220> FEATURE:
<223> OTHER INFORMATION: Modified bacterial sequence

<400> SEQUENCE: 4

Glu Val Leu Glu Ala Trp Asp Glu Ile Asp Arg Leu Pro Asn Leu Thr
1               5                   10                  15

Leu Asp Gln Trp Leu Ala Phe Ile Asn Lys Leu Asp Asp
            20                  25

<210> SEQ ID NO 5
<211> LENGTH: 29
<212> TYPE: PRT
<213> ORGANISM: artificial sequence
<220> FEATURE:
<223> OTHER INFORMATION: Modified bacterial sequence
```

```
<400> SEQUENCE: 5

Glu Val Leu Asp Ala Trp Asp Glu Ile Asp Ala Leu Pro Asn Leu Thr
1               5                   10                  15

Leu Glu Gln Trp Leu Ala Phe Ile Asn Lys Leu Asp Asp
                20                  25

<210> SEQ ID NO 6
<211> LENGTH: 29
<212> TYPE: PRT
<213> ORGANISM: artificial sequence
<220> FEATURE:
<223> OTHER INFORMATION: Modified bacterial sequence

<400> SEQUENCE: 6

Glu Val Ile Asp Ala Trp Asp Glu Ile Asp Arg Leu Pro Asn Leu Thr
1               5                   10                  15

Leu Asp Gln Trp Leu Ala Phe Ile Asn Lys Leu Asp Asp
                20                  25

<210> SEQ ID NO 7
<211> LENGTH: 29
<212> TYPE: PRT
<213> ORGANISM: artificial sequence
<220> FEATURE:
<223> OTHER INFORMATION: Modified bacterial sequence

<400> SEQUENCE: 7

Glu Thr Leu Glu Ala Trp Asp Glu Ile Asp Arg Leu Pro Asn Leu Thr
1               5                   10                  15

Ile Glu Gln Trp Leu Ala Phe Ile Asn Lys Leu Asp Asp
                20                  25

<210> SEQ ID NO 8
<211> LENGTH: 29
<212> TYPE: PRT
<213> ORGANISM: artificial sequence
<220> FEATURE:
<223> OTHER INFORMATION: Modified bacterial sequence

<400> SEQUENCE: 8

Glu Val Ile Asp Ala Trp Asn Glu Ile Asp Ala Leu Pro Asn Leu Thr
1               5                   10                  15

Leu Asp Gln Trp Leu Ala Phe Ile Asn Lys Leu Asp Asp
                20                  25

<210> SEQ ID NO 9
<211> LENGTH: 29
<212> TYPE: PRT
<213> ORGANISM: artificial sequence
<220> FEATURE:
<223> OTHER INFORMATION: Modified bacterial sequence

<400> SEQUENCE: 9

Glu Val Leu Asp Ala Trp Asp Glu Ile Asp Lys Leu Pro Asn Leu Thr
1               5                   10                  15

Ile Asp Gln Trp Leu Ala Phe Ile Asn Lys Leu Asp Asp
                20                  25

<210> SEQ ID NO 10
<211> LENGTH: 29
<212> TYPE: PRT
<213> ORGANISM: artificial sequence
<220> FEATURE:
<223> OTHER INFORMATION: Modified bacterial sequence
```

<400> SEQUENCE: 10

Glu Val Leu Glu Ala Trp Asp Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 11
<211> LENGTH: 29
<212> TYPE: PRT
<213> ORGANISM: artificial sequence
<220> FEATURE:
<223> OTHER INFORMATION: Modified bacterial sequence

<400> SEQUENCE: 11

Glu Val Leu Glu Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 12
<211> LENGTH: 29
<212> TYPE: PRT
<213> ORGANISM: artificial sequence
<220> FEATURE:
<223> OTHER INFORMATION: Modified bacterial sequence

<400> SEQUENCE: 12

Glu Val Leu Asp Ala Trp Asp Glu Ile Asp Lys Leu Pro Asn Leu Thr
1               5                   10                  15

Leu Glu Gln Trp Leu Ala Phe Ile Asn Lys Leu Asp Asp
            20                  25

<210> SEQ ID NO 13
<211> LENGTH: 29
<212> TYPE: PRT
<213> ORGANISM: artificial sequence
<220> FEATURE:
<223> OTHER INFORMATION: Modified bacterial sequence

<400> SEQUENCE: 13

Glu Thr Ile Thr Ala Trp Asp Glu Ile Asp Lys Leu Pro Asn Leu Thr
1               5                   10                  15

Ile Glu Gln Trp Leu Ala Phe Ile Gly Lys Leu Glu Asp
            20                  25

<210> SEQ ID NO 14
<211> LENGTH: 29
<212> TYPE: PRT
<213> ORGANISM: artificial sequence
<220> FEATURE:
<223> OTHER INFORMATION: Modified bacterial sequence

<400> SEQUENCE: 14

Glu Ser Met Lys Ala Trp Asp Glu Ile Asp Arg Leu Pro Asn Leu Asn
1               5                   10                  15

Ile Asn Gln Trp Val Ala Phe Ile Asp Ser Leu Tyr Asp
            20                  25

<210> SEQ ID NO 15
<211> LENGTH: 29
<212> TYPE: PRT
<213> ORGANISM: artificial sequence
<220> FEATURE:

<223> OTHER INFORMATION: Modified bacterial sequence

<400> SEQUENCE: 15

Glu Ser Ile Glu Ala Trp Thr Glu Ile Asp His Leu Pro Asn Leu Thr
1               5                   10                  15

Ile Glu Gln Trp Leu Ala Phe Ile Asn Lys Leu Thr Asp
            20                  25

<210> SEQ ID NO 16
<211> LENGTH: 29
<212> TYPE: PRT
<213> ORGANISM: artificial sequence
<220> FEATURE:
<223> OTHER INFORMATION: Modified bacterial sequence

<400> SEQUENCE: 16

Glu Val Leu Asp Ala Trp His Glu Ile Asp Thr Leu Pro Asn Leu Thr
1               5                   10                  15

Val Arg Gln Trp Leu Ala Phe Ile Ser Lys Leu Glu Asp
            20                  25

<210> SEQ ID NO 17
<211> LENGTH: 29
<212> TYPE: PRT
<213> ORGANISM: artificial sequence
<220> FEATURE:
<223> OTHER INFORMATION: Modified bacterial sequence

<400> SEQUENCE: 17

Glu His Ile Gln Ala Asn Glu Glu Ile Asp Arg Leu Pro Asn Leu Thr
1               5                   10                  15

Ile Lys Gln Trp Leu Ala Phe Ile Asn Lys Leu His Asp
            20                  25

<210> SEQ ID NO 18
<211> LENGTH: 29
<212> TYPE: PRT
<213> ORGANISM: artificial sequence
<220> FEATURE:
<223> OTHER INFORMATION: Modified bacterial sequence

<400> SEQUENCE: 18

Glu Val Leu His Ala Trp Ala Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 19
<211> LENGTH: 29
<212> TYPE: PRT
<213> ORGANISM: artificial sequence
<220> FEATURE:
<223> OTHER INFORMATION: Modified bacterial sequence

<400> SEQUENCE: 19

Glu Val Leu Ala Ala Trp Asp Glu Ile Asp Ser Leu Pro Asn Leu Thr
1               5                   10                  15

Leu Gln Gln Trp Leu Ala Phe Ile Asn Lys Leu Asp Asp
            20                  25

<210> SEQ ID NO 20
<211> LENGTH: 29
<212> TYPE: PRT
<213> ORGANISM: artificial sequence

```
<220> FEATURE:
<223> OTHER INFORMATION: Modified bacterial sequence

<400> SEQUENCE: 20

Glu Val Ile Asp Ala Trp Asn Glu Ile Asp Ala Leu Pro Asn Leu Thr
1               5                   10                  15

Leu Glu Gln Trp Leu Ala Phe Ile Asn Lys Leu Asp Asp
            20                  25

<210> SEQ ID NO 21
<211> LENGTH: 29
<212> TYPE: PRT
<213> ORGANISM: artificial sequence
<220> FEATURE:
<223> OTHER INFORMATION: Modified bacterial sequence

<400> SEQUENCE: 21

Glu Val Leu Asp Ala Trp Asn Glu Ile Asp Ala Leu Pro Asn Leu Thr
1               5                   10                  15

Ile Asp Gln Trp Leu Ala Phe Ile Asn Lys Leu Ser Asp
            20                  25

<210> SEQ ID NO 22
<211> LENGTH: 29
<212> TYPE: PRT
<213> ORGANISM: artificial sequence
<220> FEATURE:
<223> OTHER INFORMATION: Modified bacterial sequence

<400> SEQUENCE: 22

Glu Val Ile Glu Ala Trp Asp Glu Ile Asp Gly Leu Pro Asn Leu Thr
1               5                   10                  15

Ile Glu Gln Trp Leu Ala Phe Ile Asn Lys Leu Asp Asp
            20                  25

<210> SEQ ID NO 23
<211> LENGTH: 29
<212> TYPE: PRT
<213> ORGANISM: artificial sequence
<220> FEATURE:
<223> OTHER INFORMATION: Modified bacterial sequence

<400> SEQUENCE: 23

Glu Val Leu Glu Ala Trp Asp Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 24
<211> LENGTH: 29
<212> TYPE: PRT
<213> ORGANISM: artificial sequence
<220> FEATURE:
<223> OTHER INFORMATION: Modified bacterial sequence

<400> SEQUENCE: 24

Glu Val Ile Glu Ala Trp Asn Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 25
<211> LENGTH: 29
<212> TYPE: PRT
```

```
<213> ORGANISM: artificial sequence
<220> FEATURE:
<223> OTHER INFORMATION: Modified bacterial sequence

<400> SEQUENCE: 25

Glu Val Ile Ala Ala Trp Asn Glu Ile Asp Arg Leu Pro Asn Leu Thr
1               5                   10                  15

Leu Thr Gln Trp Leu Ala Phe Ile Asn Lys Leu Asp Asp
            20                  25

<210> SEQ ID NO 26
<211> LENGTH: 29
<212> TYPE: PRT
<213> ORGANISM: artificial sequence
<220> FEATURE:
<223> OTHER INFORMATION: Modified bacterial sequence

<400> SEQUENCE: 26

Glu Val Ile Glu Ala Trp Asp Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 27
<211> LENGTH: 29
<212> TYPE: PRT
<213> ORGANISM: artificial sequence
<220> FEATURE:
<223> OTHER INFORMATION: Modified bacterial sequence

<400> SEQUENCE: 27

Glu Val Ile Ala Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 28
<211> LENGTH: 29
<212> TYPE: PRT
<213> ORGANISM: artificial sequence
<220> FEATURE:
<223> OTHER INFORMATION: Modified bacterial sequence

<400> SEQUENCE: 28

Glu Val Ile Ala Ala Trp Asp Glu Ile Asp Lys Leu Pro Asn Leu Thr
1               5                   10                  15

Leu Gln Gln Trp Leu Ala Phe Ile Asn Lys Leu Asp Asp
            20                  25

<210> SEQ ID NO 29
<211> LENGTH: 29
<212> TYPE: PRT
<213> ORGANISM: artificial sequence
<220> FEATURE:
<223> OTHER INFORMATION: Modified bacterial sequence

<400> SEQUENCE: 29

Glu Thr Ile Ala Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 30
<211> LENGTH: 29
```

<212> TYPE: PRT
<213> ORGANISM: artificial sequence
<220> FEATURE:
<223> OTHER INFORMATION: Modified bacterial sequence

<400> SEQUENCE: 30

Glu Thr Ile Glu Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 31
<211> LENGTH: 29
<212> TYPE: PRT
<213> ORGANISM: artificial sequence
<220> FEATURE:
<223> OTHER INFORMATION: Modified bacterial sequence

<400> SEQUENCE: 31

Glu Val Leu Glu Ala Trp Arg Glu Ile Asp Ala Leu Pro Asn Leu Thr
1               5                   10                  15

Ile Gln Gln Trp Leu Ala Phe Ile Asn Lys Leu Asp Asp
            20                  25

<210> SEQ ID NO 32
<211> LENGTH: 29
<212> TYPE: PRT
<213> ORGANISM: artificial sequence
<220> FEATURE:
<223> OTHER INFORMATION: Modified bacterial sequence

<400> SEQUENCE: 32

Glu Val Ile Glu Ala Trp Asp Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 33
<211> LENGTH: 29
<212> TYPE: PRT
<213> ORGANISM: artificial sequence
<220> FEATURE:
<223> OTHER INFORMATION: Modified bacterial sequence

<400> SEQUENCE: 33

Glu Val Leu Arg Ala Trp Asp Glu Ile Asp His Leu Pro Asn Leu Thr
1               5                   10                  15

Leu Glu Gln Trp Leu Ala Phe Ile Asn Lys Leu Asp Asp
            20                  25

<210> SEQ ID NO 34
<211> LENGTH: 29
<212> TYPE: PRT
<213> ORGANISM: artificial sequence
<220> FEATURE:
<223> OTHER INFORMATION: Modified bacterial sequence

<400> SEQUENCE: 34

Glu Val Leu Glu Ala Trp Asp Glu Ile Asp Arg Leu Pro Asn Leu Thr
1               5                   10                  15

Leu Asn Gln Trp Leu Ala Phe Ile Asn Lys Leu Asp Asp
            20                  25

<210> SEQ ID NO 35

-continued

```
<211> LENGTH: 29
<212> TYPE: PRT
<213> ORGANISM: artificial sequence
<220> FEATURE:
<223> OTHER INFORMATION: Modified bacterial sequence

<400> SEQUENCE: 35

Glu Val Leu Asp Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 36
<211> LENGTH: 29
<212> TYPE: PRT
<213> ORGANISM: artificial sequence
<220> FEATURE:
<223> OTHER INFORMATION: Modified bacterial sequence

<400> SEQUENCE: 36

Glu Val Ile Asp Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 37
<211> LENGTH: 29
<212> TYPE: PRT
<213> ORGANISM: artificial sequence
<220> FEATURE:
<223> OTHER INFORMATION: Modified bacterial sequence

<400> SEQUENCE: 37

Glu Thr Leu Glu Ala Trp Asp Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 38
<211> LENGTH: 29
<212> TYPE: PRT
<213> ORGANISM: artificial sequence
<220> FEATURE:
<223> OTHER INFORMATION: Modified bacterial sequence

<400> SEQUENCE: 38

Glu Val Ile Glu Ala Trp Asn Glu Ile Asp Ala Leu Pro Asn Leu Thr
1               5                   10                  15

Leu Asp Gln Trp Leu Ala Phe Ile Asn Lys Leu Asp Asp
            20                  25

<210> SEQ ID NO 39
<211> LENGTH: 29
<212> TYPE: PRT
<213> ORGANISM: artificial sequence
<220> FEATURE:
<223> OTHER INFORMATION: Modified bacterial sequence

<400> SEQUENCE: 39

Glu Val Ile Asp Ala Trp Asn Glu Ile Asp Arg Leu Pro Asn Leu Thr
1               5                   10                  15

Leu Gln Gln Trp Leu Ala Phe Ile Asn Lys Leu Asp Asp
            20                  25
```

```
<210> SEQ ID NO 40
<211> LENGTH: 29
<212> TYPE: PRT
<213> ORGANISM: artificial sequence
<220> FEATURE:
<223> OTHER INFORMATION: Modified bacterial sequence

<400> SEQUENCE: 40
```

Glu Val Ile Asp Ala Trp Asn Glu Ile Asp Gln Leu Pro Asn Leu Thr
1               5                   10                  15

Leu Glu Gln Trp Leu Ala Phe Ile Asn Lys Leu Asp Asp
            20                  25

```
<210> SEQ ID NO 41
<211> LENGTH: 29
<212> TYPE: PRT
<213> ORGANISM: artificial sequence
<220> FEATURE:
<223> OTHER INFORMATION: Modified bacterial sequence

<400> SEQUENCE: 41
```

Glu Thr Ile Ala Ala Trp Asp Glu Ile Asp His Leu Pro Asn Leu Thr
1               5                   10                  15

Leu Glu Gln Trp Leu Ala Phe Ile Asn Lys Leu Asp Asp
            20                  25

```
<210> SEQ ID NO 42
<211> LENGTH: 29
<212> TYPE: PRT
<213> ORGANISM: artificial sequence
<220> FEATURE:
<223> OTHER INFORMATION: Modified bacterial sequence

<400> SEQUENCE: 42
```

Glu Val Leu Gln Ala Trp Asp Glu Ile Asp His Leu Pro Asn Leu Thr
1               5                   10                  15

Ile Gln Gln Trp Leu Ala Phe Ile Asn Lys Leu Ser Asp
            20                  25

```
<210> SEQ ID NO 43
<211> LENGTH: 29
<212> TYPE: PRT
<213> ORGANISM: artificial sequence
<220> FEATURE:
<223> OTHER INFORMATION: Modified bacterial sequence

<400> SEQUENCE: 43
```

Glu Thr Leu His Ala Trp Ala Glu Ile Asp Arg Leu Pro Asn Leu Thr
1               5                   10                  15

Ile Glu Gln Trp Leu Ala Phe Ile Asn Lys Leu Asp Asp
            20                  25

```
<210> SEQ ID NO 44
<211> LENGTH: 29
<212> TYPE: PRT
<213> ORGANISM: artificial sequence
<220> FEATURE:
<223> OTHER INFORMATION: Modified bacterial sequence

<400> SEQUENCE: 44
```

Glu Val Leu Glu Ala Trp Asn Glu Ile Asp His Leu Pro Asn Leu Thr
1               5                   10                  15

Leu Ala Gln Trp Leu Ala Phe Ile Asn Lys Leu Asp Asp
            20                  25

<210> SEQ ID NO 45
<211> LENGTH: 29
<212> TYPE: PRT
<213> ORGANISM: artificial sequence
<220> FEATURE:
<223> OTHER INFORMATION: Modified bacterial sequence

<400> SEQUENCE: 45

Glu Val Ile Glu Ala Trp Asp Glu Ile Asp Lys Leu Pro Asn Leu Thr
1               5                   10                  15

Ile Ala Gln Trp Leu Ala Phe Ile Asn Lys Leu Asp Asp
            20                  25

<210> SEQ ID NO 46
<211> LENGTH: 29
<212> TYPE: PRT
<213> ORGANISM: artificial sequence
<220> FEATURE:
<223> OTHER INFORMATION: Modified bacterial sequence

<400> SEQUENCE: 46

Glu Val Leu Asp Ala Trp Asp Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 47
<211> LENGTH: 29
<212> TYPE: PRT
<213> ORGANISM: artificial sequence
<220> FEATURE:
<223> OTHER INFORMATION: Modified bacterial sequence

<400> SEQUENCE: 47

Glu Thr Ile Glu Ala Trp Asn Glu Ile Asp Lys Leu Pro Asn Leu Thr
1               5                   10                  15

Leu Thr Gln Trp Leu Ala Phe Ile Asn Lys Leu Asp Asp
            20                  25

<210> SEQ ID NO 48
<211> LENGTH: 29
<212> TYPE: PRT
<213> ORGANISM: artificial sequence
<220> FEATURE:
<223> OTHER INFORMATION: Modified bacterial sequence

<400> SEQUENCE: 48

Glu Val Leu Glu Ala Trp Asn Glu Ile Asp Leu Leu Pro Asn Leu Thr
1               5                   10                  15

Ile Glu Gln Trp Leu Ala Phe Ile Asn Lys Leu Asp Asp
            20                  25

<210> SEQ ID NO 49
<211> LENGTH: 29
<212> TYPE: PRT
<213> ORGANISM: artificial sequence
<220> FEATURE:
<223> OTHER INFORMATION: Modified bacterial sequence

<400> SEQUENCE: 49

Glu Val Ile Glu Ala Trp Asp Glu Ile Asp His Leu Pro Asn Leu Thr
1               5                   10                  15

Ile Asp Gln Trp Leu Ala Phe Ile Asn Lys Leu Asp Asp
            20                  25

```
<210> SEQ ID NO 50
<211> LENGTH: 29
<212> TYPE: PRT
<213> ORGANISM: artificial sequence
<220> FEATURE:
<223> OTHER INFORMATION: Modified bacterial sequence

<400> SEQUENCE: 50

Glu Val Ile Ser Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 51
<211> LENGTH: 29
<212> TYPE: PRT
<213> ORGANISM: artificial sequence
<220> FEATURE:
<223> OTHER INFORMATION: Modified bacterial sequence

<400> SEQUENCE: 51

Glu Val Ile Ala Ala Trp Asn Glu Ile Asp Lys Leu Pro Asn Leu Thr
1               5                   10                  15

Leu Glu Gln Trp Leu Ala Phe Ile Asn Lys Leu Asp Asp
            20                  25

<210> SEQ ID NO 52
<211> LENGTH: 29
<212> TYPE: PRT
<213> ORGANISM: artificial sequence
<220> FEATURE:
<223> OTHER INFORMATION: Modified bacterial sequence

<400> SEQUENCE: 52

Glu Thr Ile Glu Ala Trp Asn Glu Ile Asp Ser Leu Pro Asn Leu Thr
1               5                   10                  15

Leu Asp Gln Trp Leu Ala Phe Ile Asn Lys Leu Asp Asp
            20                  25

<210> SEQ ID NO 53
<211> LENGTH: 29
<212> TYPE: PRT
<213> ORGANISM: artificial sequence
<220> FEATURE:
<223> OTHER INFORMATION: Modified bacterial sequence

<400> SEQUENCE: 53

Glu Val Leu Asp Ala Trp Asn Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 54
<211> LENGTH: 29
<212> TYPE: PRT
<213> ORGANISM: artificial sequence
<220> FEATURE:
<223> OTHER INFORMATION: Modified bacterial sequence

<400> SEQUENCE: 54

Glu Val Leu Ala Ala Trp Asn Glu Ile Asp His Leu Pro Asn Leu Thr
1               5                   10                  15

Ile Glu Gln Trp Leu Ala Phe Ile Asn Lys Leu Asp Asp
```

<210> SEQ ID NO 55
<211> LENGTH: 29
<212> TYPE: PRT
<213> ORGANISM: artificial sequence
<220> FEATURE:
<223> OTHER INFORMATION: Modified bacterial sequence

<400> SEQUENCE: 55

Glu Val Leu Glu Ala Trp Asp Glu Ile Asp His Leu Pro Asn Leu Thr
1               5                   10                  15

Ile Thr Gln Trp Leu Ala Phe Ile Asn Lys Leu Asp Asp
            20                  25

<210> SEQ ID NO 56
<211> LENGTH: 29
<212> TYPE: PRT
<213> ORGANISM: artificial sequence
<220> FEATURE:
<223> OTHER INFORMATION: Modified bacterial sequence

<400> SEQUENCE: 56

Glu Thr Ile Asp Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 57
<211> LENGTH: 29
<212> TYPE: PRT
<213> ORGANISM: artificial sequence
<220> FEATURE:
<223> OTHER INFORMATION: Modified bacterial sequence

<400> SEQUENCE: 57

Glu Val Ile Glu Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 58
<211> LENGTH: 29
<212> TYPE: PRT
<213> ORGANISM: artificial sequence
<220> FEATURE:
<223> OTHER INFORMATION: Modified bacterial sequence

<400> SEQUENCE: 58

Glu Val Ile Gln Ala Trp Asn Glu Ile Asp Ala Leu Pro Asn Leu Thr
1               5                   10                  15

Ile Ser Gln Trp Leu Ala Phe Ile Asn Lys Leu Asp Asp
            20                  25

<210> SEQ ID NO 59
<211> LENGTH: 29
<212> TYPE: PRT
<213> ORGANISM: artificial sequence
<220> FEATURE:
<223> OTHER INFORMATION: Modified bacterial sequence

<400> SEQUENCE: 59

Glu Val Ile Ala Ala Trp Asp Glu Ile Asp Ser Leu Pro Asn Leu Thr
1               5                   10                  15

Ile Glu Gln Trp Leu Ala Phe Ile Asn Lys Leu Asp Asp
            20                  25

<210> SEQ ID NO 60
<211> LENGTH: 29
<212> TYPE: PRT
<213> ORGANISM: artificial sequence
<220> FEATURE:
<223> OTHER INFORMATION: Modified bacterial sequence

<400> SEQUENCE: 60

Glu His Ile Glu Ala Trp Asn Glu Ile Asp Ala Leu Pro Asn Leu Thr
1               5                   10                  15

Ile Glu Gln Trp Leu Ala Phe Ile Asn Lys Leu Gln Asp
            20                  25

<210> SEQ ID NO 61
<211> LENGTH: 29
<212> TYPE: PRT
<213> ORGANISM: artificial sequence
<220> FEATURE:
<223> OTHER INFORMATION: Modified bacterial sequence

<400> SEQUENCE: 61

Glu Val Leu Glu Ala Trp Asn Glu Ile Asp Lys Leu Pro Asn Leu Thr
1               5                   10                  15

Leu Asp Gln Trp Leu Ala Phe Ile Asn Lys Leu Asp Asp
            20                  25

<210> SEQ ID NO 62
<211> LENGTH: 29
<212> TYPE: PRT
<213> ORGANISM: artificial sequence
<220> FEATURE:
<223> OTHER INFORMATION: Modified bacterial sequence

<400> SEQUENCE: 62

Glu Val Ile Asp Ala Trp Asn Glu Ile Asp His Leu Pro Asn Leu Thr
1               5                   10                  15

Ile Glu Gln Trp Leu Ala Phe Ile Asn Lys Leu Ala Asp
            20                  25

<210> SEQ ID NO 63
<211> LENGTH: 29
<212> TYPE: PRT
<213> ORGANISM: artificial sequence
<220> FEATURE:
<223> OTHER INFORMATION: Modified bacterial sequence

<400> SEQUENCE: 63

Glu Thr Ile Asp Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 64
<211> LENGTH: 29
<212> TYPE: PRT
<213> ORGANISM: artificial sequence
<220> FEATURE:
<223> OTHER INFORMATION: Modified bacterial sequence

<400> SEQUENCE: 64

Glu Val Ile Ala Ala Trp Asp Glu Ile Asp Leu Leu Pro Asn Leu Thr
1               5                   10                  15

Leu Gln Gln Trp Leu Ala Phe Ile Asn Lys Leu Ala Asp
            20                  25

<210> SEQ ID NO 65
<211> LENGTH: 29
<212> TYPE: PRT
<213> ORGANISM: artificial sequence
<220> FEATURE:
<223> OTHER INFORMATION: Modified bacterial sequence

<400> SEQUENCE: 65

Glu Val Ile His Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 66
<211> LENGTH: 29
<212> TYPE: PRT
<213> ORGANISM: artificial sequence
<220> FEATURE:
<223> OTHER INFORMATION: Modified bacterial sequence

<400> SEQUENCE: 66

Glu Val Ile Ala Ala Trp Asn Glu Ile Asp His Leu Pro Asn Leu Thr
1               5                   10                  15

Leu Glu Gln Trp Leu Ala Phe Ile Asn Lys Leu Asp Asp
            20                  25

<210> SEQ ID NO 67
<211> LENGTH: 29
<212> TYPE: PRT
<213> ORGANISM: artificial sequence
<220> FEATURE:
<223> OTHER INFORMATION: Modified bacterial sequence

<400> SEQUENCE: 67

Glu Thr Leu Asp Ala Trp Asn Glu Ile Asp Lys Leu Pro Asn Leu Thr
1               5                   10                  15

Leu Ser Gln Trp Leu Ala Phe Ile Asn Lys Leu Asp Asp
            20                  25

<210> SEQ ID NO 68
<211> LENGTH: 29
<212> TYPE: PRT
<213> ORGANISM: artificial sequence
<220> FEATURE:
<223> OTHER INFORMATION: Modified bacterial sequence

<400> SEQUENCE: 68

Glu Val Leu Glu Ala Trp Asn Glu Ile Asp Ala Leu Pro Asn Leu Thr
1               5                   10                  15

Leu Glu Gln Trp Leu Ala Phe Ile Asn Lys Leu Asp Asp
            20                  25

<210> SEQ ID NO 69
<211> LENGTH: 29
<212> TYPE: PRT
<213> ORGANISM: artificial sequence
<220> FEATURE:
<223> OTHER INFORMATION: Modified bacterial sequence

<400> SEQUENCE: 69

Glu Val Ile Gln Ala Trp Asp Glu Ile Asp His Leu Pro Asn Leu Thr

```
                1               5                   10                  15
Ile Ser Gln Trp Leu Ala Phe Ile Asn Lys Leu Asp Asp
                20                  25

<210> SEQ ID NO 70
<211> LENGTH: 29
<212> TYPE: PRT
<213> ORGANISM: artificial sequence
<220> FEATURE:
<223> OTHER INFORMATION: Modified bacterial sequence

<400> SEQUENCE: 70

Glu Val Leu Gln Ala Trp Asp Glu Ile Asp Ser Leu Pro Asn Leu Thr
1               5                   10                  15

Ile Glu Gln Trp Leu Ala Phe Ile Asn Lys Leu Asp Asp
                20                  25

<210> SEQ ID NO 71
<211> LENGTH: 29
<212> TYPE: PRT
<213> ORGANISM: artificial sequence
<220> FEATURE:
<223> OTHER INFORMATION: Modified bacterial sequence

<400> SEQUENCE: 71

Glu Thr Leu Glu Ala Trp Asp Glu Ile Asp His Leu Pro Asn Leu Thr
1               5                   10                  15

Ile Ala Gln Trp Leu Ala Phe Ile Asn Lys Leu Asp Asp
                20                  25

<210> SEQ ID NO 72
<211> LENGTH: 29
<212> TYPE: PRT
<213> ORGANISM: artificial sequence
<220> FEATURE:
<223> OTHER INFORMATION: Modified bacterial sequence

<400> SEQUENCE: 72

Glu Thr Ile Asp Ala Trp Asn Glu Ile Asp Arg Leu Pro Asn Leu Thr
1               5                   10                  15

Ile Ser Gln Trp Leu Ala Phe Ile Asn Lys Leu Asp Asp
                20                  25

<210> SEQ ID NO 73
<211> LENGTH: 29
<212> TYPE: PRT
<213> ORGANISM: artificial sequence
<220> FEATURE:
<223> OTHER INFORMATION: Modified bacterial sequence

<400> SEQUENCE: 73

Glu Val Leu Asp Ala Trp His Glu Ile Asp His Leu Pro Asn Leu Thr
1               5                   10                  15

Ile Gln Gln Trp Leu Ala Phe Ile Asn Lys Leu Asp Asp
                20                  25

<210> SEQ ID NO 74
<211> LENGTH: 29
<212> TYPE: PRT
<213> ORGANISM: artificial sequence
<220> FEATURE:
<223> OTHER INFORMATION: Modified bacterial sequence

<400> SEQUENCE: 74
```

```
Glu Gln Ile Arg Ala Trp Asp Glu Ile Asp Lys Leu Pro Asn Leu Thr
1               5                   10                  15

Ile Glu Gln Trp Leu Ala Phe Ile Asn Lys Leu Ala Asp
            20                  25
```

<210> SEQ ID NO 75
<211> LENGTH: 29
<212> TYPE: PRT
<213> ORGANISM: artificial sequence
<220> FEATURE:
<223> OTHER INFORMATION: Modified bacterial sequence

<400> SEQUENCE: 75

```
Glu Thr Leu Tyr Ala Trp Asn Glu Ile Asp Lys Leu Pro Asn Leu Thr
1               5                   10                  15

Ile Glu Gln Trp Leu Ala Phe Ile Glu Lys Leu Gln Asp
            20                  25
```

<210> SEQ ID NO 76
<211> LENGTH: 29
<212> TYPE: PRT
<213> ORGANISM: artificial sequence
<220> FEATURE:
<223> OTHER INFORMATION: Modified bacterial sequence

<400> SEQUENCE: 76

```
Glu Val Ile Glu Ala Trp Asn Glu Ile Asp Ala Leu Pro Asn Leu Thr
1               5                   10                  15

Ile Asp Gln Trp Leu Ala Phe Ile Asn Lys Leu Asp Asp
            20                  25
```

<210> SEQ ID NO 77
<211> LENGTH: 29
<212> TYPE: PRT
<213> ORGANISM: artificial sequence
<220> FEATURE:
<223> OTHER INFORMATION: Modified bacterial sequence

<400> SEQUENCE: 77

```
Glu Val Leu Glu Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25
```

<210> SEQ ID NO 78
<211> LENGTH: 29
<212> TYPE: PRT
<213> ORGANISM: artificial sequence
<220> FEATURE:
<223> OTHER INFORMATION: Modified bacterial sequence

<400> SEQUENCE: 78

```
Glu Thr Ile Glu Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25
```

<210> SEQ ID NO 79
<211> LENGTH: 29
<212> TYPE: PRT
<213> ORGANISM: artificial sequence
<220> FEATURE:
<223> OTHER INFORMATION: Modified bacterial sequence

<400> SEQUENCE: 79

Glu Val Ile Glu Ala Trp Asn Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 80
<211> LENGTH: 29
<212> TYPE: PRT
<213> ORGANISM: artificial sequence
<220> FEATURE:
<223> OTHER INFORMATION: Modified bacterial sequence

<400> SEQUENCE: 80

Glu Val Ile Glu Ala Trp Asn Glu Ile Asp Lys Leu Pro Asn Leu Thr
1               5                   10                  15

Ile Gln Gln Trp Leu Ala Phe Ile Asn Lys Leu Asp Asp
            20                  25

<210> SEQ ID NO 81
<211> LENGTH: 29
<212> TYPE: PRT
<213> ORGANISM: artificial sequence
<220> FEATURE:
<223> OTHER INFORMATION: Modified bacterial sequence

<400> SEQUENCE: 81

Glu Thr Leu Asp Ala Trp Ala Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 82
<211> LENGTH: 29
<212> TYPE: PRT
<213> ORGANISM: artificial sequence
<220> FEATURE:
<223> OTHER INFORMATION: Modified bacterial sequence

<400> SEQUENCE: 82

Glu His Ile Asp Ala Trp Asn Glu Ile Asp Ala Leu Pro Asn Leu Thr
1               5                   10                  15

Leu Ser Gln Trp Leu Ala Phe Ile Asn Lys Leu Asp Asp
            20                  25

<210> SEQ ID NO 83
<211> LENGTH: 29
<212> TYPE: PRT
<213> ORGANISM: artificial sequence
<220> FEATURE:
<223> OTHER INFORMATION: Modified bacterial sequence

<400> SEQUENCE: 83

Glu Val Leu Asp Ala Trp Asn Glu Ile Asp Lys Leu Pro Asn Leu Thr
1               5                   10                  15

Ile Ala Gln Trp Leu Ala Phe Ile Asn Lys Leu Asp Asp
            20                  25

<210> SEQ ID NO 84
<211> LENGTH: 29
<212> TYPE: PRT
<213> ORGANISM: artificial sequence
<220> FEATURE:
<223> OTHER INFORMATION: Modified bacterial sequence

```
<400> SEQUENCE: 84

Glu Val Ile Glu Ala Trp Thr Glu Ile Asp Tyr Leu Pro Asn Leu Thr
1               5                   10                  15

Leu Gln Gln Trp Leu Ala Phe Ile Asn Lys Leu Asp Asp
            20                  25

<210> SEQ ID NO 85
<211> LENGTH: 29
<212> TYPE: PRT
<213> ORGANISM: artificial sequence
<220> FEATURE:
<223> OTHER INFORMATION: Modified bacterial sequence

<400> SEQUENCE: 85

Glu Thr Ile Glu Ala Trp Asn Glu Ile Asp His Leu Pro Asn Leu Thr
1               5                   10                  15

Ile Ala Gln Trp Leu Ala Phe Ile Asn Lys Leu Asp Asp
            20                  25

<210> SEQ ID NO 86
<211> LENGTH: 29
<212> TYPE: PRT
<213> ORGANISM: artificial sequence
<220> FEATURE:
<223> OTHER INFORMATION: Modified bacterial sequence

<400> SEQUENCE: 86

Glu Val Ile Gln Ala Trp Asn Glu Ile Asp Lys Leu Pro Asn Leu Thr
1               5                   10                  15

Leu Glu Gln Trp Leu Ala Phe Ile Asn Lys Leu Asp Asp
            20                  25

<210> SEQ ID NO 87
<211> LENGTH: 29
<212> TYPE: PRT
<213> ORGANISM: artificial sequence
<220> FEATURE:
<223> OTHER INFORMATION: Modified bacterial sequence

<400> SEQUENCE: 87

Glu Val Ile Glu Ala Trp Asp Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 88
<211> LENGTH: 29
<212> TYPE: PRT
<213> ORGANISM: artificial sequence
<220> FEATURE:
<223> OTHER INFORMATION: Modified bacterial sequence

<400> SEQUENCE: 88

Glu Thr Ile Asp Ala Trp Asn Glu Ile Asp Leu Leu Pro Asn Leu Thr
1               5                   10                  15

Ile Glu Gln Trp Leu Ala Phe Ile Asn Lys Leu Asp Asp
            20                  25

<210> SEQ ID NO 89
<211> LENGTH: 29
<212> TYPE: PRT
<213> ORGANISM: artificial sequence
<220> FEATURE:
<223> OTHER INFORMATION: Modified bacterial sequence
```

-continued

```
<400> SEQUENCE: 89

Glu His Ile Asp Ala Trp Asn Glu Ile Asp Lys Leu Pro Asn Leu Thr
1               5                   10                  15

Leu Asp Gln Trp Leu Ala Phe Ile Asn Lys Leu Asp Asp
            20                  25

<210> SEQ ID NO 90
<211> LENGTH: 29
<212> TYPE: PRT
<213> ORGANISM: artificial sequence
<220> FEATURE:
<223> OTHER INFORMATION: Modified bacterial sequence

<400> SEQUENCE: 90

Glu Val Val Ala Ala Trp Asn Glu Ile Asp Ala Leu Pro Asn Leu Thr
1               5                   10                  15

Ile Glu Gln Trp Leu Ala Phe Ile Asn Lys Leu Asn Asp
            20                  25

<210> SEQ ID NO 91
<211> LENGTH: 29
<212> TYPE: PRT
<213> ORGANISM: artificial sequence
<220> FEATURE:
<223> OTHER INFORMATION: Modified bacterial sequence

<400> SEQUENCE: 91

Glu Val Ile Glu Ala Trp Asn Glu Ile Asp Ala Leu Pro Asn Leu Thr
1               5                   10                  15

Leu Ala Gln Trp Leu Ala Phe Ile Asn Lys Leu Asp Asp
            20                  25

<210> SEQ ID NO 92
<211> LENGTH: 29
<212> TYPE: PRT
<213> ORGANISM: artificial sequence
<220> FEATURE:
<223> OTHER INFORMATION: Modified bacterial sequence

<400> SEQUENCE: 92

Glu Val Leu Gln Ala Trp Asp Glu Ile Asp Arg Leu Pro Asn Leu Thr
1               5                   10                  15

Leu Asp Gln Trp Leu Ala Phe Ile Asn Lys Leu Asp Asp
            20                  25

<210> SEQ ID NO 93
<211> LENGTH: 29
<212> TYPE: PRT
<213> ORGANISM: artificial sequence
<220> FEATURE:
<223> OTHER INFORMATION: Modified bacterial sequence

<400> SEQUENCE: 93

Glu Val Ile Asp Ala Trp Asp Glu Ile Asp His Leu Pro Asn Leu Thr
1               5                   10                  15

Ile Glu Gln Trp Leu Ala Phe Ile Asn Lys Leu Ser Asp
            20                  25

<210> SEQ ID NO 94
<211> LENGTH: 29
<212> TYPE: PRT
<213> ORGANISM: artificial sequence
<220> FEATURE:
```

<223> OTHER INFORMATION: Modified bacterial sequence

<400> SEQUENCE: 94

Glu Val Val Glu Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 95
<211> LENGTH: 29
<212> TYPE: PRT
<213> ORGANISM: artificial sequence
<220> FEATURE:
<223> OTHER INFORMATION: Modified bacterial sequence

<400> SEQUENCE: 95

Glu Val Ile Gln Ala Trp Asn Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 96
<211> LENGTH: 29
<212> TYPE: PRT
<213> ORGANISM: artificial sequence
<220> FEATURE:
<223> OTHER INFORMATION: Modified bacterial sequence

<400> SEQUENCE: 96

Glu Val Ile Gln Ala Trp Asp Glu Ile Asp Lys Leu Pro Asn Leu Thr
1               5                   10                  15

Ile Asp Gln Trp Leu Ala Phe Ile Asn Lys Leu Ala Asp
            20                  25

<210> SEQ ID NO 97
<211> LENGTH: 29
<212> TYPE: PRT
<213> ORGANISM: artificial sequence
<220> FEATURE:
<223> OTHER INFORMATION: Modified bacterial sequence

<400> SEQUENCE: 97

Glu Val Val Ala Ala Trp Asp Glu Ile Asp Ala Leu Pro Asn Leu Thr
1               5                   10                  15

Leu Thr Gln Trp Leu Ala Phe Ile Asn Lys Leu Asp Asp
            20                  25

<210> SEQ ID NO 98
<211> LENGTH: 29
<212> TYPE: PRT
<213> ORGANISM: artificial sequence
<220> FEATURE:
<223> OTHER INFORMATION: Modified bacterial sequence

<400> SEQUENCE: 98

Glu Val Ile Gln Ala Trp Asn Glu Ile Asp Gly Leu Pro Asn Leu Thr
1               5                   10                  15

Leu Ser Gln Trp Leu Ala Phe Ile Asn Lys Leu Asp Asp
            20                  25

<210> SEQ ID NO 99
<211> LENGTH: 29
<212> TYPE: PRT
<213> ORGANISM: artificial sequence
<220> FEATURE:
<223> OTHER INFORMATION: Modified bacterial sequence

<400> SEQUENCE: 99

Glu Thr Ile Glu Ala Trp Asp Glu Ile Asp Ala Leu Pro Asn Leu Thr
1               5                   10                  15

Ile Thr Gln Trp Leu Ala Phe Ile Asn Lys Leu Asp Asp
            20                  25

<210> SEQ ID NO 100
<211> LENGTH: 29
<212> TYPE: PRT
<213> ORGANISM: artificial sequence
<220> FEATURE:
<223> OTHER INFORMATION: Modified bacterial sequence

<400> SEQUENCE: 100

Glu Val Ile Asp Ala Trp Asn Glu Ile Asp His Leu Pro Asn Leu Thr
1               5                   10                  15

Ile Gln Gln Trp Leu Ala Phe Ile Asn Lys Leu Ala Asp
            20                  25

<210> SEQ ID NO 101
<211> LENGTH: 29
<212> TYPE: PRT
<213> ORGANISM: artificial sequence
<220> FEATURE:
<223> OTHER INFORMATION: Modified bacterial sequence

<400> SEQUENCE: 101

Glu Thr Ile Glu Ala Trp Asn Glu Ile Asp Ala Leu Pro Asn Leu Thr
1               5                   10                  15

Leu Asp Gln Trp Leu Ala Phe Ile Asn Lys Leu Glu Asp
            20                  25

<210> SEQ ID NO 102
<211> LENGTH: 29
<212> TYPE: PRT
<213> ORGANISM: artificial sequence
<220> FEATURE:
<223> OTHER INFORMATION: Modified bacterial sequence

<400> SEQUENCE: 102

Glu His Ile His Ala Trp Asn Glu Ile Asp Glu Leu Pro Asn Leu Thr
1               5                   10                  15

Ile Glu Gln Trp Leu Ala Phe Ile Asn Lys Leu Ala Asp
            20                  25

<210> SEQ ID NO 103
<211> LENGTH: 29
<212> TYPE: PRT
<213> ORGANISM: artificial sequence
<220> FEATURE:
<223> OTHER INFORMATION: Modified bacterial sequence

<400> SEQUENCE: 103

Glu Val Ile Asp Ala Trp Asp Glu Ile Asp His Leu Pro Asn Leu Thr
1               5                   10                  15

Ile Asp Gln Trp Leu Ala Phe Ile Asn Lys Leu Ser Asp
            20                  25

<210> SEQ ID NO 104
<211> LENGTH: 29
<212> TYPE: PRT

<213> ORGANISM: artificial sequence
<220> FEATURE:
<223> OTHER INFORMATION: Modified bacterial sequence

<400> SEQUENCE: 104

Glu Val Ile Asp Ala Asn Asp Glu Ile Asp Ala Leu Pro Asn Leu Thr
1               5                   10                  15

Ile Ala Gln Trp Leu Ala Phe Ile Asn Lys Leu His Asp
            20                  25

<210> SEQ ID NO 105
<211> LENGTH: 29
<212> TYPE: PRT
<213> ORGANISM: artificial sequence
<220> FEATURE:
<223> OTHER INFORMATION: Modified bacterial sequence

<400> SEQUENCE: 105

Glu Thr Ile Glu Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 106
<211> LENGTH: 29
<212> TYPE: PRT
<213> ORGANISM: artificial sequence
<220> FEATURE:
<223> OTHER INFORMATION: Modified bacterial sequence

<400> SEQUENCE: 106

Glu Val Leu Leu Ala Trp Asp Glu Ile Asp His Leu Pro Asn Leu Thr
1               5                   10                  15

Leu Glu Gln Trp Leu Ala Phe Ile Asn Lys Leu Asp Asp
            20                  25

<210> SEQ ID NO 107
<211> LENGTH: 29
<212> TYPE: PRT
<213> ORGANISM: artificial sequence
<220> FEATURE:
<223> OTHER INFORMATION: Modified bacterial sequence

<400> SEQUENCE: 107

Glu His Ile Asp Ala Trp Asn Glu Ile Asp Gly Leu Pro Asn Leu Thr
1               5                   10                  15

Leu Glu Gln Trp Leu Ala Phe Ile Asn Lys Leu Asp Asp
            20                  25

<210> SEQ ID NO 108
<211> LENGTH: 29
<212> TYPE: PRT
<213> ORGANISM: artificial sequence
<220> FEATURE:
<223> OTHER INFORMATION: Modified bacterial sequence

<400> SEQUENCE: 108

Glu Val Ile Glu Ala Trp Ser Glu Ile Asp Ala Leu Pro Asn Leu Thr
1               5                   10                  15

Ile Asp Gln Trp Leu Ala Phe Ile Asn Lys Leu Ala Asp
            20                  25

<210> SEQ ID NO 109
<211> LENGTH: 29

```
<212> TYPE: PRT
<213> ORGANISM: artificial sequence
<220> FEATURE:
<223> OTHER INFORMATION: Modified bacterial sequence

<400> SEQUENCE: 109

Glu Gln Leu Asn Ala Trp Ala Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 110
<211> LENGTH: 29
<212> TYPE: PRT
<213> ORGANISM: artificial sequence
<220> FEATURE:
<223> OTHER INFORMATION: Modified bacterial sequence

<400> SEQUENCE: 110

Glu Val Ile Asp Ala Trp Asn Glu Ile Asp Ala Leu Pro Asn Leu Thr
1               5                   10                  15

Ile Ala Gln Trp Leu Ala Phe Ile Asn Lys Leu Asp Asp
            20                  25

<210> SEQ ID NO 111
<211> LENGTH: 29
<212> TYPE: PRT
<213> ORGANISM: artificial sequence
<220> FEATURE:
<223> OTHER INFORMATION: Modified bacterial sequence

<400> SEQUENCE: 111

Glu Thr Ile Asp Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 112
<211> LENGTH: 29
<212> TYPE: PRT
<213> ORGANISM: artificial sequence
<220> FEATURE:
<223> OTHER INFORMATION: Modified bacterial sequence

<400> SEQUENCE: 112

Glu Val Ile Glu Ala Trp Asp Glu Ile Asp Lys Leu Pro Asn Leu Thr
1               5                   10                  15

Leu Ala Gln Trp Leu Ala Phe Ile Asn Lys Leu Asp Asp
            20                  25

<210> SEQ ID NO 113
<211> LENGTH: 29
<212> TYPE: PRT
<213> ORGANISM: artificial sequence
<220> FEATURE:
<223> OTHER INFORMATION: Modified bacterial sequence

<400> SEQUENCE: 113

Glu Val Leu Tyr Ala Trp Ala Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 114
```

```
<211> LENGTH: 29
<212> TYPE: PRT
<213> ORGANISM: artificial sequence
<220> FEATURE:
<223> OTHER INFORMATION: Modified bacterial sequence

<400> SEQUENCE: 114

Glu Gln Ile Asp Ala Trp Asn Glu Ile Asp Arg Leu Pro Asn Leu Thr
1               5                   10                  15

Ile Gln Gln Trp Leu Ala Phe Ile Asn Lys Leu Asp Asp
            20                  25

<210> SEQ ID NO 115
<211> LENGTH: 29
<212> TYPE: PRT
<213> ORGANISM: artificial sequence
<220> FEATURE:
<223> OTHER INFORMATION: Modified bacterial sequence

<400> SEQUENCE: 115

Glu Val Leu Ala Ala Trp Asp Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 116
<211> LENGTH: 29
<212> TYPE: PRT
<213> ORGANISM: artificial sequence
<220> FEATURE:
<223> OTHER INFORMATION: Modified bacterial sequence

<400> SEQUENCE: 116

Glu Val Ile Glu Ala Trp Asp Glu Ile Asp His Leu Pro Asn Leu Thr
1               5                   10                  15

Leu His Gln Trp Leu Ala Phe Ile Asn Lys Leu Asp Asp
            20                  25

<210> SEQ ID NO 117
<211> LENGTH: 29
<212> TYPE: PRT
<213> ORGANISM: artificial sequence
<220> FEATURE:
<223> OTHER INFORMATION: Modified bacterial sequence

<400> SEQUENCE: 117

Glu Val Ile Glu Ala Trp Asn Glu Ile Asp Lys Leu Pro Asn Leu Thr
1               5                   10                  15

Leu Gln Gln Trp Leu Ala Phe Ile Asn Lys Leu Asp Asp
            20                  25

<210> SEQ ID NO 118
<211> LENGTH: 29
<212> TYPE: PRT
<213> ORGANISM: artificial sequence
<220> FEATURE:
<223> OTHER INFORMATION: Modified bacterial sequence

<400> SEQUENCE: 118

Glu Val Ile Asp Ala Asn Asp Glu Ile Asp Ala Leu Pro Asn Leu Thr
1               5                   10                  15

Ile Glu Gln Trp Leu Ala Phe Ile Asn Lys Leu His Asp
            20                  25
```

```
<210> SEQ ID NO 119
<211> LENGTH: 29
<212> TYPE: PRT
<213> ORGANISM: artificial sequence
<220> FEATURE:
<223> OTHER INFORMATION: Modified bacterial sequence

<400> SEQUENCE: 119

Glu Val Ile Ala Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 120
<211> LENGTH: 29
<212> TYPE: PRT
<213> ORGANISM: artificial sequence
<220> FEATURE:
<223> OTHER INFORMATION: Modified bacterial sequence

<400> SEQUENCE: 120

Glu Val Ile Glu Ala Trp Thr Glu Ile Asp Gln Leu Pro Asn Leu Thr
1               5                   10                  15

Leu Asp Gln Trp Leu Ala Phe Ile Asn Lys Leu Asp Asp
            20                  25

<210> SEQ ID NO 121
<211> LENGTH: 29
<212> TYPE: PRT
<213> ORGANISM: artificial sequence
<220> FEATURE:
<223> OTHER INFORMATION: Modified bacterial sequence

<400> SEQUENCE: 121

Glu Val Ile Asn Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 122
<211> LENGTH: 29
<212> TYPE: PRT
<213> ORGANISM: artificial sequence
<220> FEATURE:
<223> OTHER INFORMATION: Modified bacterial sequence

<400> SEQUENCE: 122

Glu His Ile Glu Ala Trp Asp Glu Ile Asp His Leu Pro Asn Leu Thr
1               5                   10                  15

Ile Asp Gln Trp Leu Ala Phe Ile Asn Lys Leu Ala Asp
            20                  25

<210> SEQ ID NO 123
<211> LENGTH: 29
<212> TYPE: PRT
<213> ORGANISM: artificial sequence
<220> FEATURE:
<223> OTHER INFORMATION: Modified bacterial sequence

<400> SEQUENCE: 123

Glu His Leu Glu Ala Trp Arg Glu Ile Asp Ala Leu Pro Asn Leu Thr
1               5                   10                  15

Ile Glu Gln Trp Leu Ala Phe Ile Asn Lys Leu Asp Asp
            20                  25
```

```
<210> SEQ ID NO 124
<211> LENGTH: 29
<212> TYPE: PRT
<213> ORGANISM: artificial sequence
<220> FEATURE:
<223> OTHER INFORMATION: Modified bacterial sequence

<400> SEQUENCE: 124

Glu Val Leu Asp Ala Trp Asn Glu Ile Asp Lys Leu Pro Asn Leu Thr
1               5                   10                  15

Leu Gln Gln Trp Leu Ala Phe Ile Asn Lys Leu Asp Asp
            20                  25

<210> SEQ ID NO 125
<211> LENGTH: 29
<212> TYPE: PRT
<213> ORGANISM: artificial sequence
<220> FEATURE:
<223> OTHER INFORMATION: Modified bacterial sequence

<400> SEQUENCE: 125

Glu Val Ile Ala Ala Trp Asp Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 126
<211> LENGTH: 29
<212> TYPE: PRT
<213> ORGANISM: artificial sequence
<220> FEATURE:
<223> OTHER INFORMATION: Modified bacterial sequence

<400> SEQUENCE: 126

Glu Val Ile Gln Ala Trp Asn Glu Ile Asp Ala Leu Pro Asn Leu Thr
1               5                   10                  15

Leu Glu Gln Trp Leu Ala Phe Ile Asn Lys Leu Asp Asp
            20                  25

<210> SEQ ID NO 127
<211> LENGTH: 29
<212> TYPE: PRT
<213> ORGANISM: artificial sequence
<220> FEATURE:
<223> OTHER INFORMATION: Modified bacterial sequence

<400> SEQUENCE: 127

Glu Val Ile Asp Ala Trp Asn Glu Ile Asp His Leu Pro Asn Leu Thr
1               5                   10                  15

Ile Ala Gln Trp Leu Ala Phe Ile Asn Lys Leu Asp Asp
            20                  25

<210> SEQ ID NO 128
<211> LENGTH: 29
<212> TYPE: PRT
<213> ORGANISM: artificial sequence
<220> FEATURE:
<223> OTHER INFORMATION: Modified bacterial sequence

<400> SEQUENCE: 128

Glu Gln Leu Asp Ala Trp Asp Glu Ile Asp His Leu Pro Asn Leu Thr
1               5                   10                  15

Ile Asp Gln Trp Leu Ala Phe Ile Asn Lys Leu Ser Asp
            20                  25
```

<210> SEQ ID NO 129
<211> LENGTH: 29
<212> TYPE: PRT
<213> ORGANISM: artificial sequence
<220> FEATURE:
<223> OTHER INFORMATION: Modified bacterial sequence

<400> SEQUENCE: 129

Glu Val Leu Asn Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 130
<211> LENGTH: 29
<212> TYPE: PRT
<213> ORGANISM: artificial sequence
<220> FEATURE:
<223> OTHER INFORMATION: Modified bacterial sequence

<400> SEQUENCE: 130

Glu Val Leu Glu Ala Trp Asn Glu Ile Asp His Leu Pro Asn Leu Thr
1               5                   10                  15

Ile Asp Gln Trp Leu Ala Phe Ile Asn Lys Leu Asp Asp
            20                  25

<210> SEQ ID NO 131
<211> LENGTH: 29
<212> TYPE: PRT
<213> ORGANISM: artificial sequence
<220> FEATURE:
<223> OTHER INFORMATION: Modified bacterial sequence

<400> SEQUENCE: 131

Glu Val Leu Leu Ala Trp Asp Glu Ile Asp Arg Leu Pro Asn Leu Thr
1               5                   10                  15

Ile Asp Gln Trp Leu Ala Phe Ile Asn Lys Leu Ala Asp
            20                  25

<210> SEQ ID NO 132
<211> LENGTH: 29
<212> TYPE: PRT
<213> ORGANISM: artificial sequence
<220> FEATURE:
<223> OTHER INFORMATION: Modified bacterial sequence

<400> SEQUENCE: 132

Glu Val Ile Ala Ala Trp Asn Glu Ile Asp Gln Leu Pro Asn Leu Thr
1               5                   10                  15

Leu Asp Gln Trp Leu Ala Phe Ile Asn Lys Leu Asp Asp
            20                  25

<210> SEQ ID NO 133
<211> LENGTH: 29
<212> TYPE: PRT
<213> ORGANISM: artificial sequence
<220> FEATURE:
<223> OTHER INFORMATION: Modified bacterial sequence

<400> SEQUENCE: 133

Glu Thr Leu Leu Ala Trp Asp Glu Ile Asp Ala Leu Pro Asn Leu Thr
1               5                   10                  15

Ile Glu Gln Trp Leu Ala Phe Ile Asn Lys Leu Asp Asp

```
                20                  25

<210> SEQ ID NO 134
<211> LENGTH: 29
<212> TYPE: PRT
<213> ORGANISM: artificial sequence
<220> FEATURE:
<223> OTHER INFORMATION: Modified bacterial sequence

<400> SEQUENCE: 134

Glu Val Ile Asp Ala Trp Asn Glu Ile Asp Thr Leu Pro Asn Leu Thr
1               5                   10                  15

Leu Glu Gln Trp Leu Ala Phe Ile Asn Lys Leu Asp Asp
                20                  25

<210> SEQ ID NO 135
<211> LENGTH: 29
<212> TYPE: PRT
<213> ORGANISM: artificial sequence
<220> FEATURE:
<223> OTHER INFORMATION: Modified bacterial sequence

<400> SEQUENCE: 135

Glu Val Leu His Ala Trp Asn Glu Ile Asp His Leu Pro Asn Leu Thr
1               5                   10                  15

Leu Asn Gln Trp Leu Ala Phe Ile Asn Lys Leu Gln Asp
                20                  25

<210> SEQ ID NO 136
<211> LENGTH: 29
<212> TYPE: PRT
<213> ORGANISM: artificial sequence
<220> FEATURE:
<223> OTHER INFORMATION: Modified bacterial sequence

<400> SEQUENCE: 136

Glu Val Ile Gln Ala Trp Asn Glu Ile Asp Ala Leu Pro Asn Leu Thr
1               5                   10                  15

Ile Ala Gln Trp Leu Ala Phe Ile Asn Lys Leu Asp Asp
                20                  25

<210> SEQ ID NO 137
<211> LENGTH: 29
<212> TYPE: PRT
<213> ORGANISM: artificial sequence
<220> FEATURE:
<223> OTHER INFORMATION: Modified bacterial sequence

<400> SEQUENCE: 137

Glu Thr Val Asp Ala Trp Asn Glu Ile Asp Ala Leu Pro Asn Leu Thr
1               5                   10                  15

Ile Glu Gln Trp Leu Ala Phe Ile Asn Lys Leu Asp Asp
                20                  25

<210> SEQ ID NO 138
<211> LENGTH: 29
<212> TYPE: PRT
<213> ORGANISM: artificial sequence
<220> FEATURE:
<223> OTHER INFORMATION: Modified bacterial sequence

<400> SEQUENCE: 138

Glu Val Ile Gln Ala Trp Asp Glu Ile Asp His Leu Pro Asn Leu Thr
1               5                   10                  15
```

```
Ile Asp Gln Trp Leu Ala Phe Ile Asn Lys Leu Asp Asp
            20                  25

<210> SEQ ID NO 139
<211> LENGTH: 29
<212> TYPE: PRT
<213> ORGANISM: artificial sequence
<220> FEATURE:
<223> OTHER INFORMATION: Modified bacterial sequence

<400> SEQUENCE: 139

Glu Val Leu Asp Ala Trp Asn Glu Ile Asp Gln Leu Pro Asn Leu Thr
1               5                   10                  15

Ile Gln Gln Trp Leu Ala Phe Ile Asn Lys Leu Asp Asp
            20                  25

<210> SEQ ID NO 140
<211> LENGTH: 29
<212> TYPE: PRT
<213> ORGANISM: artificial sequence
<220> FEATURE:
<223> OTHER INFORMATION: Modified bacterial sequence

<400> SEQUENCE: 140

Glu Thr Ile Glu Ala Trp Asn Glu Ile Asp Ala Leu Pro Asn Leu Thr
1               5                   10                  15

Leu Asp Gln Trp Leu Ala Phe Ile Asn Lys Leu Asp Asp
            20                  25

<210> SEQ ID NO 141
<211> LENGTH: 29
<212> TYPE: PRT
<213> ORGANISM: artificial sequence
<220> FEATURE:
<223> OTHER INFORMATION: Modified bacterial sequence

<400> SEQUENCE: 141

Glu Val Ile Glu Ala Trp Asp Glu Ile Asp Ala Leu Pro Asn Leu Thr
1               5                   10                  15

Ile Asp Gln Trp Leu Ala Phe Ile Asn Lys Leu Asp Asp
            20                  25

<210> SEQ ID NO 142
<211> LENGTH: 29
<212> TYPE: PRT
<213> ORGANISM: artificial sequence
<220> FEATURE:
<223> OTHER INFORMATION: Modified bacterial sequence

<400> SEQUENCE: 142

Glu Val Ile Glu Ala Trp Asn Glu Ile Asp Gln Leu Pro Asn Leu Thr
1               5                   10                  15

Ile Gln Gln Trp Leu Ala Phe Ile Asn Lys Leu Asp Asp
            20                  25

<210> SEQ ID NO 143
<211> LENGTH: 29
<212> TYPE: PRT
<213> ORGANISM: artificial sequence
<220> FEATURE:
<223> OTHER INFORMATION: Modified bacterial sequence

<400> SEQUENCE: 143

Glu Val Ile Glu Ala Trp Thr Glu Ile Asp His Leu Pro Asn Leu Thr
1               5                   10                  15
```

-continued

Ile Glu Gln Trp Leu Ala Phe Ile Asn Lys Leu Asp Asp
            20                  25

<210> SEQ ID NO 144
<211> LENGTH: 29
<212> TYPE: PRT
<213> ORGANISM: artificial sequence
<220> FEATURE:
<223> OTHER INFORMATION: Modified bacterial sequence

<400> SEQUENCE: 144

Glu Val Ile Gln Ala Trp Asn Glu Ile Asp His Leu Pro Asn Leu Thr
1               5                   10                  15

Leu Gln Gln Trp Leu Ala Phe Ile Asn Lys Leu Glu Asp
            20                  25

<210> SEQ ID NO 145
<211> LENGTH: 29
<212> TYPE: PRT
<213> ORGANISM: artificial sequence
<220> FEATURE:
<223> OTHER INFORMATION: Modified bacterial sequence

<400> SEQUENCE: 145

Glu Val Ile Gln Ala Asn Asn Glu Ile Asp Gln Leu Pro Asn Leu Thr
1               5                   10                  15

Ile Glu Gln Trp Leu Ala Phe Ile Asn Lys Leu His Asp
            20                  25

<210> SEQ ID NO 146
<211> LENGTH: 29
<212> TYPE: PRT
<213> ORGANISM: artificial sequence
<220> FEATURE:
<223> OTHER INFORMATION: Modified bacterial sequence

<400> SEQUENCE: 146

Glu Val Leu His Ala Trp Ser Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 147
<211> LENGTH: 29
<212> TYPE: PRT
<213> ORGANISM: artificial sequence
<220> FEATURE:
<223> OTHER INFORMATION: Modified bacterial sequence

<400> SEQUENCE: 147

Glu Thr Ile Gln Ala Trp Asp Glu Ile Asp Lys Leu Pro Asn Leu Thr
1               5                   10                  15

Leu Asp Gln Trp Leu Ala Phe Ile Asn Lys Leu Ser Asp
            20                  25

<210> SEQ ID NO 148
<211> LENGTH: 29
<212> TYPE: PRT
<213> ORGANISM: artificial sequence
<220> FEATURE:
<223> OTHER INFORMATION: Modified bacterial sequence

<400> SEQUENCE: 148

Glu Thr Leu Arg Ala Trp Asp Glu Ile Asp Lys Leu Pro Asn Leu Thr

```
                1               5                   10                  15
Ile Gln Gln Trp Leu Ala Phe Ile Asn Lys Leu Ala Asp
                20                  25

<210> SEQ ID NO 149
<211> LENGTH: 29
<212> TYPE: PRT
<213> ORGANISM: artificial sequence
<220> FEATURE:
<223> OTHER INFORMATION: Modified bacterial sequence

<400> SEQUENCE: 149

Glu Val Ile Asp Ala Trp Asn Glu Ile Asp His Leu Pro Asn Leu Thr
1               5                   10                  15

Ile Glu Gln Trp Leu Ala Phe Ile Asn Lys Leu Glu Asp
                20                  25

<210> SEQ ID NO 150
<211> LENGTH: 29
<212> TYPE: PRT
<213> ORGANISM: artificial sequence
<220> FEATURE:
<223> OTHER INFORMATION: Modified bacterial sequence

<400> SEQUENCE: 150

Glu Val Ile Asp Ala Trp Asn Glu Ile Asp His Leu Pro Asn Leu Thr
1               5                   10                  15

Leu Gln Gln Trp Leu Ala Phe Ile Asn Lys Leu Ala Asp
                20                  25

<210> SEQ ID NO 151
<211> LENGTH: 29
<212> TYPE: PRT
<213> ORGANISM: artificial sequence
<220> FEATURE:
<223> OTHER INFORMATION: Modified bacterial sequence

<400> SEQUENCE: 151

Glu Thr Ile Asp Ala Trp Asn Glu Ile Asp Ala Leu Pro Asn Leu Thr
1               5                   10                  15

Leu Asp Gln Trp Leu Ala Phe Ile Asn Lys Leu Asp Asp
                20                  25

<210> SEQ ID NO 152
<211> LENGTH: 29
<212> TYPE: PRT
<213> ORGANISM: artificial sequence
<220> FEATURE:
<223> OTHER INFORMATION: Modified bacterial sequence

<400> SEQUENCE: 152

Glu Val Ile Glu Ala Trp Asn Glu Ile Asp Gln Leu Pro Asn Leu Thr
1               5                   10                  15

Ile Glu Gln Trp Leu Ala Phe Ile Asn Lys Leu Asp Asp
                20                  25

<210> SEQ ID NO 153
<211> LENGTH: 29
<212> TYPE: PRT
<213> ORGANISM: artificial sequence
<220> FEATURE:
<223> OTHER INFORMATION: Modified bacterial sequence

<400> SEQUENCE: 153
```

```
Glu Val Ile Arg Ala Trp Asp Glu Ile Asp Gln Leu Pro Asn Leu Thr
 1               5                  10                  15

Leu Ser Gln Trp Leu Ala Phe Ile Asn Lys Leu Asp Asp
            20                  25
```

<210> SEQ ID NO 154
<211> LENGTH: 29
<212> TYPE: PRT
<213> ORGANISM: artificial sequence
<220> FEATURE:
<223> OTHER INFORMATION: Modified bacterial sequence

<400> SEQUENCE: 154

```
Glu Val Ile Glu Ala Trp Asn Glu Ile Asp Arg Leu Pro Asn Leu Thr
 1               5                  10                  15

Ile His Gln Trp Leu Ala Phe Ile Asn Lys Leu Asp Asp
            20                  25
```

<210> SEQ ID NO 155
<211> LENGTH: 29
<212> TYPE: PRT
<213> ORGANISM: artificial sequence
<220> FEATURE:
<223> OTHER INFORMATION: Modified bacterial sequence

<400> SEQUENCE: 155

```
Glu Thr Ile Glu Ala Trp Asn Glu Ile Asp Gln Leu Pro Asn Leu Thr
 1               5                  10                  15

Ile Glu Gln Trp Leu Ala Phe Ile Asn Lys Leu Asp Asp
            20                  25
```

<210> SEQ ID NO 156
<211> LENGTH: 29
<212> TYPE: PRT
<213> ORGANISM: artificial sequence
<220> FEATURE:
<223> OTHER INFORMATION: Modified bacterial sequence

<400> SEQUENCE: 156

```
Glu Val Leu Thr Ala Trp Ala Glu Ile Asp Ala Leu Pro Asn Leu Thr
 1               5                  10                  15

Leu Ser Gln Trp Leu Ala Phe Ile Asn Lys Leu Asp Asp
            20                  25
```

<210> SEQ ID NO 157
<211> LENGTH: 29
<212> TYPE: PRT
<213> ORGANISM: artificial sequence
<220> FEATURE:
<223> OTHER INFORMATION: Modified bacterial sequence

<400> SEQUENCE: 157

```
Glu Val Ile Glu Ala Trp Asp Glu Ile Asp Lys Leu Pro Asn Leu Thr
 1               5                  10                  15

Val Asp Gln Trp Leu Ala Phe Ile Asn Lys Leu Asp Asp
            20                  25
```

<210> SEQ ID NO 158
<211> LENGTH: 29
<212> TYPE: PRT
<213> ORGANISM: artificial sequence
<220> FEATURE:
<223> OTHER INFORMATION: Modified bacterial sequence

<400> SEQUENCE: 158

```
Glu Val Ile Asp Ala Trp Asn Glu Ile Asp His Leu Pro Asn Leu Thr
1               5                   10                  15

Leu Thr Gln Trp Leu Ala Phe Ile Asn Lys Leu Asp Asp
            20                  25
```

<210> SEQ ID NO 159
<211> LENGTH: 29
<212> TYPE: PRT
<213> ORGANISM: artificial sequence
<220> FEATURE:
<223> OTHER INFORMATION: Modified bacterial sequence

<400> SEQUENCE: 159

```
Glu Val Ile Glu Ala Trp Asn Glu Ile Asp Gln Leu Pro Asn Leu Thr
1               5                   10                  15

Leu Asp Gln Trp Leu Ala Phe Ile Asn Lys Leu Asp Asp
            20                  25
```

<210> SEQ ID NO 160
<211> LENGTH: 29
<212> TYPE: PRT
<213> ORGANISM: artificial sequence
<220> FEATURE:
<223> OTHER INFORMATION: Modified bacterial sequence

<400> SEQUENCE: 160

```
Glu Thr Leu Gln Ala Trp Asp Glu Ile Asp His Leu Pro Asn Leu Thr
1               5                   10                  15

Leu Asn Gln Trp Leu Ala Phe Ile Asn Lys Leu Asp Asp
            20                  25
```

<210> SEQ ID NO 161
<211> LENGTH: 29
<212> TYPE: PRT
<213> ORGANISM: artificial sequence
<220> FEATURE:
<223> OTHER INFORMATION: Modified bacterial sequence

<400> SEQUENCE: 161

```
Glu Val Ile Asp Ala Trp Asn Glu Ile Asp His Leu Pro Asn Leu Thr
1               5                   10                  15

Ile Glu Gln Trp Leu Ala Phe Ile Asn Lys Leu Asp Asp
            20                  25
```

<210> SEQ ID NO 162
<211> LENGTH: 29
<212> TYPE: PRT
<213> ORGANISM: artificial sequence
<220> FEATURE:
<223> OTHER INFORMATION: Modified bacterial sequence

<400> SEQUENCE: 162

```
Glu Val Ile Glu Ala Trp Asn Glu Ile Asp Leu Leu Pro Asn Leu Thr
1               5                   10                  15

Leu Ser Gln Trp Leu Ala Phe Ile Asn Lys Leu Asp Asp
            20                  25
```

<210> SEQ ID NO 163
<211> LENGTH: 29
<212> TYPE: PRT
<213> ORGANISM: artificial sequence
<220> FEATURE:
<223> OTHER INFORMATION: Modified bacterial sequence -continued

```
<400> SEQUENCE: 163

Glu Val Ile Asp Ala Trp Asp Glu Ile Asp Arg Leu Pro Asn Leu Thr
1               5                   10                  15

Leu Lys Gln Trp Leu Ala Phe Ile Asn Lys Leu Asp Asp
            20                  25

<210> SEQ ID NO 164
<211> LENGTH: 29
<212> TYPE: PRT
<213> ORGANISM: artificial sequence
<220> FEATURE:
<223> OTHER INFORMATION: Modified bacterial sequence

<400> SEQUENCE: 164

Glu Thr Leu His Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 165
<211> LENGTH: 29
<212> TYPE: PRT
<213> ORGANISM: artificial sequence
<220> FEATURE:
<223> OTHER INFORMATION: Modified bacterial sequence

<400> SEQUENCE: 165

Glu Val Ile Lys Ala Trp Asp Glu Ile Asp His Leu Pro Asn Leu Thr
1               5                   10                  15

Leu Asn Gln Trp Leu Ala Phe Ile Asn Lys Leu Asp Asp
            20                  25

<210> SEQ ID NO 166
<211> LENGTH: 29
<212> TYPE: PRT
<213> ORGANISM: artificial sequence
<220> FEATURE:
<223> OTHER INFORMATION: Modified bacterial sequence

<400> SEQUENCE: 166

Glu Val Ile Glu Ala Trp Asn Glu Ile Asp His Leu Pro Asn Leu Thr
1               5                   10                  15

Leu Ala Gln Trp Leu Ala Phe Ile Asn Lys Leu Asp Asp
            20                  25

<210> SEQ ID NO 167
<211> LENGTH: 29
<212> TYPE: PRT
<213> ORGANISM: artificial sequence
<220> FEATURE:
<223> OTHER INFORMATION: Modified bacterial sequence

<400> SEQUENCE: 167

Glu Val Ile Gln Ala Trp Asn Glu Ile Asp His Leu Pro Asn Leu Thr
1               5                   10                  15

Ile Asp Gln Trp Leu Ala Phe Ile Thr Lys Leu Glu Asp
            20                  25

<210> SEQ ID NO 168
<211> LENGTH: 29
<212> TYPE: PRT
<213> ORGANISM: artificial sequence
<220> FEATURE:
<223> OTHER INFORMATION: Modified bacterial sequence
```

<400> SEQUENCE: 168

Glu Val Ile Glu Ala Trp Asn Glu Ile Asp Arg Leu Pro Asn Leu Thr
1               5                   10                  15

Ile Lys Gln Trp Leu Ala Phe Ile Asn Lys Leu Asp Asp
            20                  25

<210> SEQ ID NO 169
<211> LENGTH: 29
<212> TYPE: PRT
<213> ORGANISM: artificial sequence
<220> FEATURE:
<223> OTHER INFORMATION: Modified bacterial sequence

<400> SEQUENCE: 169

Glu Val Ile Glu Ala Trp Asn Glu Ile Asp Ser Leu Pro Asn Leu Thr
1               5                   10                  15

Leu Gln Gln Trp Leu Ala Phe Ile Asn Lys Leu Asp Asp
            20                  25

<210> SEQ ID NO 170
<211> LENGTH: 29
<212> TYPE: PRT
<213> ORGANISM: artificial sequence
<220> FEATURE:
<223> OTHER INFORMATION: Modified bacterial sequence

<400> SEQUENCE: 170

Glu Thr Ile Asp Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 171
<211> LENGTH: 29
<212> TYPE: PRT
<213> ORGANISM: artificial sequence
<220> FEATURE:
<223> OTHER INFORMATION: Modified bacterial sequence

<400> SEQUENCE: 171

Glu Val Leu Glu Ala Trp Ala Glu Ile Asp Ala Leu Pro Asn Leu Thr
1               5                   10                  15

Ile Ala Gln Trp Leu Ala Phe Ile Asn Lys Leu Asp Asp
            20                  25

<210> SEQ ID NO 172
<211> LENGTH: 29
<212> TYPE: PRT
<213> ORGANISM: artificial sequence
<220> FEATURE:
<223> OTHER INFORMATION: Modified bacterial sequence

<400> SEQUENCE: 172

Glu Thr Ile Asp Ala Trp Asn Glu Ile Asp Arg Leu Pro Asn Leu Thr
1               5                   10                  15

Ile Glu Gln Trp Leu Ala Phe Ile Asn Lys Leu Asp Asp
            20                  25

<210> SEQ ID NO 173
<211> LENGTH: 29
<212> TYPE: PRT
<213> ORGANISM: artificial sequence
<220> FEATURE:

<223> OTHER INFORMATION: Modified bacterial sequence

<400> SEQUENCE: 173

Glu Thr Leu Lys Ala Trp Asp Glu Ile Asp Arg Leu Pro Asn Leu Thr
1               5                   10                  15

Leu Glu Gln Trp Leu Ala Phe Ile Asn Lys Leu Asp Asp
            20                  25

<210> SEQ ID NO 174
<211> LENGTH: 29
<212> TYPE: PRT
<213> ORGANISM: artificial sequence
<220> FEATURE:
<223> OTHER INFORMATION: Modified bacterial sequence

<400> SEQUENCE: 174

Glu Thr Ile Ala Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 175
<211> LENGTH: 29
<212> TYPE: PRT
<213> ORGANISM: artificial sequence
<220> FEATURE:
<223> OTHER INFORMATION: Modified bacterial sequence

<400> SEQUENCE: 175

Glu Val Leu Gln Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 176
<211> LENGTH: 29
<212> TYPE: PRT
<213> ORGANISM: artificial sequence
<220> FEATURE:
<223> OTHER INFORMATION: Modified bacterial sequence

<400> SEQUENCE: 176

Glu Val Ile Glu Ala Trp Ser Glu Ile Asp His Leu Pro Asn Leu Thr
1               5                   10                  15

Leu Gln Gln Trp Leu Ala Phe Ile Asn Lys Leu Asp Asp
            20                  25

<210> SEQ ID NO 177
<211> LENGTH: 29
<212> TYPE: PRT
<213> ORGANISM: artificial sequence
<220> FEATURE:
<223> OTHER INFORMATION: Modified bacterial sequence

<400> SEQUENCE: 177

Glu Val Ile Asp Ala Trp Asn Glu Ile Asp Gly Leu Pro Asn Leu Thr
1               5                   10                  15

Ile Glu Gln Trp Leu Ala Phe Ile Asn Lys Leu Asp Asp
            20                  25

<210> SEQ ID NO 178
<211> LENGTH: 29
<212> TYPE: PRT
<213> ORGANISM: artificial sequence
<220> FEATURE:
<223> OTHER INFORMATION: Modified bacterial sequence

<400> SEQUENCE: 178

Glu Val Ile His Ala Trp Asn Glu Ile Asp His Leu Pro Asn Leu Thr
1               5                   10                  15

Leu Asn Gln Trp Leu Ala Phe Ile Asn Lys Leu Glu Asp
            20                  25

<210> SEQ ID NO 179
<211> LENGTH: 29
<212> TYPE: PRT
<213> ORGANISM: artificial sequence
<220> FEATURE:
<223> OTHER INFORMATION: Modified bacterial sequence

<400> SEQUENCE: 179

Glu Val Leu Asp Ala Trp Asn Glu Ile Asp Ser Leu Pro Asn Leu Thr
1               5                   10                  15

Leu Asp Gln Trp Leu Ala Phe Ile Asn Lys Leu Asp Asp
            20                  25

<210> SEQ ID NO 180
<211> LENGTH: 29
<212> TYPE: PRT
<213> ORGANISM: artificial sequence
<220> FEATURE:
<223> OTHER INFORMATION: Modified bacterial sequence

<400> SEQUENCE: 180

Glu Gln Ile Glu Ala Trp Asn Glu Ile Asp Arg Leu Pro Asn Leu Thr
1               5                   10                  15

Leu Glu Gln Trp Leu Ala Phe Ile Asn Lys Leu Asp Asp
            20                  25

<210> SEQ ID NO 181
<211> LENGTH: 29
<212> TYPE: PRT
<213> ORGANISM: artificial sequence
<220> FEATURE:
<223> OTHER INFORMATION: Modified bacterial sequence

<400> SEQUENCE: 181

Glu Val Val Asp Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 182
<211> LENGTH: 29
<212> TYPE: PRT
<213> ORGANISM: artificial sequence
<220> FEATURE:
<223> OTHER INFORMATION: Modified bacterial sequence

<400> SEQUENCE: 182

Glu Val Ile Glu Ala Trp Asn Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 183
<211> LENGTH: 29
<212> TYPE: PRT

-continued

```
<213> ORGANISM: artificial sequence
<220> FEATURE:
<223> OTHER INFORMATION: Modified bacterial sequence

<400> SEQUENCE: 183

Glu Val Ile Glu Ala Asn Asp Glu Ile Asp Arg Leu Pro Asn Leu Thr
1               5                   10                  15

Ile Glu Gln Trp Leu Ala Phe Ile Asn Lys Leu His Asp
            20                  25

<210> SEQ ID NO 184
<211> LENGTH: 29
<212> TYPE: PRT
<213> ORGANISM: artificial sequence
<220> FEATURE:
<223> OTHER INFORMATION: Modified bacterial sequence

<400> SEQUENCE: 184

Glu Thr Leu Gln Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 185
<211> LENGTH: 29
<212> TYPE: PRT
<213> ORGANISM: artificial sequence
<220> FEATURE:
<223> OTHER INFORMATION: Modified bacterial sequence

<400> SEQUENCE: 185

Glu Val Ile Glu Ala Trp Asp Glu Ile Asp His Leu Pro Asn Leu Thr
1               5                   10                  15

Ile Asp Gln Trp Leu Ala Phe Ile Asn Lys Leu Ala Asp
            20                  25

<210> SEQ ID NO 186
<211> LENGTH: 29
<212> TYPE: PRT
<213> ORGANISM: artificial sequence
<220> FEATURE:
<223> OTHER INFORMATION: Modified bacterial sequence

<400> SEQUENCE: 186

Glu Thr Ile Asp Ala Trp Asn Glu Ile Asp His Leu Pro Asn Leu Thr
1               5                   10                  15

Leu Gln Gln Trp Leu Ala Phe Ile Asn Lys Leu Ala Asp
            20                  25

<210> SEQ ID NO 187
<211> LENGTH: 29
<212> TYPE: PRT
<213> ORGANISM: artificial sequence
<220> FEATURE:
<223> OTHER INFORMATION: Modified bacterial sequence

<400> SEQUENCE: 187

Glu Val Ile Asp Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 188
<211> LENGTH: 29
```

```
<212> TYPE: PRT
<213> ORGANISM: artificial sequence
<220> FEATURE:
<223> OTHER INFORMATION: Modified bacterial sequence

<400> SEQUENCE: 188

Glu Val Ile Glu Ala Trp Asn Glu Ile Asp Lys Leu Pro Asn Leu Thr
1               5                   10                  15

Leu Ala Gln Trp Leu Ala Phe Ile Asn Lys Leu Asp Asp
            20                  25

<210> SEQ ID NO 189
<211> LENGTH: 29
<212> TYPE: PRT
<213> ORGANISM: artificial sequence
<220> FEATURE:
<223> OTHER INFORMATION: Modified bacterial sequence

<400> SEQUENCE: 189

Glu Val Leu Gln Ala Trp Asp Glu Ile Asp Lys Leu Pro Asn Leu Thr
1               5                   10                  15

Ile Gln Gln Trp Leu Ala Phe Ile Asn Lys Leu Asp Asp
            20                  25

<210> SEQ ID NO 190
<211> LENGTH: 29
<212> TYPE: PRT
<213> ORGANISM: artificial sequence
<220> FEATURE:
<223> OTHER INFORMATION: Modified bacterial sequence

<400> SEQUENCE: 190

Glu Val Ile Ala Ala Trp Asn Glu Ile Asp Gly Leu Pro Asn Leu Thr
1               5                   10                  15

Leu Gln Gln Trp Leu Ala Phe Ile Asn Lys Leu Asp Asp
            20                  25

<210> SEQ ID NO 191
<211> LENGTH: 29
<212> TYPE: PRT
<213> ORGANISM: artificial sequence
<220> FEATURE:
<223> OTHER INFORMATION: Modified bacterial sequence

<400> SEQUENCE: 191

Glu Thr Leu Asn Ala Trp Asn Glu Ile Asp Ala Leu Pro Asn Leu Thr
1               5                   10                  15

Leu Gln Gln Trp Leu Ala Phe Ile Asn Lys Leu Asp Asp
            20                  25

<210> SEQ ID NO 192
<211> LENGTH: 29
<212> TYPE: PRT
<213> ORGANISM: artificial sequence
<220> FEATURE:
<223> OTHER INFORMATION: Modified bacterial sequence

<400> SEQUENCE: 192

Glu Val Leu Ser Ala Trp Asn Glu Ile Asp Gln Leu Pro Asn Leu Thr
1               5                   10                  15

Leu Glu Gln Trp Leu Ala Phe Ile Asn Lys Leu Asp Asp
            20                  25

<210> SEQ ID NO 193
```

```
<211> LENGTH: 29
<212> TYPE: PRT
<213> ORGANISM: artificial sequence
<220> FEATURE:
<223> OTHER INFORMATION: Modified bacterial sequence

<400> SEQUENCE: 193

Glu Thr Leu Glu Ala Trp Asp Glu Ile Asp His Leu Pro Asn Leu Thr
1               5                   10                  15

Leu His Gln Trp Leu Ala Phe Ile Asn Lys Leu Asp Asp
            20                  25

<210> SEQ ID NO 194
<211> LENGTH: 29
<212> TYPE: PRT
<213> ORGANISM: artificial sequence
<220> FEATURE:
<223> OTHER INFORMATION: Modified bacterial sequence

<400> SEQUENCE: 194

Glu Gln Ile Glu Ala Trp Asn Glu Ile Asp His Leu Pro Asn Leu Thr
1               5                   10                  15

Leu Gln Gln Trp Leu Ala Phe Ile Asn Lys Leu Ala Asp
            20                  25

<210> SEQ ID NO 195
<211> LENGTH: 29
<212> TYPE: PRT
<213> ORGANISM: artificial sequence
<220> FEATURE:
<223> OTHER INFORMATION: Modified bacterial sequence

<400> SEQUENCE: 195

Glu Val Val Glu Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 196
<211> LENGTH: 29
<212> TYPE: PRT
<213> ORGANISM: artificial sequence
<220> FEATURE:
<223> OTHER INFORMATION: Modified bacterial sequence

<400> SEQUENCE: 196

Glu Val Leu Glu Ala Trp Asn Glu Ile Asp Glu Leu Pro Asn Leu Thr
1               5                   10                  15

Ile Glu Gln Trp Leu Ala Phe Ile Asn Lys Leu Asp Asp
            20                  25

<210> SEQ ID NO 197
<211> LENGTH: 29
<212> TYPE: PRT
<213> ORGANISM: artificial sequence
<220> FEATURE:
<223> OTHER INFORMATION: Modified bacterial sequence

<400> SEQUENCE: 197

Glu Val Ile Asp Ala Trp Asn Glu Ile Asp Gln Leu Pro Asn Leu Thr
1               5                   10                  15

Leu Gln Gln Trp Leu Ala Phe Ile Asn Lys Leu Asp Asp
            20                  25
```

```
<210> SEQ ID NO 198
<211> LENGTH: 29
<212> TYPE: PRT
<213> ORGANISM: artificial sequence
<220> FEATURE:
<223> OTHER INFORMATION: Modified bacterial sequence

<400> SEQUENCE: 198

Glu Thr Ile Asp Ala Trp Asp Glu Ile Asp Lys Leu Pro Asn Leu Thr
1               5                   10                  15

Leu Ser Gln Trp Leu Ala Phe Ile Asn Lys Leu Asp Asp
            20                  25

<210> SEQ ID NO 199
<211> LENGTH: 29
<212> TYPE: PRT
<213> ORGANISM: artificial sequence
<220> FEATURE:
<223> OTHER INFORMATION: Modified bacterial sequence

<400> SEQUENCE: 199

Glu Thr Ile Asp Ala Trp Asn Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 200
<211> LENGTH: 29
<212> TYPE: PRT
<213> ORGANISM: artificial sequence
<220> FEATURE:
<223> OTHER INFORMATION: Modified bacterial sequence

<400> SEQUENCE: 200

Glu Val Ile Gln Ala Trp Asp Glu Ile Asp Ala Leu Pro Asn Leu Thr
1               5                   10                  15

Leu Asn Gln Trp Leu Ala Phe Ile Asn Lys Leu Asp Asp
            20                  25

<210> SEQ ID NO 201
<211> LENGTH: 29
<212> TYPE: PRT
<213> ORGANISM: artificial sequence
<220> FEATURE:
<223> OTHER INFORMATION: Modified bacterial sequence

<400> SEQUENCE: 201

Glu Val Leu Asp Ala Trp Ala Glu Ile Asp Gln Leu Pro Asn Leu Thr
1               5                   10                  15

Leu Gln Gln Trp Leu Ala Phe Ile Asn Lys Leu Asp Asp
            20                  25

<210> SEQ ID NO 202
<211> LENGTH: 29
<212> TYPE: PRT
<213> ORGANISM: artificial sequence
<220> FEATURE:
<223> OTHER INFORMATION: Modified bacterial sequence

<400> SEQUENCE: 202

Glu His Ile Ala Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25
```

<210> SEQ ID NO 203
<211> LENGTH: 29
<212> TYPE: PRT
<213> ORGANISM: artificial sequence
<220> FEATURE:
<223> OTHER INFORMATION: Modified bacterial sequence

<400> SEQUENCE: 203

Glu Val Ile Arg Ala Trp Asp Glu Ile Asp Ala Leu Pro Asn Leu Thr
1               5                   10                  15

Ile Glu Gln Trp Leu Ala Phe Ile Asn Lys Leu Asp Asp
            20                  25

<210> SEQ ID NO 204
<211> LENGTH: 29
<212> TYPE: PRT
<213> ORGANISM: artificial sequence
<220> FEATURE:
<223> OTHER INFORMATION: Modified bacterial sequence

<400> SEQUENCE: 204

Glu Val Ile Asp Ala Trp Asp Glu Ile Asp Ala Leu Pro Asn Leu Thr
1               5                   10                  15

Ile Asp Gln Trp Leu Ala Phe Ile Asn Lys Leu Ala Asp
            20                  25

<210> SEQ ID NO 205
<211> LENGTH: 29
<212> TYPE: PRT
<213> ORGANISM: artificial sequence
<220> FEATURE:
<223> OTHER INFORMATION: Modified bacterial sequence

<400> SEQUENCE: 205

Glu Val Ile Asp Ala Trp Asn Glu Ile Asp Arg Leu Pro Asn Leu Thr
1               5                   10                  15

Ile Gln Gln Trp Leu Ala Phe Ile Asn Lys Leu Asp Asp
            20                  25

<210> SEQ ID NO 206
<211> LENGTH: 29
<212> TYPE: PRT
<213> ORGANISM: artificial sequence
<220> FEATURE:
<223> OTHER INFORMATION: Modified bacterial sequence

<400> SEQUENCE: 206

Glu Val Ile Thr Ala Trp Asn Glu Ile Asp His Leu Pro Asn Leu Thr
1               5                   10                  15

Leu Ser Gln Trp Leu Ala Phe Ile Asn Lys Leu Asp Asp
            20                  25

<210> SEQ ID NO 207
<211> LENGTH: 29
<212> TYPE: PRT
<213> ORGANISM: artificial sequence
<220> FEATURE:
<223> OTHER INFORMATION: Modified bacterial sequence

<400> SEQUENCE: 207

Glu Val Ile Asp Ala Trp Asn Glu Ile Asp Ala Leu Pro Asn Leu Thr
1               5                   10                  15

Ile His Gln Trp Leu Ala Phe Ile Asn Lys Leu Asp Asp
            20                  25

```
<210> SEQ ID NO 208
<211> LENGTH: 29
<212> TYPE: PRT
<213> ORGANISM: artificial sequence
<220> FEATURE:
<223> OTHER INFORMATION: Modified bacterial sequence

<400> SEQUENCE: 208

Glu Gln Leu Lys Ala Trp Asp Glu Ile Asp Lys Leu Pro Asn Leu Thr
1               5                   10                  15

Ile Glu Gln Trp Leu Ala Phe Ile Glu Lys Leu Gln Asp
            20                  25

<210> SEQ ID NO 209
<211> LENGTH: 29
<212> TYPE: PRT
<213> ORGANISM: artificial sequence
<220> FEATURE:
<223> OTHER INFORMATION: Modified bacterial sequence

<400> SEQUENCE: 209

Glu His Ile Asp Ala Trp Thr Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 210
<211> LENGTH: 29
<212> TYPE: PRT
<213> ORGANISM: artificial sequence
<220> FEATURE:
<223> OTHER INFORMATION: Modified bacterial sequence

<400> SEQUENCE: 210

Glu Gln Leu Arg Ala Trp Asp Glu Ile Asp Lys Leu Pro Asn Leu Thr
1               5                   10                  15

Ile Glu Gln Trp Leu Ala Phe Ile Asn Lys Leu Gln Asp
            20                  25

<210> SEQ ID NO 211
<211> LENGTH: 29
<212> TYPE: PRT
<213> ORGANISM: artificial sequence
<220> FEATURE:
<223> OTHER INFORMATION: Modified bacterial sequence

<400> SEQUENCE: 211

Glu Val Leu Glu Ala Trp Arg Glu Ile Asp Ser Leu Pro Asn Leu Thr
1               5                   10                  15

Ile Ala Gln Trp Leu Ala Phe Ile Asn Lys Leu Asp Asp
            20                  25

<210> SEQ ID NO 212
<211> LENGTH: 29
<212> TYPE: PRT
<213> ORGANISM: artificial sequence
<220> FEATURE:
<223> OTHER INFORMATION: Modified bacterial sequence

<400> SEQUENCE: 212

Glu Val Ile Gln Ala Trp Asn Glu Ile Asp Lys Leu Pro Asn Leu Thr
1               5                   10                  15

Ile Glu Gln Trp Leu Ala Phe Ile Asn Lys Leu Asp Asp
```

```
                20                  25

<210> SEQ ID NO 213
<211> LENGTH: 29
<212> TYPE: PRT
<213> ORGANISM: artificial sequence
<220> FEATURE:
<223> OTHER INFORMATION: Modified bacterial sequence

<400> SEQUENCE: 213

Glu His Val Glu Ala Trp Asn Glu Ile Asp Gln Leu Pro Asn Leu Thr
1               5                   10                  15

Ile Glu Gln Trp Leu Ala Phe Ile Asn Lys Leu Ala Asp
                20                  25

<210> SEQ ID NO 214
<211> LENGTH: 29
<212> TYPE: PRT
<213> ORGANISM: artificial sequence
<220> FEATURE:
<223> OTHER INFORMATION: Modified bacterial sequence

<400> SEQUENCE: 214

Glu Val Ile Asp Ala Trp Asp Glu Ile Asp Ala Leu Pro Asn Leu Thr
1               5                   10                  15

Ile Asp Gln Trp Leu Ala Phe Ile Asn Lys Leu Ser Asp
                20                  25

<210> SEQ ID NO 215
<211> LENGTH: 29
<212> TYPE: PRT
<213> ORGANISM: artificial sequence
<220> FEATURE:
<223> OTHER INFORMATION: Modified bacterial sequence

<400> SEQUENCE: 215

Glu Val Ile Glu Ala Trp Asn Glu Ile Asp His Leu Pro Asn Leu Thr
1               5                   10                  15

Ile Glu Gln Trp Leu Ala Phe Ile Asn Lys Leu Asp Asp
                20                  25

<210> SEQ ID NO 216
<211> LENGTH: 29
<212> TYPE: PRT
<213> ORGANISM: artificial sequence
<220> FEATURE:
<223> OTHER INFORMATION: Modified bacterial sequence

<400> SEQUENCE: 216

Glu Val Leu Gln Ala Trp Asp Glu Ile Asp Lys Leu Pro Asn Leu Thr
1               5                   10                  15

Ile Glu Gln Trp Leu Ala Phe Ile Asn Lys Leu Ser Asp
                20                  25

<210> SEQ ID NO 217
<211> LENGTH: 29
<212> TYPE: PRT
<213> ORGANISM: artificial sequence
<220> FEATURE:
<223> OTHER INFORMATION: Modified bacterial sequence

<400> SEQUENCE: 217

Glu Val Ile Lys Ala Trp Asn Glu Ile Asp Ser Leu Pro Asn Leu Thr
1               5                   10                  15
```

Ile Glu Gln Trp Leu Ala Phe Ile Asn Lys Leu Asp Asp
            20                  25

<210> SEQ ID NO 218
<211> LENGTH: 29
<212> TYPE: PRT
<213> ORGANISM: artificial sequence
<220> FEATURE:
<223> OTHER INFORMATION: Modified bacterial sequence

<400> SEQUENCE: 218

Glu Val Leu Glu Ala Trp His Glu Ile Asp Leu Leu Pro Asn Leu Thr
1               5                   10                  15

Ile Gln Gln Trp Leu Ala Phe Ile Asn Lys Leu Asp Asp
            20                  25

<210> SEQ ID NO 219
<211> LENGTH: 29
<212> TYPE: PRT
<213> ORGANISM: artificial sequence
<220> FEATURE:
<223> OTHER INFORMATION: Modified bacterial sequence

<400> SEQUENCE: 219

Glu Val Leu Glu Ala Trp Thr Glu Ile Asp Arg Leu Pro Asn Leu Thr
1               5                   10                  15

Leu Asp Gln Trp Leu Ala Phe Ile Asn Lys Leu Asp Asp
            20                  25

<210> SEQ ID NO 220
<211> LENGTH: 29
<212> TYPE: PRT
<213> ORGANISM: artificial sequence
<220> FEATURE:
<223> OTHER INFORMATION: Modified bacterial sequence

<400> SEQUENCE: 220

Glu Gln Leu Tyr Ala Trp Asn Glu Ile Asp His Leu Pro Asn Leu Thr
1               5                   10                  15

Ile Glu Gln Trp Leu Ala Phe Ile Glu Lys Leu Gln Asp
            20                  25

<210> SEQ ID NO 221
<211> LENGTH: 29
<212> TYPE: PRT
<213> ORGANISM: artificial sequence
<220> FEATURE:
<223> OTHER INFORMATION: Modified bacterial sequence

<400> SEQUENCE: 221

Glu Val Leu Asn Ala Trp Asp Glu Ile Asp Lys Leu Pro Asn Leu Thr
1               5                   10                  15

Ile Lys Gln Trp Leu Ala Phe Ile Asn Lys Leu Asp Asp
            20                  25

<210> SEQ ID NO 222
<211> LENGTH: 29
<212> TYPE: PRT
<213> ORGANISM: artificial sequence
<220> FEATURE:
<223> OTHER INFORMATION: Modified bacterial sequence

<400> SEQUENCE: 222

Glu Val Ile Arg Ala Trp Asp Glu Ile Asp Lys Leu Pro Asn Leu Thr
1               5                   10                  15

```
Val Glu Gln Trp Leu Ala Phe Ile Asn Lys Leu Asp Asp
            20                  25

<210> SEQ ID NO 223
<211> LENGTH: 29
<212> TYPE: PRT
<213> ORGANISM: artificial sequence
<220> FEATURE:
<223> OTHER INFORMATION: Modified bacterial sequence

<400> SEQUENCE: 223

Glu Val Val Gln Ala Trp Asp Glu Ile Asp Gln Leu Pro Asn Leu Thr
1               5                   10                  15

Leu Glu Gln Trp Leu Ala Phe Ile Asn Lys Leu Asp Asp
            20                  25

<210> SEQ ID NO 224
<211> LENGTH: 29
<212> TYPE: PRT
<213> ORGANISM: artificial sequence
<220> FEATURE:
<223> OTHER INFORMATION: Modified bacterial sequence

<400> SEQUENCE: 224

Glu Val Ile Arg Ala Trp Asp Glu Ile Asp Gln Leu Pro Asn Leu Thr
1               5                   10                  15

Leu Glu Gln Trp Leu Ala Phe Ile Asn Lys Leu Asp Asp
            20                  25

<210> SEQ ID NO 225
<211> LENGTH: 29
<212> TYPE: PRT
<213> ORGANISM: artificial sequence
<220> FEATURE:
<223> OTHER INFORMATION: Modified bacterial sequence

<400> SEQUENCE: 225

Glu Thr Ile Asp Ala Trp Asn Glu Ile Asp His Leu Pro Asn Leu Thr
1               5                   10                  15

Leu Asp Gln Trp Leu Ala Phe Ile Asn Lys Leu Asp Asp
            20                  25

<210> SEQ ID NO 226
<211> LENGTH: 29
<212> TYPE: PRT
<213> ORGANISM: artificial sequence
<220> FEATURE:
<223> OTHER INFORMATION: Modified bacterial sequence

<400> SEQUENCE: 226

Glu Val Val Ala Ala Trp Thr Glu Ile Asp Leu Leu Pro Asn Leu Thr
1               5                   10                  15

Leu Asp Gln Trp Leu Ala Phe Ile Asn Lys Leu Glu Asp
            20                  25

<210> SEQ ID NO 227
<211> LENGTH: 29
<212> TYPE: PRT
<213> ORGANISM: artificial sequence
<220> FEATURE:
<223> OTHER INFORMATION: Modified bacterial sequence

<400> SEQUENCE: 227

Glu Val Val Ala Ala Trp Asp Glu Ile Asp Ala Leu Pro Asn Leu Thr
```

```
                1               5                  10                  15
Ile Glu Gln Trp Leu Ala Phe Ile Asn Lys Leu Ser Asp
            20                  25
```

<210> SEQ ID NO 228
<211> LENGTH: 29
<212> TYPE: PRT
<213> ORGANISM: artificial sequence
<220> FEATURE:
<223> OTHER INFORMATION: Modified bacterial sequence

<400> SEQUENCE: 228

```
Glu Thr Leu Glu Ala Trp Arg Glu Ile Asp Ser Leu Pro Asn Leu Thr
1               5                  10                  15

Leu Glu Gln Trp Leu Ala Phe Ile Asn Lys Leu Asp Asp
            20                  25
```

<210> SEQ ID NO 229
<211> LENGTH: 29
<212> TYPE: PRT
<213> ORGANISM: artificial sequence
<220> FEATURE:
<223> OTHER INFORMATION: Modified bacterial sequence

<400> SEQUENCE: 229

```
Glu Val Ile Lys Ala Trp Asn Glu Ile Asp His Leu Pro Asn Leu Thr
1               5                  10                  15

Leu Asp Gln Trp Leu Ala Phe Ile Asn Lys Leu Asp Asp
            20                  25
```

<210> SEQ ID NO 230
<211> LENGTH: 29
<212> TYPE: PRT
<213> ORGANISM: artificial sequence
<220> FEATURE:
<223> OTHER INFORMATION: Modified bacterial sequence

<400> SEQUENCE: 230

```
Glu Val Leu Glu Ala Trp Thr Glu Ile Asp Lys Leu Pro Asn Leu Thr
1               5                  10                  15

Ile Asp Gln Trp Leu Ala Phe Ile Asn Lys Leu Asp Asp
            20                  25
```

<210> SEQ ID NO 231
<211> LENGTH: 29
<212> TYPE: PRT
<213> ORGANISM: artificial sequence
<220> FEATURE:
<223> OTHER INFORMATION: Modified bacterial sequence

<400> SEQUENCE: 231

```
Glu Thr Leu Glu Ala Trp Asp Glu Ile Asp Lys Leu Pro Asn Leu Thr
1               5                  10                  15

Ile Asp Gln Trp Leu Ala Phe Ile Asn Lys Leu Asp Asp
            20                  25
```

<210> SEQ ID NO 232
<211> LENGTH: 29
<212> TYPE: PRT
<213> ORGANISM: artificial sequence
<220> FEATURE:
<223> OTHER INFORMATION: Modified bacterial sequence

<400> SEQUENCE: 232

Glu Val Ile Glu Ala Trp Asn Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 233
<211> LENGTH: 29
<212> TYPE: PRT
<213> ORGANISM: artificial sequence
<220> FEATURE:
<223> OTHER INFORMATION: Modified bacterial sequence

<400> SEQUENCE: 233

Glu Thr Ile Asp Ala Trp Asn Glu Ile Asp Lys Leu Pro Asn Leu Thr
1               5                   10                  15

Leu Glu Gln Trp Leu Ala Phe Ile Asn Lys Leu Asp Asp
            20                  25

<210> SEQ ID NO 234
<211> LENGTH: 29
<212> TYPE: PRT
<213> ORGANISM: artificial sequence
<220> FEATURE:
<223> OTHER INFORMATION: Modified bacterial sequence

<400> SEQUENCE: 234

Glu Thr Leu Asp Ala Trp Asp Glu Ile Asp Ala Leu Pro Asn Leu Thr
1               5                   10                  15

Ile Asp Gln Trp Leu Ala Phe Ile Asn Lys Leu Glu Asp
            20                  25

<210> SEQ ID NO 235
<211> LENGTH: 29
<212> TYPE: PRT
<213> ORGANISM: artificial sequence
<220> FEATURE:
<223> OTHER INFORMATION: Modified bacterial sequence

<400> SEQUENCE: 235

Glu Val Leu Ser Ala Trp Asn Glu Ile Asp His Leu Pro Asn Leu Thr
1               5                   10                  15

Ile Gln Gln Trp Leu Ala Phe Ile Asn Lys Leu Asp Asp
            20                  25

<210> SEQ ID NO 236
<211> LENGTH: 29
<212> TYPE: PRT
<213> ORGANISM: artificial sequence
<220> FEATURE:
<223> OTHER INFORMATION: Modified bacterial sequence

<400> SEQUENCE: 236

Glu Val Ile Gln Ala Asn Asp Glu Ile Asp Lys Leu Pro Asn Leu Thr
1               5                   10                  15

Ile Glu Gln Trp Leu Ala Phe Ile His Lys Leu His Asp
            20                  25

<210> SEQ ID NO 237
<211> LENGTH: 29
<212> TYPE: PRT
<213> ORGANISM: artificial sequence
<220> FEATURE:
<223> OTHER INFORMATION: Modified bacterial sequence

<400> SEQUENCE: 237

```
Glu His Leu Asp Ala Trp Asp Glu Ile Asp His Leu Pro Asn Leu Thr
1               5                   10                  15

Ile Gln Gln Trp Leu Ala Phe Ile Asn Lys Leu Ala Asp
            20                  25

<210> SEQ ID NO 238
<211> LENGTH: 29
<212> TYPE: PRT
<213> ORGANISM: artificial sequence
<220> FEATURE:
<223> OTHER INFORMATION: Modified bacterial sequence

<400> SEQUENCE: 238

Glu Val Ile Gln Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 239
<211> LENGTH: 29
<212> TYPE: PRT
<213> ORGANISM: artificial sequence
<220> FEATURE:
<223> OTHER INFORMATION: Modified bacterial sequence

<400> SEQUENCE: 239

Glu Val Ile Glu Ala Trp Asn Glu Ile Asp Tyr Leu Pro Asn Leu Thr
1               5                   10                  15

Ile Ala Gln Trp Ile Ala Phe Ile Asn Lys Leu Asp Asp
            20                  25

<210> SEQ ID NO 240
<211> LENGTH: 29
<212> TYPE: PRT
<213> ORGANISM: artificial sequence
<220> FEATURE:
<223> OTHER INFORMATION: Modified bacterial sequence

<400> SEQUENCE: 240

Glu Thr Ile Gln Ala Trp Asp Glu Ile Asp Arg Leu Pro Asn Leu Thr
1               5                   10                  15

Leu Gln Gln Trp Leu Ala Phe Ile Asn Lys Leu Asp Asp
            20                  25

<210> SEQ ID NO 241
<211> LENGTH: 29
<212> TYPE: PRT
<213> ORGANISM: artificial sequence
<220> FEATURE:
<223> OTHER INFORMATION: Modified bacterial sequence

<400> SEQUENCE: 241

Glu Thr Ile Gln Ala Trp Asp Glu Ile Asp Lys Leu Pro Asn Leu Thr
1               5                   10                  15

Ile Glu Gln Trp Leu Ala Phe Ile Asn Lys Leu Asp Asp
            20                  25

<210> SEQ ID NO 242
<211> LENGTH: 29
<212> TYPE: PRT
<213> ORGANISM: artificial sequence
<220> FEATURE:
<223> OTHER INFORMATION: Modified bacterial sequence
```

<400> SEQUENCE: 242

Glu Thr Leu Asp Ala Trp Ala Glu Ile Asp His Leu Pro Asn Leu Thr
1               5                   10                  15

Ile Glu Gln Trp Leu Ala Phe Ile Asn Lys Leu Asp Asp
            20                  25

<210> SEQ ID NO 243
<211> LENGTH: 29
<212> TYPE: PRT
<213> ORGANISM: artificial sequence
<220> FEATURE:
<223> OTHER INFORMATION: Modified bacterial sequence

<400> SEQUENCE: 243

Glu Val Ile Glu Ala Trp Asp Glu Ile Asp Lys Leu Pro Asn Leu Thr
1               5                   10                  15

Leu Asn Gln Trp Leu Ala Phe Ile Asn Lys Leu Asp Asp
            20                  25

<210> SEQ ID NO 244
<211> LENGTH: 29
<212> TYPE: PRT
<213> ORGANISM: artificial sequence
<220> FEATURE:
<223> OTHER INFORMATION: Modified bacterial sequence

<400> SEQUENCE: 244

Glu Val Leu Asp Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 245
<211> LENGTH: 29
<212> TYPE: PRT
<213> ORGANISM: artificial sequence
<220> FEATURE:
<223> OTHER INFORMATION: Modified bacterial sequence

<400> SEQUENCE: 245

Glu Val Leu His Ala Trp Asn Glu Ile Asp His Leu Pro Asn Leu Thr
1               5                   10                  15

Ile Glu Gln Trp Leu Ala Phe Ile Glu Lys Leu Glu Asp
            20                  25

<210> SEQ ID NO 246
<211> LENGTH: 29
<212> TYPE: PRT
<213> ORGANISM: artificial sequence
<220> FEATURE:
<223> OTHER INFORMATION: Modified bacterial sequence

<400> SEQUENCE: 246

Glu Val Ile Glu Ala Trp Gln Glu Ile Asp Lys Leu Pro Asn Leu Thr
1               5                   10                  15

Ile Asp Gln Trp Leu Ala Phe Ile Asn Lys Leu Asp Asp
            20                  25

<210> SEQ ID NO 247
<211> LENGTH: 29
<212> TYPE: PRT
<213> ORGANISM: artificial sequence
<220> FEATURE:
<223> OTHER INFORMATION: Modified bacterial sequence

<400> SEQUENCE: 247

Glu Val Val Asp Ala Trp Asn Glu Ile Asp Gln Leu Pro Asn Leu Thr
1               5                   10                  15

Ile Glu Gln Trp Leu Ala Phe Ile Asn Lys Leu Asp Asp
            20                  25

<210> SEQ ID NO 248
<211> LENGTH: 29
<212> TYPE: PRT
<213> ORGANISM: artificial sequence
<220> FEATURE:
<223> OTHER INFORMATION: Modified bacterial sequence

<400> SEQUENCE: 248

Glu Gln Ile Glu Ala Trp Asn Glu Ile Asp Ala Leu Pro Asn Leu Thr
1               5                   10                  15

Ile Glu Gln Trp Leu Ala Phe Ile Asn Lys Leu Ala Asp
            20                  25

<210> SEQ ID NO 249
<211> LENGTH: 49
<212> TYPE: PRT
<213> ORGANISM: artificial sequence
<220> FEATURE:
<223> OTHER INFORMATION: Modified bacterial sequence

<400> SEQUENCE: 249

Lys Glu Val Leu Glu Ala Trp Asp Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 250
<211> LENGTH: 49
<212> TYPE: PRT
<213> ORGANISM: artificial sequence
<220> FEATURE:
<223> OTHER INFORMATION: Modified bacterial sequence

<400> SEQUENCE: 250

Lys Glu Val Leu Glu Ala Trp Asn Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 251
<211> LENGTH: 49
<212> TYPE: PRT
<213> ORGANISM: artificial sequence
<220> FEATURE:
<223> OTHER INFORMATION: Modified bacterial sequence

<400> SEQUENCE: 251

Lys Glu Val Ile Glu Ala Trp Asn Glu Ile Asp Arg Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 252
<211> LENGTH: 49
<212> TYPE: PRT
<213> ORGANISM: artificial sequence
<220> FEATURE:
<223> OTHER INFORMATION: Modified bacterial sequence

<400> SEQUENCE: 252

Lys Glu Val Leu Glu Ala Trp Asp Glu Ile Asp Arg Leu Pro Asn Leu
1               5                   10                  15

Thr Leu Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 253
<211> LENGTH: 49
<212> TYPE: PRT
<213> ORGANISM: artificial sequence
<220> FEATURE:
<223> OTHER INFORMATION: Modified bacterial sequence

<400> SEQUENCE: 253

Lys Glu Val Leu Asp Ala Trp Asp Glu Ile Asp Ala Leu Pro Asn Leu
1               5                   10                  15

Thr Leu Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 254
<211> LENGTH: 49
<212> TYPE: PRT
<213> ORGANISM: artificial sequence
<220> FEATURE:
<223> OTHER INFORMATION: Modified bacterial sequence

<400> SEQUENCE: 254

Lys Glu Val Ile Asp Ala Trp Asp Glu Ile Asp Arg Leu Pro Asn Leu
1               5                   10                  15

Thr Leu Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 255
<211> LENGTH: 49
<212> TYPE: PRT
<213> ORGANISM: artificial sequence
<220> FEATURE:
<223> OTHER INFORMATION: Modified bacterial sequence

<400> SEQUENCE: 255

Lys Glu Thr Leu Glu Ala Trp Asp Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 256
<211> LENGTH: 49
<212> TYPE: PRT
<213> ORGANISM: artificial sequence
<220> FEATURE:
<223> OTHER INFORMATION: Modified bacterial sequence

<400> SEQUENCE: 256

Lys Glu Val Ile Asp Ala Trp Asn Glu Ile Asp Ala Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 257
<211> LENGTH: 49
<212> TYPE: PRT
<213> ORGANISM: artificial sequence
<220> FEATURE:
<223> OTHER INFORMATION: Modified bacterial sequence

<400> SEQUENCE: 257

Lys Glu Val Leu Asp Ala Trp Asp Glu Ile Asp Lys Leu Pro Asn Leu
1               5                   10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 258
<211> LENGTH: 49
<212> TYPE: PRT
<213> ORGANISM: artificial sequence
<220> FEATURE:
<223> OTHER INFORMATION: Modified bacterial sequence

<400> SEQUENCE: 258

Lys Glu Val Leu Glu Ala Trp Asp Glu Ile Asp His Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 259

<211> LENGTH: 49
<212> TYPE: PRT
<213> ORGANISM: artificial sequence
<220> FEATURE:
<223> OTHER INFORMATION: Modified bacterial sequence

<400> SEQUENCE: 259

Lys Glu Val Leu Glu Ala Trp Asp Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 260
<211> LENGTH: 49
<212> TYPE: PRT
<213> ORGANISM: artificial sequence
<220> FEATURE:
<223> OTHER INFORMATION: Modified bacterial sequence

<400> SEQUENCE: 260

Lys Glu Val Leu Asp Ala Trp Asp Glu Ile Asp Lys Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 261
<211> LENGTH: 49
<212> TYPE: PRT
<213> ORGANISM: artificial sequence
<220> FEATURE:
<223> OTHER INFORMATION: Modified bacterial sequence

<400> SEQUENCE: 261

Lys Glu Thr Ile Thr Ala Trp Asp Glu Ile Asp Lys Leu Pro Asn Leu
1               5                   10                  15

Thr Ile Glu Gln Trp Leu Ala Phe Ile Gly Lys Leu Gly Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 262
<211> LENGTH: 49
<212> TYPE: PRT
<213> ORGANISM: artificial sequence
<220> FEATURE:
<223> OTHER INFORMATION: Modified bacterial sequence

<400> SEQUENCE: 262

Lys Glu Ser Met Lys Ala Trp Asp Glu Ile Asp Arg Leu Pro Asn Leu
1               5                   10                  15

Asn Ile Asn Gln Trp Val Ala Phe Ile Asp Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 263
<211> LENGTH: 49
<212> TYPE: PRT
<213> ORGANISM: artificial sequence
<220> FEATURE:
<223> OTHER INFORMATION: Modified bacterial sequence

<400> SEQUENCE: 263

Lys Glu Ser Ile Glu Ala Trp Thr Glu Ile Asp His Leu Pro Asn Leu
1               5                   10                  15

Thr Ile Glu Gln Trp Leu Ala Phe Ile Asn Lys Leu Thr Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 264
<211> LENGTH: 49
<212> TYPE: PRT
<213> ORGANISM: artificial sequence
<220> FEATURE:
<223> OTHER INFORMATION: Modified bacterial sequence

<400> SEQUENCE: 264

Lys Glu Val Leu Asp Ala Trp His Glu Ile Asp Thr Leu Pro Asn Leu
1               5                   10                  15

Thr Val Arg Gln Trp Leu Ala Phe Ile Ser Lys Leu Glu Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 265
<211> LENGTH: 49
<212> TYPE: PRT
<213> ORGANISM: artificial sequence
<220> FEATURE:
<223> OTHER INFORMATION: Modified bacterial sequence

<400> SEQUENCE: 265

Lys Glu His Ile Gln Ala Asn Glu Glu Ile Asp Arg Leu Pro Asn Leu
1               5                   10                  15

Thr Ile Lys Gln Trp Leu Ala Phe Ile Asn Lys Leu His Asp Asp Pro
            20                  25                  30

Ser Gln Ser Ser Glu Leu Leu Ala Glu Ala Lys Lys Leu Asn Asp Ala
        35                  40                  45

Gln

<210> SEQ ID NO 266
<211> LENGTH: 49
<212> TYPE: PRT
<213> ORGANISM: artificial sequence
<220> FEATURE:
<223> OTHER INFORMATION: Modified bacterial sequence

<400> SEQUENCE: 266

Lys Glu Val Leu His Ala Trp Ala Glu Ile Asp Ala Leu Pro Asn Leu
1               5                   10                  15

-continued

```
Thr Ile Glu Gln Trp Leu Ala Phe Ile Asn Lys Leu Asp Asp Pro
            20                  25                  30
Ser Gln Ser Ser Glu Leu Leu Ser Glu Ala Lys Lys Leu Asn Asp Ser
        35                  40                  45
Gln

<210> SEQ ID NO 267
<211> LENGTH: 49
<212> TYPE: PRT
<213> ORGANISM: artificial sequence
<220> FEATURE:
<223> OTHER INFORMATION: Modified bacterial sequence

<400> SEQUENCE: 267

Lys Glu Val Leu Ala Ala Trp Asp Glu Ile Asp Ser Leu Pro Asn Leu
1               5                   10                  15
Thr Leu Gln Gln Trp Leu Ala Phe Ile Asn Lys Leu Asp Asp Pro
            20                  25                  30
Ser Gln Ser Ser Glu Leu Leu Ser Glu Ala Lys Lys Leu Asn Asp Ser
        35                  40                  45
Gln

<210> SEQ ID NO 268
<211> LENGTH: 49
<212> TYPE: PRT
<213> ORGANISM: artificial sequence
<220> FEATURE:
<223> OTHER INFORMATION: Modified bacterial sequence

<400> SEQUENCE: 268

Lys Glu Val Ile Asp Ala Trp Asn Glu Ile Asp Ala Leu Pro Asn Leu
1               5                   10                  15
Thr Leu Glu Gln Trp Leu Ala Phe Ile Asn Lys Leu Asp Asp Pro
            20                  25                  30
Ser Gln Ser Ser Glu Leu Leu Ser Glu Ala Lys Lys Leu Asn Asp Ser
        35                  40                  45
Gln

<210> SEQ ID NO 269
<211> LENGTH: 49
<212> TYPE: PRT
<213> ORGANISM: artificial sequence
<220> FEATURE:
<223> OTHER INFORMATION: Modified bacterial sequence

<400> SEQUENCE: 269

Lys Glu Val Leu Asp Ala Trp Asn Glu Ile Asp Ala Leu Pro Asn Leu
1               5                   10                  15
Thr Ile Asp Gln Trp Leu Ala Phe Ile Asn Lys Leu Ser Asp Pro
            20                  25                  30
Ser Gln Ser Ser Glu Leu Leu Ser Glu Ala Lys Lys Leu Asn Asp Ser
        35                  40                  45
Gln

<210> SEQ ID NO 270
<211> LENGTH: 49
<212> TYPE: PRT
<213> ORGANISM: artificial sequence
<220> FEATURE:
<223> OTHER INFORMATION: Modified bacterial sequence
```

-continued

```
<400> SEQUENCE: 270

Lys Glu Val Ile Glu Ala Trp Asp Glu Ile Asp Gly Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 271
<211> LENGTH: 49
<212> TYPE: PRT
<213> ORGANISM: artificial sequence
<220> FEATURE:
<223> OTHER INFORMATION: Modified bacterial sequence

<400> SEQUENCE: 271

Lys Glu Val Leu Glu Ala Trp Asp Glu Ile Asp His Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 272
<211> LENGTH: 49
<212> TYPE: PRT
<213> ORGANISM: artificial sequence
<220> FEATURE:
<223> OTHER INFORMATION: Modified bacterial sequence

<400> SEQUENCE: 272

Lys Glu Val Ile Glu Ala Trp Asn Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 273
<211> LENGTH: 49
<212> TYPE: PRT
<213> ORGANISM: artificial sequence
<220> FEATURE:
<223> OTHER INFORMATION: Modified bacterial sequence

<400> SEQUENCE: 273

Lys Glu Val Ile Ala Ala Trp Asn Glu Ile Asp Arg Leu Pro Asn Leu
1               5                   10                  15

Thr Leu Thr Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 274
<211> LENGTH: 49
```

```
<212> TYPE: PRT
<213> ORGANISM: artificial sequence
<220> FEATURE:
<223> OTHER INFORMATION: Modified bacterial sequence

<400> SEQUENCE: 274

Lys Glu Val Ile Glu Ala Trp Asp Glu Ile Asp Ala Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 275
<211> LENGTH: 49
<212> TYPE: PRT
<213> ORGANISM: artificial sequence
<220> FEATURE:
<223> OTHER INFORMATION: Modified bacterial sequence

<400> SEQUENCE: 275

Lys Glu Val Ile Ala Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 276
<211> LENGTH: 49
<212> TYPE: PRT
<213> ORGANISM: artificial sequence
<220> FEATURE:
<223> OTHER INFORMATION: Modified bacterial sequence

<400> SEQUENCE: 276

Lys Glu Val Ile Ala Ala Trp Asp Glu Ile Asp Lys Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 277
<211> LENGTH: 49
<212> TYPE: PRT
<213> ORGANISM: artificial sequence
<220> FEATURE:
<223> OTHER INFORMATION: Modified bacterial sequence

<400> SEQUENCE: 277

Lys Glu Thr Ile Ala Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 278
<211> LENGTH: 49
<212> TYPE: PRT
<213> ORGANISM: artificial sequence
<220> FEATURE:
<223> OTHER INFORMATION: Modified bacterial sequence

<400> SEQUENCE: 278

Lys Glu Thr Ile Glu Ala Trp Asn Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 279
<211> LENGTH: 49
<212> TYPE: PRT
<213> ORGANISM: artificial sequence
<220> FEATURE:
<223> OTHER INFORMATION: Modified bacterial sequence

<400> SEQUENCE: 279

Lys Glu Val Leu Glu Ala Trp Arg Glu Ile Asp Ala Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 280
<211> LENGTH: 49
<212> TYPE: PRT
<213> ORGANISM: artificial sequence
<220> FEATURE:
<223> OTHER INFORMATION: Modified bacterial sequence

<400> SEQUENCE: 280

Lys Glu Val Ile Glu Ala Trp Asp Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 281
<211> LENGTH: 49
<212> TYPE: PRT
<213> ORGANISM: artificial sequence
<220> FEATURE:
<223> OTHER INFORMATION: Modified bacterial sequence

<400> SEQUENCE: 281

Lys Glu Val Leu Arg Ala Trp Asp Glu Ile Asp His Leu Pro Asn Leu
1               5                   10                  15

Thr Leu Glu Gln Trp Leu Ala Phe Ile Asn Lys Leu Asp Asp Asp Pro

Ser Gln Ser Ser Glu Leu Leu Ser Glu Ala Lys Lys Leu Asn Asp Ser
        35                  40                  45

Gln

<210> SEQ ID NO 282
<211> LENGTH: 49
<212> TYPE: PRT
<213> ORGANISM: artificial sequence
<220> FEATURE:
<223> OTHER INFORMATION: Modified bacterial sequence

<400> SEQUENCE: 282

Lys Glu Val Leu Glu Ala Trp Asp Glu Ile Asp Arg Leu Pro Asn Leu
1               5                   10                  15

Thr Leu Asn Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 283
<211> LENGTH: 49
<212> TYPE: PRT
<213> ORGANISM: artificial sequence
<220> FEATURE:
<223> OTHER INFORMATION: Modified bacterial sequence

<400> SEQUENCE: 283

Lys Glu Val Leu Asp Ala Trp Asn Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 284
<211> LENGTH: 49
<212> TYPE: PRT
<213> ORGANISM: artificial sequence
<220> FEATURE:
<223> OTHER INFORMATION: Modified bacterial sequence

<400> SEQUENCE: 284

Lys Glu Val Ile Asp Ala Trp Asn Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 285
<211> LENGTH: 49
<212> TYPE: PRT
<213> ORGANISM: artificial sequence
<220> FEATURE:
<223> OTHER INFORMATION: Modified bacterial sequence

<400> SEQUENCE: 285

```
Lys Glu Thr Leu Glu Ala Trp Asp Glu Ile Asp Gln Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 286
<211> LENGTH: 49
<212> TYPE: PRT
<213> ORGANISM: artificial sequence
<220> FEATURE:
<223> OTHER INFORMATION: Modified bacterial sequence

<400> SEQUENCE: 286

```
Lys Glu Val Ile Glu Ala Trp Asn Glu Ile Asp Ala Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 287
<211> LENGTH: 49
<212> TYPE: PRT
<213> ORGANISM: artificial sequence
<220> FEATURE:
<223> OTHER INFORMATION: Modified bacterial sequence

<400> SEQUENCE: 287

```
Lys Glu Val Ile Asp Ala Trp Asn Glu Ile Asp Arg Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 288
<211> LENGTH: 49
<212> TYPE: PRT
<213> ORGANISM: artificial sequence
<220> FEATURE:
<223> OTHER INFORMATION: Modified bacterial sequence

<400> SEQUENCE: 288

```
Lys Glu Val Ile Asp Ala Trp Asn Glu Ile Asp Gln Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 289
<211> LENGTH: 49
<212> TYPE: PRT

```
<213> ORGANISM: artificial sequence
<220> FEATURE:
<223> OTHER INFORMATION: Modified bacterial sequence

<400> SEQUENCE: 289

Lys Glu Thr Ile Ala Ala Trp Asp Glu Ile Asp His Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 290
<211> LENGTH: 49
<212> TYPE: PRT
<213> ORGANISM: artificial sequence
<220> FEATURE:
<223> OTHER INFORMATION: Modified bacterial sequence

<400> SEQUENCE: 290

Lys Glu Val Leu Gln Ala Trp Asp Glu Ile Asp His Leu Pro Asn Leu
1               5                   10                  15

Thr Ile Gln Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 291
<211> LENGTH: 49
<212> TYPE: PRT
<213> ORGANISM: artificial sequence
<220> FEATURE:
<223> OTHER INFORMATION: Modified bacterial sequence

<400> SEQUENCE: 291

Lys Glu Thr Leu His Ala Trp Ala Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 292
<211> LENGTH: 49
<212> TYPE: PRT
<213> ORGANISM: artificial sequence
<220> FEATURE:
<223> OTHER INFORMATION: Modified bacterial sequence

<400> SEQUENCE: 292

Lys Glu Val Leu Glu Ala Trp Asn Glu Ile Asp His Leu Pro Asn Leu
1               5                   10                  15

Thr Leu Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 293
<211> LENGTH: 49
<212> TYPE: PRT
<213> ORGANISM: artificial sequence
<220> FEATURE:
<223> OTHER INFORMATION: Modified bacterial sequence

<400> SEQUENCE: 293

Lys Glu Val Ile Glu Ala Trp Asp Glu Ile Asp Lys Leu Pro Asn Leu
1               5                   10                  15

Thr Ile Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 294
<211> LENGTH: 49
<212> TYPE: PRT
<213> ORGANISM: artificial sequence
<220> FEATURE:
<223> OTHER INFORMATION: Modified bacterial sequence

<400> SEQUENCE: 294

Lys Glu Val Leu Asp Ala Trp Asp Glu Ile Asp His Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 295
<211> LENGTH: 49
<212> TYPE: PRT
<213> ORGANISM: artificial sequence
<220> FEATURE:
<223> OTHER INFORMATION: Modified bacterial sequence

<400> SEQUENCE: 295

Lys Glu Thr Ile Glu Ala Trp Asn Glu Ile Asp Lys Leu Pro Asn Leu
1               5                   10                  15

Thr Leu Thr Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 296
<211> LENGTH: 49
<212> TYPE: PRT
<213> ORGANISM: artificial sequence
<220> FEATURE:
<223> OTHER INFORMATION: Modified bacterial sequence

<400> SEQUENCE: 296

Lys Glu Val Leu Glu Ala Trp Asn Glu Ile Asp Leu Leu Pro Asn Leu
1               5                   10                  15

Thr Ile Glu Gln Trp Leu Ala Phe Ile Asn Lys Leu Asp Asp Asp Pro
            20                  25                  30

-continued

Ser Gln Ser Ser Glu Leu Leu Ser Glu Ala Lys Lys Leu Asn Asp Ser
        35                  40                  45

Gln

<210> SEQ ID NO 297
<211> LENGTH: 49
<212> TYPE: PRT
<213> ORGANISM: artificial sequence
<220> FEATURE:
<223> OTHER INFORMATION: Modified bacterial sequence

<400> SEQUENCE: 297

Lys Glu Val Ile Glu Ala Trp Asp Glu Ile Asp His Leu Pro Asn Leu
1               5                   10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 298
<211> LENGTH: 49
<212> TYPE: PRT
<213> ORGANISM: artificial sequence
<220> FEATURE:
<223> OTHER INFORMATION: Modified bacterial sequence

<400> SEQUENCE: 298

Lys Glu Val Ile Ser Ala Trp Asn Glu Ile Asp Ala Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 299
<211> LENGTH: 49
<212> TYPE: PRT
<213> ORGANISM: artificial sequence
<220> FEATURE:
<223> OTHER INFORMATION: Modified bacterial sequence

<400> SEQUENCE: 299

Lys Glu Val Ile Ala Ala Trp Asn Glu Ile Asp Lys Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 300
<211> LENGTH: 49
<212> TYPE: PRT
<213> ORGANISM: artificial sequence
<220> FEATURE:
<223> OTHER INFORMATION: Modified bacterial sequence

<400> SEQUENCE: 300

```
Lys Glu Thr Ile Glu Ala Trp Asn Glu Ile Asp Ser Leu Pro Asn Leu
1               5                   10                  15

Thr Leu Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 301
<211> LENGTH: 49
<212> TYPE: PRT
<213> ORGANISM: artificial sequence
<220> FEATURE:
<223> OTHER INFORMATION: Modified bacterial sequence

<400> SEQUENCE: 301

```
Lys Glu Val Leu Asp Ala Trp Asn Glu Ile Asp Gln Leu Pro Asn Leu
1               5                   10                  15

Thr Leu Gln Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 302
<211> LENGTH: 49
<212> TYPE: PRT
<213> ORGANISM: artificial sequence
<220> FEATURE:
<223> OTHER INFORMATION: Modified bacterial sequence

<400> SEQUENCE: 302

```
Lys Glu Val Leu Ala Ala Trp Asn Glu Ile Asp His Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 303
<211> LENGTH: 49
<212> TYPE: PRT
<213> ORGANISM: artificial sequence
<220> FEATURE:
<223> OTHER INFORMATION: Modified bacterial sequence

<400> SEQUENCE: 303

```
Lys Glu Val Leu Glu Ala Trp Asp Glu Ile Asp His Leu Pro Asn Leu
1               5                   10                  15

Thr Ile Thr Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 304
<211> LENGTH: 49
<212> TYPE: PRT
<213> ORGANISM: artificial sequence

```
<220> FEATURE:
<223> OTHER INFORMATION: Modified bacterial sequence

<400> SEQUENCE: 304

Lys Glu Thr Ile Asp Ala Trp Asn Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 305
<211> LENGTH: 49
<212> TYPE: PRT
<213> ORGANISM: artificial sequence
<220> FEATURE:
<223> OTHER INFORMATION: Modified bacterial sequence

<400> SEQUENCE: 305

Lys Glu Val Ile Glu Ala Trp Asn Glu Ile Asp His Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 306
<211> LENGTH: 49
<212> TYPE: PRT
<213> ORGANISM: artificial sequence
<220> FEATURE:
<223> OTHER INFORMATION: Modified bacterial sequence

<400> SEQUENCE: 306

Lys Glu Val Ile Gln Ala Trp Asn Glu Ile Asp Ala Leu Pro Asn Leu
1               5                   10                  15

Thr Ile Ser Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 307
<211> LENGTH: 49
<212> TYPE: PRT
<213> ORGANISM: artificial sequence
<220> FEATURE:
<223> OTHER INFORMATION: Modified bacterial sequence

<400> SEQUENCE: 307

Lys Glu Val Ile Ala Ala Trp Asp Glu Ile Asp Ser Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 308
<211> LENGTH: 49
<212> TYPE: PRT
<213> ORGANISM: artificial sequence
<220> FEATURE:
<223> OTHER INFORMATION: Modified bacterial sequence

<400> SEQUENCE: 308

Lys Glu His Ile Glu Ala Trp Asn Glu Ile Asp Ala Leu Pro Asn Leu
1               5                   10                  15

Thr Ile Glu Gln Trp Leu Ala Phe Ile Asn Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 309
<211> LENGTH: 49
<212> TYPE: PRT
<213> ORGANISM: artificial sequence
<220> FEATURE:
<223> OTHER INFORMATION: Modified bacterial sequence

<400> SEQUENCE: 309

Lys Glu Val Leu Glu Ala Trp Asn Glu Ile Asp Lys Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 310
<211> LENGTH: 49
<212> TYPE: PRT
<213> ORGANISM: artificial sequence
<220> FEATURE:
<223> OTHER INFORMATION: Modified bacterial sequence

<400> SEQUENCE: 310

Lys Glu Val Ile Asp Ala Trp Asn Glu Ile Asp His Leu Pro Asn Leu
1               5                   10                  15

Thr Ile Glu Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 311
<211> LENGTH: 49
<212> TYPE: PRT
<213> ORGANISM: artificial sequence
<220> FEATURE:
<223> OTHER INFORMATION: Modified bacterial sequence

<400> SEQUENCE: 311

Lys Glu Thr Ile Asp Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 312
<211> LENGTH: 49
<212> TYPE: PRT
<213> ORGANISM: artificial sequence
<220> FEATURE:
<223> OTHER INFORMATION: Modified bacterial sequence

<400> SEQUENCE: 312

Lys Glu Val Ile Ala Ala Trp Asp Glu Ile Asp Leu Leu Pro Asn Leu
1               5                   10                  15

Thr Leu Gln Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 313
<211> LENGTH: 49
<212> TYPE: PRT
<213> ORGANISM: artificial sequence
<220> FEATURE:
<223> OTHER INFORMATION: Modified bacterial sequence

<400> SEQUENCE: 313

Lys Glu Val Ile His Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 314
<211> LENGTH: 49
<212> TYPE: PRT
<213> ORGANISM: artificial sequence
<220> FEATURE:
<223> OTHER INFORMATION: Modified bacterial sequence

<400> SEQUENCE: 314

Lys Glu Val Ile Ala Ala Trp Asn Glu Ile Asp His Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 315
<211> LENGTH: 49
<212> TYPE: PRT
<213> ORGANISM: artificial sequence
<220> FEATURE:
<223> OTHER INFORMATION: Modified bacterial sequence

<400> SEQUENCE: 315

Lys Glu Thr Leu Asp Ala Trp Asn Glu Ile Asp Lys Leu Pro Asn Leu

```
            1               5                  10                  15
         Thr Leu Ser Gln Trp Leu Ala Phe Ile Asn Lys Leu Asp Asp Pro
                     20                  25                  30

Ser Gln Ser Ser Glu Leu Leu Ser Glu Ala Lys Lys Leu Asn Asp Ser
                     35                  40                  45

Gln

<210> SEQ ID NO 316
<211> LENGTH: 49
<212> TYPE: PRT
<213> ORGANISM: artificial sequence
<220> FEATURE:
<223> OTHER INFORMATION: Modified bacterial sequence

<400> SEQUENCE: 316

Lys Glu Val Leu Glu Ala Trp Asn Glu Ile Asp Ala Leu Pro Asn Leu
         1               5                  10                  15

Thr Leu Glu Gln Trp Leu Ala Phe Ile Asn Lys Leu Asp Asp Pro
                     20                  25                  30

Ser Gln Ser Ser Glu Leu Leu Ser Glu Ala Lys Lys Leu Asn Asp Ser
                     35                  40                  45

Gln

<210> SEQ ID NO 317
<211> LENGTH: 49
<212> TYPE: PRT
<213> ORGANISM: artificial sequence
<220> FEATURE:
<223> OTHER INFORMATION: Modified bacterial sequence

<400> SEQUENCE: 317

Lys Glu Val Ile Gln Ala Trp Asp Glu Ile Asp His Leu Pro Asn Leu
         1               5                  10                  15

Thr Ile Ser Gln Trp Leu Ala Phe Ile Asn Lys Leu Asp Asp Pro
                     20                  25                  30

Ser Gln Ser Ser Glu Leu Leu Ser Glu Ala Lys Lys Leu Asn Asp Ser
                     35                  40                  45

Gln

<210> SEQ ID NO 318
<211> LENGTH: 49
<212> TYPE: PRT
<213> ORGANISM: artificial sequence
<220> FEATURE:
<223> OTHER INFORMATION: Modified bacterial sequence

<400> SEQUENCE: 318

Lys Glu Val Leu Gln Ala Trp Asp Glu Ile Asp Ser Leu Pro Asn Leu
         1               5                  10                  15

Thr Ile Glu Gln Trp Leu Ala Phe Ile Asn Lys Leu Asp Asp Pro
                     20                  25                  30

Ser Gln Ser Ser Glu Leu Leu Ser Glu Ala Lys Lys Leu Asn Asp Ser
                     35                  40                  45

Gln

<210> SEQ ID NO 319
<211> LENGTH: 49
<212> TYPE: PRT
<213> ORGANISM: artificial sequence
<220> FEATURE:
```

<223> OTHER INFORMATION: Modified bacterial sequence

<400> SEQUENCE: 319

Lys Glu Thr Leu Glu Ala Trp Asp Glu Ile Asp His Leu Pro Asn Leu
1               5                   10                  15

Thr Ile Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 320
<211> LENGTH: 49
<212> TYPE: PRT
<213> ORGANISM: artificial sequence
<220> FEATURE:
<223> OTHER INFORMATION: Modified bacterial sequence

<400> SEQUENCE: 320

Lys Glu Thr Ile Asp Ala Trp Asn Glu Ile Asp Arg Leu Pro Asn Leu
1               5                   10                  15

Thr Ile Ser Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 321
<211> LENGTH: 49
<212> TYPE: PRT
<213> ORGANISM: artificial sequence
<220> FEATURE:
<223> OTHER INFORMATION: Modified bacterial sequence

<400> SEQUENCE: 321

Lys Glu Val Leu Asp Ala Trp His Glu Ile Asp His Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 322
<211> LENGTH: 49
<212> TYPE: PRT
<213> ORGANISM: artificial sequence
<220> FEATURE:
<223> OTHER INFORMATION: Modified bacterial sequence

<400> SEQUENCE: 322

Lys Glu Gln Ile Arg Ala Trp Asp Glu Ile Asp Lys Leu Pro Asn Leu
1               5                   10                  15

Thr Ile Glu Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

-continued

```
<210> SEQ ID NO 323
<211> LENGTH: 49
<212> TYPE: PRT
<213> ORGANISM: artificial sequence
<220> FEATURE:
<223> OTHER INFORMATION: Modified bacterial sequence

<400> SEQUENCE: 323

Lys Glu Thr Leu Tyr Ala Trp Asn Glu Ile Asp Lys Leu Pro Asn Leu
1               5                   10                  15

Thr Ile Glu Gln Trp Leu Ala Phe Ile Glu Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 324
<211> LENGTH: 49
<212> TYPE: PRT
<213> ORGANISM: artificial sequence
<220> FEATURE:
<223> OTHER INFORMATION: Modified bacterial sequence

<400> SEQUENCE: 324

Lys Glu Val Ile Glu Ala Trp Asn Glu Ile Asp Ala Leu Pro Asn Leu
1               5                   10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 325
<211> LENGTH: 49
<212> TYPE: PRT
<213> ORGANISM: artificial sequence
<220> FEATURE:
<223> OTHER INFORMATION: Modified bacterial sequence

<400> SEQUENCE: 325

Lys Glu Val Leu Glu Ala Trp Asn Glu Ile Asp His Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 326
<211> LENGTH: 49
<212> TYPE: PRT
<213> ORGANISM: artificial sequence
<220> FEATURE:
<223> OTHER INFORMATION: Modified bacterial sequence

<400> SEQUENCE: 326

Lys Glu Thr Ile Glu Ala Trp Asp Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
```

-continued

```
            35                  40                  45
Gln

<210> SEQ ID NO 327
<211> LENGTH: 49
<212> TYPE: PRT
<213> ORGANISM: artificial sequence
<220> FEATURE:
<223> OTHER INFORMATION: Modified bacterial sequence

<400> SEQUENCE: 327

Lys Glu Val Ile Glu Ala Trp Asn Glu Ile Asp His Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 328
<211> LENGTH: 49
<212> TYPE: PRT
<213> ORGANISM: artificial sequence
<220> FEATURE:
<223> OTHER INFORMATION: Modified bacterial sequence

<400> SEQUENCE: 328

Lys Glu Val Ile Glu Ala Trp Asn Glu Ile Asp Lys Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 329
<211> LENGTH: 49
<212> TYPE: PRT
<213> ORGANISM: artificial sequence
<220> FEATURE:
<223> OTHER INFORMATION: Modified bacterial sequence

<400> SEQUENCE: 329

Lys Glu Thr Leu Asp Ala Trp Ala Glu Ile Asp His Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 330
<211> LENGTH: 49
<212> TYPE: PRT
<213> ORGANISM: artificial sequence
<220> FEATURE:
<223> OTHER INFORMATION: Modified bacterial sequence

<400> SEQUENCE: 330

Lys Glu His Ile Asp Ala Trp Asn Glu Ile Asp Ala Leu Pro Asn Leu
1               5                   10                  15
```

```
Thr Leu Ser Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 331
<211> LENGTH: 49
<212> TYPE: PRT
<213> ORGANISM: artificial sequence
<220> FEATURE:
<223> OTHER INFORMATION: Modified bacterial sequence

<400> SEQUENCE: 331

Lys Glu Val Leu Asp Ala Trp Asn Gly Ile Asp Lys Leu Pro Asn Leu
1               5                   10                  15

Thr Ile Ala Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 332
<211> LENGTH: 49
<212> TYPE: PRT
<213> ORGANISM: artificial sequence
<220> FEATURE:
<223> OTHER INFORMATION: Modified bacterial sequence

<400> SEQUENCE: 332

Lys Glu Val Ile Glu Ala Trp Thr Glu Ile Asp Tyr Leu Pro Asn Leu
1               5                   10                  15

Thr Leu Gln Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 333
<211> LENGTH: 49
<212> TYPE: PRT
<213> ORGANISM: artificial sequence
<220> FEATURE:
<223> OTHER INFORMATION: Modified bacterial sequence

<400> SEQUENCE: 333

Lys Glu Thr Ile Glu Ala Trp Asn Glu Ile Asp His Leu Pro Asn Leu
1               5                   10                  15

Thr Ile Ala Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 334
<211> LENGTH: 49
<212> TYPE: PRT
<213> ORGANISM: artificial sequence
<220> FEATURE:
<223> OTHER INFORMATION: Modified bacterial sequence
```

<400> SEQUENCE: 334

Lys Glu Val Ile Gln Ala Trp Asn Glu Ile Asp Lys Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 335
<211> LENGTH: 49
<212> TYPE: PRT
<213> ORGANISM: artificial sequence
<220> FEATURE:
<223> OTHER INFORMATION: Modified bacterial sequence

<400> SEQUENCE: 335

Lys Glu Val Ile Glu Ala Trp Asp Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 336
<211> LENGTH: 49
<212> TYPE: PRT
<213> ORGANISM: artificial sequence
<220> FEATURE:
<223> OTHER INFORMATION: Modified bacterial sequence

<400> SEQUENCE: 336

Lys Glu Thr Ile Asp Ala Trp Asn Glu Ile Asp Leu Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 337
<211> LENGTH: 49
<212> TYPE: PRT
<213> ORGANISM: artificial sequence
<220> FEATURE:
<223> OTHER INFORMATION: Modified bacterial sequence

<400> SEQUENCE: 337

Lys Glu His Ile Asp Ala Trp Asn Glu Ile Asp Lys Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 338

```
<211> LENGTH: 49
<212> TYPE: PRT
<213> ORGANISM: artificial sequence
<220> FEATURE:
<223> OTHER INFORMATION: Modified bacterial sequence

<400> SEQUENCE: 338

Lys Glu Val Val Ala Ala Trp Asn Glu Ile Asp Ala Leu Pro Asn Leu
1               5                   10                  15

Thr Ile Glu Gln Trp Leu Ala Phe Ile Asn Lys Leu Asn Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 339
<211> LENGTH: 49
<212> TYPE: PRT
<213> ORGANISM: artificial sequence
<220> FEATURE:
<223> OTHER INFORMATION: Modified bacterial sequence

<400> SEQUENCE: 339

Lys Glu Val Ile Glu Ala Trp Asn Glu Ile Asp Ala Leu Pro Asn Leu
1               5                   10                  15

Thr Leu Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 340
<211> LENGTH: 49
<212> TYPE: PRT
<213> ORGANISM: artificial sequence
<220> FEATURE:
<223> OTHER INFORMATION: Modified bacterial sequence

<400> SEQUENCE: 340

Lys Glu Val Leu Gln Ala Trp Asp Glu Ile Asp Arg Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 341
<211> LENGTH: 49
<212> TYPE: PRT
<213> ORGANISM: artificial sequence
<220> FEATURE:
<223> OTHER INFORMATION: Modified bacterial sequence

<400> SEQUENCE: 341

Lys Glu Val Ile Asp Ala Trp Asp Glu Ile Asp His Leu Pro Asn Leu
1               5                   10                  15

Thr Ile Glu Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 342
<211> LENGTH: 49
<212> TYPE: PRT
<213> ORGANISM: artificial sequence
<220> FEATURE:
<223> OTHER INFORMATION: Modified bacterial sequence

<400> SEQUENCE: 342

Lys Glu Val Val Glu Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 343
<211> LENGTH: 49
<212> TYPE: PRT
<213> ORGANISM: artificial sequence
<220> FEATURE:
<223> OTHER INFORMATION: Modified bacterial sequence

<400> SEQUENCE: 343

Lys Glu Val Ile Gln Ala Trp Asn Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 344
<211> LENGTH: 49
<212> TYPE: PRT
<213> ORGANISM: artificial sequence
<220> FEATURE:
<223> OTHER INFORMATION: Modified bacterial sequence

<400> SEQUENCE: 344

Lys Glu Val Ile Gln Ala Trp Asp Glu Ile Asp Lys Leu Pro Asn Leu
1               5                   10                  15

Thr Ile Asp Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 345
<211> LENGTH: 49
<212> TYPE: PRT
<213> ORGANISM: artificial sequence
<220> FEATURE:
<223> OTHER INFORMATION: Modified bacterial sequence

<400> SEQUENCE: 345

Lys Glu Val Val Ala Ala Trp Asp Glu Ile Asp Ala Leu Pro Asn Leu
1               5                   10                  15

```
Thr Leu Thr Gln Trp Leu Ala Phe Ile Asn Lys Leu Asp Asp Pro
        20                  25                  30

Ser Gln Ser Ser Glu Leu Leu Ser Glu Ala Lys Lys Leu Asn Asp Ser
        35                  40                  45

Gln
```

<210> SEQ ID NO 346
<211> LENGTH: 49
<212> TYPE: PRT
<213> ORGANISM: artificial sequence
<220> FEATURE:
<223> OTHER INFORMATION: Modified bacterial sequence

<400> SEQUENCE: 346

```
Lys Glu Val Ile Gln Ala Trp Asn Glu Ile Asp Gly Leu Pro Asn Leu
1               5                   10                  15

Thr Leu Ser Gln Trp Leu Ala Phe Ile Asn Lys Leu Asp Asp Asp Pro
        20                  25                  30

Ser Gln Ser Ser Glu Leu Leu Ser Glu Ala Lys Lys Leu Asn Asp Ser
        35                  40                  45

Gln
```

<210> SEQ ID NO 347
<211> LENGTH: 49
<212> TYPE: PRT
<213> ORGANISM: artificial sequence
<220> FEATURE:
<223> OTHER INFORMATION: Modified bacterial sequence

<400> SEQUENCE: 347

```
Lys Glu Thr Ile Glu Ala Trp Asp Glu Ile Asp Ala Leu Pro Asn Leu
1               5                   10                  15

Thr Ile Thr Gln Trp Leu Ala Phe Ile Asn Lys Leu Asp Asp Asp Pro
        20                  25                  30

Ser Gln Ser Ser Glu Leu Leu Ser Glu Ala Lys Lys Leu Asn Asp Ser
        35                  40                  45

Gln
```

<210> SEQ ID NO 348
<211> LENGTH: 49
<212> TYPE: PRT
<213> ORGANISM: artificial sequence
<220> FEATURE:
<223> OTHER INFORMATION: Modified bacterial sequence

<400> SEQUENCE: 348

```
Lys Glu Val Ile Asp Ala Trp Asn Glu Ile Asp His Leu Pro Asn Leu
1               5                   10                  15

Thr Ile Gln Gln Trp Leu Ala Phe Ile Asn Lys Leu Ala Asp Asp Pro
        20                  25                  30

Ser Gln Ser Ser Glu Leu Leu Ser Glu Ala Lys Lys Leu Asn Asp Ser
        35                  40                  45

Gln
```

<210> SEQ ID NO 349
<211> LENGTH: 49
<212> TYPE: PRT
<213> ORGANISM: artificial sequence
<220> FEATURE:
<223> OTHER INFORMATION: Modified bacterial sequence

<400> SEQUENCE: 349

Lys Glu Thr Ile Glu Ala Trp Asn Glu Ile Asp Ala Leu Pro Asn Leu
1               5                   10                  15

Thr Leu Asp Gln Trp Leu Ala Phe Ile Asn Lys Leu Glu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 350
<211> LENGTH: 49
<212> TYPE: PRT
<213> ORGANISM: artificial sequence
<220> FEATURE:
<223> OTHER INFORMATION: Modified bacterial sequence

<400> SEQUENCE: 350

Lys Glu His Ile His Ala Trp Asn Glu Ile Asp Glu Leu Pro Asn Leu
1               5                   10                  15

Thr Ile Glu Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 351
<211> LENGTH: 49
<212> TYPE: PRT
<213> ORGANISM: artificial sequence
<220> FEATURE:
<223> OTHER INFORMATION: Modified bacterial sequence

<400> SEQUENCE: 351

Lys Glu Val Ile Asp Ala Trp Asp Glu Ile Asp His Leu Pro Asn Leu
1               5                   10                  15

Thr Ile Asp Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 352
<211> LENGTH: 49
<212> TYPE: PRT
<213> ORGANISM: artificial sequence
<220> FEATURE:
<223> OTHER INFORMATION: Modified bacterial sequence

<400> SEQUENCE: 352

Lys Glu Val Ile Asp Ala Asn Asp Glu Ile Asp Ala Leu Pro Asn Leu
1               5                   10                  15

Thr Ile Ala Gln Trp Leu Ala Phe Ile Asn Lys Leu His Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 353
<211> LENGTH: 49

```
<212> TYPE: PRT
<213> ORGANISM: artificial sequence
<220> FEATURE:
<223> OTHER INFORMATION: Modified bacterial sequence

<400> SEQUENCE: 353

Lys Glu Thr Ile Glu Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 354
<211> LENGTH: 49
<212> TYPE: PRT
<213> ORGANISM: artificial sequence
<220> FEATURE:
<223> OTHER INFORMATION: Modified bacterial sequence

<400> SEQUENCE: 354

Lys Glu Val Leu Leu Ala Trp Asp Glu Ile Asp His Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 355
<211> LENGTH: 49
<212> TYPE: PRT
<213> ORGANISM: artificial sequence
<220> FEATURE:
<223> OTHER INFORMATION: Modified bacterial sequence

<400> SEQUENCE: 355

Lys Glu His Ile Asp Ala Trp Asn Glu Ile Asp Gly Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 356
<211> LENGTH: 49
<212> TYPE: PRT
<213> ORGANISM: artificial sequence
<220> FEATURE:
<223> OTHER INFORMATION: Modified bacterial sequence

<400> SEQUENCE: 356

Lys Glu Val Ile Glu Ala Trp Ser Glu Ile Asp Ala Leu Pro Asn Leu
1               5                   10                  15

Thr Ile Asp Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 357
<211> LENGTH: 49
<212> TYPE: PRT
<213> ORGANISM: artificial sequence
<220> FEATURE:
<223> OTHER INFORMATION: Modified bacterial sequence

<400> SEQUENCE: 357

Lys Glu Gln Leu Asn Ala Trp Ala Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 358
<211> LENGTH: 49
<212> TYPE: PRT
<213> ORGANISM: artificial sequence
<220> FEATURE:
<223> OTHER INFORMATION: Modified bacterial sequence

<400> SEQUENCE: 358

Lys Glu Val Ile Asp Ala Trp Asn Glu Ile Asp Ala Leu Pro Asn Leu
1               5                   10                  15

Thr Ile Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 359
<211> LENGTH: 49
<212> TYPE: PRT
<213> ORGANISM: artificial sequence
<220> FEATURE:
<223> OTHER INFORMATION: Modified bacterial sequence

<400> SEQUENCE: 359

Lys Glu Thr Ile Asp Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 360
<211> LENGTH: 49
<212> TYPE: PRT
<213> ORGANISM: artificial sequence
<220> FEATURE:
<223> OTHER INFORMATION: Modified bacterial sequence

<400> SEQUENCE: 360

Lys Glu Val Ile Glu Ala Trp Asp Glu Ile Asp Lys Leu Pro Asn Leu
1               5                   10                  15

Thr Leu Ala Gln Trp Leu Ala Phe Ile Asn Lys Leu Asp Asp Asp Pro 20                  25                  30

Ser Gln Ser Ser Glu Leu Leu Ser Glu Ala Lys Lys Leu Asn Asp Ser
        35                  40                  45

Gln

<210> SEQ ID NO 361
<211> LENGTH: 49
<212> TYPE: PRT
<213> ORGANISM: artificial sequence
<220> FEATURE:
<223> OTHER INFORMATION: Modified bacterial sequence

<400> SEQUENCE: 361

Lys Glu Val Leu Tyr Ala Trp Ala Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 362
<211> LENGTH: 49
<212> TYPE: PRT
<213> ORGANISM: artificial sequence
<220> FEATURE:
<223> OTHER INFORMATION: Modified bacterial sequence

<400> SEQUENCE: 362

Lys Glu Gln Ile Asp Ala Trp Asn Glu Ile Asp Arg Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 363
<211> LENGTH: 49
<212> TYPE: PRT
<213> ORGANISM: artificial sequence
<220> FEATURE:
<223> OTHER INFORMATION: Modified bacterial sequence

<400> SEQUENCE: 363

Lys Glu Val Leu Ala Ala Trp Asp Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 364
<211> LENGTH: 49
<212> TYPE: PRT
<213> ORGANISM: artificial sequence
<220> FEATURE:
<223> OTHER INFORMATION: Modified bacterial sequence

<400> SEQUENCE: 364

-continued

Lys Glu Val Ile Glu Ala Trp Asp Glu Ile Asp His Leu Pro Asn Leu
1               5                   10                  15

Thr Leu His Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 365
<211> LENGTH: 49
<212> TYPE: PRT
<213> ORGANISM: artificial sequence
<220> FEATURE:
<223> OTHER INFORMATION: Modified bacterial sequence

<400> SEQUENCE: 365

Lys Glu Val Ile Glu Ala Trp Asn Glu Ile Asp Lys Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 366
<211> LENGTH: 49
<212> TYPE: PRT
<213> ORGANISM: artificial sequence
<220> FEATURE:
<223> OTHER INFORMATION: Modified bacterial sequence

<400> SEQUENCE: 366

Lys Glu Val Ile Asp Ala Asn Asp Glu Ile Asp Ala Leu Pro Asn Leu
1               5                   10                  15

Thr Ile Glu Gln Trp Leu Ala Phe Ile Asn Lys Leu His Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 367
<211> LENGTH: 49
<212> TYPE: PRT
<213> ORGANISM: artificial sequence
<220> FEATURE:
<223> OTHER INFORMATION: Modified bacterial sequence

<400> SEQUENCE: 367

Lys Glu Val Ile Ala Ala Trp Asp Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 368
<211> LENGTH: 49
<212> TYPE: PRT

<213> ORGANISM: artificial sequence
<220> FEATURE:
<223> OTHER INFORMATION: Modified bacterial sequence

<400> SEQUENCE: 368

```
Lys Glu Val Ile Glu Ala Trp Thr Glu Ile Asp Gln Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 369
<211> LENGTH: 49
<212> TYPE: PRT
<213> ORGANISM: artificial sequence
<220> FEATURE:
<223> OTHER INFORMATION: Modified bacterial sequence

<400> SEQUENCE: 369

```
Lys Glu Val Ile Asn Ala Trp Asn Glu Ile Asp Ala Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 370
<211> LENGTH: 49
<212> TYPE: PRT
<213> ORGANISM: artificial sequence
<220> FEATURE:
<223> OTHER INFORMATION: Modified bacterial sequence

<400> SEQUENCE: 370

```
Lys Glu His Ile Glu Ala Trp Asp Glu Ile Asp His Leu Pro Asn Leu
1               5                   10                  15

Thr Ile Asp Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 371
<211> LENGTH: 49
<212> TYPE: PRT
<213> ORGANISM: artificial sequence
<220> FEATURE:
<223> OTHER INFORMATION: Modified bacterial sequence

<400> SEQUENCE: 371

```
Lys Glu His Leu Glu Ala Trp Arg Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 372
<211> LENGTH: 49
<212> TYPE: PRT
<213> ORGANISM: artificial sequence
<220> FEATURE:
<223> OTHER INFORMATION: Modified bacterial sequence

<400> SEQUENCE: 372

Lys Glu Val Leu Asp Ala Trp Asn Glu Ile Asp Lys Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 373
<211> LENGTH: 49
<212> TYPE: PRT
<213> ORGANISM: artificial sequence
<220> FEATURE:
<223> OTHER INFORMATION: Modified bacterial sequence

<400> SEQUENCE: 373

Lys Glu Val Ile Ala Ala Trp Asp Glu Ile Asp His Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 374
<211> LENGTH: 49
<212> TYPE: PRT
<213> ORGANISM: artificial sequence
<220> FEATURE:
<223> OTHER INFORMATION: Modified bacterial sequence

<400> SEQUENCE: 374

Lys Glu Val Ile Gln Ala Trp Asn Glu Ile Asp Ala Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 375
<211> LENGTH: 49
<212> TYPE: PRT
<213> ORGANISM: artificial sequence
<220> FEATURE:
<223> OTHER INFORMATION: Modified bacterial sequence

<400> SEQUENCE: 375

Lys Glu Val Ile Asp Ala Trp Asn Glu Ile Asp His Leu Pro Asn Leu
1               5                   10                  15

Thr Ile Ala Gln Trp Leu Ala Phe Ile Asn Lys Leu Asp Asp Asp Pro
            20                  25                  30

-continued

Ser Gln Ser Ser Glu Leu Leu Ser Glu Ala Lys Lys Leu Asn Asp Ser
        35                  40                  45

Gln

<210> SEQ ID NO 376
<211> LENGTH: 49
<212> TYPE: PRT
<213> ORGANISM: artificial sequence
<220> FEATURE:
<223> OTHER INFORMATION: Modified bacterial sequence

<400> SEQUENCE: 376

Lys Glu Gln Leu Asp Ala Trp Asp Glu Ile Asp His Leu Pro Asn Leu
1               5                   10                  15

Thr Ile Asp Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 377
<211> LENGTH: 49
<212> TYPE: PRT
<213> ORGANISM: artificial sequence
<220> FEATURE:
<223> OTHER INFORMATION: Modified bacterial sequence

<400> SEQUENCE: 377

Lys Glu Val Leu Asn Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 378
<211> LENGTH: 49
<212> TYPE: PRT
<213> ORGANISM: artificial sequence
<220> FEATURE:
<223> OTHER INFORMATION: Modified bacterial sequence

<400> SEQUENCE: 378

Lys Glu Val Leu Glu Ala Trp Asn Glu Ile Asp His Leu Pro Asn Leu
1               5                   10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 379
<211> LENGTH: 49
<212> TYPE: PRT
<213> ORGANISM: artificial sequence
<220> FEATURE:
<223> OTHER INFORMATION: Modified bacterial sequence

<400> SEQUENCE: 379

-continued

Lys Glu Val Leu Leu Ala Trp Asp Glu Ile Asp Arg Leu Pro Asn Leu
1               5                   10                  15

Thr Ile Asp Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 380
<211> LENGTH: 49
<212> TYPE: PRT
<213> ORGANISM: artificial sequence
<220> FEATURE:
<223> OTHER INFORMATION: Modified bacterial sequence

<400> SEQUENCE: 380

Lys Glu Val Ile Ala Ala Trp Asn Glu Ile Asp Gln Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 381
<211> LENGTH: 49
<212> TYPE: PRT
<213> ORGANISM: artificial sequence
<220> FEATURE:
<223> OTHER INFORMATION: Modified bacterial sequence

<400> SEQUENCE: 381

Lys Glu Thr Leu Leu Ala Trp Asp Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 382
<211> LENGTH: 49
<212> TYPE: PRT
<213> ORGANISM: artificial sequence
<220> FEATURE:
<223> OTHER INFORMATION: Modified bacterial sequence

<400> SEQUENCE: 382

Lys Glu Val Ile Asp Ala Trp Asn Glu Ile Asp Thr Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 383
<211> LENGTH: 49
<212> TYPE: PRT
<213> ORGANISM: artificial sequence
<220> FEATURE:
<223> OTHER INFORMATION: Modified bacterial sequence

<400> SEQUENCE: 383

Lys Glu Val Leu His Ala Trp Asn Glu Ile Asp His Leu Pro Asn Leu
1               5                   10                  15

Thr Leu Asn Gln Trp Leu Ala Phe Ile Asn Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 384
<211> LENGTH: 49
<212> TYPE: PRT
<213> ORGANISM: artificial sequence
<220> FEATURE:
<223> OTHER INFORMATION: Modified bacterial sequence

<400> SEQUENCE: 384

Lys Glu Val Ile Gln Ala Trp Asn Glu Ile Asp Ala Leu Pro Asn Leu
1               5                   10                  15

Thr Ile Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 385
<211> LENGTH: 49
<212> TYPE: PRT
<213> ORGANISM: artificial sequence
<220> FEATURE:
<223> OTHER INFORMATION: Modified bacterial sequence

<400> SEQUENCE: 385

Lys Glu Thr Val Asp Ala Trp Asn Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 386
<211> LENGTH: 49
<212> TYPE: PRT
<213> ORGANISM: artificial sequence
<220> FEATURE:
<223> OTHER INFORMATION: Modified bacterial sequence

<400> SEQUENCE: 386

Lys Glu Val Ile Gln Ala Trp Asp Glu Ile Asp His Leu Pro Asn Leu
1               5                   10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 387
<211> LENGTH: 49
<212> TYPE: PRT
<213> ORGANISM: artificial sequence
<220> FEATURE:
<223> OTHER INFORMATION: Modified bacterial sequence

<400> SEQUENCE: 387

Lys Glu Val Leu Asp Ala Trp Asn Glu Ile Asp Gln Leu Pro Asn Leu
1               5                  10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 388
<211> LENGTH: 49
<212> TYPE: PRT
<213> ORGANISM: artificial sequence
<220> FEATURE:
<223> OTHER INFORMATION: Modified bacterial sequence

<400> SEQUENCE: 388

Lys Glu Thr Ile Glu Ala Trp Asn Glu Ile Asp Ala Leu Pro Asn Leu
1               5                  10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 389
<211> LENGTH: 49
<212> TYPE: PRT
<213> ORGANISM: artificial sequence
<220> FEATURE:
<223> OTHER INFORMATION: Modified bacterial sequence

<400> SEQUENCE: 389

Lys Glu Val Ile Glu Ala Trp Asp Glu Ile Asp Ala Leu Pro Asn Leu
1               5                  10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 390
<211> LENGTH: 49
<212> TYPE: PRT
<213> ORGANISM: artificial sequence
<220> FEATURE:
<223> OTHER INFORMATION: Modified bacterial sequence

<400> SEQUENCE: 390

Lys Glu Val Ile Glu Ala Trp Asn Glu Ile Asp Gln Leu Pro Asn Leu
1               5                  10                  15

Thr Ile Gln Gln Trp Leu Ala Phe Ile Asn Lys Leu Asp Asp Asp Pro
            20                  25                  30

```
Ser Gln Ser Ser Glu Leu Leu Ser Glu Ala Lys Lys Leu Asn Asp Ser
        35                  40                  45

Gln

<210> SEQ ID NO 391
<211> LENGTH: 49
<212> TYPE: PRT
<213> ORGANISM: artificial sequence
<220> FEATURE:
<223> OTHER INFORMATION: Modified bacterial sequence

<400> SEQUENCE: 391

Lys Glu Val Ile Glu Ala Trp Thr Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 392
<211> LENGTH: 49
<212> TYPE: PRT
<213> ORGANISM: artificial sequence
<220> FEATURE:
<223> OTHER INFORMATION: Modified bacterial sequence

<400> SEQUENCE: 392

Lys Glu Val Ile Gln Ala Trp Asn Glu Ile Asp His Leu Pro Asn Leu
1               5                   10                  15

Thr Leu Gln Gln Trp Leu Ala Phe Ile Asn Lys Leu Glu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 393
<211> LENGTH: 49
<212> TYPE: PRT
<213> ORGANISM: artificial sequence
<220> FEATURE:
<223> OTHER INFORMATION: Modified bacterial sequence

<400> SEQUENCE: 393

Lys Glu Val Ile Gln Ala Asn Asn Glu Ile Asp Gln Leu Pro Asn Leu
1               5                   10                  15

Thr Ile Glu Gln Trp Leu Ala Phe Ile Asn Lys Leu His Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 394
<211> LENGTH: 49
<212> TYPE: PRT
<213> ORGANISM: artificial sequence
<220> FEATURE:
<223> OTHER INFORMATION: Modified bacterial sequence

<400> SEQUENCE: 394

Lys Glu Val Leu His Ala Trp Ser Glu Ile Asp Lys Leu Pro Asn Leu
```

```
                1               5                  10                 15
            Thr Ile Glu Gln Trp Leu Ala Phe Ile Asn Lys Leu Asp Asp Pro
                        20                  25                  30
            Ser Gln Ser Ser Glu Leu Leu Ser Glu Ala Lys Lys Leu Asn Asp Ser
                    35                  40                  45

Gln
```

<210> SEQ ID NO 395
<211> LENGTH: 49
<212> TYPE: PRT
<213> ORGANISM: artificial sequence
<220> FEATURE:
<223> OTHER INFORMATION: Modified bacterial sequence

<400> SEQUENCE: 395

```
            Lys Glu Thr Ile Gln Ala Trp Asp Glu Ile Asp Lys Leu Pro Asn Leu
            1               5                   10                  15
            Thr Leu Asp Gln Trp Leu Ala Phe Ile Asn Lys Leu Ser Asp Pro
                        20                  25                  30
            Ser Gln Ser Ser Glu Leu Leu Ser Glu Ala Lys Lys Leu Asn Asp Ser
                    35                  40                  45

Gln
```

<210> SEQ ID NO 396
<211> LENGTH: 49
<212> TYPE: PRT
<213> ORGANISM: artificial sequence
<220> FEATURE:
<223> OTHER INFORMATION: Modified bacterial sequence

<400> SEQUENCE: 396

```
            Lys Glu Thr Leu Arg Ala Trp Asp Glu Ile Asp Lys Leu Pro Asn Leu
            1               5                   10                  15
            Thr Ile Gln Gln Trp Leu Ala Phe Ile Asn Lys Leu Ala Asp Asp Pro
                        20                  25                  30
            Ser Gln Ser Ser Glu Leu Leu Ser Glu Ala Lys Lys Leu Asn Asp Ser
                    35                  40                  45

Gln
```

<210> SEQ ID NO 397
<211> LENGTH: 49
<212> TYPE: PRT
<213> ORGANISM: artificial sequence
<220> FEATURE:
<223> OTHER INFORMATION: Modified bacterial sequence

<400> SEQUENCE: 397

```
            Lys Glu Val Ile Asp Ala Trp Asn Glu Ile Asp His Leu Pro Asn Leu
            1               5                   10                  15
            Thr Ile Glu Gln Trp Leu Ala Phe Ile Asn Lys Leu Glu Asp Asp Pro
                        20                  25                  30
            Ser Gln Ser Ser Glu Leu Leu Ser Glu Ala Lys Lys Leu Asn Asp Ser
                    35                  40                  45

Gln
```

<210> SEQ ID NO 398
<211> LENGTH: 49
<212> TYPE: PRT
<213> ORGANISM: artificial sequence
<220> FEATURE:

<223> OTHER INFORMATION: Modified bacterial sequence

<400> SEQUENCE: 398

Lys Glu Val Ile Asp Ala Trp Asn Glu Ile Asp His Leu Pro Asn Leu
1               5                   10                  15

Thr Leu Gln Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 399
<211> LENGTH: 49
<212> TYPE: PRT
<213> ORGANISM: artificial sequence
<220> FEATURE:
<223> OTHER INFORMATION: Modified bacterial sequence

<400> SEQUENCE: 399

Lys Glu Thr Ile Asp Ala Trp Asn Glu Ile Asp Ala Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 400
<211> LENGTH: 49
<212> TYPE: PRT
<213> ORGANISM: artificial sequence
<220> FEATURE:
<223> OTHER INFORMATION: Modified bacterial sequence

<400> SEQUENCE: 400

Lys Glu Val Ile Glu Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 401
<211> LENGTH: 49
<212> TYPE: PRT
<213> ORGANISM: artificial sequence
<220> FEATURE:
<223> OTHER INFORMATION: Modified bacterial sequence

<400> SEQUENCE: 401

Lys Glu Val Ile Arg Ala Trp Asp Glu Ile Asp Gln Leu Pro Asn Leu
1               5                   10                  15

Thr Leu Ser Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

```
<210> SEQ ID NO 402
<211> LENGTH: 49
<212> TYPE: PRT
<213> ORGANISM: artificial sequence
<220> FEATURE:
<223> OTHER INFORMATION: Modified bacterial sequence

<400> SEQUENCE: 402

Lys Glu Val Ile Glu Ala Trp Asn Glu Ile Asp Arg Leu Pro Asn Leu
1               5                   10                  15

Thr Ile His Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 403
<211> LENGTH: 49
<212> TYPE: PRT
<213> ORGANISM: artificial sequence
<220> FEATURE:
<223> OTHER INFORMATION: Modified bacterial sequence

<400> SEQUENCE: 403

Lys Glu Thr Ile Glu Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 404
<211> LENGTH: 49
<212> TYPE: PRT
<213> ORGANISM: artificial sequence
<220> FEATURE:
<223> OTHER INFORMATION: Modified bacterial sequence

<400> SEQUENCE: 404

Lys Glu Val Leu Thr Ala Trp Ala Glu Ile Asp Ala Leu Pro Asn Leu
1               5                   10                  15

Thr Leu Ser Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 405
<211> LENGTH: 49
<212> TYPE: PRT
<213> ORGANISM: artificial sequence
<220> FEATURE:
<223> OTHER INFORMATION: Modified bacterial sequence

<400> SEQUENCE: 405

Lys Glu Val Ile Glu Ala Trp Asp Glu Ile Asp Lys Leu Pro Asn Leu
1               5                   10                  15

Thr Val Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
```

35                  40                  45

Gln

<210> SEQ ID NO 406
<211> LENGTH: 49
<212> TYPE: PRT
<213> ORGANISM: artificial sequence
<220> FEATURE:
<223> OTHER INFORMATION: Modified bacterial sequence

<400> SEQUENCE: 406

Lys Glu Val Ile Asp Ala Trp Asn Glu Ile Asp His Leu Pro Asn Leu
1               5                   10                  15

Thr Leu Thr Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 407
<211> LENGTH: 49
<212> TYPE: PRT
<213> ORGANISM: artificial sequence
<220> FEATURE:
<223> OTHER INFORMATION: Modified bacterial sequence

<400> SEQUENCE: 407

Lys Glu Val Ile Glu Ala Trp Asn Glu Ile Asp Gln Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 408
<211> LENGTH: 49
<212> TYPE: PRT
<213> ORGANISM: artificial sequence
<220> FEATURE:
<223> OTHER INFORMATION: Modified bacterial sequence

<400> SEQUENCE: 408

Lys Glu Thr Leu Gln Ala Trp Asp Glu Ile Asp His Leu Pro Asn Leu
1               5                   10                  15

Thr Leu Asn Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 409
<211> LENGTH: 49
<212> TYPE: PRT
<213> ORGANISM: artificial sequence
<220> FEATURE:
<223> OTHER INFORMATION: Modified bacterial sequence

<400> SEQUENCE: 409

Lys Glu Val Ile Asp Ala Trp Asn Glu Ile Asp His Leu Pro Asn Leu
1               5                   10                  15

```
Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 410
<211> LENGTH: 49
<212> TYPE: PRT
<213> ORGANISM: artificial sequence
<220> FEATURE:
<223> OTHER INFORMATION: Modified bacterial sequence

<400> SEQUENCE: 410

Lys Glu Val Ile Glu Ala Trp Asn Gly Ile Asp Leu Leu Pro Asn Leu
1               5                   10                  15

Thr Leu Ser Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 411
<211> LENGTH: 49
<212> TYPE: PRT
<213> ORGANISM: artificial sequence
<220> FEATURE:
<223> OTHER INFORMATION: Modified bacterial sequence

<400> SEQUENCE: 411

Lys Glu Val Ile Asp Ala Trp Asp Glu Ile Asp Arg Leu Pro Asn Leu
1               5                   10                  15

Thr Leu Lys Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 412
<211> LENGTH: 49
<212> TYPE: PRT
<213> ORGANISM: artificial sequence
<220> FEATURE:
<223> OTHER INFORMATION: Modified bacterial sequence

<400> SEQUENCE: 412

Lys Glu Thr Leu His Ala Trp Asp Glu Ile Asp Lys Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 413
<211> LENGTH: 49
<212> TYPE: PRT
<213> ORGANISM: artificial sequence
<220> FEATURE:
<223> OTHER INFORMATION: Modified bacterial sequence
```

<400> SEQUENCE: 413

Lys Glu Val Ile Lys Ala Trp Asp Glu Ile Asp His Leu Pro Asn Leu
1               5                   10                  15

Thr Leu Asn Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 414
<211> LENGTH: 49
<212> TYPE: PRT
<213> ORGANISM: artificial sequence
<220> FEATURE:
<223> OTHER INFORMATION: Modified bacterial sequence

<400> SEQUENCE: 414

Lys Glu Val Ile Glu Ala Trp Asn Glu Ile Asp His Leu Pro Asn Leu
1               5                   10                  15

Thr Leu Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 415
<211> LENGTH: 49
<212> TYPE: PRT
<213> ORGANISM: artificial sequence
<220> FEATURE:
<223> OTHER INFORMATION: Modified bacterial sequence

<400> SEQUENCE: 415

Lys Glu Val Ile Gln Ala Trp Asn Glu Ile Asp His Leu Pro Asn Leu
1               5                   10                  15

Thr Ile Asp Gln Trp Leu Ala Phe Ile Thr Lys Leu Glu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 416
<211> LENGTH: 49
<212> TYPE: PRT
<213> ORGANISM: artificial sequence
<220> FEATURE:
<223> OTHER INFORMATION: Modified bacterial sequence

<400> SEQUENCE: 416

Lys Glu Val Ile Glu Ala Trp Asn Glu Ile Asp Arg Leu Pro Asn Leu
1               5                   10                  15

Thr Ile Lys Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 417

-continued

```
<211> LENGTH: 49
<212> TYPE: PRT
<213> ORGANISM: artificial sequence
<220> FEATURE:
<223> OTHER INFORMATION: Modified bacterial sequence

<400> SEQUENCE: 417

Lys Glu Val Ile Glu Ala Trp Asn Glu Ile Asp Ser Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 418
<211> LENGTH: 49
<212> TYPE: PRT
<213> ORGANISM: artificial sequence
<220> FEATURE:
<223> OTHER INFORMATION: Modified bacterial sequence

<400> SEQUENCE: 418

Lys Glu Thr Ile Asp Ala Trp Asn Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 419
<211> LENGTH: 49
<212> TYPE: PRT
<213> ORGANISM: artificial sequence
<220> FEATURE:
<223> OTHER INFORMATION: Modified bacterial sequence

<400> SEQUENCE: 419

Lys Glu Val Leu Glu Ala Trp Ala Glu Ile Asp Ala Leu Pro Asn Leu
1               5                   10                  15

Thr Ile Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 420
<211> LENGTH: 49
<212> TYPE: PRT
<213> ORGANISM: artificial sequence
<220> FEATURE:
<223> OTHER INFORMATION: Modified bacterial sequence

<400> SEQUENCE: 420

Lys Glu Thr Ile Asp Ala Trp Asn Glu Ile Asp Arg Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 421
<211> LENGTH: 49
<212> TYPE: PRT
<213> ORGANISM: artificial sequence
<220> FEATURE:
<223> OTHER INFORMATION: Modified bacterial sequence

<400> SEQUENCE: 421

Lys Glu Thr Leu Lys Ala Trp Asp Glu Ile Asp Arg Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 422
<211> LENGTH: 49
<212> TYPE: PRT
<213> ORGANISM: artificial sequence
<220> FEATURE:
<223> OTHER INFORMATION: Modified bacterial sequence

<400> SEQUENCE: 422

Lys Glu Thr Ile Ala Ala Trp Asn Glu Ile Asp Ala Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 423
<211> LENGTH: 49
<212> TYPE: PRT
<213> ORGANISM: artificial sequence
<220> FEATURE:
<223> OTHER INFORMATION: Modified bacterial sequence

<400> SEQUENCE: 423

Lys Glu Val Leu Gln Ala Trp Asn Glu Ile Asp His Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 424
<211> LENGTH: 49
<212> TYPE: PRT
<213> ORGANISM: artificial sequence
<220> FEATURE:
<223> OTHER INFORMATION: Modified bacterial sequence

<400> SEQUENCE: 424

Lys Glu Val Ile Glu Ala Trp Ser Glu Ile Asp His Leu Pro Asn Leu
1               5                   10                  15

Thr Leu Gln Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 425
<211> LENGTH: 49
<212> TYPE: PRT
<213> ORGANISM: artificial sequence
<220> FEATURE:
<223> OTHER INFORMATION: Modified bacterial sequence

<400> SEQUENCE: 425

Lys Glu Val Ile Asp Ala Trp Asn Glu Ile Asp Gly Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 426
<211> LENGTH: 49
<212> TYPE: PRT
<213> ORGANISM: artificial sequence
<220> FEATURE:
<223> OTHER INFORMATION: Modified bacterial sequence

<400> SEQUENCE: 426

Lys Glu Val Ile His Ala Trp Asn Glu Ile Asp His Leu Pro Asn Leu
1               5                   10                  15

Thr Leu Asn Gln Trp Leu Ala Phe Ile Asn Lys Leu Glu Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 427
<211> LENGTH: 49
<212> TYPE: PRT
<213> ORGANISM: artificial sequence
<220> FEATURE:
<223> OTHER INFORMATION: Modified bacterial sequence

<400> SEQUENCE: 427

Lys Glu Val Leu Asp Ala Trp Asn Glu Ile Asp Ser Leu Pro Asn Leu
1               5                   10                  15

Thr Leu Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 428
<211> LENGTH: 49
<212> TYPE: PRT
<213> ORGANISM: artificial sequence
<220> FEATURE:
<223> OTHER INFORMATION: Modified bacterial sequence -continued

```
<400> SEQUENCE: 428

Lys Glu Gln Ile Glu Ala Trp Asn Glu Ile Asp Arg Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 429
<211> LENGTH: 49
<212> TYPE: PRT
<213> ORGANISM: artificial sequence
<220> FEATURE:
<223> OTHER INFORMATION: Modified bacterial sequence

<400> SEQUENCE: 429

Lys Glu Val Val Asp Ala Trp Asn Glu Ile Asp Ala Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 430
<211> LENGTH: 49
<212> TYPE: PRT
<213> ORGANISM: artificial sequence
<220> FEATURE:
<223> OTHER INFORMATION: Modified bacterial sequence

<400> SEQUENCE: 430

Lys Glu Val Ile Glu Ala Trp Asn Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 431
<211> LENGTH: 49
<212> TYPE: PRT
<213> ORGANISM: artificial sequence
<220> FEATURE:
<223> OTHER INFORMATION: Modified bacterial sequence

<400> SEQUENCE: 431

Lys Glu Val Ile Glu Ala Asn Asp Glu Ile Asp Arg Leu Pro Asn Leu
1               5                   10                  15

Thr Ile Glu Gln Trp Leu Ala Phe Ile Asn Lys Leu His Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 432
<211> LENGTH: 49
```

```
<212> TYPE: PRT
<213> ORGANISM: artificial sequence
<220> FEATURE:
<223> OTHER INFORMATION: Modified bacterial sequence

<400> SEQUENCE: 432

Lys Glu Thr Leu Gln Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 433
<211> LENGTH: 49
<212> TYPE: PRT
<213> ORGANISM: artificial sequence
<220> FEATURE:
<223> OTHER INFORMATION: Modified bacterial sequence

<400> SEQUENCE: 433

Lys Glu Val Ile Glu Ala Trp Asp Glu Ile Asp His Leu Pro Asn Leu
1               5                   10                  15

Thr Ile Asp Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 434
<211> LENGTH: 49
<212> TYPE: PRT
<213> ORGANISM: artificial sequence
<220> FEATURE:
<223> OTHER INFORMATION: Modified bacterial sequence

<400> SEQUENCE: 434

Lys Glu Thr Ile Asp Ala Trp Asn Glu Ile Asp His Leu Pro Asn Leu
1               5                   10                  15

Thr Leu Gln Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 435
<211> LENGTH: 49
<212> TYPE: PRT
<213> ORGANISM: artificial sequence
<220> FEATURE:
<223> OTHER INFORMATION: Modified bacterial sequence

<400> SEQUENCE: 435

Lys Glu Val Ile Asp Ala Trp Asp Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45
```

Gln

<210> SEQ ID NO 436
<211> LENGTH: 49
<212> TYPE: PRT
<213> ORGANISM: artificial sequence
<220> FEATURE:
<223> OTHER INFORMATION: Modified bacterial sequence

<400> SEQUENCE: 436

Lys Glu Val Ile Glu Ala Trp Asn Glu Ile Asp Lys Leu Pro Asn Leu
1               5                   10                  15

Thr Leu Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 437
<211> LENGTH: 49
<212> TYPE: PRT
<213> ORGANISM: artificial sequence
<220> FEATURE:
<223> OTHER INFORMATION: Modified bacterial sequence

<400> SEQUENCE: 437

Lys Glu Val Leu Gln Ala Trp Asp Glu Ile Asp Lys Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 438
<211> LENGTH: 49
<212> TYPE: PRT
<213> ORGANISM: artificial sequence
<220> FEATURE:
<223> OTHER INFORMATION: Modified bacterial sequence

<400> SEQUENCE: 438

Lys Glu Val Ile Ala Ala Trp Asn Glu Ile Asp Gly Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 439
<211> LENGTH: 49
<212> TYPE: PRT
<213> ORGANISM: artificial sequence
<220> FEATURE:
<223> OTHER INFORMATION: Modified bacterial sequence

<400> SEQUENCE: 439

Lys Glu Thr Leu Asn Ala Trp Asn Glu Ile Asp Ala Leu Pro Asn Leu
1               5                   10                  15

Thr Leu Gln Gln Trp Leu Ala Phe Ile Asn Lys Leu Asp Asp Asp Pro 20                  25                  30

Ser Gln Ser Ser Glu Leu Leu Ser Glu Ala Lys Lys Leu Asn Asp Ser
        35                  40                  45

Gln

<210> SEQ ID NO 440
<211> LENGTH: 49
<212> TYPE: PRT
<213> ORGANISM: artificial sequence
<220> FEATURE:
<223> OTHER INFORMATION: Modified bacterial sequence

<400> SEQUENCE: 440

Lys Glu Val Leu Ser Ala Trp Asn Glu Ile Asp Gln Leu Pro Asn Leu
1               5                   10                  15

Thr Leu Glu Gln Trp Leu Ala Phe Ile Asn Lys Leu Asp Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 441
<211> LENGTH: 49
<212> TYPE: PRT
<213> ORGANISM: artificial sequence
<220> FEATURE:
<223> OTHER INFORMATION: Modified bacterial sequence

<400> SEQUENCE: 441

Lys Glu Thr Leu Glu Ala Trp Asp Glu Ile Asp His Leu Pro Asn Leu
1               5                   10                  15

Thr Leu His Gln Trp Leu Ala Phe Ile Asn Lys Leu Asp Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 442
<211> LENGTH: 49
<212> TYPE: PRT
<213> ORGANISM: artificial sequence
<220> FEATURE:
<223> OTHER INFORMATION: Modified bacterial sequence

<400> SEQUENCE: 442

Lys Glu Gln Ile Glu Ala Trp Asn Glu Ile Asp His Leu Pro Asn Leu
1               5                   10                  15

Thr Leu Gln Gln Trp Leu Ala Phe Ile Asn Lys Leu Ala Asp Asp Pro
                20                  25                  30

Ser Gln Ser Ser Glu Leu Leu Ser Glu Ala Lys Lys Leu Asn Asp Ser
        35                  40                  45

Gln

<210> SEQ ID NO 443
<211> LENGTH: 49
<212> TYPE: PRT
<213> ORGANISM: artificial sequence
<220> FEATURE:
<223> OTHER INFORMATION: Modified bacterial sequence

<400> SEQUENCE: 443

-continued

Lys Glu Val Glu Ala Trp Asp Glu Ile Asp Lys Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 444
<211> LENGTH: 49
<212> TYPE: PRT
<213> ORGANISM: artificial sequence
<220> FEATURE:
<223> OTHER INFORMATION: Modified bacterial sequence

<400> SEQUENCE: 444

Lys Glu Val Leu Glu Ala Trp Asn Glu Ile Asp Glu Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 445
<211> LENGTH: 49
<212> TYPE: PRT
<213> ORGANISM: artificial sequence
<220> FEATURE:
<223> OTHER INFORMATION: Modified bacterial sequence

<400> SEQUENCE: 445

Lys Glu Val Ile Asp Ala Trp Asn Glu Ile Asp Gln Leu Pro Asn Leu
1               5                   10                  15

Thr Leu Gln Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 446
<211> LENGTH: 49
<212> TYPE: PRT
<213> ORGANISM: artificial sequence
<220> FEATURE:
<223> OTHER INFORMATION: Modified bacterial sequence

<400> SEQUENCE: 446

Lys Glu Thr Ile Asp Ala Trp Asp Glu Ile Asp Lys Leu Pro Asn Leu
1               5                   10                  15

Thr Leu Ser Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 447
<211> LENGTH: 49
<212> TYPE: PRT

-continued

<213> ORGANISM: artificial sequence
<220> FEATURE:
<223> OTHER INFORMATION: Modified bacterial sequence

<400> SEQUENCE: 447

```
Lys Glu Thr Ile Asp Ala Trp Asn Glu Ile Asp Gln Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 448
<211> LENGTH: 49
<212> TYPE: PRT
<213> ORGANISM: artificial sequence
<220> FEATURE:
<223> OTHER INFORMATION: Modified bacterial sequence

<400> SEQUENCE: 448

```
Lys Glu Val Ile Gln Ala Trp Asp Glu Ile Asp Ala Leu Pro Asn Leu
1               5                   10                  15

Thr Leu Asn Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 449
<211> LENGTH: 49
<212> TYPE: PRT
<213> ORGANISM: artificial sequence
<220> FEATURE:
<223> OTHER INFORMATION: Modified bacterial sequence

<400> SEQUENCE: 449

```
Lys Glu Val Leu Asp Ala Trp Ala Glu Ile Asp Gln Leu Pro Asn Leu
1               5                   10                  15

Thr Leu Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 450
<211> LENGTH: 49
<212> TYPE: PRT
<213> ORGANISM: artificial sequence
<220> FEATURE:
<223> OTHER INFORMATION: Modified bacterial sequence

<400> SEQUENCE: 450

```
Lys Glu His Ile Ala Ala Trp Asp Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 451
<211> LENGTH: 49
<212> TYPE: PRT
<213> ORGANISM: artificial sequence
<220> FEATURE:
<223> OTHER INFORMATION: Modified bacterial sequence

<400> SEQUENCE: 451

Lys Glu Val Ile Arg Ala Trp Asp Glu Ile Asp Ala Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 452
<211> LENGTH: 49
<212> TYPE: PRT
<213> ORGANISM: artificial sequence
<220> FEATURE:
<223> OTHER INFORMATION: Modified bacterial sequence

<400> SEQUENCE: 452

Lys Glu Val Ile Asp Ala Trp Asp Glu Ile Asp Ala Leu Pro Asn Leu
1               5                   10                  15

Thr Ile Asp Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 453
<211> LENGTH: 49
<212> TYPE: PRT
<213> ORGANISM: artificial sequence
<220> FEATURE:
<223> OTHER INFORMATION: Modified bacterial sequence

<400> SEQUENCE: 453

Lys Glu Val Ile Asp Ala Trp Asn Glu Ile Asp Arg Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 454
<211> LENGTH: 49
<212> TYPE: PRT
<213> ORGANISM: artificial sequence
<220> FEATURE:
<223> OTHER INFORMATION: Modified bacterial sequence

<400> SEQUENCE: 454

Lys Glu Val Ile Thr Ala Trp Asn Glu Ile Asp His Leu Pro Asn Leu
1               5                   10                  15

Thr Leu Ser Gln Trp Leu Ala Phe Ile Asn Lys Leu Asp Asp Asp Pro
            20                  25                  30

-continued

Ser Gln Ser Ser Glu Leu Leu Ser Glu Ala Lys Lys Leu Asn Asp Ser
        35                  40                  45

Gln

<210> SEQ ID NO 455
<211> LENGTH: 49
<212> TYPE: PRT
<213> ORGANISM: artificial sequence
<220> FEATURE:
<223> OTHER INFORMATION: Modified bacterial sequence

<400> SEQUENCE: 455

Lys Glu Val Ile Asp Ala Trp Asn Glu Ile Asp Ala Leu Pro Asn Leu
1               5                   10                  15

Thr Ile His Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 456
<211> LENGTH: 49
<212> TYPE: PRT
<213> ORGANISM: artificial sequence
<220> FEATURE:
<223> OTHER INFORMATION: Modified bacterial sequence

<400> SEQUENCE: 456

Lys Glu Gln Leu Lys Ala Trp Asp Glu Ile Asp Lys Leu Pro Asn Leu
1               5                   10                  15

Thr Ile Glu Gln Trp Leu Ala Phe Ile Glu Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 457
<211> LENGTH: 49
<212> TYPE: PRT
<213> ORGANISM: artificial sequence
<220> FEATURE:
<223> OTHER INFORMATION: Modified bacterial sequence

<400> SEQUENCE: 457

Lys Glu His Ile Asp Ala Trp Thr Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 458
<211> LENGTH: 49
<212> TYPE: PRT
<213> ORGANISM: artificial sequence
<220> FEATURE:
<223> OTHER INFORMATION: Modified bacterial sequence

<400> SEQUENCE: 458

-continued

```
Lys Glu Gln Leu Arg Ala Trp Asp Glu Ile Asp Lys Leu Pro Asn Leu
1               5                   10                  15

Thr Ile Glu Gln Trp Leu Ala Phe Ile Asn Lys Leu Gln Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 459
<211> LENGTH: 49
<212> TYPE: PRT
<213> ORGANISM: artificial sequence
<220> FEATURE:
<223> OTHER INFORMATION: Modified bacterial sequence

<400> SEQUENCE: 459

```
Lys Glu Val Leu Glu Ala Trp Arg Glu Ile Asp Ser Leu Pro Asn Leu
1               5                   10                  15

Thr Ile Ala Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 460
<211> LENGTH: 49
<212> TYPE: PRT
<213> ORGANISM: artificial sequence
<220> FEATURE:
<223> OTHER INFORMATION: Modified bacterial sequence

<400> SEQUENCE: 460

```
Lys Glu Val Ile Gln Ala Trp Asn Glu Ile Asp Lys Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 461
<211> LENGTH: 49
<212> TYPE: PRT
<213> ORGANISM: artificial sequence
<220> FEATURE:
<223> OTHER INFORMATION: Modified bacterial sequence

<400> SEQUENCE: 461

```
Lys Glu His Val Glu Ala Trp Asn Glu Ile Asp Gln Leu Pro Asn Leu
1               5                   10                  15

Thr Ile Glu Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln
```

<210> SEQ ID NO 462
<211> LENGTH: 49
<212> TYPE: PRT
<213> ORGANISM: artificial sequence -continued

```
<220> FEATURE:
<223> OTHER INFORMATION: Modified bacterial sequence

<400> SEQUENCE: 462

Lys Glu Val Ile Asp Ala Trp Asp Glu Ile Asp Ala Leu Pro Asn Leu
1               5                   10                  15

Thr Ile Asp Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 463
<211> LENGTH: 49
<212> TYPE: PRT
<213> ORGANISM: artificial sequence
<220> FEATURE:
<223> OTHER INFORMATION: Modified bacterial sequence

<400> SEQUENCE: 463

Lys Glu Val Ile Glu Ala Trp Asn Glu Ile Asp His Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 464
<211> LENGTH: 49
<212> TYPE: PRT
<213> ORGANISM: artificial sequence
<220> FEATURE:
<223> OTHER INFORMATION: Modified bacterial sequence

<400> SEQUENCE: 464

Lys Glu Val Leu Gln Ala Trp Asp Glu Ile Asp Lys Leu Pro Asn Leu
1               5                   10                  15

Thr Ile Glu Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 465
<211> LENGTH: 49
<212> TYPE: PRT
<213> ORGANISM: artificial sequence
<220> FEATURE:
<223> OTHER INFORMATION: Modified bacterial sequence

<400> SEQUENCE: 465

Lys Glu Val Ile Lys Ala Trp Asn Glu Ile Asp Ser Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln
```

```
<210> SEQ ID NO 466
<211> LENGTH: 49
<212> TYPE: PRT
<213> ORGANISM: artificial sequence
<220> FEATURE:
<223> OTHER INFORMATION: Modified bacterial sequence

<400> SEQUENCE: 466

Lys Glu Val Leu Glu Ala Trp His Glu Ile Asp Leu Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 467
<211> LENGTH: 49
<212> TYPE: PRT
<213> ORGANISM: artificial sequence
<220> FEATURE:
<223> OTHER INFORMATION: Modified bacterial sequence

<400> SEQUENCE: 467

Lys Glu Val Leu Glu Ala Trp Thr Glu Ile Asp Arg Leu Pro Asn Leu
1               5                   10                  15

Thr Leu Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 468
<211> LENGTH: 49
<212> TYPE: PRT
<213> ORGANISM: artificial sequence
<220> FEATURE:
<223> OTHER INFORMATION: Modified bacterial sequence

<400> SEQUENCE: 468

Lys Glu Gln Leu Tyr Ala Trp Asn Glu Ile Asp His Leu Pro Asn Leu
1               5                   10                  15

Thr Ile Glu Gln Trp Leu Ala Phe Ile Glu Lys Leu Gln Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 469
<211> LENGTH: 49
<212> TYPE: PRT
<213> ORGANISM: artificial sequence
<220> FEATURE:
<223> OTHER INFORMATION: Modified bacterial sequence

<400> SEQUENCE: 469

Lys Glu Val Leu Asn Ala Trp Asp Glu Ile Asp Lys Leu Pro Asn Leu
1               5                   10                  15

Thr Ile Lys Gln Trp Leu Ala Phe Ile Asn Lys Leu Asp Asp Asp Pro
            20                  25                  30
```

Ser Gln Ser Ser Glu Leu Leu Ser Glu Ala Lys Lys Leu Asn Asp Ser
        35                  40                  45

Gln

<210> SEQ ID NO 470
<211> LENGTH: 49
<212> TYPE: PRT
<213> ORGANISM: artificial sequence
<220> FEATURE:
<223> OTHER INFORMATION: Modified bacterial sequence

<400> SEQUENCE: 470

Lys Glu Val Ile Arg Ala Trp Asp Glu Ile Asp Lys Leu Pro Asn Leu
1               5                   10                  15

Thr Val Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 471
<211> LENGTH: 49
<212> TYPE: PRT
<213> ORGANISM: artificial sequence
<220> FEATURE:
<223> OTHER INFORMATION: Modified bacterial sequence

<400> SEQUENCE: 471

Lys Glu Val Val Gln Ala Trp Asp Glu Ile Asp Gln Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 472
<211> LENGTH: 49
<212> TYPE: PRT
<213> ORGANISM: artificial sequence
<220> FEATURE:
<223> OTHER INFORMATION: Modified bacterial sequence

<400> SEQUENCE: 472

Lys Glu Val Ile Arg Ala Trp Asp Glu Ile Asp Gln Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 473
<211> LENGTH: 49
<212> TYPE: PRT
<213> ORGANISM: artificial sequence
<220> FEATURE:
<223> OTHER INFORMATION: Modified bacterial sequence

<400> SEQUENCE: 473

Lys Glu Thr Ile Asp Ala Trp Asn Glu Ile Asp His Leu Pro Asn Leu

```
                1               5                  10                  15
Thr Leu Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 474
<211> LENGTH: 49
<212> TYPE: PRT
<213> ORGANISM: artificial sequence
<220> FEATURE:
<223> OTHER INFORMATION: Modified bacterial sequence

<400> SEQUENCE: 474

Lys Glu Val Val Ala Ala Trp Thr Glu Ile Asp Leu Leu Pro Asn Leu
1               5                  10                  15

Thr Leu Asp Gln Trp Leu Ala Phe Ile Asn Lys Leu Glu Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 475
<211> LENGTH: 49
<212> TYPE: PRT
<213> ORGANISM: artificial sequence
<220> FEATURE:
<223> OTHER INFORMATION: Modified bacterial sequence

<400> SEQUENCE: 475

Lys Glu Val Val Ala Ala Trp Asp Glu Ile Asp Ala Leu Pro Asn Leu
1               5                  10                  15

Thr Ile Glu Gln Trp Leu Ala Phe Ile Asn Lys Leu Ser Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 476
<211> LENGTH: 49
<212> TYPE: PRT
<213> ORGANISM: artificial sequence
<220> FEATURE:
<223> OTHER INFORMATION: Modified bacterial sequence

<400> SEQUENCE: 476

Lys Glu Thr Leu Glu Ala Trp Arg Glu Ile Asp Ser Leu Pro Asn Leu
1               5                  10                  15

Thr Leu Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 477
<211> LENGTH: 49
<212> TYPE: PRT
<213> ORGANISM: artificial sequence
<220> FEATURE:
```

<223> OTHER INFORMATION: Modified bacterial sequence

<400> SEQUENCE: 477

Lys Glu Val Ile Lys Ala Trp Asn Glu Ile Asp His Leu Pro Asn Leu
1               5                   10                  15

Thr Leu Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 478
<211> LENGTH: 49
<212> TYPE: PRT
<213> ORGANISM: artificial sequence
<220> FEATURE:
<223> OTHER INFORMATION: Modified bacterial sequence

<400> SEQUENCE: 478

Lys Glu Val Leu Glu Ala Trp Thr Glu Ile Asp Lys Leu Pro Asn Leu
1               5                   10                  15

Thr Ile Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 479
<211> LENGTH: 49
<212> TYPE: PRT
<213> ORGANISM: artificial sequence
<220> FEATURE:
<223> OTHER INFORMATION: Modified bacterial sequence

<400> SEQUENCE: 479

Lys Glu Thr Leu Glu Ala Trp Asp Glu Ile Asp Lys Leu Pro Asn Leu
1               5                   10                  15

Thr Ile Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 480
<211> LENGTH: 49
<212> TYPE: PRT
<213> ORGANISM: artificial sequence
<220> FEATURE:
<223> OTHER INFORMATION: Modified bacterial sequence

<400> SEQUENCE: 480

Lys Glu Val Ile Glu Ala Trp Asn Glu Ile Asp Lys Leu Pro Asn Leu
1               5                   10                  15

Thr Ile Asp Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

```
<210> SEQ ID NO 481
<211> LENGTH: 49
<212> TYPE: PRT
<213> ORGANISM: artificial sequence
<220> FEATURE:
<223> OTHER INFORMATION: Modified bacterial sequence

<400> SEQUENCE: 481

Lys Glu Thr Ile Asp Ala Trp Asn Glu Ile Asp Lys Leu Pro Asn Leu
1               5                   10                  15

Thr Leu Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 482
<211> LENGTH: 49
<212> TYPE: PRT
<213> ORGANISM: artificial sequence
<220> FEATURE:
<223> OTHER INFORMATION: Modified bacterial sequence

<400> SEQUENCE: 482

Lys Glu Thr Leu Asp Ala Trp Asp Glu Ile Asp Ala Leu Pro Asn Leu
1               5                   10                  15

Thr Ile Asp Gln Trp Leu Ala Phe Ile Asn Lys Leu Glu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 483
<211> LENGTH: 49
<212> TYPE: PRT
<213> ORGANISM: artificial sequence
<220> FEATURE:
<223> OTHER INFORMATION: Modified bacterial sequence

<400> SEQUENCE: 483

Lys Glu Val Leu Ser Ala Trp Asn Glu Ile Asp His Leu Pro Asn Leu
1               5                   10                  15

Thr Ile Gln Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 484
<211> LENGTH: 49
<212> TYPE: PRT
<213> ORGANISM: artificial sequence
<220> FEATURE:
<223> OTHER INFORMATION: Modified bacterial sequence

<400> SEQUENCE: 484

Lys Glu Val Ile Gln Ala Asn Asp Glu Ile Asp Lys Leu Pro Asn Leu
1               5                   10                  15

Thr Ile Glu Gln Trp Leu Ala Phe Ile His Lys Leu His Asp Asp Pro
            20                  25                  30

Ser Gln Ser Ser Glu Leu Leu Ser Glu Ala Lys Lys Leu Asn Asp Ser
```

Gln

<210> SEQ ID NO 485
<211> LENGTH: 49
<212> TYPE: PRT
<213> ORGANISM: artificial sequence
<220> FEATURE:
<223> OTHER INFORMATION: Modified bacterial sequence

<400> SEQUENCE: 485

Lys Glu His Leu Asp Ala Trp Asp Glu Ile Asp His Leu Pro Asn Leu
1               5                   10                  15

Thr Ile Gln Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 486
<211> LENGTH: 49
<212> TYPE: PRT
<213> ORGANISM: artificial sequence
<220> FEATURE:
<223> OTHER INFORMATION: Modified bacterial sequence

<400> SEQUENCE: 486

Lys Glu Val Ile Gln Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 487
<211> LENGTH: 49
<212> TYPE: PRT
<213> ORGANISM: artificial sequence
<220> FEATURE:
<223> OTHER INFORMATION: Modified bacterial sequence

<400> SEQUENCE: 487

Lys Glu Val Ile Glu Ala Trp Asn Glu Ile Asp Tyr Leu Pro Asn Leu
1               5                   10                  15

Thr Ile Ala Gln Trp Ile Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 488
<211> LENGTH: 49
<212> TYPE: PRT
<213> ORGANISM: artificial sequence
<220> FEATURE:
<223> OTHER INFORMATION: Modified bacterial sequence

<400> SEQUENCE: 488

Lys Glu Thr Ile Gln Ala Trp Asp Glu Ile Asp Arg Leu Pro Asn Leu
1               5                   10                  15

Thr Leu Gln Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 489
<211> LENGTH: 49
<212> TYPE: PRT
<213> ORGANISM: artificial sequence
<220> FEATURE:
<223> OTHER INFORMATION: Modified bacterial sequence

<400> SEQUENCE: 489

Lys Glu Thr Ile Gln Ala Trp Asp Glu Ile Asp Lys Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 490
<211> LENGTH: 49
<212> TYPE: PRT
<213> ORGANISM: artificial sequence
<220> FEATURE:
<223> OTHER INFORMATION: Modified bacterial sequence

<400> SEQUENCE: 490

Lys Glu Thr Leu Asp Ala Trp Ala Glu Ile Asp His Leu Pro Asn Leu
1               5                   10                  15

Thr Ile Glu Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 491
<211> LENGTH: 49
<212> TYPE: PRT
<213> ORGANISM: artificial sequence
<220> FEATURE:
<223> OTHER INFORMATION: Modified bacterial sequence

<400> SEQUENCE: 491

Lys Glu Val Ile Glu Ala Trp Asp Glu Ile Asp Lys Leu Pro Asn Leu
1               5                   10                  15

Thr Leu Asn Gln Trp Leu Ala Phe Ile Asn Lys Leu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 492
<211> LENGTH: 49
<212> TYPE: PRT
<213> ORGANISM: artificial sequence
<220> FEATURE:
<223> OTHER INFORMATION: Modified bacterial sequence

```
<400> SEQUENCE: 492

Lys Glu Val Leu Asp Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 493
<211> LENGTH: 49
<212> TYPE: PRT
<213> ORGANISM: artificial sequence
<220> FEATURE:
<223> OTHER INFORMATION: Modified bacterial sequence

<400> SEQUENCE: 493

Lys Glu Val Leu His Ala Trp Asn Glu Ile Asp His Leu Pro Asn Leu
1               5                   10                  15

Thr Ile Glu Gln Trp Leu Ala Phe Ile Glu Lys Leu Glu Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 494
<211> LENGTH: 49
<212> TYPE: PRT
<213> ORGANISM: artificial sequence
<220> FEATURE:
<223> OTHER INFORMATION: Modified bacterial sequence

<400> SEQUENCE: 494

Lys Glu Val Ile Glu Ala Trp Gln Glu Ile Asp Lys Leu Pro Asn Leu
1               5                   10                  15

Thr Ile Asp Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 495
<211> LENGTH: 49
<212> TYPE: PRT
<213> ORGANISM: artificial sequence
<220> FEATURE:
<223> OTHER INFORMATION: Modified bacterial sequence

<400> SEQUENCE: 495

Lys Glu Val Val Asp Ala Trp Asn Glu Ile Asp Gln Leu Pro Asn Leu
1               5                   10                  15

Thr Ile Glu Gln Trp Leu Ala Phe Ile Asn Lys Leu Asp Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 496
```

```
<211> LENGTH: 49
<212> TYPE: PRT
<213> ORGANISM: artificial sequence
<220> FEATURE:
<223> OTHER INFORMATION: Modified bacterial sequence

<400> SEQUENCE: 496

Lys Glu Gln Ile Glu Ala Trp Asn Glu Ile Asp Ala Leu Pro Asn Leu
1               5                   10                  15

Thr Ile Glu Gln Trp Leu Ala Phe Ile Asn Lys Leu Ala Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 497
<211> LENGTH: 58
<212> TYPE: PRT
<213> ORGANISM: artificial sequence
<220> FEATURE:
<223> OTHER INFORMATION: Modified bacterial sequence

<400> SEQUENCE: 497

Val Asp Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 498
<211> LENGTH: 58
<212> TYPE: PRT
<213> ORGANISM: artificial sequence
<220> FEATURE:
<223> OTHER INFORMATION: Modified bacterial sequence

<400> SEQUENCE: 498

Val Asp Ala Lys Tyr Ala Lys Glu Val Leu Glu Ala Trp Asn Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 499
<211> LENGTH: 58
<212> TYPE: PRT
<213> ORGANISM: artificial sequence
<220> FEATURE:
<223> OTHER INFORMATION: Modified bacterial sequence

<400> SEQUENCE: 499

Val Asp Ala Lys Tyr Ala Lys Glu Val Ile Glu Ala Trp Asn Glu Ile
1               5                   10                  15

Asp Arg Leu Pro Asn Leu Thr Ile Glu Gln Trp Leu Ala Phe Ile Asn
            20                  25                  30
```

Lys Leu Asp Asp Asp Pro Ser Gln Ser Ser Glu Leu Ser Glu Ala
         35                  40                  45

Lys Lys Leu Asn Asp Ser Gln Ala Pro Lys
     50                  55

<210> SEQ ID NO 500
<211> LENGTH: 58
<212> TYPE: PRT
<213> ORGANISM: artificial sequence
<220> FEATURE:
<223> OTHER INFORMATION: Modified bacterial sequence

<400> SEQUENCE: 500

Val Asp Ala Lys Tyr Ala Lys Glu Val Leu Glu Ala Trp Asp Glu Ile
1               5                   10                  15

Asp Arg Leu Pro Asn Leu Thr Leu Asp Gln Trp Leu Ala Phe Ile Asn
             20                  25                  30

Lys Leu Asp Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 501
<211> LENGTH: 58
<212> TYPE: PRT
<213> ORGANISM: artificial sequence
<220> FEATURE:
<223> OTHER INFORMATION: Modified bacterial sequence

<400> SEQUENCE: 501

Val Asp Ala Lys Tyr Ala Lys Glu Val Leu Asp Ala Trp Asp Glu Ile
1               5                   10                  15

Asp Ala Leu Pro Asn Leu Thr Leu Glu Gln Trp Leu Ala Phe Ile Asn
             20                  25                  30

Lys Leu Asp Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 502
<211> LENGTH: 58
<212> TYPE: PRT
<213> ORGANISM: artificial sequence
<220> FEATURE:
<223> OTHER INFORMATION: Modified bacterial sequence

<400> SEQUENCE: 502

Val Asp Ala Lys Tyr Ala Lys Glu Val Ile Asp Ala Trp Asp Glu Ile
1               5                   10                  15

Asp Arg Leu Pro Asn Leu Thr Leu Asp Gln Trp Leu Ala Phe Ile Asn
             20                  25                  30

Lys Leu Asp Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 503
<211> LENGTH: 58
<212> TYPE: PRT
<213> ORGANISM: artificial sequence
<220> FEATURE:
<223> OTHER INFORMATION: Modified bacterial sequence

<400> SEQUENCE: 503

Val Asp Ala Lys Tyr Ala Lys Glu Thr Leu Glu Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 504
<211> LENGTH: 58
<212> TYPE: PRT
<213> ORGANISM: artificial sequence
<220> FEATURE:
<223> OTHER INFORMATION: Modified bacterial sequence

<400> SEQUENCE: 504

Val Asp Ala Lys Tyr Ala Lys Glu Val Ile Asp Ala Trp Asn Glu Ile
1               5                   10                  15

Asp Ala Leu Pro Asn Leu Thr Leu Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 505
<211> LENGTH: 58
<212> TYPE: PRT
<213> ORGANISM: artificial sequence
<220> FEATURE:
<223> OTHER INFORMATION: Modified bacterial sequence

<400> SEQUENCE: 505

Val Asp Ala Lys Tyr Ala Lys Glu Val Leu Asp Ala Trp Asp Glu Ile
1               5                   10                  15

Asp Lys Leu Pro Asn Leu Thr Ile Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 506
<211> LENGTH: 58
<212> TYPE: PRT
<213> ORGANISM: artificial sequence
<220> FEATURE:
<223> OTHER INFORMATION: Modified bacterial sequence

<400> SEQUENCE: 506

Val Asp Ala Lys Tyr Ala Lys Glu Val Leu Glu Ala Trp Asp Glu Ile
1               5                   10                  15

Asp His Leu Pro Asn Leu Thr Leu Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys

```
<210> SEQ ID NO 507
<211> LENGTH: 58
<212> TYPE: PRT
<213> ORGANISM: artificial sequence
<220> FEATURE:
<223> OTHER INFORMATION: Modified bacterial sequence

<400> SEQUENCE: 507

Val Asp Ala Lys Tyr Ala Lys Glu Val Leu Glu Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 508
<211> LENGTH: 58
<212> TYPE: PRT
<213> ORGANISM: artificial sequence
<220> FEATURE:
<223> OTHER INFORMATION: Modified bacterial sequence

<400> SEQUENCE: 508

Val Asp Ala Lys Tyr Ala Lys Glu Val Leu Asp Ala Trp Asp Glu Ile
1               5                   10                  15

Asp Lys Leu Pro Asn Leu Thr Leu Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 509
<211> LENGTH: 58
<212> TYPE: PRT
<213> ORGANISM: artificial sequence
<220> FEATURE:
<223> OTHER INFORMATION: Modified bacterial sequence

<400> SEQUENCE: 509

Val Asp Ala Lys Tyr Ala Lys Glu Thr Ile Thr Ala Trp Asp Glu Ile
1               5                   10                  15

Asp Lys Leu Pro Asn Leu Thr Ile Glu Gln Trp Leu Ala Phe Ile Gly
            20                  25                  30

Lys Leu Glu Asp Pro Ser Gln Ser Ser Glu Leu Leu Ala Glu Ala
        35                  40                  45

Lys Lys Leu Asn Asp Ala Gln Ala Pro Lys
    50                  55

<210> SEQ ID NO 510
<211> LENGTH: 58
<212> TYPE: PRT
<213> ORGANISM: artificial sequence
<220> FEATURE:
<223> OTHER INFORMATION: Modified bacterial sequence

<400> SEQUENCE: 510

Val Asp Asn Lys Phe Asn Lys Glu Ser Met Lys Ala Trp Asp Glu Ile
```

```
            1               5                  10                  15
         Asp Arg Leu Pro Asn Leu Asn Ile Asn Gln Trp Val Ala Phe Ile Asp
                        20                  25                  30

Ser Leu Tyr Asp Asp Pro Ser Gln Ser Ala Asn Leu Leu Ala Glu Ala
                        35                  40                  45

Lys Lys Leu Asn Asp Ala Gln Ala Pro Lys
                        50                  55

<210> SEQ ID NO 511
<211> LENGTH: 58
<212> TYPE: PRT
<213> ORGANISM: artificial sequence
<220> FEATURE:
<223> OTHER INFORMATION: Modified bacterial sequence

<400> SEQUENCE: 511

Val Asp Ala Lys Tyr Ala Lys Glu Ser Ile Glu Ala Trp Thr Glu Ile
1               5                  10                  15

Asp His Leu Pro Asn Leu Thr Ile Glu Gln Trp Leu Ala Phe Ile Asn
                20                  25                  30

Lys Leu Thr Asp Asp Pro Ser Gln Ser Ser Glu Leu Leu Ala Glu Ala
                35                  40                  45

Lys Lys Leu Asn Asp Ala Gln Ala Pro Lys
                50                  55

<210> SEQ ID NO 512
<211> LENGTH: 58
<212> TYPE: PRT
<213> ORGANISM: artificial sequence
<220> FEATURE:
<223> OTHER INFORMATION: Modified bacterial sequence

<400> SEQUENCE: 512

Val Asp Ala Lys Tyr Ala Lys Glu Val Leu Asp Ala Trp His Glu Ile
1               5                  10                  15

Asp Thr Leu Pro Asn Leu Thr Val Arg Gln Trp Leu Ala Phe Ile Ser
                20                  25                  30

Lys Leu Glu Asp Asp Pro Ser Gln Ser Ser Glu Leu Leu Ala Glu Ala
                35                  40                  45

Lys Lys Leu Asn Asp Ala Gln Ala Pro Lys
                50                  55

<210> SEQ ID NO 513
<211> LENGTH: 58
<212> TYPE: PRT
<213> ORGANISM: artificial sequence
<220> FEATURE:
<223> OTHER INFORMATION: Modified bacterial sequence

<400> SEQUENCE: 513

Val Asp Ala Lys Tyr Ala Lys Glu His Ile Gln Ala Asn Glu Glu Ile
1               5                  10                  15

Asp Arg Leu Pro Asn Leu Thr Ile Lys Gln Trp Leu Ala Phe Ile Asn
                20                  25                  30

Lys Leu His Asp Asp Pro Ser Gln Ser Ser Glu Leu Leu Ala Glu Ala
                35                  40                  45

Lys Lys Leu Asn Asp Ala Gln Ala Pro Lys
                50                  55

<210> SEQ ID NO 514
```

<211> LENGTH: 58
<212> TYPE: PRT
<213> ORGANISM: artificial sequence
<220> FEATURE:
<223> OTHER INFORMATION: Modified bacterial sequence

<400> SEQUENCE: 514

Val Asp Ala Lys Tyr Ala Lys Glu Val Leu His Ala Trp Ala Glu Ile
1               5                   10                  15

Asp Ala Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 515
<211> LENGTH: 58
<212> TYPE: PRT
<213> ORGANISM: artificial sequence
<220> FEATURE:
<223> OTHER INFORMATION: Modified bacterial sequence

<400> SEQUENCE: 515

Val Asp Ala Lys Tyr Ala Lys Glu Val Leu Ala Ala Trp Asp Glu Ile
1               5                   10                  15

Asp Ser Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 516
<211> LENGTH: 58
<212> TYPE: PRT
<213> ORGANISM: artificial sequence
<220> FEATURE:
<223> OTHER INFORMATION: Modified bacterial sequence

<400> SEQUENCE: 516

Val Asp Ala Lys Tyr Ala Lys Glu Val Ile Asp Ala Trp Asn Glu Ile
1               5                   10                  15

Asp Ala Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 517
<211> LENGTH: 58
<212> TYPE: PRT
<213> ORGANISM: artificial sequence
<220> FEATURE:
<223> OTHER INFORMATION: Modified bacterial sequence

<400> SEQUENCE: 517

Val Asp Ala Lys Tyr Ala Lys Glu Val Leu Asp Ala Trp Asn Glu Ile
1               5                   10                  15

Asp Ala Leu Pro Asn Leu Thr Ile Asp Gln Trp Leu Ala Phe Ile Asn
            20                  25                  30

-continued

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 518
<211> LENGTH: 58
<212> TYPE: PRT
<213> ORGANISM: artificial sequence
<220> FEATURE:
<223> OTHER INFORMATION: Modified bacterial sequence

<400> SEQUENCE: 518

Val Asp Ala Lys Tyr Ala Lys Glu Val Ile Glu Ala Trp Asp Glu Ile
 1               5                  10                  15

Asp Gly Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 519
<211> LENGTH: 58
<212> TYPE: PRT
<213> ORGANISM: artificial sequence
<220> FEATURE:
<223> OTHER INFORMATION: Modified bacterial sequence

<400> SEQUENCE: 519

Val Asp Ala Lys Tyr Ala Lys Glu Val Leu Glu Ala Trp Asp Glu Ile
 1               5                  10                  15

Asp His Leu Pro Asn Leu Thr Leu Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 520
<211> LENGTH: 58
<212> TYPE: PRT
<213> ORGANISM: artificial sequence
<220> FEATURE:
<223> OTHER INFORMATION: Modified bacterial sequence

<400> SEQUENCE: 520

Val Asp Ala Lys Tyr Ala Lys Glu Val Ile Glu Ala Trp Asn Glu Ile
 1               5                  10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 521
<211> LENGTH: 58
<212> TYPE: PRT
<213> ORGANISM: artificial sequence
<220> FEATURE:

<223> OTHER INFORMATION: Modified bacterial sequence

<400> SEQUENCE: 521

Val Asp Ala Lys Tyr Ala Lys Glu Val Ile Ala Ala Trp Asn Glu Ile
1               5                   10                  15

Asp Arg Leu Pro Asn Leu Thr Leu Thr Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 522
<211> LENGTH: 58
<212> TYPE: PRT
<213> ORGANISM: artificial sequence
<220> FEATURE:
<223> OTHER INFORMATION: Modified bacterial sequence

<400> SEQUENCE: 522

Val Asp Ala Lys Tyr Ala Lys Glu Val Ile Glu Ala Trp Asp Glu Ile
1               5                   10                  15

Asp Ala Leu Pro Asn Leu Thr Leu Gln Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 523
<211> LENGTH: 58
<212> TYPE: PRT
<213> ORGANISM: artificial sequence
<220> FEATURE:
<223> OTHER INFORMATION: Modified bacterial sequence

<400> SEQUENCE: 523

Val Asp Ala Lys Tyr Ala Lys Glu Val Ile Ala Ala Trp Asp Glu Ile
1               5                   10                  15

Asp Lys Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 524
<211> LENGTH: 58
<212> TYPE: PRT
<213> ORGANISM: artificial sequence
<220> FEATURE:
<223> OTHER INFORMATION: Modified bacterial sequence

<400> SEQUENCE: 524

Val Asp Ala Lys Tyr Ala Lys Glu Val Ile Ala Ala Trp Asp Glu Ile
1               5                   10                  15

Asp Lys Leu Pro Asn Leu Thr Leu Gln Gln Trp Leu Ala Phe Ile Asn
                20                  25                  30

Lys Leu Asp Asp Pro Ser Gln Ser Ser Glu Leu Leu Ser Glu Ala
            35                  40                  45

```
Lys Lys Leu Asn Asp Ser Gln Ala Pro Lys
    50                  55

<210> SEQ ID NO 525
<211> LENGTH: 58
<212> TYPE: PRT
<213> ORGANISM: artificial sequence
<220> FEATURE:
<223> OTHER INFORMATION: Modified bacterial sequence

<400> SEQUENCE: 525

Val Asp Ala Lys Tyr Ala Lys Glu Thr Ile Ala Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 526
<211> LENGTH: 58
<212> TYPE: PRT
<213> ORGANISM: artificial sequence
<220> FEATURE:
<223> OTHER INFORMATION: Modified bacterial sequence

<400> SEQUENCE: 526

Val Asp Ala Lys Tyr Ala Lys Glu Thr Ile Glu Ala Trp Asn Glu Ile
1               5                   10                  15

Asp Arg Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 527
<211> LENGTH: 58
<212> TYPE: PRT
<213> ORGANISM: artificial sequence
<220> FEATURE:
<223> OTHER INFORMATION: Modified bacterial sequence

<400> SEQUENCE: 527

Val Asp Ala Lys Tyr Ala Lys Glu Val Leu Glu Ala Trp Arg Glu Ile
1               5                   10                  15

Asp Ala Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 528
<211> LENGTH: 58
<212> TYPE: PRT
<213> ORGANISM: artificial sequence
<220> FEATURE:
<223> OTHER INFORMATION: Modified bacterial sequence

<400> SEQUENCE: 528
```

-continued

Val Asp Ala Lys Tyr Ala Lys Glu Val Ile Glu Ala Trp Asp Glu Ile
1               5                   10                  15

Asp Gln Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 529
<211> LENGTH: 58
<212> TYPE: PRT
<213> ORGANISM: artificial sequence
<220> FEATURE:
<223> OTHER INFORMATION: Modified bacterial sequence

<400> SEQUENCE: 529

Val Asp Ala Lys Tyr Ala Lys Glu Val Leu Arg Ala Trp Asp Glu Ile
1               5                   10                  15

Asp His Leu Pro Asn Leu Thr Leu Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 530
<211> LENGTH: 58
<212> TYPE: PRT
<213> ORGANISM: artificial sequence
<220> FEATURE:
<223> OTHER INFORMATION: Modified bacterial sequence

<400> SEQUENCE: 530

Val Asp Ala Lys Tyr Ala Lys Glu Val Leu Glu Ala Trp Asp Glu Ile
1               5                   10                  15

Asp Arg Leu Pro Asn Leu Thr Leu Asn Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 531
<211> LENGTH: 58
<212> TYPE: PRT
<213> ORGANISM: artificial sequence
<220> FEATURE:
<223> OTHER INFORMATION: Modified bacterial sequence

<400> SEQUENCE: 531

Val Asp Ala Lys Tyr Ala Lys Glu Val Leu Asp Ala Trp Asn Glu Ile
1               5                   10                  15

Asp His Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 532
<211> LENGTH: 58
<212> TYPE: PRT
<213> ORGANISM: artificial sequence
<220> FEATURE:
<223> OTHER INFORMATION: Modified bacterial sequence

<400> SEQUENCE: 532

Val Asp Ala Lys Tyr Ala Lys Glu Val Ile Asp Ala Trp Asn Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 533
<211> LENGTH: 58
<212> TYPE: PRT
<213> ORGANISM: artificial sequence
<220> FEATURE:
<223> OTHER INFORMATION: Modified bacterial sequence

<400> SEQUENCE: 533

Val Asp Ala Lys Tyr Ala Lys Glu Thr Leu Glu Ala Trp Asp Glu Ile
1               5                   10                  15

Asp Gln Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 534
<211> LENGTH: 58
<212> TYPE: PRT
<213> ORGANISM: artificial sequence
<220> FEATURE:
<223> OTHER INFORMATION: Modified bacterial sequence

<400> SEQUENCE: 534

Val Asp Ala Lys Tyr Ala Lys Glu Val Ile Glu Ala Trp Asn Glu Ile
1               5                   10                  15

Asp Ala Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 535
<211> LENGTH: 58
<212> TYPE: PRT
<213> ORGANISM: artificial sequence
<220> FEATURE:
<223> OTHER INFORMATION: Modified bacterial sequence

<400> SEQUENCE: 535

Val Asp Ala Lys Tyr Ala Lys Glu Val Ile Asp Ala Trp Asn Glu Ile
1               5                   10                  15

Asp Arg Leu Pro Asn Leu Thr Leu Gln Gln Trp Leu Ala Phe Ile Asn
```

```
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 536
<211> LENGTH: 58
<212> TYPE: PRT
<213> ORGANISM: artificial sequence
<220> FEATURE:
<223> OTHER INFORMATION: Modified bacterial sequence

<400> SEQUENCE: 536

Val Asp Ala Lys Tyr Ala Lys Glu Val Ile Asp Ala Trp Asn Glu Ile
1               5                   10                  15

Asp Gln Leu Pro Asn Leu Thr Leu Glu Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 537
<211> LENGTH: 58
<212> TYPE: PRT
<213> ORGANISM: artificial sequence
<220> FEATURE:
<223> OTHER INFORMATION: Modified bacterial sequence

<400> SEQUENCE: 537

Val Asp Ala Lys Tyr Ala Lys Glu Thr Ile Ala Ala Trp Asp Glu Ile
1               5                   10                  15

Asp His Leu Pro Asn Leu Thr Leu Glu Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 538
<211> LENGTH: 58
<212> TYPE: PRT
<213> ORGANISM: artificial sequence
<220> FEATURE:
<223> OTHER INFORMATION: Modified bacterial sequence

<400> SEQUENCE: 538

Val Asp Ala Lys Tyr Ala Lys Glu Val Leu Gln Ala Trp Asp Glu Ile
1               5                   10                  15

Asp His Leu Pro Asn Leu Thr Ile Gln Gln Trp Leu Ala Phe Ile Asn
                20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 539
<211> LENGTH: 58
<212> TYPE: PRT
<213> ORGANISM: artificial sequence
```

-continued

```
<220> FEATURE:
<223> OTHER INFORMATION: Modified bacterial sequence

<400> SEQUENCE: 539

Val Asp Ala Lys Tyr Ala Lys Glu Thr Leu His Ala Trp Ala Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 540
<211> LENGTH: 58
<212> TYPE: PRT
<213> ORGANISM: artificial sequence
<220> FEATURE:
<223> OTHER INFORMATION: Modified bacterial sequence

<400> SEQUENCE: 540

Val Asp Ala Lys Tyr Ala Lys Glu Val Leu Glu Ala Trp Asn Glu Ile
1               5                   10                  15

Asp His Leu Pro Asn Leu Thr Leu Ala Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 541
<211> LENGTH: 58
<212> TYPE: PRT
<213> ORGANISM: artificial sequence
<220> FEATURE:
<223> OTHER INFORMATION: Modified bacterial sequence

<400> SEQUENCE: 541

Val Asp Ala Lys Tyr Ala Lys Glu Val Ile Glu Ala Trp Asp Glu Ile
1               5                   10                  15

Asp Lys Leu Pro Asn Leu Thr Ile Ala Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 542
<211> LENGTH: 58
<212> TYPE: PRT
<213> ORGANISM: artificial sequence
<220> FEATURE:
<223> OTHER INFORMATION: Modified bacterial sequence

<400> SEQUENCE: 542

Val Asp Ala Lys Tyr Ala Lys Glu Val Leu Asp Ala Trp Asp Glu Ile
1               5                   10                  15

Asp His Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45
```

```
Lys Lys Leu Asn Asp Ser Gln Ala Pro Lys
    50                  55

<210> SEQ ID NO 543
<211> LENGTH: 58
<212> TYPE: PRT
<213> ORGANISM: artificial sequence
<220> FEATURE:
<223> OTHER INFORMATION: Modified bacterial sequence

<400> SEQUENCE: 543

Val Asp Ala Lys Tyr Ala Lys Glu Thr Ile Glu Ala Trp Asn Glu Ile
1               5                   10                  15

Asp Lys Leu Pro Asn Leu Thr Leu Thr Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 544
<211> LENGTH: 58
<212> TYPE: PRT
<213> ORGANISM: artificial sequence
<220> FEATURE:
<223> OTHER INFORMATION: Modified bacterial sequence

<400> SEQUENCE: 544

Val Asp Ala Lys Tyr Ala Lys Glu Val Leu Glu Ala Trp Asn Glu Ile
1               5                   10                  15

Asp Leu Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 545
<211> LENGTH: 58
<212> TYPE: PRT
<213> ORGANISM: artificial sequence
<220> FEATURE:
<223> OTHER INFORMATION: Modified bacterial sequence

<400> SEQUENCE: 545

Val Asp Ala Lys Tyr Ala Lys Glu Val Ile Glu Ala Trp Asp Glu Ile
1               5                   10                  15

Asp His Leu Pro Asn Leu Thr Ile Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 546
<211> LENGTH: 58
<212> TYPE: PRT
<213> ORGANISM: artificial sequence
<220> FEATURE:
<223> OTHER INFORMATION: Modified bacterial sequence

<400> SEQUENCE: 546
```

-continued

Val Asp Ala Lys Tyr Ala Lys Glu Val Ile Ser Ala Trp Asn Glu Ile
1               5                   10                  15

Asp Ala Leu Pro Asn Leu Thr Leu Gln Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 547
<211> LENGTH: 58
<212> TYPE: PRT
<213> ORGANISM: artificial sequence
<220> FEATURE:
<223> OTHER INFORMATION: Modified bacterial sequence

<400> SEQUENCE: 547

Val Asp Ala Lys Tyr Ala Lys Glu Val Ile Ala Ala Trp Asn Glu Ile
1               5                   10                  15

Asp Lys Leu Pro Asn Leu Thr Leu Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 548
<211> LENGTH: 58
<212> TYPE: PRT
<213> ORGANISM: artificial sequence
<220> FEATURE:
<223> OTHER INFORMATION: Modified bacterial sequence

<400> SEQUENCE: 548

Val Asp Ala Lys Tyr Ala Lys Glu Thr Ile Glu Ala Trp Asn Glu Ile
1               5                   10                  15

Asp Ser Leu Pro Asn Leu Thr Leu Asp Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 549
<211> LENGTH: 58
<212> TYPE: PRT
<213> ORGANISM: artificial sequence
<220> FEATURE:
<223> OTHER INFORMATION: Modified bacterial sequence

<400> SEQUENCE: 549

Val Asp Ala Lys Tyr Ala Lys Glu Val Leu Asp Ala Trp Asn Glu Ile
1               5                   10                  15

Asp Gln Leu Pro Asn Leu Thr Leu Gln Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 550
<211> LENGTH: 58
<212> TYPE: PRT
<213> ORGANISM: artificial sequence
<220> FEATURE:
<223> OTHER INFORMATION: Modified bacterial sequence

<400> SEQUENCE: 550

Val Asp Ala Lys Tyr Ala Lys Glu Val Leu Ala Ala Trp Asn Glu Ile
1               5                   10                  15

Asp His Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 551
<211> LENGTH: 58
<212> TYPE: PRT
<213> ORGANISM: artificial sequence
<220> FEATURE:
<223> OTHER INFORMATION: Modified bacterial sequence

<400> SEQUENCE: 551

Val Asp Ala Lys Tyr Ala Lys Glu Val Leu Gly Ala Trp Asp Glu Ile
1               5                   10                  15

Asp His Leu Pro Asn Leu Thr Ile Thr Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 552
<211> LENGTH: 58
<212> TYPE: PRT
<213> ORGANISM: artificial sequence
<220> FEATURE:
<223> OTHER INFORMATION: Modified bacterial sequence

<400> SEQUENCE: 552

Val Asp Ala Lys Tyr Ala Lys Glu Thr Ile Asp Ala Trp Asn Glu Ile
1               5                   10                  15

Asp His Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 553
<211> LENGTH: 58
<212> TYPE: PRT
<213> ORGANISM: artificial sequence
<220> FEATURE:
<223> OTHER INFORMATION: Modified bacterial sequence

<400> SEQUENCE: 553

Val Asp Ala Lys Tyr Ala Lys Glu Val Ile Glu Ala Trp Asn Glu Ile
1               5                   10                  15

Asp His Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 554
<211> LENGTH: 58
<212> TYPE: PRT
<213> ORGANISM: artificial sequence
<220> FEATURE:
<223> OTHER INFORMATION: Modified bacterial sequence

<400> SEQUENCE: 554

Val Asp Ala Lys Tyr Ala Lys Glu Val Ile Gln Ala Trp Asn Glu Ile
1               5                   10                  15

Asp Ala Leu Pro Asn Leu Thr Ile Ser Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 555
<211> LENGTH: 58
<212> TYPE: PRT
<213> ORGANISM: artificial sequence
<220> FEATURE:
<223> OTHER INFORMATION: Modified bacterial sequence

<400> SEQUENCE: 555

Val Asp Ala Lys Tyr Ala Lys Glu Val Ile Ala Ala Trp Asp Glu Ile
1               5                   10                  15

Asp Ser Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 556
<211> LENGTH: 58
<212> TYPE: PRT
<213> ORGANISM: artificial sequence
<220> FEATURE:
<223> OTHER INFORMATION: Modified bacterial sequence

<400> SEQUENCE: 556

Val Asp Ala Lys Tyr Ala Lys Glu His Ile Glu Ala Trp Asn Glu Ile
1               5                   10                  15

Asp Ala Leu Pro Asn Leu Thr Ile Glu Gln Trp Leu Ala Phe Ile Asn
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 557
<211> LENGTH: 58
<212> TYPE: PRT

<213> ORGANISM: artificial sequence
<220> FEATURE:
<223> OTHER INFORMATION: Modified bacterial sequence

<400> SEQUENCE: 557

```
Val Asp Ala Lys Tyr Ala Lys Glu Val Leu Glu Ala Trp Asn Glu Ile
1               5                   10                  15

Asp Lys Leu Pro Asn Leu Thr Leu Asp Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
    50                  55
```

<210> SEQ ID NO 558
<211> LENGTH: 58
<212> TYPE: PRT
<213> ORGANISM: artificial sequence
<220> FEATURE:
<223> OTHER INFORMATION: Modified bacterial sequence

<400> SEQUENCE: 558

```
Val Asp Ala Lys Tyr Ala Lys Glu Val Ile Asp Ala Trp Asn Glu Ile
1               5                   10                  15

Asp His Leu Pro Asn Leu Thr Ile Glu Gln Trp Leu Ala Phe Ile Asn
                20                  25                  30

Lys Leu Ala Asp Pro Ser Gln Ser Ser Glu Leu Leu Ser Glu Ala
            35                  40                  45

Lys Lys Leu Asn Asp Ser Gln Ala Pro Lys
    50                  55
```

<210> SEQ ID NO 559
<211> LENGTH: 58
<212> TYPE: PRT
<213> ORGANISM: artificial sequence
<220> FEATURE:
<223> OTHER INFORMATION: Modified bacterial sequence

<400> SEQUENCE: 559

```
Val Asp Ala Lys Tyr Ala Lys Glu Thr Ile Asp Ala Trp Asp Glu Ile
1               5                   10                  15

Asp Lys Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
    50                  55
```

<210> SEQ ID NO 560
<211> LENGTH: 58
<212> TYPE: PRT
<213> ORGANISM: artificial sequence
<220> FEATURE:
<223> OTHER INFORMATION: Modified bacterial sequence

<400> SEQUENCE: 560

```
Val Asp Ala Lys Tyr Ala Lys Glu Val Ile Ala Ala Trp Asp Glu Ile
1               5                   10                  15

Asp Leu Leu Pro Asn Leu Thr Leu Gln Gln Trp Leu Ala Phe Ile Asn
                20                  25                  30

Lys Leu Ala Asp Pro Ser Gln Ser Ser Glu Leu Leu Ser Glu Ala
```

-continued

```
            35                  40                  45

Lys Lys Leu Asn Asp Ser Gln Ala Pro Lys
    50                  55

<210> SEQ ID NO 561
<211> LENGTH: 58
<212> TYPE: PRT
<213> ORGANISM: artificial sequence
<220> FEATURE:
<223> OTHER INFORMATION: Modified bacterial sequence

<400> SEQUENCE: 561

Val Asp Ala Lys Tyr Ala Lys Glu Val Ile His Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 562
<211> LENGTH: 58
<212> TYPE: PRT
<213> ORGANISM: artificial sequence
<220> FEATURE:
<223> OTHER INFORMATION: Modified bacterial sequence

<400> SEQUENCE: 562

Val Asp Ala Lys Tyr Ala Lys Glu Val Ile Ala Ala Trp Asn Glu Ile
1               5                   10                  15

Asp His Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 563
<211> LENGTH: 58
<212> TYPE: PRT
<213> ORGANISM: artificial sequence
<220> FEATURE:
<223> OTHER INFORMATION: Modified bacterial sequence

<400> SEQUENCE: 563

Val Asp Ala Lys Tyr Ala Lys Glu Thr Leu Asp Ala Trp Asn Glu Ile
1               5                   10                  15

Asp Lys Leu Pro Asn Leu Thr Leu Ser Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 564
<211> LENGTH: 58
<212> TYPE: PRT
<213> ORGANISM: artificial sequence
<220> FEATURE:
<223> OTHER INFORMATION: Modified bacterial sequence
```

<400> SEQUENCE: 564

Val Asp Ala Lys Tyr Ala Lys Glu Val Leu Glu Ala Trp Asn Glu Ile
1               5                   10                  15

Asp Ala Leu Pro Asn Leu Thr Leu Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 565
<211> LENGTH: 58
<212> TYPE: PRT
<213> ORGANISM: artificial sequence
<220> FEATURE:
<223> OTHER INFORMATION: Modified bacterial sequence

<400> SEQUENCE: 565

Val Asp Ala Lys Tyr Ala Lys Glu Val Ile Gln Ala Trp Asp Glu Ile
1               5                   10                  15

Asp His Leu Pro Asn Leu Thr Ile Ser Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 566
<211> LENGTH: 58
<212> TYPE: PRT
<213> ORGANISM: artificial sequence
<220> FEATURE:
<223> OTHER INFORMATION: Modified bacterial sequence

<400> SEQUENCE: 566

Val Asp Ala Lys Tyr Ala Lys Glu Val Leu Gln Ala Trp Asp Glu Ile
1               5                   10                  15

Asp Ser Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 567
<211> LENGTH: 58
<212> TYPE: PRT
<213> ORGANISM: artificial sequence
<220> FEATURE:
<223> OTHER INFORMATION: Modified bacterial sequence

<400> SEQUENCE: 567

Val Asp Ala Lys Tyr Ala Lys Glu Thr Leu Glu Ala Trp Asp Glu Ile
1               5                   10                  15

Asp His Leu Pro Asn Leu Thr Ile Ala Gln Trp Leu Ala Phe Ile Asn
                20                  25                  30

Lys Leu Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 568
<211> LENGTH: 58
<212> TYPE: PRT
<213> ORGANISM: artificial sequence
<220> FEATURE:
<223> OTHER INFORMATION: Modified bacterial sequence

<400> SEQUENCE: 568

Val Asp Ala Lys Tyr Ala Lys Glu Thr Ile Asp Ala Trp Asn Glu Ile
1               5                   10                  15

Asp Arg Leu Pro Asn Leu Thr Ile Ser Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 569
<211> LENGTH: 58
<212> TYPE: PRT
<213> ORGANISM: artificial sequence
<220> FEATURE:
<223> OTHER INFORMATION: Modified bacterial sequence

<400> SEQUENCE: 569

Val Asp Ala Lys Tyr Ala Lys Glu Val Leu Asp Ala Trp His Glu Ile
1               5                   10                  15

Asp His Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 570
<211> LENGTH: 58
<212> TYPE: PRT
<213> ORGANISM: artificial sequence
<220> FEATURE:
<223> OTHER INFORMATION: Modified bacterial sequence

<400> SEQUENCE: 570

Val Asp Ala Lys Tyr Ala Lys Glu Gln Ile Arg Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 571
<211> LENGTH: 58
<212> TYPE: PRT
<213> ORGANISM: artificial sequence
<220> FEATURE:
<223> OTHER INFORMATION: Modified bacterial sequence

<400> SEQUENCE: 571

Val Asp Ala Lys Tyr Ala Lys Glu Thr Leu Tyr Ala Trp Asn Glu Ile
1               5                   10                  15

```
Asp Lys Leu Pro Asn Leu Thr Ile Glu Gln Trp Leu Ala Phe Ile Glu
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 572
<211> LENGTH: 58
<212> TYPE: PRT
<213> ORGANISM: artificial sequence
<220> FEATURE:
<223> OTHER INFORMATION: Modified bacterial sequence

<400> SEQUENCE: 572

```
Val Asp Ala Lys Tyr Ala Lys Glu Val Ile Glu Ala Trp Asn Glu Ile
1               5                   10                  15

Asp Ala Leu Pro Asn Leu Thr Ile Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 573
<211> LENGTH: 58
<212> TYPE: PRT
<213> ORGANISM: artificial sequence
<220> FEATURE:
<223> OTHER INFORMATION: Modified bacterial sequence

<400> SEQUENCE: 573

```
Val Asp Ala Lys Tyr Ala Lys Glu Val Leu Glu Ala Trp Asn Glu Ile
1               5                   10                  15

Asp His Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 574
<211> LENGTH: 58
<212> TYPE: PRT
<213> ORGANISM: artificial sequence
<220> FEATURE:
<223> OTHER INFORMATION: Modified bacterial sequence

<400> SEQUENCE: 574

```
Val Asp Ala Lys Tyr Ala Lys Glu Thr Ile Glu Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 575
<211> LENGTH: 58

```
<212> TYPE: PRT
<213> ORGANISM: artificial sequence
<220> FEATURE:
<223> OTHER INFORMATION: Modified bacterial sequence

<400> SEQUENCE: 575

Val Asp Ala Lys Tyr Ala Lys Glu Val Ile Glu Ala Trp Asn Glu Ile
1               5                   10                  15

Asp His Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 576
<211> LENGTH: 58
<212> TYPE: PRT
<213> ORGANISM: artificial sequence
<220> FEATURE:
<223> OTHER INFORMATION: Modified bacterial sequence

<400> SEQUENCE: 576

Val Asp Ala Lys Tyr Ala Lys Glu Val Ile Glu Ala Trp Asn Glu Ile
1               5                   10                  15

Asp Lys Leu Pro Asn Leu Thr Ile Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 577
<211> LENGTH: 58
<212> TYPE: PRT
<213> ORGANISM: artificial sequence
<220> FEATURE:
<223> OTHER INFORMATION: Modified bacterial sequence

<400> SEQUENCE: 577

Val Asp Ala Lys Tyr Ala Lys Glu Thr Leu Asp Ala Trp Ala Glu Ile
1               5                   10                  15

Asp His Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 578
<211> LENGTH: 58
<212> TYPE: PRT
<213> ORGANISM: artificial sequence
<220> FEATURE:
<223> OTHER INFORMATION: Modified bacterial sequence

<400> SEQUENCE: 578

Val Asp Ala Lys Tyr Ala Lys Glu His Ile Asp Ala Trp Asn Glu Ile
1               5                   10                  15

Asp Ala Leu Pro Asn Leu Thr Ser Gln Trp Leu Ala Phe Ile Asn
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 579
<211> LENGTH: 58
<212> TYPE: PRT
<213> ORGANISM: artificial sequence
<220> FEATURE:
<223> OTHER INFORMATION: Modified bacterial sequence

<400> SEQUENCE: 579

Val Asp Ala Lys Tyr Ala Lys Glu Val Leu Asp Ala Trp Asn Glu Ile
1               5                   10                  15

Asp Lys Leu Pro Asn Leu Thr Ile Ala Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 580
<211> LENGTH: 58
<212> TYPE: PRT
<213> ORGANISM: artificial sequence
<220> FEATURE:
<223> OTHER INFORMATION: Modified bacterial sequence

<400> SEQUENCE: 580

Val Asp Ala Lys Tyr Ala Lys Glu Val Ile Glu Ala Trp Thr Glu Ile
1               5                   10                  15

Asp Tyr Leu Pro Asn Leu Thr Leu Gln Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 581
<211> LENGTH: 58
<212> TYPE: PRT
<213> ORGANISM: artificial sequence
<220> FEATURE:
<223> OTHER INFORMATION: Modified bacterial sequence

<400> SEQUENCE: 581

Val Asp Ala Lys Tyr Ala Lys Glu Thr Ile Glu Ala Trp Asn Glu Ile
1               5                   10                  15

Asp His Leu Pro Asn Leu Thr Ile Ala Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 582
<211> LENGTH: 58
<212> TYPE: PRT
<213> ORGANISM: artificial sequence
<220> FEATURE:
<223> OTHER INFORMATION: Modified bacterial sequence
```

-continued

```
<400> SEQUENCE: 582

Val Asp Ala Lys Tyr Ala Lys Glu Val Ile Gln Ala Trp Asn Glu Ile
1               5                   10                  15

Asp Lys Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 583
<211> LENGTH: 58
<212> TYPE: PRT
<213> ORGANISM: artificial sequence
<220> FEATURE:
<223> OTHER INFORMATION: Modified bacterial sequence

<400> SEQUENCE: 583

Val Asp Ala Lys Tyr Ala Lys Glu Val Ile Glu Ala Trp Asp Glu Ile
1               5                   10                  15

Asp His Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 584
<211> LENGTH: 58
<212> TYPE: PRT
<213> ORGANISM: artificial sequence
<220> FEATURE:
<223> OTHER INFORMATION: Modified bacterial sequence

<400> SEQUENCE: 584

Val Asp Ala Lys Tyr Ala Lys Glu Thr Ile Asp Ala Trp Asn Glu Ile
1               5                   10                  15

Asp Leu Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 585
<211> LENGTH: 58
<212> TYPE: PRT
<213> ORGANISM: artificial sequence
<220> FEATURE:
<223> OTHER INFORMATION: Modified bacterial sequence

<400> SEQUENCE: 585

Val Asp Ala Lys Tyr Ala Lys Glu His Ile Asp Ala Trp Asn Glu Ile
1               5                   10                  15

Asp Lys Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
```

<210> SEQ ID NO 586
<211> LENGTH: 58
<212> TYPE: PRT
<213> ORGANISM: artificial sequence
<220> FEATURE:
<223> OTHER INFORMATION: Modified bacterial sequence

<400> SEQUENCE: 586

Val Asp Ala Lys Tyr Ala Lys Glu Val Val Ala Ala Trp Asn Glu Ile
1               5                   10                  15

Asp Ala Leu Pro Asn Leu Thr Ile Glu Gln Trp Leu Ala Phe Ile Asn
            20                  25                  30

Lys Leu Asn Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 587
<211> LENGTH: 58
<212> TYPE: PRT
<213> ORGANISM: artificial sequence
<220> FEATURE:
<223> OTHER INFORMATION: Modified bacterial sequence

<400> SEQUENCE: 587

Val Asp Ala Lys Tyr Ala Lys Glu Val Ile Glu Ala Trp Asn Glu Ile
1               5                   10                  15

Asp Ala Leu Pro Asn Leu Thr Leu Ala Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 588
<211> LENGTH: 58
<212> TYPE: PRT
<213> ORGANISM: artificial sequence
<220> FEATURE:
<223> OTHER INFORMATION: Modified bacterial sequence

<400> SEQUENCE: 588

Val Asp Ala Lys Tyr Ala Lys Glu Val Leu Gln Ala Trp Asp Glu Ile
1               5                   10                  15

Asp Arg Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 589
<211> LENGTH: 58
<212> TYPE: PRT
<213> ORGANISM: artificial sequence
<220> FEATURE:
<223> OTHER INFORMATION: Modified bacterial sequence

<400> SEQUENCE: 589

Val Asp Ala Lys Tyr Ala Lys Glu Val Ile Asp Ala Trp Asp Glu Ile

```
                 1               5                  10                 15
Asp His Leu Pro Asn Leu Thr Ile Glu Gln Trp Leu Ala Phe Ile Asn
                 20                 25                 30

Lys Leu Ser Asp Asp Pro Ser Gln Ser Ser Glu Leu Leu Ser Glu Ala
             35                 40                 45

Lys Lys Leu Asn Asp Ser Gln Ala Pro Lys
         50                 55
```

<210> SEQ ID NO 590
<211> LENGTH: 58
<212> TYPE: PRT
<213> ORGANISM: artificial sequence
<220> FEATURE:
<223> OTHER INFORMATION: Modified bacterial sequence

<400> SEQUENCE: 590

```
Val Asp Ala Lys Tyr Ala Lys Glu Val Val Glu Ala Trp Asn Glu Ile
1               5                  10                 15

Asp Gln Leu Pro Asn Leu Thr Ile Glu Gln Trp Leu Ala Phe Ile Asn
                 20                 25                 30

Lys Leu Asp Asp Asp Pro Ser Gln Ser Ser Glu Leu Leu Ser Glu Ala
             35                 40                 45

Lys Lys Leu Asn Asp Ser Gln Ala Pro Lys
         50                 55
```

<210> SEQ ID NO 591
<211> LENGTH: 58
<212> TYPE: PRT
<213> ORGANISM: artificial sequence
<220> FEATURE:
<223> OTHER INFORMATION: Modified bacterial sequence

<400> SEQUENCE: 591

```
Val Asp Ala Lys Tyr Ala Lys Glu Val Ile Gln Ala Trp Asn Glu Ile
1               5                  10                 15

Asp Ala Leu Pro Asn Leu Thr Ile Glu Gln Trp Leu Ala Phe Ile Asn
                 20                 25                 30

Lys Leu Asp Asp Asp Pro Ser Gln Ser Ser Glu Leu Leu Ser Glu Ala
             35                 40                 45

Lys Lys Leu Asn Asp Ser Gln Ala Pro Lys
         50                 55
```

<210> SEQ ID NO 592
<211> LENGTH: 58
<212> TYPE: PRT
<213> ORGANISM: artificial sequence
<220> FEATURE:
<223> OTHER INFORMATION: Modified bacterial sequence

<400> SEQUENCE: 592

```
Val Asp Ala Lys Tyr Ala Lys Glu Val Ile Gln Ala Trp Asp Glu Ile
1               5                  10                 15

Asp Lys Leu Pro Asn Leu Thr Ile Asp Gln Trp Leu Ala Phe Ile Asn
                 20                 25                 30

Lys Leu Ala Asp Asp Pro Ser Gln Ser Ser Glu Leu Leu Ser Glu Ala
             35                 40                 45

Lys Lys Leu Asn Asp Ser Gln Ala Pro Lys
         50                 55
```

<210> SEQ ID NO 593

```
<211> LENGTH: 58
<212> TYPE: PRT
<213> ORGANISM: artificial sequence
<220> FEATURE:
<223> OTHER INFORMATION: Modified bacterial sequence

<400> SEQUENCE: 593

Val Asp Ala Lys Tyr Ala Lys Glu Val Val Ala Ala Trp Asp Glu Ile
1               5                   10                  15

Asp Ala Leu Pro Asn Leu Thr Leu Thr Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 594
<211> LENGTH: 58
<212> TYPE: PRT
<213> ORGANISM: artificial sequence
<220> FEATURE:
<223> OTHER INFORMATION: Modified bacterial sequence

<400> SEQUENCE: 594

Val Asp Ala Lys Tyr Ala Lys Glu Val Ile Gln Ala Trp Asn Glu Ile
1               5                   10                  15

Asp Gly Leu Pro Asn Leu Thr Leu Ser Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 595
<211> LENGTH: 58
<212> TYPE: PRT
<213> ORGANISM: artificial sequence
<220> FEATURE:
<223> OTHER INFORMATION: Modified bacterial sequence

<400> SEQUENCE: 595

Val Asp Ala Lys Tyr Ala Lys Glu Thr Ile Glu Ala Trp Asp Glu Ile
1               5                   10                  15

Asp Ala Leu Pro Asn Leu Thr Ile Thr Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 596
<211> LENGTH: 58
<212> TYPE: PRT
<213> ORGANISM: artificial sequence
<220> FEATURE:
<223> OTHER INFORMATION: Modified bacterial sequence

<400> SEQUENCE: 596

Val Asp Ala Lys Tyr Ala Lys Glu Val Ile Asp Ala Trp Asn Glu Ile
1               5                   10                  15

Asp His Leu Pro Asn Leu Thr Ile Gln Gln Trp Leu Ala Phe Ile Asn
            20                  25                  30
```

```
Lys Leu Ala Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 597
<211> LENGTH: 58
<212> TYPE: PRT
<213> ORGANISM: artificial sequence
<220> FEATURE:
<223> OTHER INFORMATION: Modified bacterial sequence

<400> SEQUENCE: 597

Val Asp Ala Lys Tyr Ala Lys Glu Thr Ile Glu Ala Trp Asn Glu Ile
  1               5                  10                  15

Asp Ala Leu Pro Asn Leu Thr Leu Asp Gln Trp Leu Ala Phe Ile Asn
             20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 598
<211> LENGTH: 58
<212> TYPE: PRT
<213> ORGANISM: artificial sequence
<220> FEATURE:
<223> OTHER INFORMATION: Modified bacterial sequence

<400> SEQUENCE: 598

Val Asp Ala Lys Tyr Ala Lys Glu His Ile His Ala Trp Asn Glu Ile
  1               5                  10                  15

Asp Glu Leu Pro Asn Leu Thr Ile Glu Gln Trp Leu Ala Phe Ile Asn
             20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 599
<211> LENGTH: 58
<212> TYPE: PRT
<213> ORGANISM: artificial sequence
<220> FEATURE:
<223> OTHER INFORMATION: Modified bacterial sequence

<400> SEQUENCE: 599

Val Asp Ala Lys Tyr Ala Lys Glu Val Ile Asp Ala Trp Asp Glu Ile
  1               5                  10                  15

Asp His Leu Pro Asn Leu Thr Ile Asp Gln Trp Leu Ala Phe Ile Asn
             20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
 50                  55

<210> SEQ ID NO 600
<211> LENGTH: 58
<212> TYPE: PRT
<213> ORGANISM: artificial sequence
<220> FEATURE:
```

<223> OTHER INFORMATION: Modified bacterial sequence

<400> SEQUENCE: 600

Val Asp Ala Lys Tyr Ala Lys Glu Val Ile Asp Ala Asn Asp Glu Ile
1               5                   10                  15

Asp Ala Leu Pro Asn Leu Thr Ile Ala Gln Trp Leu Ala Phe Ile Asn
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 601
<211> LENGTH: 58
<212> TYPE: PRT
<213> ORGANISM: artificial sequence
<220> FEATURE:
<223> OTHER INFORMATION: Modified bacterial sequence

<400> SEQUENCE: 601

Val Asp Ala Lys Tyr Ala Lys Glu Thr Ile Glu Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 602
<211> LENGTH: 58
<212> TYPE: PRT
<213> ORGANISM: artificial sequence
<220> FEATURE:
<223> OTHER INFORMATION: Modified bacterial sequence

<400> SEQUENCE: 602

Val Asp Ala Lys Tyr Ala Lys Glu Val Leu Leu Ala Trp Asp Glu Ile
1               5                   10                  15

Asp His Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 603
<211> LENGTH: 58
<212> TYPE: PRT
<213> ORGANISM: artificial sequence
<220> FEATURE:
<223> OTHER INFORMATION: Modified bacterial sequence

<400> SEQUENCE: 603

Val Asp Ala Lys Tyr Ala Lys Glu His Ile Asp Ala Trp Asn Glu Ile
1               5                   10                  15

Asp Gly Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 604
<211> LENGTH: 58
<212> TYPE: PRT
<213> ORGANISM: artificial sequence
<220> FEATURE:
<223> OTHER INFORMATION: Modified bacterial sequence

<400> SEQUENCE: 604

Val Asp Ala Lys Tyr Ala Lys Glu Val Ile Glu Ala Trp Ser Glu Ile
1               5                   10                  15

Asp Ala Leu Pro Asn Leu Thr Ile Asp Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 605
<211> LENGTH: 58
<212> TYPE: PRT
<213> ORGANISM: artificial sequence
<220> FEATURE:
<223> OTHER INFORMATION: Modified bacterial sequence

<400> SEQUENCE: 605

Val Asp Ala Lys Tyr Ala Lys Glu Gln Leu Asn Ala Trp Ala Glu Ile
1               5                   10                  15

Asp Ala Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 606
<211> LENGTH: 58
<212> TYPE: PRT
<213> ORGANISM: artificial sequence
<220> FEATURE:
<223> OTHER INFORMATION: Modified bacterial sequence

<400> SEQUENCE: 606

Val Asp Ala Lys Tyr Ala Lys Glu Val Ile Asp Ala Trp Asn Glu Ile
1               5                   10                  15

Asp Ala Leu Pro Asn Leu Thr Ile Ala Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 607
<211> LENGTH: 58
<212> TYPE: PRT
<213> ORGANISM: artificial sequence
<220> FEATURE:
<223> OTHER INFORMATION: Modified bacterial sequence

<400> SEQUENCE: 607

```
Val Asp Ala Lys Tyr Ala Lys Glu Thr Ile Asp Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 608
<211> LENGTH: 58
<212> TYPE: PRT
<213> ORGANISM: artificial sequence
<220> FEATURE:
<223> OTHER INFORMATION: Modified bacterial sequence

<400> SEQUENCE: 608

```
Val Asp Ala Lys Tyr Ala Lys Glu Val Ile Glu Ala Trp Asp Glu Ile
1               5                   10                  15

Asp Lys Leu Pro Asn Leu Thr Leu Ala Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 609
<211> LENGTH: 58
<212> TYPE: PRT
<213> ORGANISM: artificial sequence
<220> FEATURE:
<223> OTHER INFORMATION: Modified bacterial sequence

<400> SEQUENCE: 609

```
Val Asp Ala Lys Tyr Ala Lys Glu Val Leu Tyr Ala Trp Ala Glu Ile
1               5                   10                  15

Asp His Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 610
<211> LENGTH: 58
<212> TYPE: PRT
<213> ORGANISM: artificial sequence
<220> FEATURE:
<223> OTHER INFORMATION: Modified bacterial sequence

<400> SEQUENCE: 610

```
Val Asp Ala Lys Tyr Ala Lys Glu Gln Ile Asp Ala Trp Asn Glu Ile
1               5                   10                  15

Asp Arg Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 611
<211> LENGTH: 58
<212> TYPE: PRT
<213> ORGANISM: artificial sequence
<220> FEATURE:
<223> OTHER INFORMATION: Modified bacterial sequence

<400> SEQUENCE: 611

Val Asp Ala Lys Tyr Ala Lys Glu Val Leu Ala Ala Trp Asp Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 612
<211> LENGTH: 58
<212> TYPE: PRT
<213> ORGANISM: artificial sequence
<220> FEATURE:
<223> OTHER INFORMATION: Modified bacterial sequence

<400> SEQUENCE: 612

Val Asp Ala Lys Tyr Ala Lys Glu Val Ile Glu Ala Trp Asp Glu Ile
1               5                   10                  15

Asp His Leu Pro Asn Leu Thr Leu His Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 613
<211> LENGTH: 58
<212> TYPE: PRT
<213> ORGANISM: artificial sequence
<220> FEATURE:
<223> OTHER INFORMATION: Modified bacterial sequence

<400> SEQUENCE: 613

Val Asp Ala Lys Tyr Ala Lys Glu Val Ile Glu Ala Trp Asn Glu Ile
1               5                   10                  15

Asp Lys Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 614
<211> LENGTH: 58
<212> TYPE: PRT
<213> ORGANISM: artificial sequence
<220> FEATURE:
<223> OTHER INFORMATION: Modified bacterial sequence

<400> SEQUENCE: 614

Val Asp Ala Lys Tyr Ala Lys Glu Val Ile Asp Ala Asn Asp Glu Ile
1               5                   10                  15

Asp Ala Leu Pro Asn Leu Thr Ile Glu Gln Trp Leu Ala Phe Ile Asn
```

```
                    20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 615
<211> LENGTH: 58
<212> TYPE: PRT
<213> ORGANISM: artificial sequence
<220> FEATURE:
<223> OTHER INFORMATION: Modified bacterial sequence

<400> SEQUENCE: 615

Val Asp Ala Lys Tyr Ala Lys Glu Val Ile Ala Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 616
<211> LENGTH: 58
<212> TYPE: PRT
<213> ORGANISM: artificial sequence
<220> FEATURE:
<223> OTHER INFORMATION: Modified bacterial sequence

<400> SEQUENCE: 616

Val Asp Ala Lys Tyr Ala Lys Glu Val Ile Glu Ala Trp Thr Glu Ile
1               5                   10                  15

Asp Gln Leu Pro Asn Leu Thr Leu Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 617
<211> LENGTH: 58
<212> TYPE: PRT
<213> ORGANISM: artificial sequence
<220> FEATURE:
<223> OTHER INFORMATION: Modified bacterial sequence

<400> SEQUENCE: 617

Val Asp Ala Lys Tyr Ala Lys Glu Val Ile Asn Ala Trp Asn Glu Ile
1               5                   10                  15

Asp Ala Leu Pro Asn Leu Thr Leu Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 618
<211> LENGTH: 58
<212> TYPE: PRT
<213> ORGANISM: artificial sequence
```

```
<220> FEATURE:
<223> OTHER INFORMATION: Modified bacterial sequence

<400> SEQUENCE: 618

Val Asp Ala Lys Tyr Ala Lys Glu His Ile Glu Ala Trp Asp Glu Ile
1               5                   10                  15

Asp His Leu Pro Asn Leu Thr Ile Asp Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 619
<211> LENGTH: 58
<212> TYPE: PRT
<213> ORGANISM: artificial sequence
<220> FEATURE:
<223> OTHER INFORMATION: Modified bacterial sequence

<400> SEQUENCE: 619

Val Asp Ala Lys Tyr Ala Lys Glu His Leu Glu Ala Trp Arg Glu Ile
1               5                   10                  15

Asp Ala Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 620
<211> LENGTH: 58
<212> TYPE: PRT
<213> ORGANISM: artificial sequence
<220> FEATURE:
<223> OTHER INFORMATION: Modified bacterial sequence

<400> SEQUENCE: 620

Val Asp Ala Lys Tyr Ala Lys Glu Val Leu Asp Ala Trp Asn Glu Ile
1               5                   10                  15

Asp Lys Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 621
<211> LENGTH: 58
<212> TYPE: PRT
<213> ORGANISM: artificial sequence
<220> FEATURE:
<223> OTHER INFORMATION: Modified bacterial sequence

<400> SEQUENCE: 621

Val Asp Ala Lys Tyr Ala Lys Glu Val Ile Ala Ala Trp Asp Glu Ile
1               5                   10                  15

Asp His Leu Pro Asn Leu Thr Ile Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45
```

```
Lys Lys Leu Asn Asp Ser Gln Ala Pro Lys
    50                  55
```

<210> SEQ ID NO 622
<211> LENGTH: 58
<212> TYPE: PRT
<213> ORGANISM: artificial sequence
<220> FEATURE:
<223> OTHER INFORMATION: Modified bacterial sequence

<400> SEQUENCE: 622

```
Val Asp Ala Lys Tyr Ala Lys Glu Val Ile Gln Ala Trp Asn Glu Ile
1               5                   10                  15

Asp Ala Leu Pro Asn Leu Thr Leu Glu Gln Trp Leu Ala Phe Ile Asn
            20                  25                  30

Lys Leu Asp Asp Pro Ser Gln Ser Ser Leu Leu Ser Glu Ala
        35                  40                  45

Lys Lys Leu Asn Asp Ser Gln Ala Pro Lys
    50                  55
```

<210> SEQ ID NO 623
<211> LENGTH: 58
<212> TYPE: PRT
<213> ORGANISM: artificial sequence
<220> FEATURE:
<223> OTHER INFORMATION: Modified bacterial sequence

<400> SEQUENCE: 623

```
Val Asp Ala Lys Tyr Ala Lys Glu Val Ile Asp Ala Trp Asn Glu Ile
1               5                   10                  15

Asp His Leu Pro Asn Leu Thr Ile Ala Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 624
<211> LENGTH: 58
<212> TYPE: PRT
<213> ORGANISM: artificial sequence
<220> FEATURE:
<223> OTHER INFORMATION: Modified bacterial sequence

<400> SEQUENCE: 624

```
Val Asp Ala Lys Tyr Ala Lys Glu Gln Leu Asp Ala Trp Asp Glu Ile
1               5                   10                  15

Asp His Leu Pro Asn Leu Thr Ile Asp Gln Trp Leu Ala Phe Ile Asn
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 625
<211> LENGTH: 58
<212> TYPE: PRT
<213> ORGANISM: artificial sequence
<220> FEATURE:
<223> OTHER INFORMATION: Modified bacterial sequence

<400> SEQUENCE: 625

Val Asp Ala Lys Tyr Ala Lys Glu Val Leu Asn Ala Trp Asp Glu Ile
1               5                   10                  15

Asp Lys Leu Pro Asn Leu Thr Ile Glu Gln Trp Leu Ala Phe Ile Asn
                20                  25                  30

Lys Leu Asp Asp Pro Ser Gln Ser Ser Glu Leu Leu Ser Glu Ala
                35                  40                  45

Lys Lys Leu Asn Asp Ser Gln Ala Pro Lys
        50                  55

<210> SEQ ID NO 626
<211> LENGTH: 58
<212> TYPE: PRT
<213> ORGANISM: artificial sequence
<220> FEATURE:
<223> OTHER INFORMATION: Modified bacterial sequence

<400> SEQUENCE: 626

Val Asp Ala Lys Tyr Ala Lys Glu Val Leu Glu Ala Trp Asn Glu Ile
1               5                   10                  15

Asp His Leu Pro Asn Leu Thr Ile Asp Gln Trp Leu Ala Phe Ile Asn
                20                  25                  30

Lys Leu Asp Asp Pro Ser Gln Ser Ser Glu Leu Leu Ser Glu Ala
                35                  40                  45

Lys Lys Leu Asn Asp Ser Gln Ala Pro Lys
        50                  55

<210> SEQ ID NO 627
<211> LENGTH: 58
<212> TYPE: PRT
<213> ORGANISM: artificial sequence
<220> FEATURE:
<223> OTHER INFORMATION: Modified bacterial sequence

<400> SEQUENCE: 627

Val Asp Ala Lys Tyr Ala Lys Glu Val Leu Leu Ala Trp Asp Glu Ile
1               5                   10                  15

Asp Arg Leu Pro Asn Leu Thr Ile Asp Gln Trp Leu Ala Phe Ile Asn
                20                  25                  30

Lys Leu Ala Asp Pro Ser Gln Ser Ser Glu Leu Leu Ser Glu Ala
                35                  40                  45

Lys Lys Leu Asn Asp Ser Gln Ala Pro Lys
        50                  55

<210> SEQ ID NO 628
<211> LENGTH: 58
<212> TYPE: PRT
<213> ORGANISM: artificial sequence
<220> FEATURE:
<223> OTHER INFORMATION: Modified bacterial sequence

<400> SEQUENCE: 628

Val Asp Ala Lys Tyr Ala Lys Glu Val Ile Ala Ala Trp Asn Glu Ile
1               5                   10                  15

Asp Gln Leu Pro Asn Leu Thr Leu Asp Gln Trp Leu Ala Phe Ile Asn
                20                  25                  30

Lys Leu Asp Asp Pro Ser Gln Ser Ser Glu Leu Leu Ser Glu Ala
                35                  40                  45

Lys Lys Leu Asn Asp Ser Gln Ala Pro Lys
        50                  55

<210> SEQ ID NO 629
<211> LENGTH: 58
<212> TYPE: PRT
<213> ORGANISM: artificial sequence
<220> FEATURE:
<223> OTHER INFORMATION: Modified bacterial sequence

<400> SEQUENCE: 629

Val Asp Ala Lys Tyr Ala Lys Glu Thr Leu Leu Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Leu Leu Ser Glu Ala
        35                  40                  45

Lys Lys Leu Asn Asp Ser Gln Ala Pro Lys
    50                  55

<210> SEQ ID NO 630
<211> LENGTH: 58
<212> TYPE: PRT
<213> ORGANISM: artificial sequence
<220> FEATURE:
<223> OTHER INFORMATION: Modified bacterial sequence

<400> SEQUENCE: 630

Val Asp Ala Lys Tyr Ala Lys Glu Val Ile Asp Ala Trp Asn Glu Ile
1               5                   10                  15

Asp Thr Leu Pro Asn Leu Thr Leu Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 631
<211> LENGTH: 58
<212> TYPE: PRT
<213> ORGANISM: artificial sequence
<220> FEATURE:
<223> OTHER INFORMATION: Modified bacterial sequence

<400> SEQUENCE: 631

Val Asp Ala Lys Tyr Ala Lys Glu Val Leu His Ala Trp Asn Glu Ile
1               5                   10                  15

Asp His Leu Pro Asn Leu Thr Leu Asn Gln Trp Leu Ala Phe Ile Asn
            20                  25                  30

Lys Leu Gln Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 632
<211> LENGTH: 58
<212> TYPE: PRT
<213> ORGANISM: artificial sequence
<220> FEATURE:
<223> OTHER INFORMATION: Modified bacterial sequence

<400> SEQUENCE: 632

Val Asp Ala Lys Tyr Ala Lys Glu Val Ile Gln Ala Trp Asn Glu Ile
1               5                   10                  15

```
Asp Ala Leu Pro Asn Leu Thr Ile Ala Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 633
<211> LENGTH: 58
<212> TYPE: PRT
<213> ORGANISM: artificial sequence
<220> FEATURE:
<223> OTHER INFORMATION: Modified bacterial sequence

<400> SEQUENCE: 633

Val Asp Ala Lys Tyr Ala Lys Glu Thr Val Asp Ala Trp Asn Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 634
<211> LENGTH: 58
<212> TYPE: PRT
<213> ORGANISM: artificial sequence
<220> FEATURE:
<223> OTHER INFORMATION: Modified bacterial sequence

<400> SEQUENCE: 634

Val Asp Ala Lys Tyr Ala Lys Glu Val Ile Gln Ala Trp Asp Glu Ile
1               5                   10                  15

Asp His Leu Pro Asn Leu Thr Ile Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 635
<211> LENGTH: 58
<212> TYPE: PRT
<213> ORGANISM: artificial sequence
<220> FEATURE:
<223> OTHER INFORMATION: Modified bacterial sequence

<400> SEQUENCE: 635

Val Asp Ala Lys Tyr Ala Lys Glu Val Leu Asp Ala Trp Asn Glu Ile
1               5                   10                  15

Asp Gln Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 636
<211> LENGTH: 58
<212> TYPE: PRT
```

```
<213> ORGANISM: artificial sequence
<220> FEATURE:
<223> OTHER INFORMATION: Modified bacterial sequence

<400> SEQUENCE: 636

Val Asp Ala Lys Tyr Ala Lys Glu Thr Ile Glu Ala Trp Asn Glu Ile
1               5                   10                  15

Asp Ala Leu Pro Asn Leu Thr Leu Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 637
<211> LENGTH: 58
<212> TYPE: PRT
<213> ORGANISM: artificial sequence
<220> FEATURE:
<223> OTHER INFORMATION: Modified bacterial sequence

<400> SEQUENCE: 637

Val Asp Ala Lys Tyr Ala Lys Glu Val Ile Glu Ala Trp Asp Glu Ile
1               5                   10                  15

Asp Ala Leu Pro Asn Leu Thr Ile Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 638
<211> LENGTH: 58
<212> TYPE: PRT
<213> ORGANISM: artificial sequence
<220> FEATURE:
<223> OTHER INFORMATION: Modified bacterial sequence

<400> SEQUENCE: 638

Val Asp Ala Lys Tyr Ala Lys Glu Val Ile Glu Ala Trp Asn Glu Ile
1               5                   10                  15

Asp Gln Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 639
<211> LENGTH: 58
<212> TYPE: PRT
<213> ORGANISM: artificial sequence
<220> FEATURE:
<223> OTHER INFORMATION: Modified bacterial sequence

<400> SEQUENCE: 639

Val Asp Ala Lys Tyr Ala Lys Glu Val Ile Glu Ala Trp Thr Glu Ile
1               5                   10                  15

Asp His Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
```

```
<210> SEQ ID NO 640
<211> LENGTH: 58
<212> TYPE: PRT
<213> ORGANISM: artificial sequence
<220> FEATURE:
<223> OTHER INFORMATION: Modified bacterial sequence

<400> SEQUENCE: 640

Val Asp Ala Lys Tyr Ala Lys Glu Val Ile Gln Ala Trp Asn Glu Ile
1               5                   10                  15

Asp His Leu Pro Asn Leu Thr Leu Gln Gln Trp Leu Ala Phe Ile Asn
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 641
<211> LENGTH: 58
<212> TYPE: PRT
<213> ORGANISM: artificial sequence
<220> FEATURE:
<223> OTHER INFORMATION: Modified bacterial sequence

<400> SEQUENCE: 641

Val Asp Ala Lys Tyr Ala Lys Glu Val Ile Gln Ala Asn Asn Glu Ile
1               5                   10                  15

Asp Gln Leu Pro Asn Leu Thr Ile Glu Gln Trp Leu Ala Phe Ile Asn
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 642
<211> LENGTH: 58
<212> TYPE: PRT
<213> ORGANISM: artificial sequence
<220> FEATURE:
<223> OTHER INFORMATION: Modified bacterial sequence

<400> SEQUENCE: 642

Val Asp Ala Lys Tyr Ala Lys Glu Val Leu His Ala Trp Ser Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 643
<211> LENGTH: 58
<212> TYPE: PRT
<213> ORGANISM: artificial sequence
<220> FEATURE:
<223> OTHER INFORMATION: Modified bacterial sequence
```

<400> SEQUENCE: 643

Val Asp Ala Lys Tyr Ala Lys Glu Thr Ile Gln Ala Trp Asp Glu Ile
1               5                   10                  15

Asp Lys Leu Pro Asn Leu Thr Leu Asp Gln Trp Leu Ala Phe Ile Asn
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 644
<211> LENGTH: 58
<212> TYPE: PRT
<213> ORGANISM: artificial sequence
<220> FEATURE:
<223> OTHER INFORMATION: Modified bacterial sequence

<400> SEQUENCE: 644

Val Asp Ala Lys Tyr Ala Lys Glu Thr Leu Arg Ala Trp Asp Glu Ile
1               5                   10                  15

Asp Lys Leu Pro Asn Leu Thr Ile Gln Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 645
<211> LENGTH: 58
<212> TYPE: PRT
<213> ORGANISM: artificial sequence
<220> FEATURE:
<223> OTHER INFORMATION: Modified bacterial sequence

<400> SEQUENCE: 645

Val Asp Ala Lys Tyr Ala Lys Glu Val Ile Asp Ala Trp Asn Glu Ile
1               5                   10                  15

Asp His Leu Pro Asn Leu Thr Ile Glu Gln Trp Leu Ala Phe Ile Asn
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 646
<211> LENGTH: 58
<212> TYPE: PRT
<213> ORGANISM: artificial sequence
<220> FEATURE:
<223> OTHER INFORMATION: Modified bacterial sequence

<400> SEQUENCE: 646

Val Asp Ala Lys Tyr Ala Lys Glu Val Ile Asp Ala Trp Asn Glu Ile
1               5                   10                  15

Asp His Leu Pro Asn Leu Thr Leu Gln Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 647
<211> LENGTH: 58
<212> TYPE: PRT
<213> ORGANISM: artificial sequence
<220> FEATURE:
<223> OTHER INFORMATION: Modified bacterial sequence

<400> SEQUENCE: 647

Val Asp Ala Lys Tyr Ala Lys Glu Thr Ile Asp Ala Trp Asn Glu Ile
1               5                   10                  15

Asp Ala Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 648
<211> LENGTH: 58
<212> TYPE: PRT
<213> ORGANISM: artificial sequence
<220> FEATURE:
<223> OTHER INFORMATION: Modified bacterial sequence

<400> SEQUENCE: 648

Val Asp Ala Lys Tyr Ala Lys Glu Val Ile Glu Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 649
<211> LENGTH: 58
<212> TYPE: PRT
<213> ORGANISM: artificial sequence
<220> FEATURE:
<223> OTHER INFORMATION: Modified bacterial sequence

<400> SEQUENCE: 649

Val Asp Ala Lys Tyr Ala Lys Glu Val Ile Arg Ala Trp Asp Glu Ile
1               5                   10                  15

Asp Gln Leu Pro Asn Leu Thr Leu Ser Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 650
<211> LENGTH: 58
<212> TYPE: PRT
<213> ORGANISM: artificial sequence
<220> FEATURE:
<223> OTHER INFORMATION: Modified bacterial sequence

<400> SEQUENCE: 650

Val Asp Ala Lys Tyr Ala Lys Glu Val Ile Glu Ala Trp Asn Glu Ile
1               5                   10                  15

Asp Arg Leu Pro Asn Leu Thr Ile His Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 651
<211> LENGTH: 58
<212> TYPE: PRT
<213> ORGANISM: artificial sequence
<220> FEATURE:
<223> OTHER INFORMATION: Modified bacterial sequence

<400> SEQUENCE: 651

Val Asp Ala Lys Tyr Ala Lys Glu Thr Ile Glu Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 652
<211> LENGTH: 58
<212> TYPE: PRT
<213> ORGANISM: artificial sequence
<220> FEATURE:
<223> OTHER INFORMATION: Modified bacterial sequence

<400> SEQUENCE: 652

Val Asp Ala Lys Tyr Ala Lys Glu Val Leu Thr Ala Trp Ala Glu Ile
1               5                   10                  15

Asp Ala Leu Pro Asn Leu Thr Leu Ser Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 653
<211> LENGTH: 58
<212> TYPE: PRT
<213> ORGANISM: artificial sequence
<220> FEATURE:
<223> OTHER INFORMATION: Modified bacterial sequence

<400> SEQUENCE: 653

Val Asp Ala Lys Tyr Ala Lys Glu Val Ile Glu Ala Trp Asp Glu Ile
1               5                   10                  15

Asp Lys Leu Pro Asn Leu Thr Val Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 654
<211> LENGTH: 58

```
<212> TYPE: PRT
<213> ORGANISM: artificial sequence
<220> FEATURE:
<223> OTHER INFORMATION: Modified bacterial sequence

<400> SEQUENCE: 654

Val Asp Ala Lys Tyr Ala Lys Glu Val Ile Asp Ala Trp Asn Glu Ile
1               5                   10                  15

Asp His Leu Pro Asn Leu Thr Leu Thr Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 655
<211> LENGTH: 58
<212> TYPE: PRT
<213> ORGANISM: artificial sequence
<220> FEATURE:
<223> OTHER INFORMATION: Modified bacterial sequence

<400> SEQUENCE: 655

Val Asp Ala Lys Tyr Ala Lys Glu Val Ile Glu Ala Trp Asn Glu Ile
1               5                   10                  15

Asp Gln Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 656
<211> LENGTH: 58
<212> TYPE: PRT
<213> ORGANISM: artificial sequence
<220> FEATURE:
<223> OTHER INFORMATION: Modified bacterial sequence

<400> SEQUENCE: 656

Val Asp Ala Lys Tyr Ala Lys Glu Thr Leu Gln Ala Trp Asp Glu Ile
1               5                   10                  15

Asp His Leu Pro Asn Leu Thr Leu Asn Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 657
<211> LENGTH: 58
<212> TYPE: PRT
<213> ORGANISM: artificial sequence
<220> FEATURE:
<223> OTHER INFORMATION: Modified bacterial sequence

<400> SEQUENCE: 657

Val Asp Ala Lys Tyr Ala Lys Glu Val Ile Asp Ala Trp Asn Glu Ile
1               5                   10                  15

Asp His Leu Pro Asn Leu Thr Ile Glu Gln Trp Leu Ala Phe Ile Asn
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 658
<211> LENGTH: 58
<212> TYPE: PRT
<213> ORGANISM: artificial sequence
<220> FEATURE:
<223> OTHER INFORMATION: Modified bacterial sequence

<400> SEQUENCE: 658

Val Asp Ala Lys Tyr Ala Lys Glu Val Ile Glu Ala Trp Asn Glu Ile
1               5                   10                  15

Asp Leu Leu Pro Asn Leu Thr Leu Ser Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 659
<211> LENGTH: 58
<212> TYPE: PRT
<213> ORGANISM: artificial sequence
<220> FEATURE:
<223> OTHER INFORMATION: Modified bacterial sequence

<400> SEQUENCE: 659

Val Asp Ala Lys Tyr Ala Lys Glu Val Ile Asp Ala Trp Asp Glu Ile
1               5                   10                  15

Asp Arg Leu Pro Asn Leu Thr Leu Lys Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 660
<211> LENGTH: 58
<212> TYPE: PRT
<213> ORGANISM: artificial sequence
<220> FEATURE:
<223> OTHER INFORMATION: Modified bacterial sequence

<400> SEQUENCE: 660

Val Asp Ala Lys Tyr Ala Lys Glu Thr Leu His Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 661
<211> LENGTH: 58
<212> TYPE: PRT
<213> ORGANISM: artificial sequence
<220> FEATURE:
<223> OTHER INFORMATION: Modified bacterial sequence
```

```
<400> SEQUENCE: 661

Val Asp Ala Lys Tyr Ala Lys Glu Val Ile Lys Ala Trp Asp Glu Ile
1               5                   10                  15

Asp His Leu Pro Asn Leu Thr Leu Asn Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 662
<211> LENGTH: 58
<212> TYPE: PRT
<213> ORGANISM: artificial sequence
<220> FEATURE:
<223> OTHER INFORMATION: Modified bacterial sequence

<400> SEQUENCE: 662

Val Asp Ala Lys Tyr Ala Lys Glu Val Ile Glu Ala Trp Asn Glu Ile
1               5                   10                  15

Asp His Leu Pro Asn Leu Thr Leu Ala Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 663
<211> LENGTH: 58
<212> TYPE: PRT
<213> ORGANISM: artificial sequence
<220> FEATURE:
<223> OTHER INFORMATION: Modified bacterial sequence

<400> SEQUENCE: 663

Val Asp Ala Lys Tyr Ala Lys Glu Val Ile Gln Ala Trp Asn Glu Ile
1               5                   10                  15

Asp His Leu Pro Asn Leu Thr Ile Asp Gln Trp Leu Ala Phe Ile Thr
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 664
<211> LENGTH: 58
<212> TYPE: PRT
<213> ORGANISM: artificial sequence
<220> FEATURE:
<223> OTHER INFORMATION: Modified bacterial sequence

<400> SEQUENCE: 664

Val Asp Ala Lys Tyr Ala Lys Glu Val Ile Glu Ala Trp Asn Glu Ile
1               5                   10                  15

Asp Arg Leu Pro Asn Leu Thr Ile Lys Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
```

<210> SEQ ID NO 665
<211> LENGTH: 58
<212> TYPE: PRT
<213> ORGANISM: artificial sequence
<220> FEATURE:
<223> OTHER INFORMATION: Modified bacterial sequence

<400> SEQUENCE: 665

Val Asp Ala Lys Tyr Ala Lys Glu Val Ile Glu Ala Trp Asn Glu Ile
1               5                   10                  15

Asp Ser Leu Pro Asn Leu Thr Leu Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 666
<211> LENGTH: 58
<212> TYPE: PRT
<213> ORGANISM: artificial sequence
<220> FEATURE:
<223> OTHER INFORMATION: Modified bacterial sequence

<400> SEQUENCE: 666

Val Asp Ala Lys Tyr Ala Lys Glu Thr Ile Asp Ala Trp Asn Glu Ile
1               5                   10                  15

Asp Lys Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 667
<211> LENGTH: 58
<212> TYPE: PRT
<213> ORGANISM: artificial sequence
<220> FEATURE:
<223> OTHER INFORMATION: Modified bacterial sequence

<400> SEQUENCE: 667

Val Asp Ala Lys Tyr Ala Lys Glu Val Leu Glu Ala Trp Ala Glu Ile
1               5                   10                  15

Asp Ala Leu Pro Asn Leu Thr Ile Ala Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 668
<211> LENGTH: 58
<212> TYPE: PRT
<213> ORGANISM: artificial sequence
<220> FEATURE:
<223> OTHER INFORMATION: Modified bacterial sequence

<400> SEQUENCE: 668

Val Asp Ala Lys Tyr Ala Lys Glu Thr Ile Asp Ala Trp Asn Glu Ile

```
                 1               5                  10                 15
Asp Arg Leu Pro Asn Leu Thr Ile Glu Gln Trp Leu Ala Phe Ile Asn
                20                  25                 30

Lys Leu Asp Asp Pro Ser Gln Ser Ser Glu Leu Leu Ser Glu Ala
       35                  40                 45

Lys Lys Leu Asn Asp Ser Gln Ala Pro Lys
       50                  55
```

<210> SEQ ID NO 669
<211> LENGTH: 58
<212> TYPE: PRT
<213> ORGANISM: artificial sequence
<220> FEATURE:
<223> OTHER INFORMATION: Modified bacterial sequence

<400> SEQUENCE: 669

```
Val Asp Ala Lys Tyr Ala Lys Glu Thr Leu Lys Ala Trp Asp Glu Ile
1               5                  10                 15

Asp Arg Leu Pro Asn Leu Thr Leu Glu Gln Trp Leu Ala Phe Ile Asn
                20                  25                 30

Lys Leu Asp Asp Pro Ser Gln Ser Ser Glu Leu Leu Ser Glu Ala
       35                  40                 45

Lys Lys Leu Asn Asp Ser Gln Ala Pro Lys
       50                  55
```

<210> SEQ ID NO 670
<211> LENGTH: 58
<212> TYPE: PRT
<213> ORGANISM: artificial sequence
<220> FEATURE:
<223> OTHER INFORMATION: Modified bacterial sequence

<400> SEQUENCE: 670

```
Val Asp Ala Lys Tyr Ala Lys Glu Thr Ile Ala Ala Trp Asn Glu Ile
1               5                  10                 15

Asp Ala Leu Pro Asn Leu Thr Leu Gln Gln Trp Leu Ala Phe Ile Asn
                20                  25                 30

Lys Leu Asp Asp Pro Ser Gln Ser Ser Glu Leu Leu Ser Glu Ala
       35                  40                 45

Lys Lys Leu Asn Asp Ser Gln Ala Pro Lys
       50                  55
```

<210> SEQ ID NO 671
<211> LENGTH: 58
<212> TYPE: PRT
<213> ORGANISM: artificial sequence
<220> FEATURE:
<223> OTHER INFORMATION: Modified bacterial sequence

<400> SEQUENCE: 671

```
Val Asp Ala Lys Tyr Ala Lys Glu Val Leu Gln Ala Trp Asn Glu Ile
1               5                  10                 15

Asp His Leu Pro Asn Leu Thr Ile Gln Gln Trp Leu Ala Phe Ile Asn
                20                  25                 30

Lys Leu Asp Asp Pro Ser Gln Ser Ser Glu Leu Leu Ser Glu Ala
       35                  40                 45

Lys Lys Leu Asn Asp Ser Gln Ala Pro Lys
       50                  55
```

<210> SEQ ID NO 672

```
<211> LENGTH: 58
<212> TYPE: PRT
<213> ORGANISM: artificial sequence
<220> FEATURE:
<223> OTHER INFORMATION: Modified bacterial sequence

<400> SEQUENCE: 672

Val Asp Ala Lys Tyr Ala Lys Glu Val Ile Glu Ala Trp Ser Glu Ile
1               5                   10                  15

Asp His Leu Pro Asn Leu Thr Leu Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 673
<211> LENGTH: 58
<212> TYPE: PRT
<213> ORGANISM: artificial sequence
<220> FEATURE:
<223> OTHER INFORMATION: Modified bacterial sequence

<400> SEQUENCE: 673

Val Asp Ala Lys Tyr Ala Lys Glu Val Ile Asp Ala Trp Asn Glu Ile
1               5                   10                  15

Asp Gly Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 674
<211> LENGTH: 58
<212> TYPE: PRT
<213> ORGANISM: artificial sequence
<220> FEATURE:
<223> OTHER INFORMATION: Modified bacterial sequence

<400> SEQUENCE: 674

Val Asp Ala Lys Tyr Ala Lys Glu Val Ile His Ala Trp Asn Glu Ile
1               5                   10                  15

Asp His Leu Pro Asn Leu Thr Leu Asn Gln Trp Leu Ala Phe Ile Asn
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 675
<211> LENGTH: 58
<212> TYPE: PRT
<213> ORGANISM: artificial sequence
<220> FEATURE:
<223> OTHER INFORMATION: Modified bacterial sequence

<400> SEQUENCE: 675

Val Asp Ala Lys Tyr Ala Lys Glu Val Leu Asp Ala Trp Asn Glu Ile
1               5                   10                  15

Asp Ser Leu Pro Asn Leu Thr Leu Asp Gln Trp Leu Ala Phe Ile Asn
            20                  25                  30
```

```
Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 676
<211> LENGTH: 58
<212> TYPE: PRT
<213> ORGANISM: artificial sequence
<220> FEATURE:
<223> OTHER INFORMATION: Modified bacterial sequence

<400> SEQUENCE: 676

Val Asp Ala Lys Tyr Ala Lys Glu Gln Ile Glu Ala Trp Asn Glu Ile
1               5                   10                  15

Asp Arg Leu Pro Asn Leu Thr Leu Glu Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 677
<211> LENGTH: 58
<212> TYPE: PRT
<213> ORGANISM: artificial sequence
<220> FEATURE:
<223> OTHER INFORMATION: Modified bacterial sequence

<400> SEQUENCE: 677

Val Asp Ala Lys Tyr Ala Lys Glu Val Val Asp Ala Trp Asn Glu Ile
1               5                   10                  15

Asp Ala Leu Pro Asn Leu Thr Leu Gln Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 678
<211> LENGTH: 58
<212> TYPE: PRT
<213> ORGANISM: artificial sequence
<220> FEATURE:
<223> OTHER INFORMATION: Modified bacterial sequence

<400> SEQUENCE: 678

Val Asp Ala Lys Tyr Ala Lys Glu Val Ile Glu Ala Trp Asn Glu Ile
1               5                   10                  15

Asp Lys Leu Pro Asn Leu Thr Ile Glu Gln Trp Leu Ala Phe Ile Asn
                20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 679
<211> LENGTH: 58
<212> TYPE: PRT
<213> ORGANISM: artificial sequence
<220> FEATURE:
```

<223> OTHER INFORMATION: Modified bacterial sequence

<400> SEQUENCE: 679

Val Asp Ala Lys Tyr Ala Lys Glu Val Ile Glu Ala Asn Asp Glu Ile
1               5                   10                  15

Asp Arg Leu Pro Asn Leu Thr Ile Glu Gln Trp Leu Ala Phe Ile Asn
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 680
<211> LENGTH: 58
<212> TYPE: PRT
<213> ORGANISM: artificial sequence
<220> FEATURE:
<223> OTHER INFORMATION: Modified bacterial sequence

<400> SEQUENCE: 680

Val Asp Ala Lys Tyr Ala Lys Glu Thr Leu Gln Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 681
<211> LENGTH: 58
<212> TYPE: PRT
<213> ORGANISM: artificial sequence
<220> FEATURE:
<223> OTHER INFORMATION: Modified bacterial sequence

<400> SEQUENCE: 681

Val Asp Ala Lys Tyr Ala Lys Glu Val Ile Glu Ala Trp Asp Glu Ile
1               5                   10                  15

Asp His Leu Pro Asn Leu Thr Ile Asp Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 682
<211> LENGTH: 58
<212> TYPE: PRT
<213> ORGANISM: artificial sequence
<220> FEATURE:
<223> OTHER INFORMATION: Modified bacterial sequence

<400> SEQUENCE: 682

Val Asp Ala Lys Tyr Ala Lys Glu Thr Ile Asp Ala Trp Asn Glu Ile
1               5                   10                  15

Asp His Leu Pro Asn Leu Thr Leu Gln Gln Trp Leu Ala Phe Ile Asn
            20                  25                  30

Lys Leu Ala Asp Asp Pro Ser Gln Ser Ser Glu Leu Leu Ser Glu Ala
        35                  40                  45

```
Lys Lys Leu Asn Asp Ser Gln Ala Pro Lys
    50                  55
```

<210> SEQ ID NO 683
<211> LENGTH: 58
<212> TYPE: PRT
<213> ORGANISM: artificial sequence
<220> FEATURE:
<223> OTHER INFORMATION: Modified bacterial sequence

<400> SEQUENCE: 683

```
Val Asp Ala Lys Tyr Ala Lys Glu Val Ile Asp Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 684
<211> LENGTH: 58
<212> TYPE: PRT
<213> ORGANISM: artificial sequence
<220> FEATURE:
<223> OTHER INFORMATION: Modified bacterial sequence

<400> SEQUENCE: 684

```
Val Asp Ala Lys Tyr Ala Lys Glu Val Ile Glu Ala Trp Asn Glu Ile
1               5                   10                  15

Asp Lys Leu Pro Asn Leu Thr Leu Ala Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 685
<211> LENGTH: 58
<212> TYPE: PRT
<213> ORGANISM: artificial sequence
<220> FEATURE:
<223> OTHER INFORMATION: Modified bacterial sequence

<400> SEQUENCE: 685

```
Val Asp Ala Lys Tyr Ala Lys Glu Val Leu Gln Ala Trp Asp Glu Ile
1               5                   10                  15

Asp Lys Leu Pro Asn Leu Thr Ile Gln Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

<210> SEQ ID NO 686
<211> LENGTH: 58
<212> TYPE: PRT
<213> ORGANISM: artificial sequence
<220> FEATURE:
<223> OTHER INFORMATION: Modified bacterial sequence

<400> SEQUENCE: 686

Val Asp Ala Lys Tyr Ala Lys Glu Val Ile Ala Ala Trp Asn Glu Ile
1               5                   10                  15

Asp Gly Leu Pro Asn Leu Thr Leu Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 687
<211> LENGTH: 58
<212> TYPE: PRT
<213> ORGANISM: artificial sequence
<220> FEATURE:
<223> OTHER INFORMATION: Modified bacterial sequence

<400> SEQUENCE: 687

Val Asp Ala Lys Tyr Ala Lys Glu Thr Leu Asn Ala Trp Asn Glu Ile
1               5                   10                  15

Asp Ala Leu Pro Asn Leu Thr Leu Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 688
<211> LENGTH: 58
<212> TYPE: PRT
<213> ORGANISM: artificial sequence
<220> FEATURE:
<223> OTHER INFORMATION: Modified bacterial sequence

<400> SEQUENCE: 688

Val Asp Ala Lys Tyr Ala Lys Glu Val Leu Ser Ala Trp Asn Glu Ile
1               5                   10                  15

Asp Gln Leu Pro Asn Leu Thr Leu Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 689
<211> LENGTH: 58
<212> TYPE: PRT
<213> ORGANISM: artificial sequence
<220> FEATURE:
<223> OTHER INFORMATION: Modified bacterial sequence

<400> SEQUENCE: 689

Val Asp Ala Lys Tyr Ala Lys Glu Thr Leu Gly Ala Trp Asp Glu Ile
1               5                   10                  15

Asp His Leu Pro Asn Leu Thr Leu His Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

```
<210> SEQ ID NO 690
<211> LENGTH: 58
<212> TYPE: PRT
<213> ORGANISM: artificial sequence
<220> FEATURE:
<223> OTHER INFORMATION: Modified bacterial sequence

<400> SEQUENCE: 690

Val Asp Ala Lys Tyr Ala Lys Glu Gln Ile Glu Ala Trp Asn Glu Ile
1               5                   10                  15

Asp His Leu Pro Asn Leu Thr Leu Gln Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 691
<211> LENGTH: 58
<212> TYPE: PRT
<213> ORGANISM: artificial sequence
<220> FEATURE:
<223> OTHER INFORMATION: Modified bacterial sequence

<400> SEQUENCE: 691

Val Asp Ala Lys Tyr Ala Lys Glu Val Val Glu Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 692
<211> LENGTH: 58
<212> TYPE: PRT
<213> ORGANISM: artificial sequence
<220> FEATURE:
<223> OTHER INFORMATION: Modified bacterial sequence

<400> SEQUENCE: 692

Val Asp Ala Lys Tyr Ala Lys Glu Val Leu Glu Ala Trp Asn Glu Ile
1               5                   10                  15

Asp Glu Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 693
<211> LENGTH: 58
<212> TYPE: PRT
<213> ORGANISM: artificial sequence
<220> FEATURE:
<223> OTHER INFORMATION: Modified bacterial sequence

<400> SEQUENCE: 693

Val Asp Ala Lys Tyr Ala Lys Glu Val Ile Asp Ala Trp Asn Glu Ile
1               5                   10                  15

Asp Gln Leu Pro Asn Leu Thr Leu Gln Gln Trp Leu Ala Phe Ile Asn
```

```
                20                  25                  30
Lys Leu Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 694
<211> LENGTH: 58
<212> TYPE: PRT
<213> ORGANISM: artificial sequence
<220> FEATURE:
<223> OTHER INFORMATION: Modified bacterial sequence

<400> SEQUENCE: 694

Val Asp Ala Lys Tyr Ala Lys Glu Thr Ile Asp Ala Trp Asp Glu Ile
1               5                  10                  15
Asp Lys Leu Pro Asn Leu Thr Leu Ser Gln Trp Leu Ala Phe Ile Asn
                20                  25                  30
Lys Leu Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 695
<211> LENGTH: 58
<212> TYPE: PRT
<213> ORGANISM: artificial sequence
<220> FEATURE:
<223> OTHER INFORMATION: Modified bacterial sequence

<400> SEQUENCE: 695

Val Asp Ala Lys Tyr Ala Lys Glu Thr Ile Asp Ala Trp Asn Glu Ile
1               5                  10                  15
Asp Gln Leu Pro Asn Leu Thr Leu Gln Gln Trp Leu Ala Phe Ile Asn
                20                  25                  30
Lys Leu Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 696
<211> LENGTH: 58
<212> TYPE: PRT
<213> ORGANISM: artificial sequence
<220> FEATURE:
<223> OTHER INFORMATION: Modified bacterial sequence

<400> SEQUENCE: 696

Val Asp Ala Lys Tyr Ala Lys Glu Val Ile Gln Ala Trp Asp Glu Ile
1               5                  10                  15
Asp Ala Leu Pro Asn Leu Thr Leu Asn Gln Trp Leu Ala Phe Ile Asn
                20                  25                  30
Lys Leu Asp Asp Pro Ser Gln Ser Ser Glu Leu Leu Ser Glu Ala
        35                  40                  45
Lys Lys Leu Asn Asp Ser Gln Ala Pro Lys
    50                  55

<210> SEQ ID NO 697
<211> LENGTH: 58
<212> TYPE: PRT
<213> ORGANISM: artificial sequence
```

```
<220> FEATURE:
<223> OTHER INFORMATION: Modified bacterial sequence

<400> SEQUENCE: 697

Val Asp Ala Lys Tyr Ala Lys Glu Val Leu Asp Ala Trp Ala Glu Ile
1               5                   10                  15

Asp Gln Leu Pro Asn Leu Thr Leu Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 698
<211> LENGTH: 58
<212> TYPE: PRT
<213> ORGANISM: artificial sequence
<220> FEATURE:
<223> OTHER INFORMATION: Modified bacterial sequence

<400> SEQUENCE: 698

Val Asp Ala Lys Tyr Ala Lys Glu His Ile Ala Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 699
<211> LENGTH: 58
<212> TYPE: PRT
<213> ORGANISM: artificial sequence
<220> FEATURE:
<223> OTHER INFORMATION: Modified bacterial sequence

<400> SEQUENCE: 699

Val Asp Ala Lys Tyr Ala Lys Glu Val Ile Arg Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 700
<211> LENGTH: 58
<212> TYPE: PRT
<213> ORGANISM: artificial sequence
<220> FEATURE:
<223> OTHER INFORMATION: Modified bacterial sequence

<400> SEQUENCE: 700

Val Asp Ala Lys Tyr Ala Lys Glu Val Ile Asp Ala Trp Asp Glu Ile
1               5                   10                  15

Asp Ala Leu Pro Asn Leu Thr Ile Asp Gln Trp Leu Ala Phe Ile Asn
            20                  25                  30

Lys Leu Ala Asp Asp Pro Ser Gln Ser Ser Glu Leu Leu Ser Glu Ala
        35                  40                  45
```

```
Lys Lys Leu Asn Asp Ser Gln Ala Pro Lys
    50                  55

<210> SEQ ID NO 701
<211> LENGTH: 58
<212> TYPE: PRT
<213> ORGANISM: artificial sequence
<220> FEATURE:
<223> OTHER INFORMATION: Modified bacterial sequence

<400> SEQUENCE: 701

Val Asp Ala Lys Tyr Ala Lys Glu Val Ile Asp Ala Trp Asn Glu Ile
1               5                   10                  15

Asp Arg Leu Pro Asn Leu Thr Ile Gln Gln Trp Leu Ala Phe Ile Asn
            20                  25                  30

Lys Leu Asp Asp Asp Pro Ser Gln Ser Ser Leu Leu Ser Glu Ala
        35                  40                  45

Lys Lys Leu Asn Asp Ser Gln Ala Pro Lys
    50                  55

<210> SEQ ID NO 702
<211> LENGTH: 58
<212> TYPE: PRT
<213> ORGANISM: artificial sequence
<220> FEATURE:
<223> OTHER INFORMATION: Modified bacterial sequence

<400> SEQUENCE: 702

Val Asp Ala Lys Tyr Ala Lys Glu Val Ile Thr Ala Trp Asn Glu Ile
1               5                   10                  15

Asp His Leu Pro Asn Leu Thr Leu Ser Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 703
<211> LENGTH: 58
<212> TYPE: PRT
<213> ORGANISM: artificial sequence
<220> FEATURE:
<223> OTHER INFORMATION: Modified bacterial sequence

<400> SEQUENCE: 703

Val Asp Ala Lys Tyr Ala Lys Glu Val Ile Asp Ala Trp Asn Glu Ile
1               5                   10                  15

Asp Ala Leu Pro Asn Leu Thr Ile His Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 704
<211> LENGTH: 58
<212> TYPE: PRT
<213> ORGANISM: artificial sequence
<220> FEATURE:
<223> OTHER INFORMATION: Modified bacterial sequence

<400> SEQUENCE: 704
```

-continued

Val Asp Ala Lys Tyr Ala Lys Glu Gln Leu Lys Ala Trp Asp Glu Ile
1               5                   10                  15

Asp Lys Leu Pro Asn Leu Thr Ile Glu Gln Trp Leu Ala Phe Ile Glu
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 705
<211> LENGTH: 58
<212> TYPE: PRT
<213> ORGANISM: artificial sequence
<220> FEATURE:
<223> OTHER INFORMATION: Modified bacterial sequence

<400> SEQUENCE: 705

Val Asp Ala Lys Tyr Ala Lys Glu His Ile Asp Ala Trp Thr Glu Ile
1               5                   10                  15

Asp His Leu Pro Asn Leu Thr Ile Glu Gln Trp Leu Ala Phe Ile Asn
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 706
<211> LENGTH: 58
<212> TYPE: PRT
<213> ORGANISM: artificial sequence
<220> FEATURE:
<223> OTHER INFORMATION: Modified bacterial sequence

<400> SEQUENCE: 706

Val Asp Ala Lys Tyr Ala Lys Glu Gln Leu Arg Ala Trp Asp Glu Ile
1               5                   10                  15

Asp Lys Leu Pro Asn Leu Thr Ile Glu Gln Trp Leu Ala Phe Ile Asn
                20                  25                  30

Lys Leu Gln Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 707
<211> LENGTH: 58
<212> TYPE: PRT
<213> ORGANISM: artificial sequence
<220> FEATURE:
<223> OTHER INFORMATION: Modified bacterial sequence

<400> SEQUENCE: 707

Val Asp Ala Lys Tyr Ala Lys Glu Val Leu Glu Ala Trp Arg Glu Ile
1               5                   10                  15

Asp Ser Leu Pro Asn Leu Thr Ile Ala Gln Trp Leu Ala Phe Ile Asn
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys
        50                  55

<210> SEQ ID NO 708
<211> LENGTH: 58
<212> TYPE: PRT
<213> ORGANISM: artificial sequence
<220> FEATURE:
<223> OTHER INFORMATION: Modified bacterial sequence

<400> SEQUENCE: 708

Val Asp Ala Lys Tyr Ala Lys Glu Val Ile Gln Ala Trp Asn Glu Ile
1               5                   10                  15

Asp Lys Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 709
<211> LENGTH: 58
<212> TYPE: PRT
<213> ORGANISM: artificial sequence
<220> FEATURE:
<223> OTHER INFORMATION: Modified bacterial sequence

<400> SEQUENCE: 709

Val Asp Ala Lys Tyr Ala Lys Glu His Val Glu Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 710
<211> LENGTH: 58
<212> TYPE: PRT
<213> ORGANISM: artificial sequence
<220> FEATURE:
<223> OTHER INFORMATION: Modified bacterial sequence

<400> SEQUENCE: 710

Val Asp Ala Lys Tyr Ala Lys Glu Val Ile Asp Ala Trp Asp Glu Ile
1               5                   10                  15

Asp Ala Leu Pro Asn Leu Thr Ile Asp Gln Trp Leu Ala Phe Ile Asn
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 711
<211> LENGTH: 58
<212> TYPE: PRT
<213> ORGANISM: artificial sequence
<220> FEATURE:
<223> OTHER INFORMATION: Modified bacterial sequence

<400> SEQUENCE: 711

Val Asp Ala Lys Tyr Ala Lys Glu Val Ile Glu Ala Trp Asn Glu Ile
1               5                   10                  15

-continued

Asp His Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 712
<211> LENGTH: 58
<212> TYPE: PRT
<213> ORGANISM: artificial sequence
<220> FEATURE:
<223> OTHER INFORMATION: Modified bacterial sequence

<400> SEQUENCE: 712

Val Asp Ala Lys Tyr Ala Lys Glu Val Leu Gln Ala Trp Asp Glu Ile
1               5                   10                  15

Asp Lys Leu Pro Asn Leu Thr Ile Glu Gln Trp Leu Ala Phe Ile Asn
            20                  25                  30

Lys Leu Ser Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 713
<211> LENGTH: 58
<212> TYPE: PRT
<213> ORGANISM: artificial sequence
<220> FEATURE:
<223> OTHER INFORMATION: Modified bacterial sequence

<400> SEQUENCE: 713

Val Asp Ala Lys Tyr Ala Lys Glu Val Ile Lys Ala Trp Asn Glu Ile
1               5                   10                  15

Asp Ser Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 714
<211> LENGTH: 58
<212> TYPE: PRT
<213> ORGANISM: artificial sequence
<220> FEATURE:
<223> OTHER INFORMATION: Modified bacterial sequence

<400> SEQUENCE: 714

Val Asp Ala Lys Tyr Ala Lys Glu Val Leu Glu Ala Trp His Glu Ile
1               5                   10                  15

Asp Leu Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 715
<211> LENGTH: 58
<212> TYPE: PRT

```
<213> ORGANISM: artificial sequence
<220> FEATURE:
<223> OTHER INFORMATION: Modified bacterial sequence

<400> SEQUENCE: 715

Val Asp Ala Lys Tyr Ala Lys Glu Val Leu Glu Ala Trp Thr Glu Ile
1               5                   10                  15

Asp Arg Leu Pro Asn Leu Thr Leu Asp Gln Trp Leu Ala Phe Ile Asn
            20                  25                  30

Lys Leu Asp Asp Pro Ser Gln Ser Ser Glu Leu Ser Glu Ala
        35                  40                  45

Lys Lys Leu Asn Asp Ser Gln Ala Pro Lys
    50                  55

<210> SEQ ID NO 716
<211> LENGTH: 58
<212> TYPE: PRT
<213> ORGANISM: artificial sequence
<220> FEATURE:
<223> OTHER INFORMATION: Modified bacterial sequence

<400> SEQUENCE: 716

Val Asp Ala Lys Tyr Ala Lys Glu Gln Leu Tyr Ala Trp Asn Glu Ile
1               5                   10                  15

Asp His Leu Pro Asn Leu Thr Ile Glu Gln Trp Leu Ala Phe Ile Glu
            20                  25                  30

Lys Leu Gln Asp Asp Pro Ser Gln Ser Ser Glu Leu Ser Glu Ala
        35                  40                  45

Lys Lys Leu Asn Asp Ser Gln Ala Pro Lys
    50                  55

<210> SEQ ID NO 717
<211> LENGTH: 58
<212> TYPE: PRT
<213> ORGANISM: artificial sequence
<220> FEATURE:
<223> OTHER INFORMATION: Modified bacterial sequence

<400> SEQUENCE: 717

Val Asp Ala Lys Tyr Ala Lys Glu Val Leu Asn Ala Trp Asp Glu Ile
1               5                   10                  15

Asp Lys Leu Pro Asn Leu Thr Ile Lys Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 718
<211> LENGTH: 58
<212> TYPE: PRT
<213> ORGANISM: artificial sequence
<220> FEATURE:
<223> OTHER INFORMATION: Modified bacterial sequence

<400> SEQUENCE: 718

Val Asp Ala Lys Tyr Ala Lys Glu Val Ile Arg Ala Trp Asp Glu Ile
1               5                   10                  15

Asp Lys Leu Pro Asn Leu Thr Val Glu Gln Trp Leu Ala Phe Ile Asn
            20                  25                  30

Lys Leu Asp Asp Asp Pro Ser Gln Ser Ser Glu Leu Leu Ser Glu Ala
```

Lys Lys Leu Asn Asp Ser Gln Ala Pro Lys
        50                  55

<210> SEQ ID NO 719
<211> LENGTH: 58
<212> TYPE: PRT
<213> ORGANISM: artificial sequence
<220> FEATURE:
<223> OTHER INFORMATION: Modified bacterial sequence

<400> SEQUENCE: 719

Val Asp Ala Lys Tyr Ala Lys Glu Val Val Gln Ala Trp Asp Glu Ile
1               5                   10                  15

Asp Gln Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 720
<211> LENGTH: 58
<212> TYPE: PRT
<213> ORGANISM: artificial sequence
<220> FEATURE:
<223> OTHER INFORMATION: Modified bacterial sequence

<400> SEQUENCE: 720

Val Asp Ala Lys Tyr Ala Lys Glu Val Ile Arg Ala Trp Asp Glu Ile
1               5                   10                  15

Asp Gln Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 721
<211> LENGTH: 58
<212> TYPE: PRT
<213> ORGANISM: artificial sequence
<220> FEATURE:
<223> OTHER INFORMATION: Modified bacterial sequence

<400> SEQUENCE: 721

Val Asp Ala Lys Tyr Ala Lys Glu Thr Ile Asp Ala Trp Asn Glu Ile
1               5                   10                  15

Asp His Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
        50                  55

<210> SEQ ID NO 722
<211> LENGTH: 58
<212> TYPE: PRT
<213> ORGANISM: artificial sequence
<220> FEATURE:
<223> OTHER INFORMATION: Modified bacterial sequence

```
<400> SEQUENCE: 722

Val Asp Ala Lys Tyr Ala Lys Glu Val Ala Ala Trp Thr Glu Ile
1               5                   10                  15

Asp Leu Leu Pro Asn Leu Thr Leu Asp Gln Trp Leu Ala Phe Ile Asn
            20                  25                  30

Lys Leu Glu Asp Asp Pro Ser Gln Ser Ser Leu Leu Ser Glu Ala
        35                  40                  45

Lys Lys Leu Asn Asp Ser Gln Ala Pro Lys
    50                  55

<210> SEQ ID NO 723
<211> LENGTH: 58
<212> TYPE: PRT
<213> ORGANISM: artificial sequence
<220> FEATURE:
<223> OTHER INFORMATION: Modified bacterial sequence

<400> SEQUENCE: 723

Val Asp Ala Lys Tyr Ala Lys Glu Val Val Ala Ala Trp Asp Glu Ile
1               5                   10                  15

Asp Ala Leu Pro Asn Leu Thr Ile Glu Gln Trp Leu Ala Phe Ile Asn
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 724
<211> LENGTH: 58
<212> TYPE: PRT
<213> ORGANISM: artificial sequence
<220> FEATURE:
<223> OTHER INFORMATION: Modified bacterial sequence

<400> SEQUENCE: 724

Val Asp Ala Lys Tyr Ala Lys Glu Thr Leu Glu Ala Trp Arg Glu Ile
1               5                   10                  15

Asp Ser Leu Pro Asn Leu Thr Leu Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 725
<211> LENGTH: 58
<212> TYPE: PRT
<213> ORGANISM: artificial sequence
<220> FEATURE:
<223> OTHER INFORMATION: Modified bacterial sequence

<400> SEQUENCE: 725

Val Asp Ala Lys Tyr Ala Lys Glu Val Ile Lys Ala Trp Asn Glu Ile
1               5                   10                  15

Asp His Leu Pro Asn Leu Thr Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55
```

```
<210> SEQ ID NO 726
<211> LENGTH: 58
<212> TYPE: PRT
<213> ORGANISM: artificial sequence
<220> FEATURE:
<223> OTHER INFORMATION: Modified bacterial sequence

<400> SEQUENCE: 726

Val Asp Ala Lys Tyr Ala Lys Glu Val Leu Glu Ala Trp Thr Glu Ile
1               5                   10                  15

Asp Lys Leu Pro Asn Leu Thr Ile Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 727
<211> LENGTH: 58
<212> TYPE: PRT
<213> ORGANISM: artificial sequence
<220> FEATURE:
<223> OTHER INFORMATION: Modified bacterial sequence

<400> SEQUENCE: 727

Val Asp Ala Lys Tyr Ala Lys Glu Thr Leu Glu Ala Trp Asp Glu Ile
1               5                   10                  15

Asp Lys Leu Pro Asn Leu Thr Ile Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 728
<211> LENGTH: 58
<212> TYPE: PRT
<213> ORGANISM: artificial sequence
<220> FEATURE:
<223> OTHER INFORMATION: Modified bacterial sequence

<400> SEQUENCE: 728

Val Asp Ala Lys Tyr Ala Lys Glu Val Ile Glu Ala Trp Asn Glu Ile
1               5                   10                  15

Asp Lys Leu Pro Asn Leu Thr Ile Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 729
<211> LENGTH: 58
<212> TYPE: PRT
<213> ORGANISM: artificial sequence
<220> FEATURE:
<223> OTHER INFORMATION: Modified bacterial sequence

<400> SEQUENCE: 729

Val Asp Ala Lys Tyr Ala Lys Glu Thr Ile Asp Ala Trp Asn Glu Ile
1               5                   10                  15
```

-continued

Asp Lys Leu Pro Asn Leu Thr Leu Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 730
<211> LENGTH: 58
<212> TYPE: PRT
<213> ORGANISM: artificial sequence
<220> FEATURE:
<223> OTHER INFORMATION: Modified bacterial sequence

<400> SEQUENCE: 730

Val Asp Ala Lys Tyr Ala Lys Glu Thr Leu Asp Ala Trp Asp Glu Ile
1               5                   10                  15

Asp Ala Leu Pro Asn Leu Thr Ile Asp Gln Trp Leu Ala Phe Ile Asn
            20                  25                  30

Lys Leu Glu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 731
<211> LENGTH: 58
<212> TYPE: PRT
<213> ORGANISM: artificial sequence
<220> FEATURE:
<223> OTHER INFORMATION: Modified bacterial sequence

<400> SEQUENCE: 731

Val Asp Ala Lys Tyr Ala Lys Glu Val Leu Ser Ala Trp Asn Glu Ile
1               5                   10                  15

Asp His Leu Pro Asn Leu Thr Ile Gln Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 732
<211> LENGTH: 58
<212> TYPE: PRT
<213> ORGANISM: artificial sequence
<220> FEATURE:
<223> OTHER INFORMATION: Modified bacterial sequence

<400> SEQUENCE: 732

Val Asp Ala Lys Tyr Ala Lys Glu Val Ile Gln Ala Asn Asp Glu Ile
1               5                   10                  15

Asp Lys Leu Pro Asn Leu Thr Ile Glu Gln Trp Leu Ala Phe Ile His
            20                  25                  30

Lys Leu His Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 733
<211> LENGTH: 58

```
<212> TYPE: PRT
<213> ORGANISM: artificial sequence
<220> FEATURE:
<223> OTHER INFORMATION: Modified bacterial sequence

<400> SEQUENCE: 733

Val Asp Ala Lys Tyr Ala Lys Glu His Leu Asp Ala Trp Asp Glu Ile
1               5                   10                  15

Asp His Leu Pro Asn Leu Thr Ile Gln Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 734
<211> LENGTH: 58
<212> TYPE: PRT
<213> ORGANISM: artificial sequence
<220> FEATURE:
<223> OTHER INFORMATION: Modified bacterial sequence

<400> SEQUENCE: 734

Val Asp Ala Lys Tyr Ala Lys Glu Val Ile Gln Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 735
<211> LENGTH: 58
<212> TYPE: PRT
<213> ORGANISM: artificial sequence
<220> FEATURE:
<223> OTHER INFORMATION: Modified bacterial sequence

<400> SEQUENCE: 735

Val Asp Ala Lys Tyr Ala Lys Glu Val Ile Glu Ala Trp Asn Glu Ile
1               5                   10                  15

Asp Tyr Leu Pro Asn Leu Thr Ile Ala Gln Trp Ile Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 736
<211> LENGTH: 58
<212> TYPE: PRT
<213> ORGANISM: artificial sequence
<220> FEATURE:
<223> OTHER INFORMATION: Modified bacterial sequence

<400> SEQUENCE: 736

Val Asp Ala Lys Tyr Ala Lys Glu Thr Ile Gln Ala Trp Asp Glu Ile
1               5                   10                  15

Asp Arg Leu Pro Asn Leu Thr Leu Gln Gln Trp Leu Ala Phe Ile Asn
            20                  25                  30
```

-continued

Lys Leu Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 737
<211> LENGTH: 58
<212> TYPE: PRT
<213> ORGANISM: artificial sequence
<220> FEATURE:
<223> OTHER INFORMATION: Modified bacterial sequence

<400> SEQUENCE: 737

Val Asp Ala Lys Tyr Ala Lys Glu Thr Ile Gln Ala Trp Asp Glu Ile
1               5                   10                  15

Asp Lys Leu Pro Asn Leu Thr Ile Glu Gln Trp Leu Ala Phe Ile Asn
             20                  25                  30

Lys Leu Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 738
<211> LENGTH: 58
<212> TYPE: PRT
<213> ORGANISM: artificial sequence
<220> FEATURE:
<223> OTHER INFORMATION: Modified bacterial sequence

<400> SEQUENCE: 738

Val Asp Ala Lys Tyr Ala Lys Glu Thr Leu Asp Ala Trp Ala Glu Ile
1               5                   10                  15

Asp His Leu Pro Asn Leu Thr Ile Glu Gln Trp Leu Ala Phe Ile Asn
             20                  25                  30

Lys Leu Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 739
<211> LENGTH: 58
<212> TYPE: PRT
<213> ORGANISM: artificial sequence
<220> FEATURE:
<223> OTHER INFORMATION: Modified bacterial sequence

<400> SEQUENCE: 739

Val Asp Ala Lys Tyr Ala Lys Glu Val Ile Glu Ala Trp Asp Glu Ile
1               5                   10                  15

Asp Lys Leu Pro Asn Leu Thr Leu Asn Gln Trp Leu Ala Phe Ile Asn
             20                  25                  30

Lys Leu Asp Asp Pro Ser Gln Ser Ser Glu Leu Leu Ser Glu Ala
         35                  40                  45

Lys Lys Leu Asn Asp Ser Gln Ala Pro Lys
     50                  55

<210> SEQ ID NO 740
<211> LENGTH: 58
<212> TYPE: PRT
<213> ORGANISM: artificial sequence
<220> FEATURE:
<223> OTHER INFORMATION: Modified bacterial sequence

```
<400> SEQUENCE: 740

Val Asp Ala Lys Tyr Ala Lys Glu Val Leu Asp Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 741
<211> LENGTH: 58
<212> TYPE: PRT
<213> ORGANISM: artificial sequence
<220> FEATURE:
<223> OTHER INFORMATION: Modified bacterial sequence

<400> SEQUENCE: 741

Val Asp Ala Lys Tyr Ala Lys Glu Val Leu His Ala Trp Asn Glu Ile
1               5                   10                  15

Asp His Leu Pro Asn Leu Thr Ile Glu Gln Trp Leu Ala Phe Ile Glu
            20                  25                  30

Lys Leu Glu Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 742
<211> LENGTH: 58
<212> TYPE: PRT
<213> ORGANISM: artificial sequence
<220> FEATURE:
<223> OTHER INFORMATION: Modified bacterial sequence

<400> SEQUENCE: 742

Val Asp Ala Lys Tyr Ala Lys Glu Val Ile Glu Ala Trp Gln Glu Ile
1               5                   10                  15

Asp Lys Leu Pro Asn Leu Thr Ile Asp Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 743
<211> LENGTH: 58
<212> TYPE: PRT
<213> ORGANISM: artificial sequence
<220> FEATURE:
<223> OTHER INFORMATION: Modified bacterial sequence

<400> SEQUENCE: 743

Val Asp Ala Lys Tyr Ala Lys Glu Val Val Asp Ala Trp Asn Glu Ile
1               5                   10                  15

Asp Gln Leu Pro Asn Leu Thr Ile Glu Gln Trp Leu Ala Phe Ile Asn
            20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys
```

-continued

```
        50                  55

<210> SEQ ID NO 744
<211> LENGTH: 58
<212> TYPE: PRT
<213> ORGANISM: artificial sequence
<220> FEATURE:
<223> OTHER INFORMATION: Modified bacterial sequence

<400> SEQUENCE: 744

Val Asp Ala Lys Tyr Ala Lys Glu Gln Ile Glu Ala Trp Asn Glu Ile
1               5                   10                  15

Asp Ala Leu Pro Asn Leu Thr Ile Glu Gln Trp Leu Ala Phe Ile Asn
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 745
<211> LENGTH: 60
<212> TYPE: PRT
<213> ORGANISM: artificial sequence
<220> FEATURE:
<223> OTHER INFORMATION: Modified bacterial sequence

<400> SEQUENCE: 745

Val Asp Ala Lys Tyr Ala Lys Glu Thr Ile Thr Ala Trp Asp Glu Ile
1               5                   10                  15

Asp Lys Leu Pro Asn Leu Thr Ile Glu Gln Trp Leu Ala Phe Ile Gly
            20                  25                  30

Lys Leu Glu Asp Asp Pro Ser Gln Ser Ser Glu Leu Leu Ala Glu Ala
        35                  40                  45

Lys Lys Leu Asn Asp Ala Gln Ala Pro Lys Val Asp
    50                  55                  60

<210> SEQ ID NO 746
<211> LENGTH: 60
<212> TYPE: PRT
<213> ORGANISM: artificial sequence
<220> FEATURE:
<223> OTHER INFORMATION: Modified bacterial sequence

<400> SEQUENCE: 746

Ala Glu Ala Lys Tyr Ala Lys Glu Val Ile Glu Ala Trp Asn Glu Ile
1               5                   10                  15

Asp Arg Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp
    50                  55                  60

<210> SEQ ID NO 747
<211> LENGTH: 60
<212> TYPE: PRT
<213> ORGANISM: artificial sequence
<220> FEATURE:
<223> OTHER INFORMATION: Modified bacterial sequence

<400> SEQUENCE: 747

Ala Glu Ala Lys Tyr Ala Lys Glu Val Leu Glu Ala Trp Asn Glu Ile
```

```
                1               5                  10                 15
Asp Arg Leu Pro Asn Leu Thr Ile Glu Gln Trp Leu Ala Phe Ile Asn
                    20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp
    50                  55                  60

<210> SEQ ID NO 748
<211> LENGTH: 60
<212> TYPE: PRT
<213> ORGANISM: artificial sequence
<220> FEATURE:
<223> OTHER INFORMATION: Modified bacterial sequence

<400> SEQUENCE: 748

Ala Glu Ala Lys Tyr Ala Lys Glu Val Leu Glu Ala Trp Asp Glu Ile
1               5                   10                  15

Asp Arg Leu Pro Asn Leu Thr Leu Asp Gln Trp Leu Ala Phe Ile Asn
                    20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp
    50                  55                  60

<210> SEQ ID NO 749
<211> LENGTH: 60
<212> TYPE: PRT
<213> ORGANISM: artificial sequence
<220> FEATURE:
<223> OTHER INFORMATION: Modified bacterial sequence

<400> SEQUENCE: 749

Ala Glu Ala Lys Tyr Ala Lys Glu Val Leu Asp Ala Trp Asp Glu Ile
1               5                   10                  15

Asp Lys Leu Pro Asn Leu Thr Leu Glu Gln Trp Leu Ala Phe Ile Asn
                    20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp
    50                  55                  60

<210> SEQ ID NO 750
<211> LENGTH: 60
<212> TYPE: PRT
<213> ORGANISM: artificial sequence
<220> FEATURE:
<223> OTHER INFORMATION: Modified bacterial sequence

<400> SEQUENCE: 750

Ala Glu Ala Lys Tyr Ala Lys Glu Val Leu Asp Ala Trp Asp Glu Ile
1               5                   10                  15

Asp Ala Leu Pro Asn Leu Thr Leu Glu Gln Trp Leu Ala Phe Ile Asn
                    20                  25                  30

Lys Leu Asp Asp Pro Ser Gln Ser Ser Glu Leu Leu Ser Glu Ala
        35                  40                  45

Lys Lys Leu Asn Asp Ser Gln Ala Pro Lys Val Asp
    50                  55                  60

<210> SEQ ID NO 751
```

```
<211> LENGTH: 60
<212> TYPE: PRT
<213> ORGANISM: artificial sequence
<220> FEATURE:
<223> OTHER INFORMATION: Modified bacterial sequence

<400> SEQUENCE: 751

Ala Glu Ala Lys Tyr Ala Lys Glu Val Ile Asp Ala Trp Asp Glu Ile
1               5                   10                  15

Asp Arg Leu Pro Asn Leu Thr Leu Asp Gln Trp Leu Ala Phe Ile Asn
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys Val Asp
        50                  55                  60

<210> SEQ ID NO 752
<211> LENGTH: 60
<212> TYPE: PRT
<213> ORGANISM: artificial sequence
<220> FEATURE:
<223> OTHER INFORMATION: Modified bacterial sequence

<400> SEQUENCE: 752

Ala Glu Ala Lys Tyr Ala Lys Glu Thr Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys Val Asp
        50                  55                  60

<210> SEQ ID NO 753
<211> LENGTH: 60
<212> TYPE: PRT
<213> ORGANISM: artificial sequence
<220> FEATURE:
<223> OTHER INFORMATION: Modified bacterial sequence

<400> SEQUENCE: 753

Ala Glu Ala Lys Tyr Ala Lys Glu Val Leu Glu Ala Trp Asp Glu Ile
1               5                   10                  15

Asp Arg Leu Pro Asn Leu Thr Ile Glu Gln Trp Leu Ala Phe Ile Asn
                20                  25                  30

Lys Leu Asp Asp Asp Pro Ser Gln Ser Ser Glu Leu Leu Ser Glu Ala
            35                  40                  45

Lys Lys Leu Asn Asp Ser Gln Ala Pro Lys Val Asp
        50                  55                  60

<210> SEQ ID NO 754
<211> LENGTH: 60
<212> TYPE: PRT
<213> ORGANISM: artificial sequence
<220> FEATURE:
<223> OTHER INFORMATION: Modified bacterial sequence

<400> SEQUENCE: 754

Ala Glu Ala Lys Tyr Ala Lys Glu Val Ile Asp Ala Trp Asn Glu Ile
1               5                   10                  15

Asp Ala Leu Pro Asn Leu Thr Leu Asp Gln Trp Leu Ala Phe Ile Asn
                20                  25                  30
```

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp
 50                  55                  60

<210> SEQ ID NO 755
<211> LENGTH: 60
<212> TYPE: PRT
<213> ORGANISM: artificial sequence
<220> FEATURE:
<223> OTHER INFORMATION: Modified bacterial sequence

<400> SEQUENCE: 755

Ala Glu Ala Lys Tyr Ala Lys Glu Val Leu Asp Ala Trp Asp Glu Ile
 1               5                  10                  15

Asp Lys Leu Pro Asn Leu Thr Ile Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp
 50                  55                  60

<210> SEQ ID NO 756
<211> LENGTH: 60
<212> TYPE: PRT
<213> ORGANISM: artificial sequence
<220> FEATURE:
<223> OTHER INFORMATION: Modified bacterial sequence

<400> SEQUENCE: 756

Ala Glu Ala Lys Tyr Ala Lys Glu Val Leu Glu Ala Trp Asp Glu Ile
 1               5                  10                  15

Asp His Leu Pro Asn Leu Thr Leu Asp Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp
 50                  55                  60

<210> SEQ ID NO 757
<211> LENGTH: 60
<212> TYPE: PRT
<213> ORGANISM: artificial sequence
<220> FEATURE:
<223> OTHER INFORMATION: Modified bacterial sequence

<400> SEQUENCE: 757

Ala Glu Ala Lys Tyr Ala Lys Glu Val Leu Glu Ala Trp Asp Glu Ile
 1               5                  10                  15

Asp Ala Leu Pro Asn Leu Thr Ile Glu Gln Trp Leu Ala Phe Ile Asn
            20                  25                  30

Lys Leu Asp Asp Asp Pro Ser Gln Ser Ser Glu Leu Leu Ser Glu Ala
        35                  40                  45

Lys Lys Leu Asn Asp Ser Gln Ala Pro Lys Val Asp
 50                  55                  60

<210> SEQ ID NO 758
<211> LENGTH: 58
<212> TYPE: PRT
<213> ORGANISM: artificial sequence
<220> FEATURE:

<223> OTHER INFORMATION: Modified bacterial sequence

<400> SEQUENCE: 758

| Val | Asp | Asn | Lys | Phe | Asn | Lys | Glu | Gln | Gln | Asn | Ala | Phe | Tyr | Glu | Ile |
|---|---|---|---|---|---|---|---|---|---|---|---|---|---|---|---|
| 1 | | | | 5 | | | | | 10 | | | | | 15 | |

| Leu | His | Leu | Pro | Asn | Leu | Asn | Glu | Glu | Gln | Arg | Asn | Ala | Phe | Ile | Gln |
|---|---|---|---|---|---|---|---|---|---|---|---|---|---|---|---|
| | | | 20 | | | | | 25 | | | | | 30 | | |

| Ser | Leu | Lys | Asp | Asp | Pro | Ser | Gln | Ser | Ala | Asn | Leu | Leu | Ala | Glu | Ala |
|---|---|---|---|---|---|---|---|---|---|---|---|---|---|---|---|
| | | 35 | | | | | 40 | | | | | 45 | | | |

| Lys | Lys | Leu | Asn | Asp | Ala | Gln | Ala | Pro | Lys |
|---|---|---|---|---|---|---|---|---|---|
| 50 | | | | | 55 | | | | |

<210> SEQ ID NO 759
<211> LENGTH: 46
<212> TYPE: PRT
<213> ORGANISM: artificial sequence
<220> FEATURE:
<223> OTHER INFORMATION: Modified bacterial sequence

<400> SEQUENCE: 759

| Leu | Ala | Glu | Ala | Lys | Glu | Ala | Ala | Asn | Ala | Glu | Leu | Asp | Ser | Tyr | Gly |
|---|---|---|---|---|---|---|---|---|---|---|---|---|---|---|---|
| 1 | | | | 5 | | | | | 10 | | | | | 15 | |

| Val | Ser | Asp | Phe | Tyr | Lys | Arg | Leu | Ile | Asp | Lys | Ala | Lys | Thr | Val | Glu |
|---|---|---|---|---|---|---|---|---|---|---|---|---|---|---|---|
| | | | 20 | | | | | 25 | | | | | 30 | | |

| Gly | Val | Glu | Ala | Leu | Lys | Asp | Ala | Ile | Leu | Ala | Ala | Leu | Pro |
|---|---|---|---|---|---|---|---|---|---|---|---|---|---|
| | | 35 | | | | | 40 | | | | | 45 | |

<210> SEQ ID NO 760
<211> LENGTH: 1676
<212> TYPE: PRT
<213> ORGANISM: Homo sapiens

<400> SEQUENCE: 760

| Met | Gly | Leu | Leu | Gly | Ile | Leu | Cys | Phe | Leu | Ile | Phe | Leu | Gly | Lys | Thr |
|---|---|---|---|---|---|---|---|---|---|---|---|---|---|---|---|
| 1 | | | | 5 | | | | | 10 | | | | | 15 | |

| Trp | Gly | Gln | Glu | Gln | Thr | Tyr | Val | Ile | Ser | Ala | Pro | Lys | Ile | Phe | Arg |
|---|---|---|---|---|---|---|---|---|---|---|---|---|---|---|---|
| | | | 20 | | | | | 25 | | | | | 30 | | |

| Val | Gly | Ala | Ser | Glu | Asn | Ile | Val | Ile | Gln | Val | Tyr | Gly | Tyr | Thr | Glu |
|---|---|---|---|---|---|---|---|---|---|---|---|---|---|---|---|
| | | 35 | | | | | 40 | | | | | 45 | | | |

| Ala | Phe | Asp | Ala | Thr | Ile | Ser | Ile | Lys | Ser | Tyr | Pro | Asp | Lys | Lys | Phe |
|---|---|---|---|---|---|---|---|---|---|---|---|---|---|---|---|
| 50 | | | | | 55 | | | | | 60 | | | | | |

| Ser | Tyr | Ser | Ser | Gly | His | Val | His | Leu | Ser | Ser | Glu | Asn | Lys | Phe | Gln |
|---|---|---|---|---|---|---|---|---|---|---|---|---|---|---|---|
| 65 | | | | 70 | | | | | 75 | | | | | 80 | |

| Asn | Ser | Ala | Ile | Leu | Thr | Ile | Gln | Pro | Lys | Gln | Leu | Pro | Gly | Gly | Gln |
|---|---|---|---|---|---|---|---|---|---|---|---|---|---|---|---|
| | | | 85 | | | | | 90 | | | | | 95 | | |

| Asn | Pro | Val | Ser | Tyr | Val | Tyr | Leu | Glu | Val | Val | Ser | Lys | His | Phe | Ser |
|---|---|---|---|---|---|---|---|---|---|---|---|---|---|---|---|
| | | 100 | | | | | 105 | | | | | 110 | | | |

| Lys | Ser | Lys | Arg | Met | Pro | Ile | Thr | Tyr | Asp | Asn | Gly | Phe | Leu | Phe | Ile |
|---|---|---|---|---|---|---|---|---|---|---|---|---|---|---|---|
| | 115 | | | | | 120 | | | | | 125 | | | | |

| His | Thr | Asp | Lys | Pro | Val | Tyr | Thr | Pro | Asp | Gln | Ser | Val | Lys | Val | Arg |
|---|---|---|---|---|---|---|---|---|---|---|---|---|---|---|---|
| | 130 | | | | | 135 | | | | | 140 | | | | |

| Val | Tyr | Ser | Leu | Asn | Asp | Asp | Leu | Lys | Pro | Ala | Lys | Arg | Glu | Thr | Val |
|---|---|---|---|---|---|---|---|---|---|---|---|---|---|---|---|
| 145 | | | | | 150 | | | | | 155 | | | | | 160 |

| Leu | Thr | Phe | Ile | Asp | Pro | Glu | Gly | Ser | Glu | Val | Asp | Met | Val | Glu | Glu |
|---|---|---|---|---|---|---|---|---|---|---|---|---|---|---|---|
| | | | 165 | | | | | 170 | | | | | 175 | | |

| Ile | Asp | His | Ile | Gly | Ile | Ile | Ser | Phe | Pro | Asp | Phe | Lys | Ile | Pro | Ser |
|---|---|---|---|---|---|---|---|---|---|---|---|---|---|---|---|
| | | | 180 | | | | | 185 | | | | | 190 | | |

```
Asn Pro Arg Tyr Gly Met Trp Thr Ile Lys Ala Lys Tyr Lys Glu Asp
            195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
    275                 280                 285

Asn Thr Met Leu Ile Asn Gly Ile Ala Gln Val Thr Phe Asp Ser Glu
290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
    355                 360                 365

Tyr Pro Ile Lys Val Gln Val Lys Asp Ser Leu Asp Gln Leu Val Gly
370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
    435                 440                 445

Arg Glu Gly Tyr Arg Ala Ile Ala Tyr Ser Ser Leu Ser Gln Ser Tyr
450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
    515                 520                 525

Pro Val Thr Gln Asn Met Val Pro Ser Ser Arg Leu Leu Val Tyr Tyr
530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
    595                 600                 605

Val Tyr Gly Val Gln Arg Gly Ala Lys Lys Pro Leu Glu Arg Val Phe
```

```
                610                 615                 620
Gln Phe Leu Glu Lys Ser Asp Leu Gly Cys Gly Ala Gly Gly Leu
625                 630                 635                 640

Asn Asn Ala Asn Val Phe His Leu Ala Gly Leu Thr Phe Leu Thr Asn
                    645                 650                 655

Ala Asn Ala Asp Asp Ser Gln Glu Asn Asp Glu Pro Cys Lys Glu Ile
                660                 665                 670

Leu Arg Pro Arg Arg Thr Leu Gln Lys Lys Ile Glu Glu Ile Ala Ala
            675                 680                 685

Lys Tyr Lys His Ser Val Val Lys Cys Cys Tyr Asp Gly Ala Cys
        690                 695                 700

Val Asn Asn Asp Glu Thr Cys Glu Gln Arg Ala Ala Arg Ile Ser Leu
705                 710                 715                 720

Gly Pro Arg Cys Ile Lys Ala Phe Thr Glu Cys Cys Val Val Ala Ser
                    725                 730                 735

Gln Leu Arg Ala Asn Ile Ser His Lys Asp Met Gln Leu Gly Arg Leu
                740                 745                 750

His Met Lys Thr Leu Leu Pro Val Ser Lys Pro Glu Ile Arg Ser Tyr
            755                 760                 765

Phe Pro Glu Ser Trp Leu Trp Glu Val His Leu Val Pro Arg Arg Lys
770                 775                 780

Gln Leu Gln Phe Ala Leu Pro Asp Ser Leu Thr Thr Trp Glu Ile Gln
785                 790                 795                 800

Gly Val Gly Ile Ser Asn Thr Gly Ile Cys Val Ala Asp Thr Val Lys
                    805                 810                 815

Ala Lys Val Phe Lys Asp Val Phe Leu Glu Met Asn Ile Pro Tyr Ser
                820                 825                 830

Val Val Arg Gly Glu Gln Ile Gln Leu Lys Gly Thr Val Tyr Asn Tyr
            835                 840                 845

Arg Thr Ser Gly Met Gln Phe Cys Val Lys Met Ser Ala Val Glu Gly
850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser His Leu Val
                    885                 890                 895

Thr Phe Thr Val Leu Pro Leu Glu Ile Gly Leu His Asn Ile Asn Phe
                900                 905                 910

Ser Leu Glu Thr Trp Phe Gly Lys Glu Ile Leu Val Lys Thr Leu Arg
            915                 920                 925

Val Val Pro Glu Gly Val Lys Arg Glu Ser Tyr Ser Gly Val Thr Leu
930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                    965                 970                 975

Leu Ser Val Lys Gly Leu Leu Val Gly Glu Ile Leu Ser Ala Val Leu
                980                 985                 990

Ser Gln Glu Gly Ile Asn Ile Leu  Thr His Leu Pro Lys  Gly Ser Ala
            995                 1000                1005

Glu Ala  Glu Leu Met Ser Val  Pro Val Phe Tyr  Val Phe His
    1010                1015                1020

Tyr Leu  Glu Thr Gly Asn His  Trp Asn Ile Phe His  Ser Asp Pro
    1025                1030                1035
```

-continued

| | | | | | | | | | | |
|---|---|---|---|---|---|---|---|---|---|---|
| Leu | Ile | Glu | Lys | Gln | Lys | Leu | Lys | Lys | Lys | Leu | Lys | Glu | Gly | Met |
| | 1040 | | | | 1045 | | | | 1050 | |
| Leu | Ser | Ile | Met | Ser | Tyr | Arg | Asn | Ala | Asp | Tyr | Ser | Tyr | Ser | Val |
| | 1055 | | | | 1060 | | | | 1065 | |
| Trp | Lys | Gly | Gly | Ser | Ala | Ser | Thr | Trp | Leu | Thr | Ala | Phe | Ala | Leu |
| | 1070 | | | | 1075 | | | | 1080 | |
| Arg | Val | Leu | Gly | Gln | Val | Asn | Lys | Tyr | Val | Glu | Gln | Asn | Gln | Asn |
| | 1085 | | | | 1090 | | | | 1095 | |
| Ser | Ile | Cys | Asn | Ser | Leu | Leu | Trp | Leu | Val | Glu | Asn | Tyr | Gln | Leu |
| | 1100 | | | | 1105 | | | | 1110 | |
| Asp | Asn | Gly | Ser | Phe | Lys | Glu | Asn | Ser | Gln | Tyr | Gln | Pro | Ile | Lys |
| | 1115 | | | | 1120 | | | | 1125 | |
| Leu | Gln | Gly | Thr | Leu | Pro | Val | Glu | Ala | Arg | Glu | Asn | Ser | Leu | Tyr |
| | 1130 | | | | 1135 | | | | 1140 | |
| Leu | Thr | Ala | Phe | Thr | Val | Ile | Gly | Ile | Arg | Lys | Ala | Phe | Asp | Ile |
| | 1145 | | | | 1150 | | | | 1155 | |
| Cys | Pro | Leu | Val | Lys | Ile | Asp | Thr | Ala | Leu | Ile | Lys | Ala | Asp | Asn |
| | 1160 | | | | 1165 | | | | 1170 | |
| Phe | Leu | Leu | Glu | Asn | Thr | Leu | Pro | Ala | Gln | Ser | Thr | Phe | Thr | Leu |
| | 1175 | | | | 1180 | | | | 1185 | |
| Ala | Ile | Ser | Ala | Tyr | Ala | Leu | Ser | Leu | Gly | Asp | Lys | Thr | His | Pro |
| | 1190 | | | | 1195 | | | | 1200 | |
| Gln | Phe | Arg | Ser | Ile | Val | Ser | Ala | Leu | Lys | Arg | Glu | Ala | Leu | Val |
| | 1205 | | | | 1210 | | | | 1215 | |
| Lys | Gly | Asn | Pro | Pro | Ile | Tyr | Arg | Phe | Trp | Lys | Asp | Asn | Leu | Gln |
| | 1220 | | | | 1225 | | | | 1230 | |
| His | Lys | Asp | Ser | Ser | Val | Pro | Asn | Thr | Gly | Thr | Ala | Arg | Met | Val |
| | 1235 | | | | 1240 | | | | 1245 | |
| Glu | Thr | Thr | Ala | Tyr | Ala | Leu | Leu | Thr | Ser | Leu | Asn | Leu | Lys | Asp |
| | 1250 | | | | 1255 | | | | 1260 | |
| Ile | Asn | Tyr | Val | Asn | Pro | Val | Ile | Lys | Trp | Leu | Ser | Glu | Glu | Gln |
| | 1265 | | | | 1270 | | | | 1275 | |
| Arg | Tyr | Gly | Gly | Gly | Phe | Tyr | Ser | Thr | Gln | Asp | Thr | Ile | Asn | Ala |
| | 1280 | | | | 1285 | | | | 1290 | |
| Ile | Glu | Gly | Leu | Thr | Glu | Tyr | Ser | Leu | Leu | Val | Lys | Gln | Leu | Arg |
| | 1295 | | | | 1300 | | | | 1305 | |
| Leu | Ser | Met | Asp | Ile | Asp | Val | Ser | Tyr | Lys | His | Lys | Gly | Ala | Leu |
| | 1310 | | | | 1315 | | | | 1320 | |
| His | Asn | Tyr | Lys | Met | Thr | Asp | Lys | Asn | Phe | Leu | Gly | Arg | Pro | Val |
| | 1325 | | | | 1330 | | | | 1335 | |
| Glu | Val | Leu | Leu | Asn | Asp | Asp | Leu | Ile | Val | Ser | Thr | Gly | Phe | Gly |
| | 1340 | | | | 1345 | | | | 1350 | |
| Ser | Gly | Leu | Ala | Thr | Val | His | Val | Thr | Thr | Val | Val | His | Lys | Thr |
| | 1355 | | | | 1360 | | | | 1365 | |
| Ser | Thr | Ser | Glu | Glu | Val | Cys | Ser | Phe | Tyr | Leu | Lys | Ile | Asp | Thr |
| | 1370 | | | | 1375 | | | | 1380 | |
| Gln | Asp | Ile | Glu | Ala | Ser | His | Tyr | Arg | Gly | Tyr | Gly | Asn | Ser | Asp |
| | 1385 | | | | 1390 | | | | 1395 | |
| Tyr | Lys | Arg | Ile | Val | Ala | Cys | Ala | Ser | Tyr | Lys | Pro | Ser | Arg | Glu |
| | 1400 | | | | 1405 | | | | 1410 | |
| Glu | Ser | Ser | Ser | Gly | Ser | Ser | His | Ala | Val | Met | Asp | Ile | Ser | Leu |
| | 1415 | | | | 1420 | | | | 1425 | |

```
Pro  Thr  Gly  Ile  Ser  Ala  Asn  Glu  Glu  Asp  Leu  Lys  Ala  Leu  Val
     1430                     1435                1440

Glu  Gly  Val  Asp  Gln  Leu  Phe  Thr  Asp  Tyr  Gln  Ile  Lys  Asp  Gly
     1445                     1450                1455

His  Val  Ile  Leu  Gln  Leu  Asn  Ser  Ile  Pro  Ser  Ser  Asp  Phe  Leu
     1460                     1465                1470

Cys  Val  Arg  Phe  Arg  Ile  Phe  Glu  Leu  Phe  Glu  Val  Gly  Phe  Leu
     1475                     1480                1485

Ser  Pro  Ala  Thr  Phe  Thr  Val  Tyr  Glu  Tyr  His  Arg  Pro  Asp  Lys
     1490                     1495                1500

Gln  Cys  Thr  Met  Phe  Tyr  Ser  Thr  Ser  Asn  Ile  Lys  Ile  Gln  Lys
     1505                     1510                1515

Val  Cys  Glu  Gly  Ala  Ala  Cys  Lys  Cys  Val  Glu  Ala  Asp  Cys  Gly
     1520                     1525                1530

Gln  Met  Gln  Glu  Glu  Leu  Asp  Leu  Thr  Ile  Ser  Ala  Glu  Thr  Arg
     1535                     1540                1545

Lys  Gln  Thr  Ala  Cys  Lys  Pro  Glu  Ile  Ala  Tyr  Ala  Tyr  Lys  Val
     1550                     1555                1560

Ser  Ile  Thr  Ser  Ile  Thr  Val  Glu  Asn  Val  Phe  Val  Lys  Tyr  Lys
     1565                     1570                1575

Ala  Thr  Leu  Leu  Asp  Ile  Tyr  Lys  Thr  Gly  Glu  Ala  Val  Ala  Glu
     1580                     1585                1590

Lys  Asp  Ser  Glu  Ile  Thr  Phe  Ile  Lys  Lys  Val  Thr  Cys  Thr  Asn
     1595                     1600                1605

Ala  Glu  Leu  Val  Lys  Gly  Arg  Gln  Tyr  Leu  Ile  Met  Gly  Lys  Glu
     1610                     1615                1620

Ala  Leu  Gln  Ile  Lys  Tyr  Asn  Phe  Ser  Phe  Arg  Tyr  Ile  Tyr  Pro
     1625                     1630                1635

Leu  Asp  Ser  Leu  Thr  Trp  Ile  Glu  Tyr  Trp  Pro  Arg  Asp  Thr  Thr
     1640                     1645                1650

Cys  Ser  Ser  Cys  Gln  Ala  Phe  Leu  Ala  Asn  Leu  Asp  Glu  Phe  Ala
     1655                     1660                1665

Glu  Asp  Ile  Phe  Leu  Asn  Gly  Cys
     1670                     1675

<210> SEQ ID NO 761
<211> LENGTH: 170
<212> TYPE: PRT
<213> ORGANISM: Ornithodoros moubata

<400> SEQUENCE: 761

Met  Asp  Ser  Glu  Ser  Asp  Cys  Thr  Gly  Ser  Glu  Pro  Val  Asp  Ala  Phe
1                  5                    10                   15

Gln  Ala  Phe  Ser  Glu  Gly  Lys  Glu  Ala  Tyr  Val  Leu  Val  Arg  Ser  Thr
                  20                   25                   30

Asp  Pro  Lys  Ala  Arg  Asp  Cys  Leu  Lys  Gly  Glu  Pro  Ala  Gly  Glu  Lys
             35                   40                   45

Gln  Asp  Asn  Thr  Leu  Pro  Val  Met  Met  Thr  Phe  Lys  Asn  Gly  Thr  Asp
         50                   55                   60

Trp  Ala  Ser  Thr  Asp  Trp  Thr  Phe  Thr  Leu  Asp  Gly  Ala  Lys  Val  Thr
65                   70                   75                   80

Ala  Thr  Leu  Gly  Asn  Leu  Thr  Gln  Asn  Arg  Glu  Val  Val  Tyr  Asp  Ser
                 85                   90                   95

Gln  Ser  His  His  Cys  His  Val  Asp  Lys  Val  Glu  Lys  Glu  Val  Pro  Asp
             100                  105                  110
```

-continued

```
Tyr Glu Met Trp Met Leu Asp Ala Gly Gly Leu Glu Val Glu Val Glu
            115                 120                 125

Cys Cys Arg Gln Lys Leu Glu Glu Leu Ala Ser Gly Arg Asn Gln Met
        130                 135                 140

Tyr Pro His Leu Lys Asp Cys Gly Gly Gly Ser Glu Asn Leu Tyr
145                 150                 155                 160

Phe Gln Gly Ser His His His His His His
                165                 170

<210> SEQ ID NO 762
<211> LENGTH: 1676
<212> TYPE: PRT
<213> ORGANISM: Macaca fascicularis
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (1346)..(1346)
<223> OTHER INFORMATION: Xaa can be any naturally occurring amino acid

<400> SEQUENCE: 762

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Xaa Phe
    50                  55                  60

Ser Tyr Ser Ser Gly His Val His Leu Ser Ser Glu Asn Lys Phe Gln
65                  70                  75                  80

Asn Ser Ala Val Leu Thr Ile Gln Pro Lys Gln Leu Pro Gly Gly Gln
                85                  90                  95

Asn Gln Val Ser Tyr Val Tyr Leu Glu Val Val Ser Lys His Phe Ser
            100                 105                 110

Lys Ser Lys Lys Ile Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Ile Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Gln Ala Lys Tyr Lys Glu Asp
        195                 200                 205

Phe Ser Thr Thr Gly Thr Ala Phe Phe Glu Val Lys Glu Tyr Val Leu
    210                 215                 220

Pro His Phe Ser Val Ser Val Glu Pro Glu Ser Asn Phe Ile Gly Tyr
225                 230                 235                 240

Lys Asn Phe Lys Asn Phe Glu Ile Thr Ile Lys Ala Arg Ile Phe Tyr
                245                 250                 255

Asn Lys Val Val Thr Glu Ala Asp Val Tyr Ile Thr Phe Gly Ile Arg
            260                 265                 270
```

```
Glu Asp Leu Lys Asp Asp Gln Lys Glu Met Met Gln Thr Ala Met Gln
        275                 280                 285

Asn Thr Met Leu Ile Asn Gly Ile Ala Glu Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Ser Ile Lys Val Gln Val Lys Asp Ala Leu Asp Gln Leu Val Gly
    370                 375                 380

Gly Val Pro Val Thr Leu Asn Ala Gln Thr Ile Asp Val Asn Gln Glu
385                 390                 395                 400

Thr Ser Asp Leu Glu Pro Arg Lys Ser Val Thr Arg Val Asp Asp Gly
                405                 410                 415

Val Ala Ser Phe Val Val Asn Leu Pro Ser Gly Val Thr Val Leu Glu
            420                 425                 430

Phe Asn Val Lys Thr Asp Ala Pro Asp Leu Pro Asp Glu Asn Gln Ala
        435                 440                 445

Arg Glu Gly Tyr Arg Ala Ile Ala Tyr Ser Ser Leu Ser Gln Ser Tyr
    450                 455                 460

Leu Tyr Ile Asp Trp Thr Asp Asn His Lys Ala Leu Leu Val Gly Glu
465                 470                 475                 480

Tyr Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Leu Ser Asp Ala Ser Tyr Gln Ser Ile Asn Ile
        515                 520                 525

Pro Val Thr Gln Asn Met Val Pro Ser Ser Arg Leu Leu Val Tyr Tyr
    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Thr Tyr Ser Pro Gly Gln Thr Val Ser Leu Asn Met
            580                 585                 590

Val Thr Gly Met Asp Ser Trp Val Ala Leu Thr Ala Val Asp Ser Ala
        595                 600                 605

Val Tyr Gly Val Gln Arg Arg Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Ile Arg Pro Arg Arg Met Leu Gln Glu Lys Ile Glu Glu Ile Ala Ala
        675                 680                 685
```

```
Lys Tyr Lys His Leu Val Val Lys Lys Cys Cys Tyr Asp Gly Val Arg
    690                 695                 700

Ile Asn His Asp Glu Thr Cys Glu Gln Arg Ala Ala Arg Ile Ser Val
705                 710                 715                 720

Gly Pro Arg Cys Val Lys Ala Phe Thr Glu Cys Cys Val Val Ala Ser
                725                 730                 735

Gln Leu Arg Ala Asn Asn Ser His Lys Asp Leu Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
770                 775                 780

Gln Leu Gln Phe Ala Leu Pro Asp Ser Val Thr Thr Trp Glu Ile Gln
785                 790                 795                 800

Gly Val Gly Ile Ser Asn Ser Gly Ile Cys Val Ala Asp Thr Ile Lys
                805                 810                 815

Ala Lys Val Phe Lys Asp Val Phe Leu Glu Met Asn Ile Pro Tyr Ser
            820                 825                 830

Val Val Arg Gly Glu Gln Val Gln Leu Lys Gly Thr Val Tyr Asn Tyr
        835                 840                 845

Arg Thr Ser Gly Met Gln Phe Cys Val Lys Met Ser Ala Val Glu Gly
850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser Asn His Leu Val
                885                 890                 895

Thr Phe Thr Val Leu Pro Leu Glu Ile Gly Leu Gln Asn Ile Asn Phe
            900                 905                 910

Ser Leu Glu Thr Ser Phe Gly Lys Glu Ile Leu Val Lys Ser Leu Arg
        915                 920                 925

Val Val Pro Glu Gly Val Lys Arg Glu Ser Tyr Ser Gly Ile Thr Leu
930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Arg Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His
        1010                1015                1020

Tyr Leu Glu Thr Gly Asn His Trp Asn Ile Phe His Ser Asp Pro
        1025                1030                1035

Leu Ile Glu Lys Arg Asn Leu Glu Lys Lys Leu Lys Glu Gly Met
        1040                1045                1050

Val Ser Ile Met Ser Tyr Arg Asn Ala Asp Tyr Ser Tyr Ser Val
        1055                1060                1065

Trp Lys Gly Gly Ser Ala Ser Thr Trp Leu Thr Ala Phe Ala Leu
        1070                1075                1080

Arg Val Leu Gly Gln Val His Lys Tyr Val Glu Gln Asn Gln Asn
        1085                1090                1095

Ser Ile Cys Asn Ser Leu Leu Trp Leu Val Glu Asn Tyr Gln Leu
```

```
                  1100                1105                1110

Asp Asn Gly Ser Phe Lys Glu Asn Ser Gln Tyr Gln Pro Ile Lys
                  1115                1120                1125

Leu Gln Gly Thr Leu Pro Val Glu Ala Arg Glu Asn Ser Leu Tyr
                  1130                1135                1140

Leu Thr Ala Phe Thr Val Ile Gly Ile Arg Lys Ala Phe Asp Ile
                  1145                1150                1155

Cys Pro Leu Val Lys Ile Asn Thr Ala Leu Ile Lys Ala Asp Thr
                  1160                1165                1170

Phe Leu Leu Glu Asn Thr Leu Pro Ala Gln Ser Thr Phe Thr Leu
                  1175                1180                1185

Ala Ile Ser Ala Tyr Ala Leu Ser Leu Gly Asp Lys Thr His Pro
                  1190                1195                1200

Gln Phe Arg Ser Ile Val Ser Ala Leu Lys Arg Glu Ala Leu Val
                  1205                1210                1215

Lys Gly Asn Pro Pro Ile Tyr Arg Phe Trp Lys Asp Ser Leu Gln
                  1220                1225                1230

His Lys Asp Ser Ser Val Pro Asn Thr Gly Thr Ala Arg Met Val
                  1235                1240                1245

Glu Thr Thr Ala Tyr Ala Leu Leu Thr Ser Leu Asn Leu Lys Asp
                  1250                1255                1260

Ile Asn Tyr Val Asn Pro Ile Ile Lys Trp Leu Ser Glu Glu Gln
                  1265                1270                1275

Arg Tyr Gly Gly Gly Phe Tyr Ser Thr Gln Asp Thr Ile Asn Ala
                  1280                1285                1290

Ile Glu Gly Leu Thr Glu Tyr Ser Leu Leu Val Lys Gln Leu Arg
                  1295                1300                1305

Leu Asn Met Asp Ile Asp Val Ala Tyr Lys His Lys Gly Pro Leu
                  1310                1315                1320

His Asn Tyr Lys Met Thr Asp Lys Asn Phe Leu Gly Arg Pro Val
                  1325                1330                1335

Glu Val Leu Leu Asn Asp Asp Xaa Val Val Ser Thr Gly Phe Gly
                  1340                1345                1350

Ser Gly Leu Ala Thr Val His Val Thr Thr Val His Lys Thr
                  1355                1360                1365

Ser Thr Ser Glu Glu Val Cys Ser Phe Tyr Leu Lys Ile Asp Thr
                  1370                1375                1380

Gln Asp Val Glu Ala Ser His Tyr Arg Gly Tyr Gly Asn Ser Asp
                  1385                1390                1395

Tyr Lys Arg Ile Val Ala Cys Ala Ser Tyr Lys Pro Ser Lys Glu
                  1400                1405                1410

Glu Ser Ser Gly Ser Ser His Ala Val Met Asp Ile Ser Leu
                  1415                1420                1425

Pro Thr Gly Ile Asn Ala Asn Glu Glu Asp Leu Lys Ala Leu Val
                  1430                1435                1440

Glu Gly Val Asp Gln Leu Phe Thr Asp Tyr Gln Ile Lys Asp Gly
                  1445                1450                1455

His Val Ile Leu Gln Leu Asn Ser Ile Pro Ser Ser Asp Phe Leu
                  1460                1465                1470

Cys Val Arg Phe Arg Ile Phe Glu Leu Phe Glu Val Gly Phe Leu
                  1475                1480                1485

Ser Pro Ala Thr Phe Thr Val Tyr Glu Tyr His Arg Pro Asp Lys
                  1490                1495                1500
```

```
Gln Cys Thr Met Phe Tyr Ser Thr Ser Asn Ile Lys Ile Gln Lys
    1505                1510                1515

Val Cys Glu Gly Ala Thr Cys Lys Cys Ile Glu Ala Asp Cys Gly
    1520                1525                1530

Gln Met Gln Lys Glu Leu Asp Leu Thr Ile Ser Ala Glu Thr Arg
    1535                1540                1545

Lys Gln Thr Ala Cys Asn Pro Glu Ile Ala Tyr Ala Tyr Lys Val
    1550                1555                1560

Ile Ile Thr Ser Ile Thr Thr Glu Asn Val Phe Val Lys Tyr Lys
    1565                1570                1575

Ala Thr Leu Leu Asp Ile Tyr Lys Thr Gly Glu Ala Val Ala Glu
    1580                1585                1590

Lys Asp Ser Glu Ile Thr Phe Ile Lys Lys Val Thr Cys Thr Asn
    1595                1600                1605

Ala Glu Leu Val Lys Gly Arg Gln Tyr Leu Ile Met Gly Lys Glu
    1610                1615                1620

Ala Leu Gln Ile Lys Tyr Asn Phe Thr Phe Arg Tyr Ile Tyr Pro
    1625                1630                1635

Leu Asp Ser Leu Thr Trp Ile Glu Tyr Trp Pro Arg Asp Thr Thr
    1640                1645                1650

Cys Ser Ser Cys Gln Ala Phe Leu Ala Asn Leu Asp Glu Phe Ala
    1655                1660                1665

Glu Asp Ile Phe Leu Asn Gly Cys
    1670                1675

<210> SEQ ID NO 763
<211> LENGTH: 29
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (2)..(2)
<223> OTHER INFORMATION: Amino acid selected from H, Q, S, T and V
<220> FEATURE:
<221> NAME/KEY: MISC_FEATURE
<222> LOCATION: (3)..(3)
<223> OTHER INFORMATION: Amino acid selected from I, L, M, and V
<220> FEATURE:
<221> NAME/KEY: MISC_FEATURE
<222> LOCATION: (4)..(4)
<223> OTHER INFORMATION: Amino acid selected from A, D, E, H, K, L, N,
    Q, R, S, T and Y
<220> FEATURE:
<221> NAME/KEY: MISC_FEATURE
<222> LOCATION: (6)..(6)
<223> OTHER INFORMATION: Amino acid selected from N and W
<220> FEATURE:
<221> NAME/KEY: MISC_FEATURE
<222> LOCATION: (7)..(7)
<223> OTHER INFORMATION: Amino acid selected from A, D, E, H, N, Q, R,
    S and T
<220> FEATURE:
<221> NAME/KEY: MISC_FEATURE
<222> LOCATION: (11)..(11)
<223> OTHER INFORMATION: Amino acid selected from A, E, G, H, K, L, Q,
    R, S, T and Y
<220> FEATURE:
<221> NAME/KEY: MISC_FEATURE
<222> LOCATION: (16)..(16)
<223> OTHER INFORMATION: Amino acid selected from N and T
<220> FEATURE:
<221> NAME/KEY: MISC_FEATURE
<222> LOCATION: (17)..(17)
<223> OTHER INFORMATION: Amino acid selected from I, L and V
```

```
<220> FEATURE:
<221> NAME/KEY: MISC_FEATURE
<222> LOCATION: (18)..(18)
<223> OTHER INFORMATION: Amino acid selected from A, D, E, H, K, N, Q,
      R, S and T
<220> FEATURE:
<221> NAME/KEY: MISC_FEATURE
<222> LOCATION: (21)..(21)
<223> OTHER INFORMATION: Amino acid selected from I, L and V
<220> FEATURE:
<221> NAME/KEY: MISC_FEATURE
<222> LOCATION: (25)..(25)
<223> OTHER INFORMATION: Amino acid selected from D, E, G, H, N, S and T
<220> FEATURE:
<221> NAME/KEY: MISC_FEATURE
<222> LOCATION: (26)..(26)
<223> OTHER INFORMATION: Amino acid selected from K and S
<220> FEATURE:
<221> NAME/KEY: MISC_FEATURE
<222> LOCATION: (28)..(28)
<223> OTHER INFORMATION: Amino acid selected from A, D, E, H, N, Q, S, T
      and Y

<400> SEQUENCE: 763

Glu Xaa Xaa Xaa Ala Xaa Xaa Glu Ile Asp Xaa Leu Pro Asn Leu Xaa
1               5                   10                  15

Xaa Xaa Gln Trp Xaa Ala Phe Ile Xaa Xaa Leu Xaa Asp
            20                  25

<210> SEQ ID NO 764
<211> LENGTH: 20
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(2)
<223> OTHER INFORMATION: BM is a C5 binding motif
<220> FEATURE:
<221> NAME/KEY: MISC_FEATURE
<222> LOCATION: (7)..(7)
<223> OTHER INFORMATION: Xaa selected from A and S
<220> FEATURE:
<221> NAME/KEY: MISC_FEATURE
<222> LOCATION: (8)..(8)
<223> OTHER INFORMATION: Xaa selected from N and E
<220> FEATURE:
<221> NAME/KEY: MISC_FEATURE
<222> LOCATION: (11)..(11)
<223> OTHER INFORMATION: Xaa selected from A, S and C
<220> FEATURE:
<221> NAME/KEY: MISC_FEATURE
<222> LOCATION: (19)..(19)
<223> OTHER INFORMATION: Xaa selected from A and S

<400> SEQUENCE: 764

Lys Asp Pro Ser Gln Ser Xaa Xaa Leu Leu Xaa Glu Ala Lys Lys Leu
1               5                   10                  15

Asn Asp Xaa Gln
            20

<210> SEQ ID NO 765
<211> LENGTH: 24
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(4)
<223> OTHER INFORMATION: BM is a C5 binding motif
<220> FEATURE:
```

<221> NAME/KEY: MISC_FEATURE
<222> LOCATION: (13)..(13)
<223> OTHER INFORMATION: Xaa selected from S and C

<400> SEQUENCE: 765

Tyr Ala Lys Asp Pro Ser Gln Ser Ser Glu Leu Leu Xaa Glu Ala Lys
1               5                   10                  15

Lys Leu Asn Asp Ser Gln Ala Pro
            20

<210> SEQ ID NO 766
<211> LENGTH: 24
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (3)..(4)
<223> OTHER INFORMATION: BM is a C5 binding motif
<220> FEATURE:
<221> NAME/KEY: MISC_FEATURE
<222> LOCATION: (13)..(13)
<223> OTHER INFORMATION: Xaa selected from A and C

<400> SEQUENCE: 766

Phe Asn Lys Asp Pro Ser Gln Ser Ala Asn Leu Leu Xaa Glu Ala Lys
1               5                   10                  15

Lys Leu Asn Asp Ala Gln Ala Pro
            20

<210> SEQ ID NO 767
<211> LENGTH: 16
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (8)..(9)
<223> OTHER INFORMATION: Individual Z variant
<220> FEATURE:
<221> NAME/KEY: MISC_FEATURE
<222> LOCATION: (12)..(13)
<223> OTHER INFORMATION: Albumin binding domain

<400> SEQUENCE: 767

Ala Gln His Asp Glu Ala Leu Glu Val Asp Tyr Val Tyr Val Pro Gly
1               5                   10                  15

<210> SEQ ID NO 768
<211> LENGTH: 16
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (8)..(9)
<223> OTHER INFORMATION: Individual Z variant
<220> FEATURE:
<221> NAME/KEY: MISC_FEATURE
<222> LOCATION: (12)..(13)
<223> OTHER INFORMATION: Z variant Z03639

<400> SEQUENCE: 768

Ala Gln His Asp Glu Ala Leu Glu Val Asp Tyr Val Tyr Val Pro Gly
1               5                   10                  15

```
<210> SEQ ID NO 769
<211> LENGTH: 16
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (8)..(9)
<223> OTHER INFORMATION: Z variant Z03938
<220> FEATURE:
<221> NAME/KEY: MISC_FEATURE
<222> LOCATION: (12)..(13)
<223> OTHER INFORMATION: Z variant Z03639

<400> SEQUENCE: 769

Ala Gln His Asp Glu Ala Leu Glu Val Asp Tyr Val Tyr Val Pro Gly
1               5                   10                  15

<210> SEQ ID NO 770
<211> LENGTH: 24
<212> TYPE: DNA
<213> ORGANISM: Artificial Sequence
<220> FEATURE:
<223> OTHER INFORMATION: Primer Sequence

<400> SEQUENCE: 770
tgcttccggc tcgtatgttg tgtg                                          24

<210> SEQ ID NO 771
<211> LENGTH: 21
<212> TYPE: DNA
<213> ORGANISM: Artificial Sequence
<220> FEATURE:
<223> OTHER INFORMATION: Primer sequence

<400> SEQUENCE: 771
cggaaccaga gccaccaccg g                                             21

<210> SEQ ID NO 772
<211> LENGTH: 21
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)..(1)
<223> OTHER INFORMATION: 5' biotin cap

<400> SEQUENCE: 772
cggaaccaga gccaccaccg g                                             21

<210> SEQ ID NO 773
<211> LENGTH: 14
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (12)..(13)
<223> OTHER INFORMATION: Two individual Z variants

<400> SEQUENCE: 773

Met Gly Ser Ser His His His His His His Leu Gln Val Asp
1               5                   10

<210> SEQ ID NO 774
```

```
<211> LENGTH: 183
<212> TYPE: DNA
<213> ORGANISM: Artificial Sequence
<220> FEATURE:
<223> OTHER INFORMATION: Library coding sequence
<220> FEATURE:
<221> NAME/KEY: misc_feature
<222> LOCATION: (42)..(44)
<223> OTHER INFORMATION: Randomized codon
<220> FEATURE:
<221> NAME/KEY: misc_feature
<222> LOCATION: (45)..(47)
<223> OTHER INFORMATION: Randomized codon
<220> FEATURE:
<221> NAME/KEY: misc_feature
<222> LOCATION: (48)..(50)
<223> OTHER INFORMATION: Randomized codon
<220> FEATURE:
<221> NAME/KEY: misc_feature
<222> LOCATION: (55)..(59)
<223> OTHER INFORMATION: Randomized codon
<220> FEATURE:
<221> NAME/KEY: misc_feature
<222> LOCATION: (60)..(62)
<223> OTHER INFORMATION: Randomized codon
<220> FEATURE:
<221> NAME/KEY: misc_feature
<222> LOCATION: (75)..(77)
<223> OTHER INFORMATION: Randomized codon
<220> FEATURE:
<221> NAME/KEY: misc_feature
<222> LOCATION: (78)..(80)
<223> OTHER INFORMATION: Randomized codon
<220> FEATURE:
<221> NAME/KEY: misc_feature
<222> LOCATION: (102)..(104)
<223> OTHER INFORMATION: Randomized codon
<220> FEATURE:
<221> NAME/KEY: misc_feature
<222> LOCATION: (105)..(107)
<223> OTHER INFORMATION: Randomized codon
<220> FEATURE:
<221> NAME/KEY: misc_feature
<222> LOCATION: (117)..(119)
<223> OTHER INFORMATION: Randomized codon
<220> FEATURE:
<221> NAME/KEY: misc_feature
<222> LOCATION: (135)..(137)
<223> OTHER INFORMATION: Randomized codon
<220> FEATURE:
<221> NAME/KEY: misc_feature
<222> LOCATION: (150)..(152)
<223> OTHER INFORMATION: Randomized codon

<400> SEQUENCE: 774
aaataaatct cgaggtagat gccaaatacg ccaaagaaga gnnnnnnnnn gcagccnnnn      60
nngaggaaat cattnnnnnn ttactgccta acttaaccac tnnnnnncaa cagtggnnng     120
ccgcgttcat cattnnnaaa aagttactgn nngatgacga cccaagccag agctcattat     180
tta                                                                  183

<210> SEQ ID NO 775
<211> LENGTH: 14
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (12)..(13)
<223> OTHER INFORMATION: Individual Z variant

<400> SEQUENCE: 775

Met Gly Ser Ser His His His His His His Leu Gln Val Asp
```

```
1               5                   10
```

<210> SEQ ID NO 776
<211> LENGTH: 12
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (1)..(1)
<223> OTHER INFORMATION: Individual Z variant Z06175a
<220> FEATURE:
<221> NAME/KEY: MISC_FEATURE
<222> LOCATION: (12)..(12)
<223> OTHER INFORMATION: Albumin Binding Domain 094

<400> SEQUENCE: 776

```
Gly Ser Gly Gly Gly Gly Ser Gly Gly Gly Gly Ser
1               5                   10
```

<210> SEQ ID NO 777
<211> LENGTH: 14
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: Z is an individual Z variant Z06175a
<220> FEATURE:
<221> NAME/KEY: MISC_FEATURE
<222> LOCATION: (2)..(3)
<223> OTHER INFORMATION: Albumin binding domain 094
<220> FEATURE:
<221> NAME/KEY: MISC_FEATURE
<222> LOCATION: (14)..(14)
<223> OTHER INFORMATION: Z is an individual Z variant Z06175a

<400> SEQUENCE: 777

```
Gly Ser Gly Ser Gly Gly Gly Gly Ser Gly Gly Gly Gly Ser
1               5                   10
```

<210> SEQ ID NO 778
<211> LENGTH: 12
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: Z is an individual Z variant Z06175a
<220> FEATURE:
<221> NAME/KEY: MISC_FEATURE
<222> LOCATION: (12)..(12)
<223> OTHER INFORMATION: Albumin binding domain 094

<400> SEQUENCE: 778

```
Gly Ser Gly Gly Gly Gly Ser Gly Gly Gly Gly Ser
1               5                   10
```

<210> SEQ ID NO 779
<211> LENGTH: 12
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)

-continued

```
<223> OTHER INFORMATION: Z is individual Z variant Z06175a
<220> FEATURE:
<221> NAME/KEY: MISC_FEATURE
<222> LOCATION: (12)..(12)
<223> OTHER INFORMATION: Albumin binding domain 094

<400> SEQUENCE: 779

Gly Ser Gly Gly Gly Gly Ser Gly Gly Gly Gly Ser
1               5                   10

<210> SEQ ID NO 780
<211> LENGTH: 15
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (1)..(1)
<223> OTHER INFORMATION: Individual Z variant is Z06175a
<220> FEATURE:
<221> NAME/KEY: MISC_FEATURE
<222> LOCATION: (2)..(3)
<223> OTHER INFORMATION: Albumin binding domain 094
<220> FEATURE:
<221> NAME/KEY: MISC_FEATURE
<222> LOCATION: (14)..(14)
<223> OTHER INFORMATION: Individual Z variant is Z06175a

<400> SEQUENCE: 780

Ala Gly Ser Gly Ser Gly Gly Gly Gly Ser Gly Gly Gly Gly Ser
1               5                   10                  15

<210> SEQ ID NO 781
<211> LENGTH: 15
<212> TYPE: PRT
<213> ORGANISM: Artificial Sequence
<220> FEATURE:
<223> OTHER INFORMATION: Artificial Sequence
<220> FEATURE:
<221> NAME/KEY: MISC_FEATURE
<222> LOCATION: (1)..(1)
<223> OTHER INFORMATION: Individual Z variant is Z06175a
<220> FEATURE:
<221> NAME/KEY: MISC_FEATURE
<222> LOCATION: (2)..(3)
<223> OTHER INFORMATION: Albumin binding domain 094
<220> FEATURE:
<221> NAME/KEY: MISC_FEATURE
<222> LOCATION: (14)..(14)
<223> OTHER INFORMATION: Individual Z variant is Z06175a

<400> SEQUENCE: 781

Ala Gly Ser Gly Ser Gly Gly Gly Gly Ser Gly Gly Gly Gly Ser
1               5                   10                  15

<210> SEQ ID NO 782
<211> LENGTH: 14
<212> TYPE: PRT
<213> ORGANISM: Artificial Sequence
<220> FEATURE:
<223> OTHER INFORMATION: Artificial Sequence
<220> FEATURE:
<221> NAME/KEY: MISC_FEATURE
<222> LOCATION: (2)..(2)
<223> OTHER INFORMATION: Sequence contains carbon 13 and nitrogen 15

<400> SEQUENCE: 782

Ile Asn Lys Leu Asp Asp Asp Pro Ser Gln Ser Ser Glu Leu
1               5                   10
```

```
<210> SEQ ID NO 783
<211> LENGTH: 4
<212> TYPE: PRT
<213> ORGANISM: Artificial Sequence
<220> FEATURE:
<223> OTHER INFORMATION: linking moiety
<220> FEATURE:
<221> NAME/KEY: MISC_FEATURE
<222> LOCATION: (1)..(4)
<223> OTHER INFORMATION: Repeated 0-7 times

<400> SEQUENCE: 783

Gly Gly Gly Ser
1

<210> SEQ ID NO 784
<211> LENGTH: 5
<212> TYPE: PRT
<213> ORGANISM: Artificial Sequence
<220> FEATURE:
<223> OTHER INFORMATION: linking moiety
<220> FEATURE:
<221> NAME/KEY: MISC_FEATURE
<222> LOCATION: (1)..(5)
<223> OTHER INFORMATION: Repeated 0-7 times

<400> SEQUENCE: 784

Gly Gly Gly Gly Ser
1               5

<210> SEQ ID NO 785
<211> LENGTH: 7
<212> TYPE: PRT
<213> ORGANISM: Artificial Sequence
<220> FEATURE:
<223> OTHER INFORMATION: linking moiety
<220> FEATURE:
<221> NAME/KEY: MISC_FEATURE
<222> LOCATION: (3)..(7)
<223> OTHER INFORMATION: Repeated 0-7 times

<400> SEQUENCE: 785

Gly Ser Gly Gly Gly Gly Ser
1               5

<210> SEQ ID NO 786
<211> LENGTH: 4
<212> TYPE: PRT
<213> ORGANISM: Artificial Sequence
<220> FEATURE:
<223> OTHER INFORMATION: linking moiety
<220> FEATURE:
<221> NAME/KEY: MISC_FEATURE
<222> LOCATION: (1)..(4)
<223> OTHER INFORMATION: Repeated 0-7 times

<400> SEQUENCE: 786

Ser Ser Ser Gly
1

<210> SEQ ID NO 787
<211> LENGTH: 5
<212> TYPE: PRT
<213> ORGANISM: Artificial Sequence
<220> FEATURE:
<223> OTHER INFORMATION: linking moiety
<220> FEATURE:
<221> NAME/KEY: MISC_FEATURE
<222> LOCATION: (1)..(5)
<223> OTHER INFORMATION: Repeated 0-7 times
```

```
<400> SEQUENCE: 787

Ser Ser Ser Ser Gly
1               5

<210> SEQ ID NO 788
<211> LENGTH: 4
<212> TYPE: PRT
<213> ORGANISM: Artificial Sequence
<220> FEATURE:
<223> OTHER INFORMATION: linking moiety

<400> SEQUENCE: 788

Val Asp Gly Ser
1

<210> SEQ ID NO 789
<211> LENGTH: 13
<212> TYPE: PRT
<213> ORGANISM: Artificial Sequence
<220> FEATURE:
<223> OTHER INFORMATION: C5 binding moiety
<220> FEATURE:
<221> NAME/KEY: MISC_FEATURE
<222> LOCATION: (1)..(1)
<223> OTHER INFORMATION: Individual Z variant Z06175a
<220> FEATURE:
<221> NAME/KEY: MISC_FEATURE
<222> LOCATION: (2)..(3)
<223> OTHER INFORMATION: Albumin Binding Domain 094
<220> FEATURE:
<221> NAME/KEY: MISC_FEATURE
<222> LOCATION: (13)..(13)
<223> OTHER INFORMATION: Individual Z variant Z06175a

<400> SEQUENCE: 789

Gly Ser Gly Ser Gly Gly Gly Gly Ser Gly Gly Gly Ser
1               5                   10
```